US011535627B2

(12) United States Patent
Park et al.

(10) Patent No.: US 11,535,627 B2
(45) Date of Patent: Dec. 27, 2022

(54) PYRIMIDINE DERIVATIVE COMPOUND, PHARMACEUTICALLY ACCEPTABLE SALT THEREOF, PREPARATION PROCESS THEREOF, AND PHARMACEUTICAL COMPOSITION USING THE SAME

(71) Applicant: Spark Biopharma, Inc., Seoul (KR)

(72) Inventors: Seung Bum Park, Seoul (KR); Jonghoon Kim, Seoul (KR)

(73) Assignee: Spark Biopharma, Inc., Seoul (KR)

( * ) Notice: Subject to any disclaimer, the term of this patent is extended or adjusted under 35 U.S.C. 154(b) by 37 days.

(21) Appl. No.: 16/338,139

(22) PCT Filed: Sep. 15, 2017

(86) PCT No.: PCT/KR2017/010120

§ 371 (c)(1),
(2) Date: Mar. 29, 2019

(87) PCT Pub. No.: WO2018/062732

PCT Pub. Date: Apr. 5, 2018

(65) Prior Publication Data

US 2020/0190099 A1 Jun. 18, 2020

(30) Foreign Application Priority Data

Sep. 30, 2016 (KR) ........................ 10-2016-0127045

(51) Int. Cl.

| | |
|---|---|
| ***A61K 31/551*** | (2006.01) |
| ***A61P 35/00*** | (2006.01) |
| ***C07D 487/04*** | (2006.01) |
| ***C07D 498/14*** | (2006.01) |
| ***C07D 515/14*** | (2006.01) |
| ***C07D 487/22*** | (2006.01) |
| ***C07D 471/18*** | (2006.01) |
| ***C07D 487/14*** | (2006.01) |
| ***C07D 487/16*** | (2006.01) |
| ***C07D 498/04*** | (2006.01) |
| ***C07D 498/08*** | (2006.01) |

(52) U.S. Cl.

CPC ............ *C07D 487/22* (2013.01); *A61P 35/00* (2018.01); *C07D 471/18* (2013.01); *C07D 487/04* (2013.01); *C07D 487/14* (2013.01); *C07D 487/16* (2013.01); *C07D 498/04* (2013.01); *C07D 498/08* (2013.01); *C07D 515/14* (2013.01)

(58) Field of Classification Search

CPC ..... A61K 31/551; A61P 35/00; C07D 487/04; C07D 498/14; C07D 515/14

See application file for complete search history.

(56) References Cited

FOREIGN PATENT DOCUMENTS

| | | | |
|---|---|---|---|
| WO | 93-08171 | A1 | 4/1993 |
| WO | 2004-030635 | A2 | 4/2004 |
| WO | 2013-064231 | A1 | 5/2013 |

OTHER PUBLICATIONS

Heaney, F. et al, "Pyrimidine Annelated Heterocycles-synthesis and Cycloaddition of the First Pyrimido[1,4] diazepine N-oxides", Perkin1: An International Journal of Organic and Bio-organic Chemistry, 2001, vol. 6, pp. 622-632.**

Huddleston, N. E. et al., "Synthesis of 2-amino-4-chloro-6,9-bis-(2,4-dimethoxy benzyl)-6,7,8,9-tetrahydro-5H-pyrimido [4,5-e][1,4]diazepine. A Potentially Useful Intermediate to Pyrimido[4,5-e][1,4]diazepine-based Folates", Heterocyclic Communications, 2004, vol. 10, No. 6, pp. 405-406.**

Kim, J. et al., "Diversity-oriented Synthetic Strategy for Developing a Chemical Modulator of Protein-protein Interaction", Nature Communications, Oct. 24, 2016, vol. 7, Article No. 13196, inner pp. 1-10.**

*Primary Examiner* — Brenda L Coleman

(74) *Attorney, Agent, or Firm* — United One Law Group LLC; Kongsik Kim; Jhongwoo Peck

(57) ABSTRACT

The present invention is related to a novel pyrimidine derivative compound or a pharmaceutically acceptable salt thereof, a process for preparing the same, and a pharmaceutical composition using the same.

6 Claims, 127 Drawing Sheets

[Figure 1]
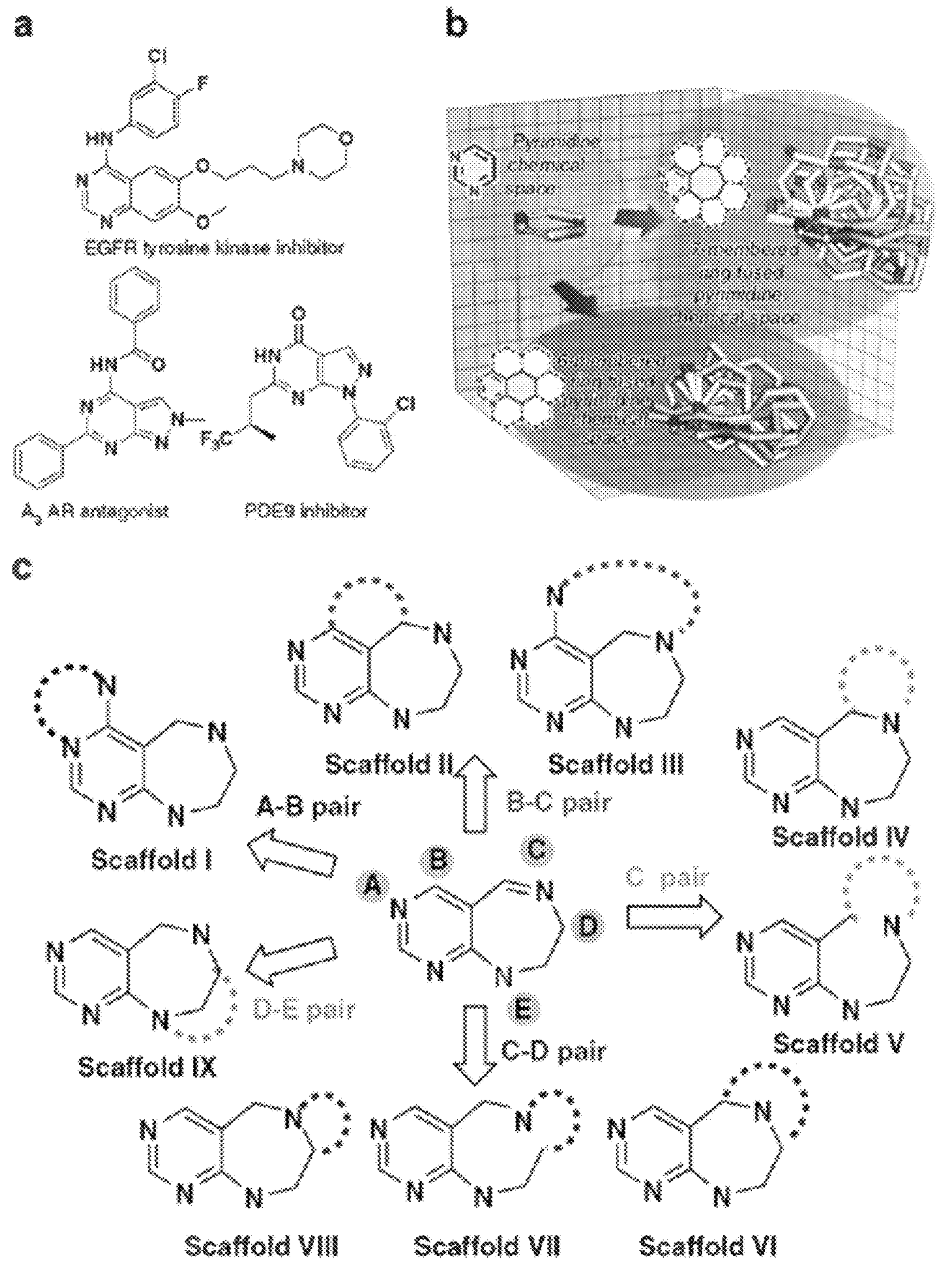

[Figure 2]
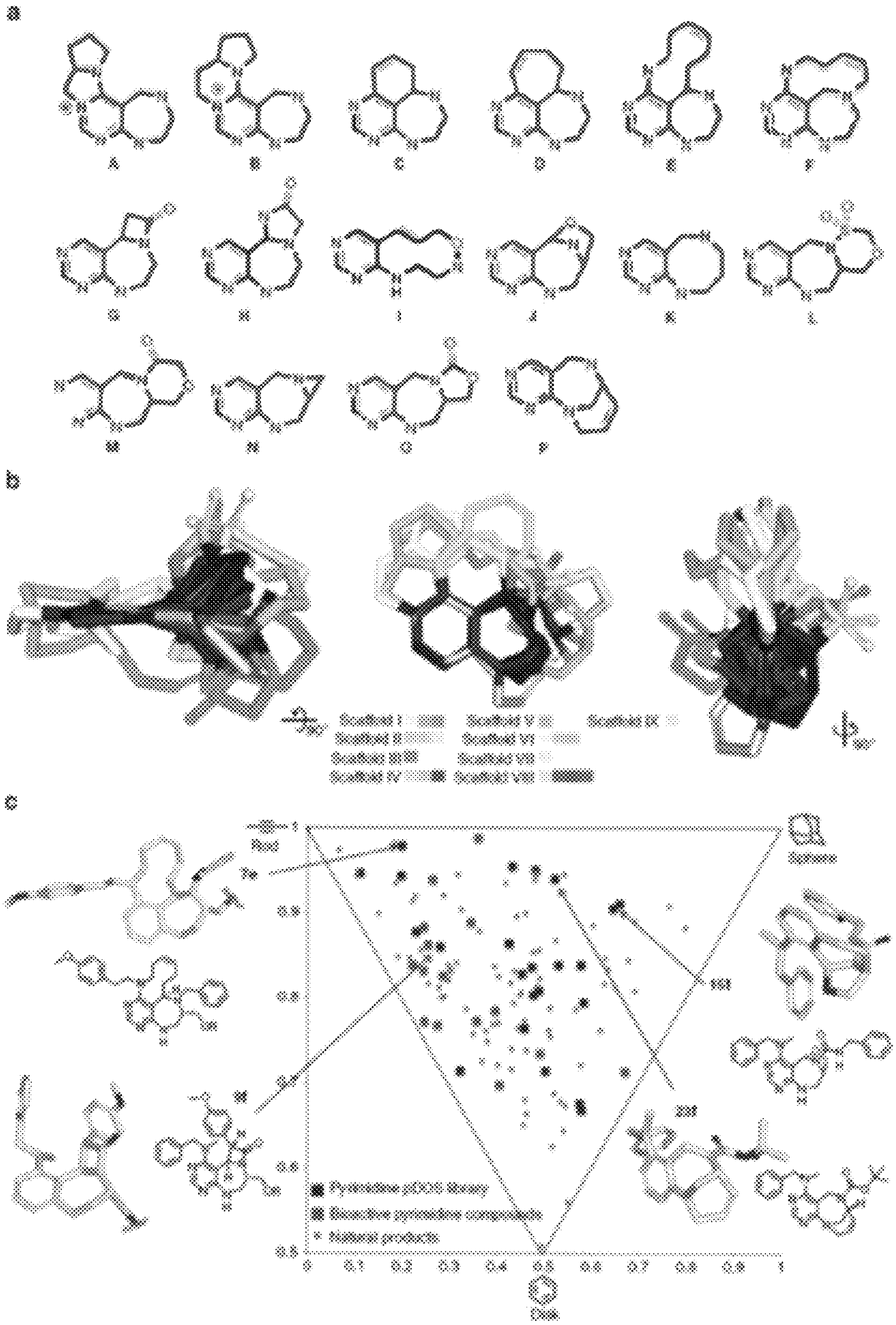

[Figure 3]
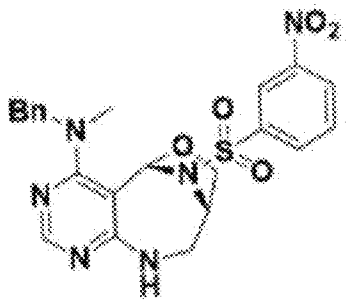
16f
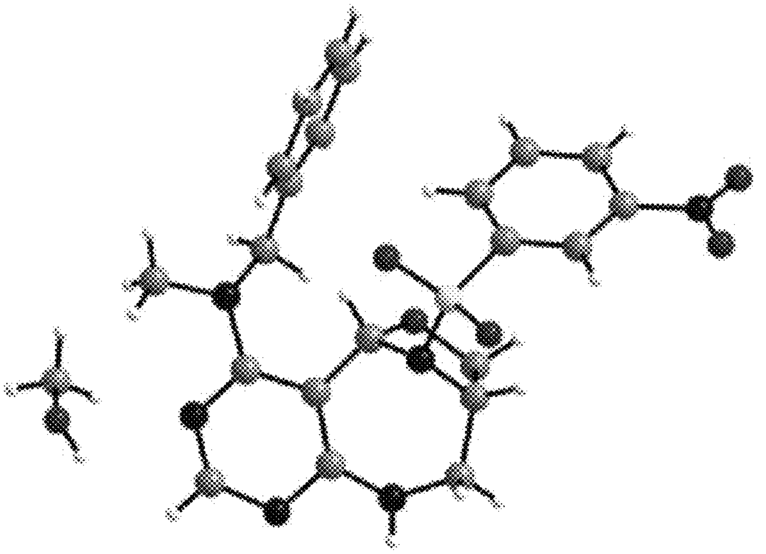
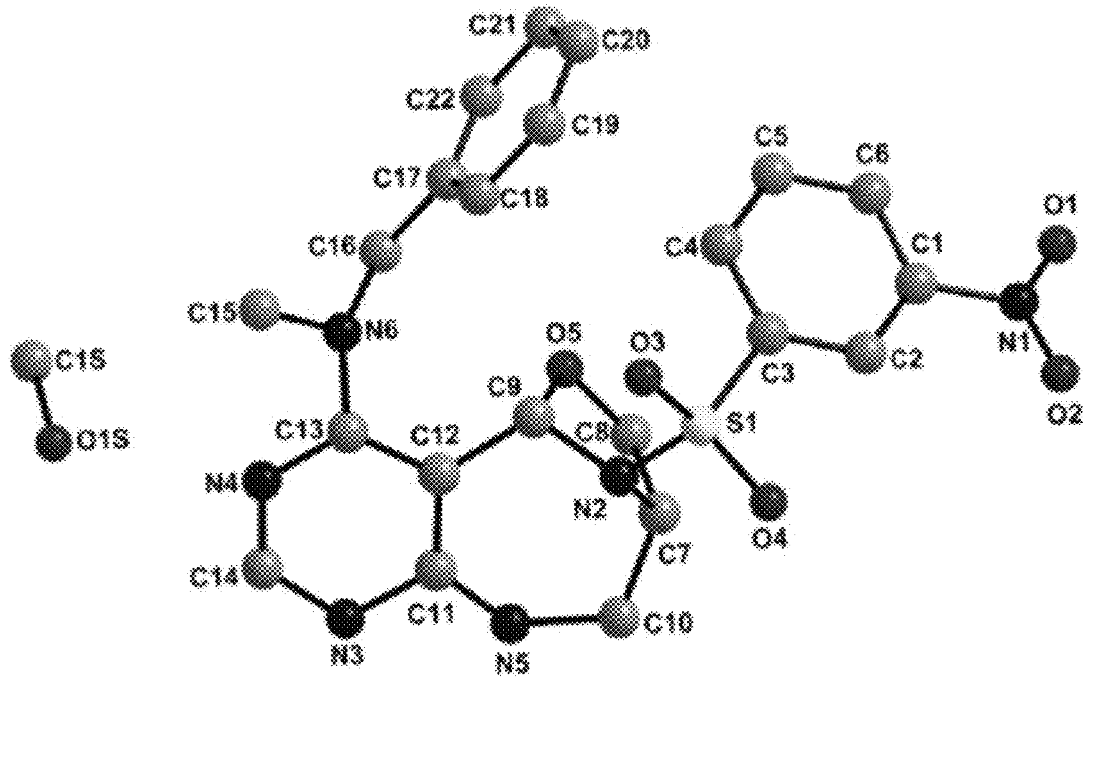

[Figure 4]
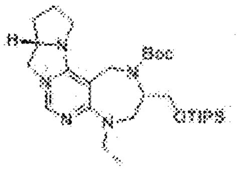
2a
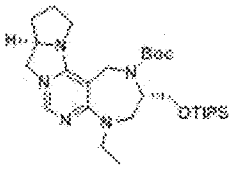
3b
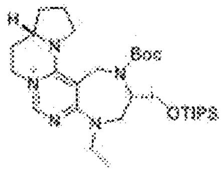
4c
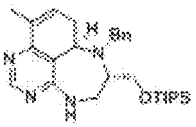
5d
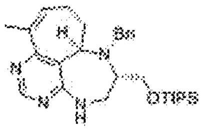
6d
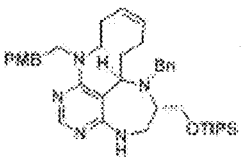
7e
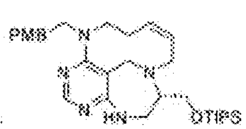
8e
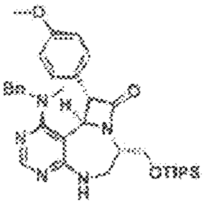
9f
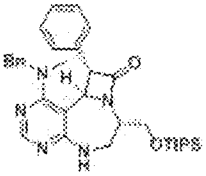
10f
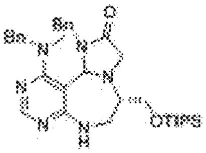
11f
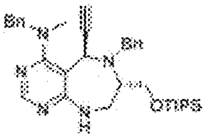
12f
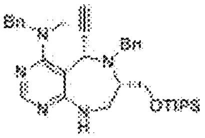
12f'
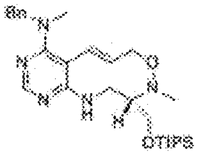
13f
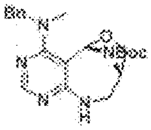
14f
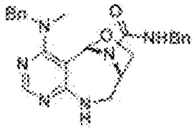
15f
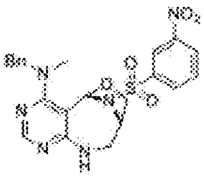
16f
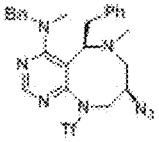
17f
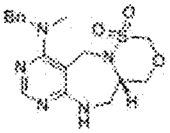
18f
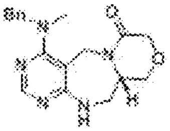
19f
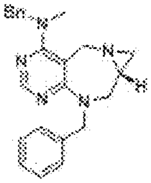
20f
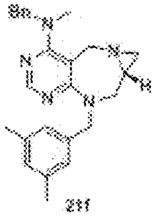
21f
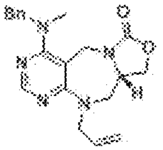
22f
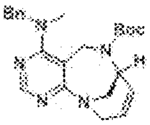
23f

[Figure 5]
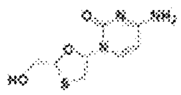
Lamivudine
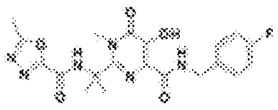
Raltegravir
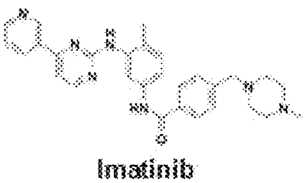
Imatinib
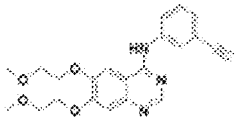
Erlotinib
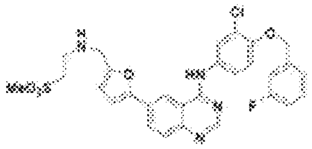
Lapatinib
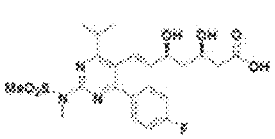
Rosuvastatin
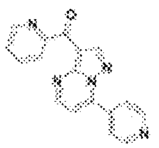
Ocinaplon
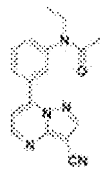
Zaleplon
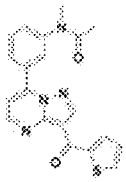
Indiplon
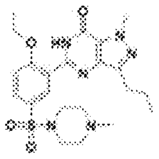
Sildenafil
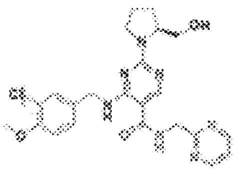
Avanafil
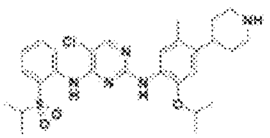
Ceritinib
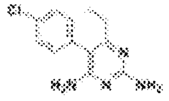
Pyrimethamine
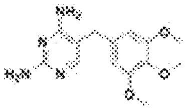
Trimethoprim
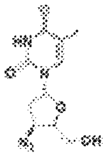
ZIDOVUDINE

[Figure 6A]
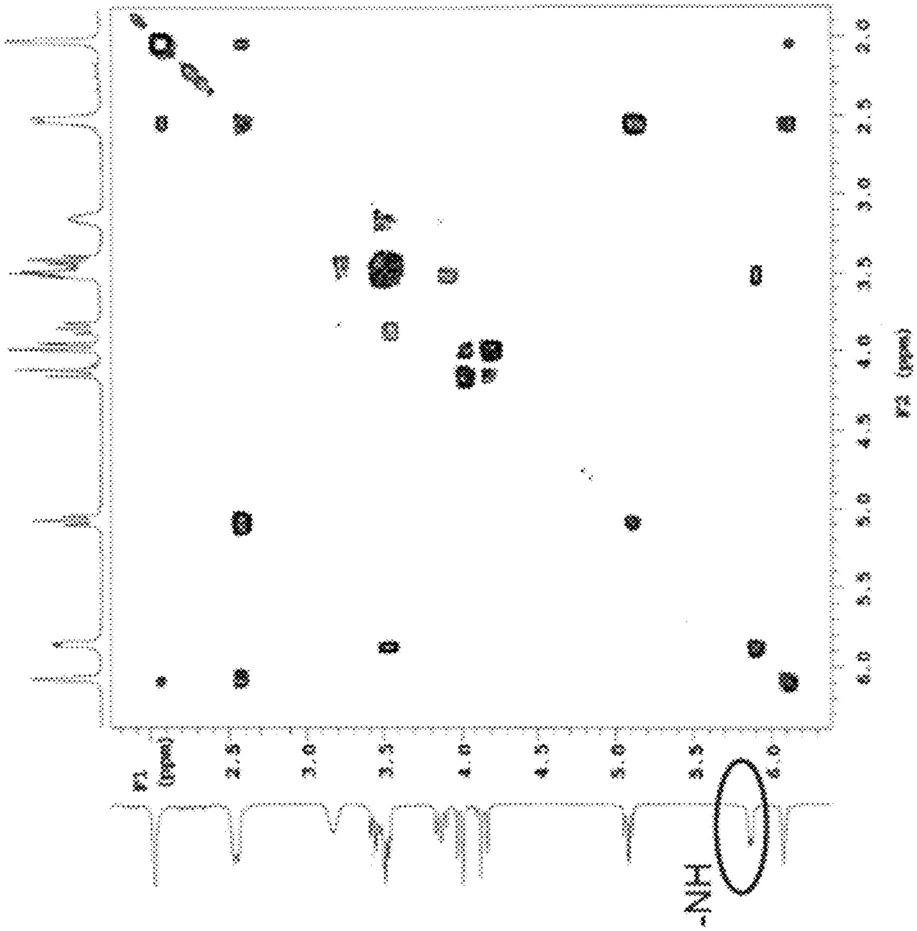

[Figure 6B]
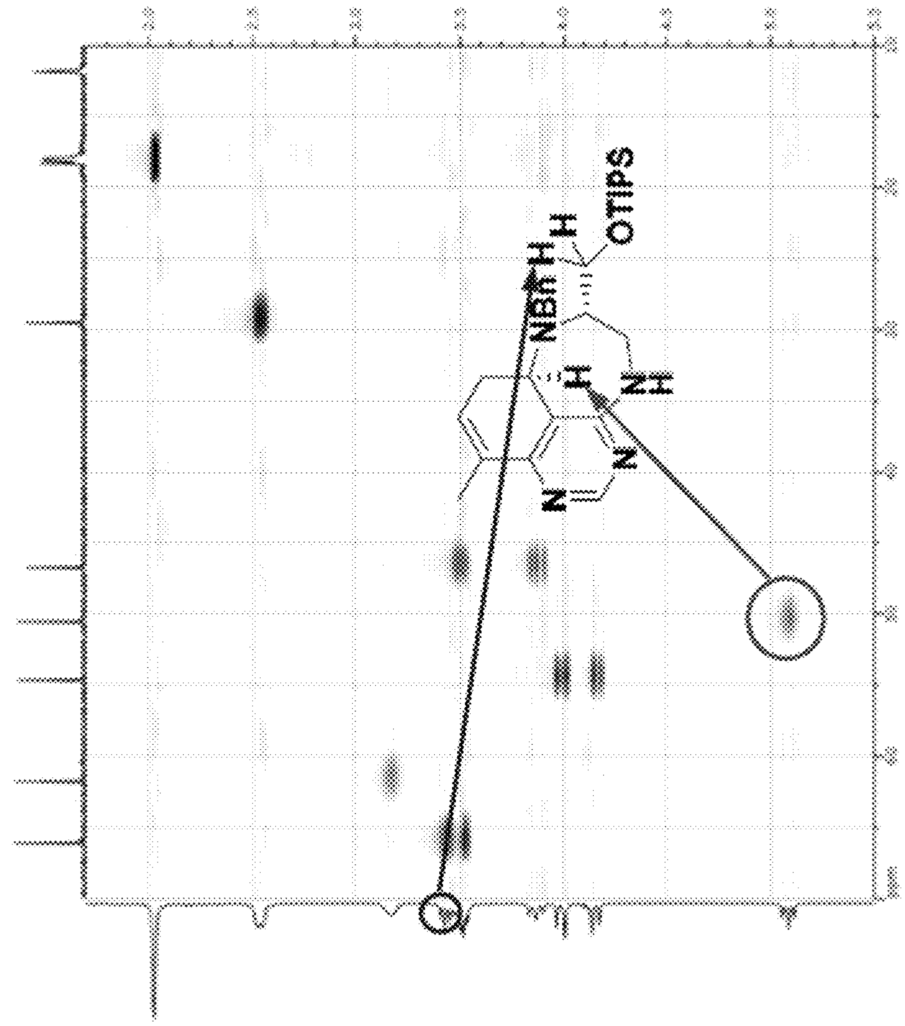

[Figure 6C]
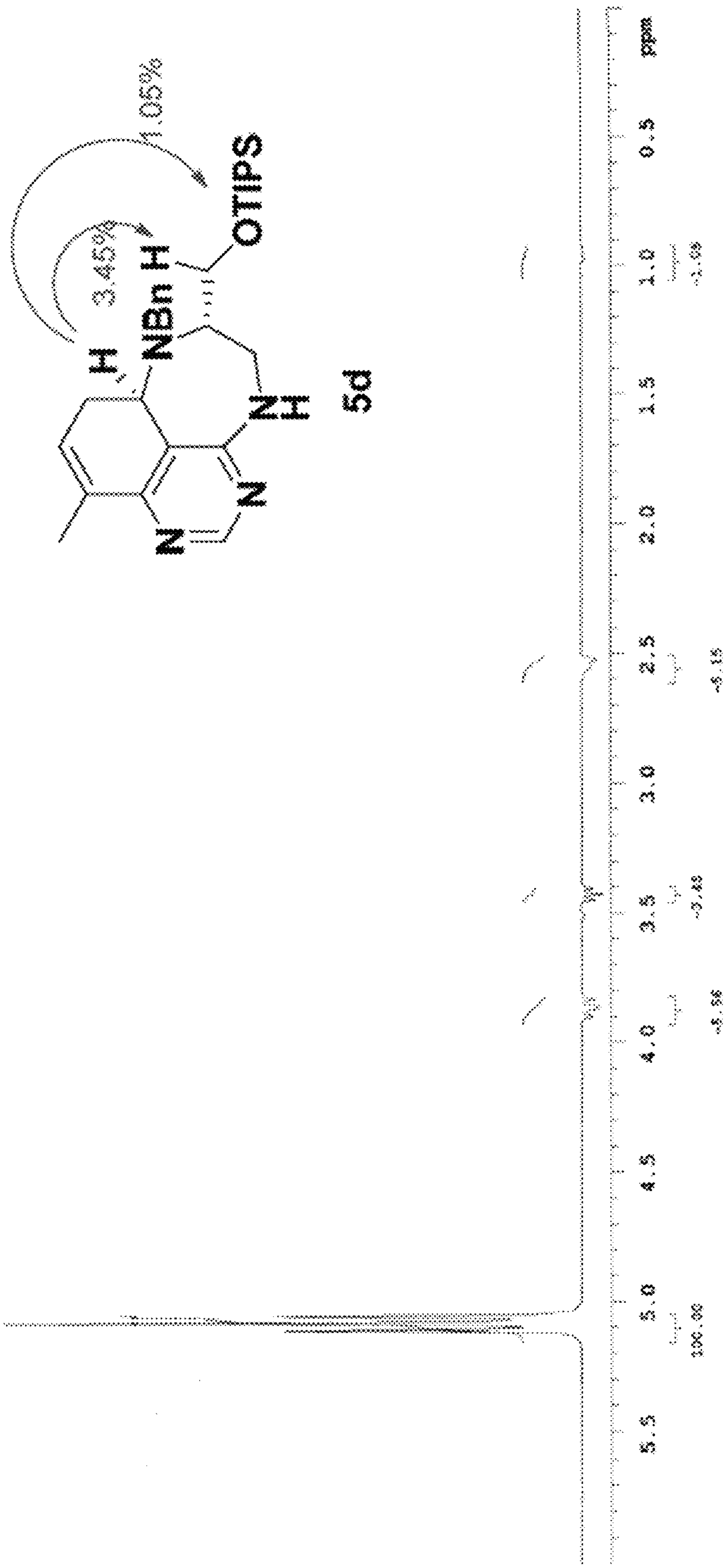
5d

[Figure 7A]
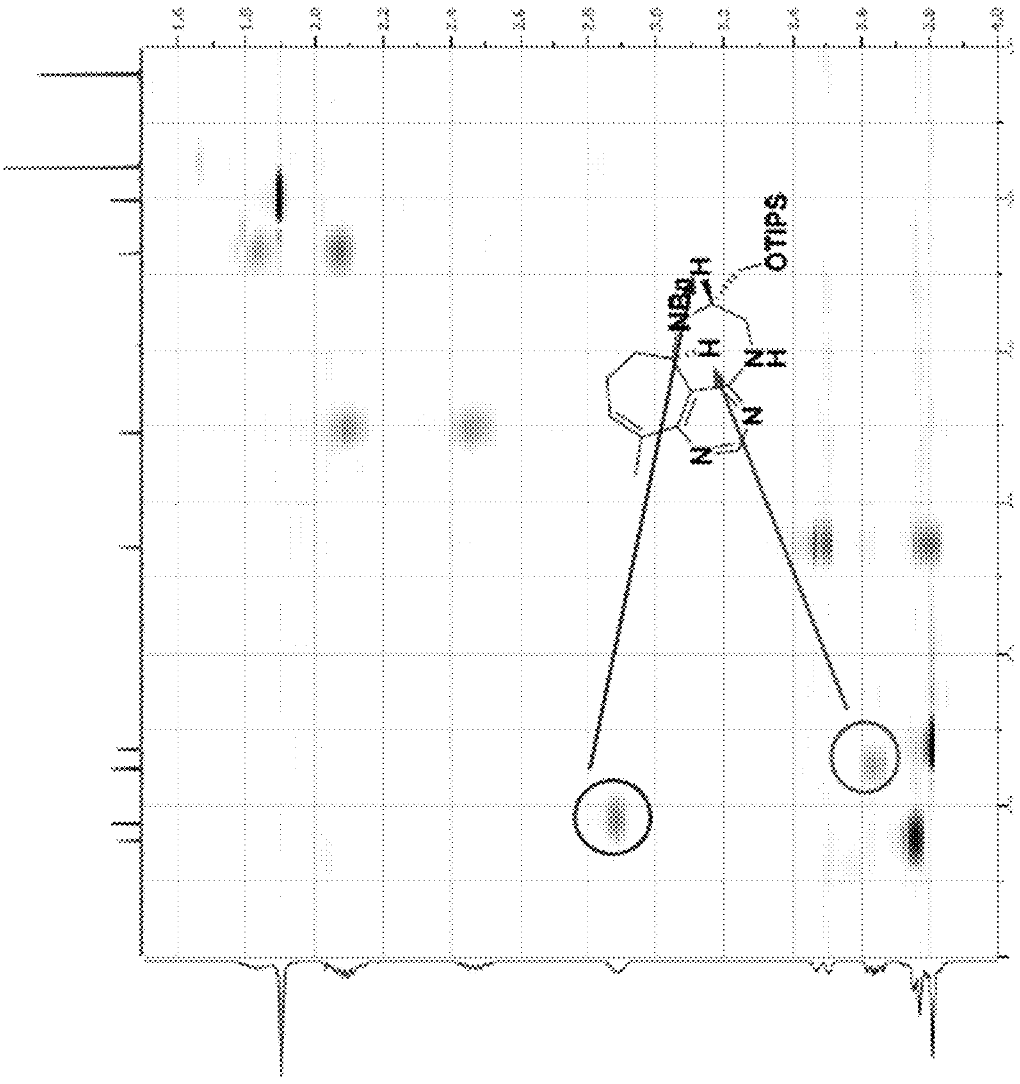

[Figure 7B]
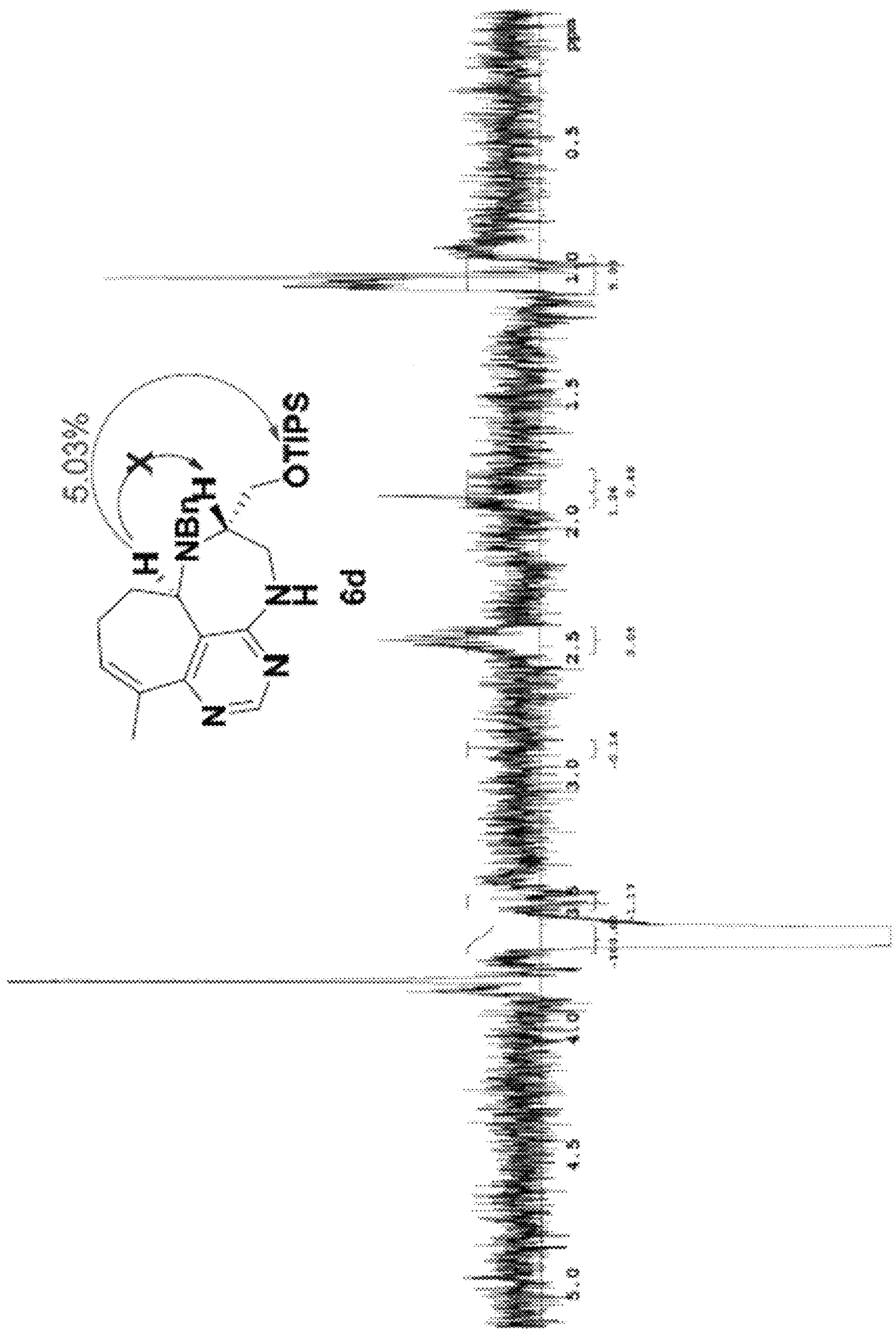
6d

[Figure 8A]
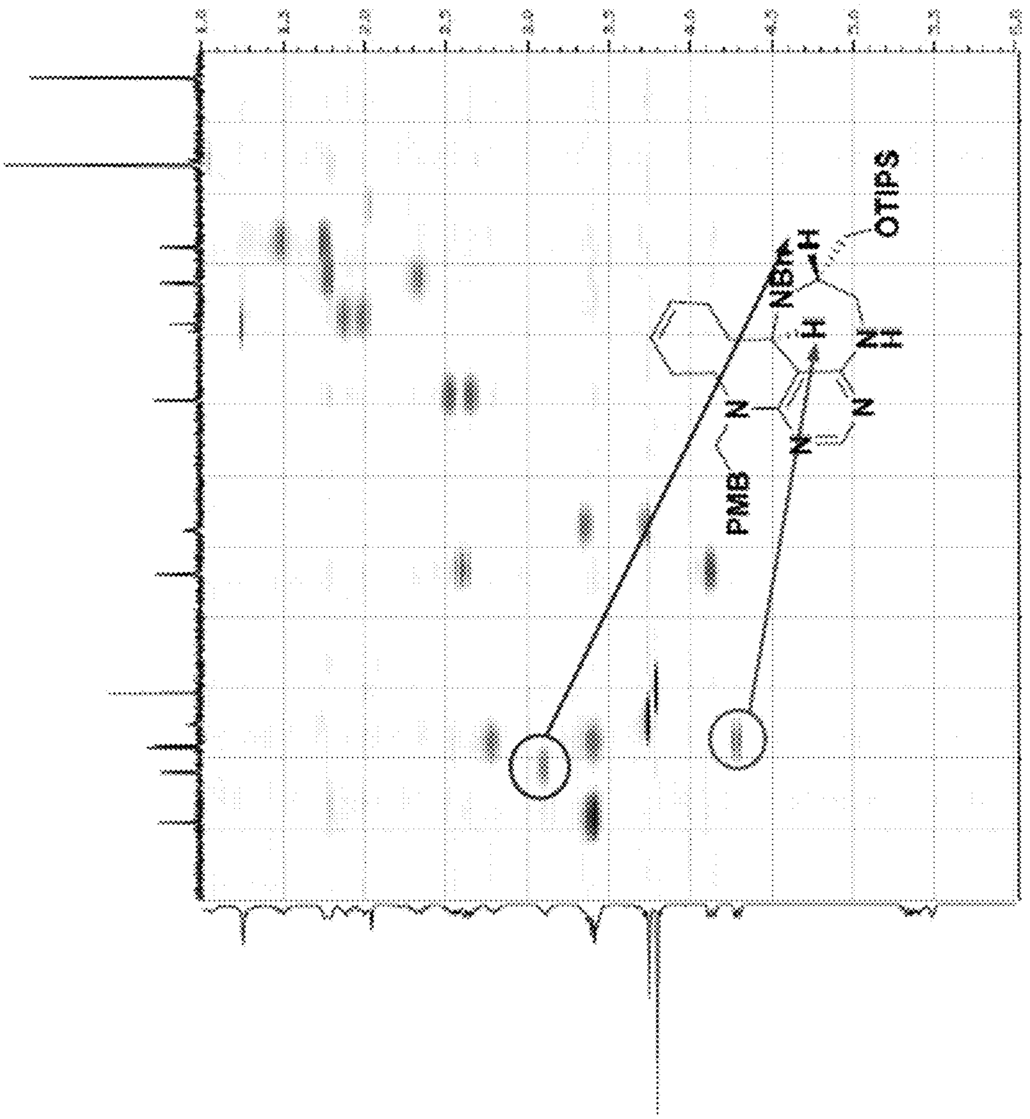

[Figure 8B]
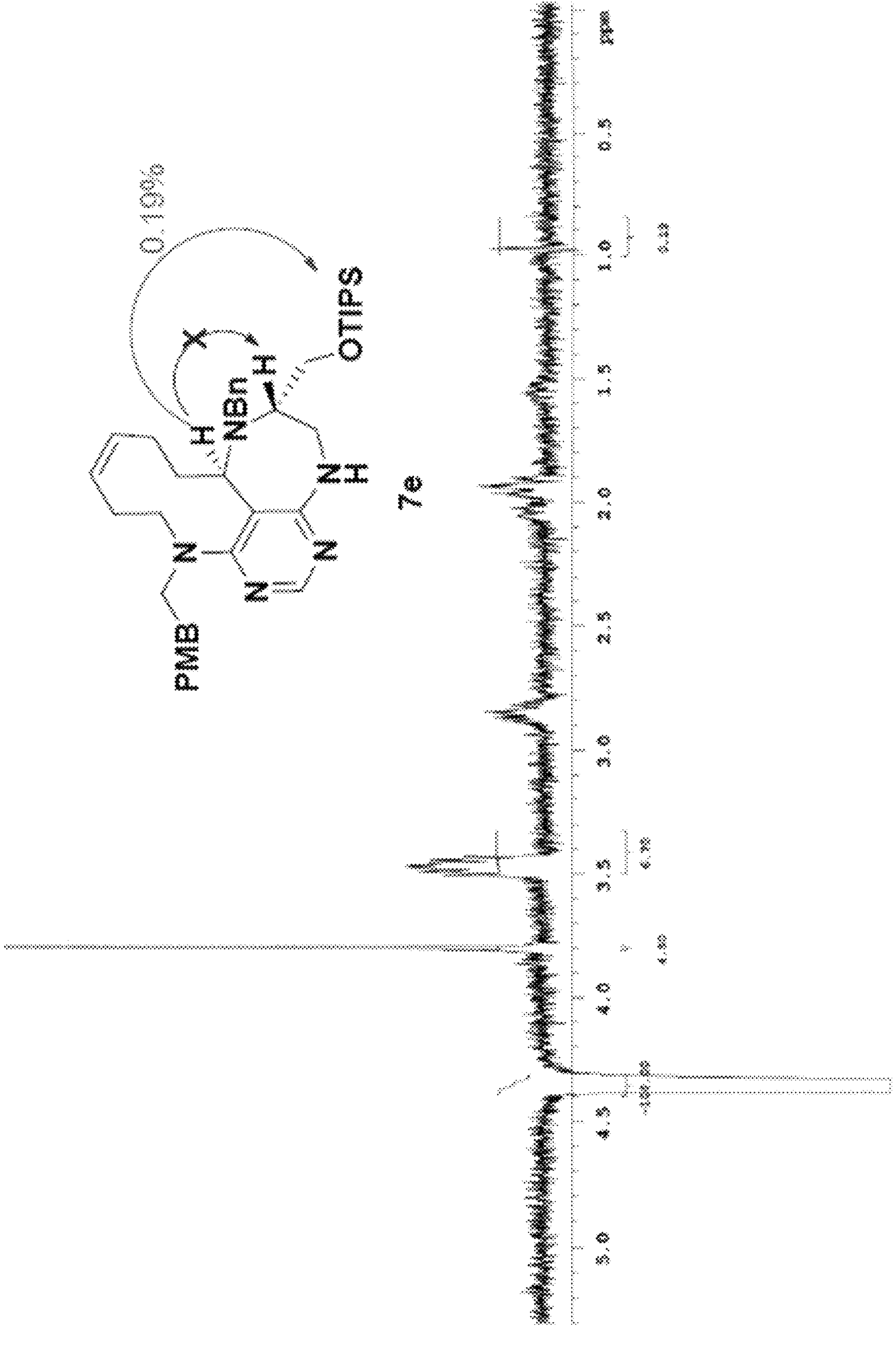
7e

[Figure 9A]
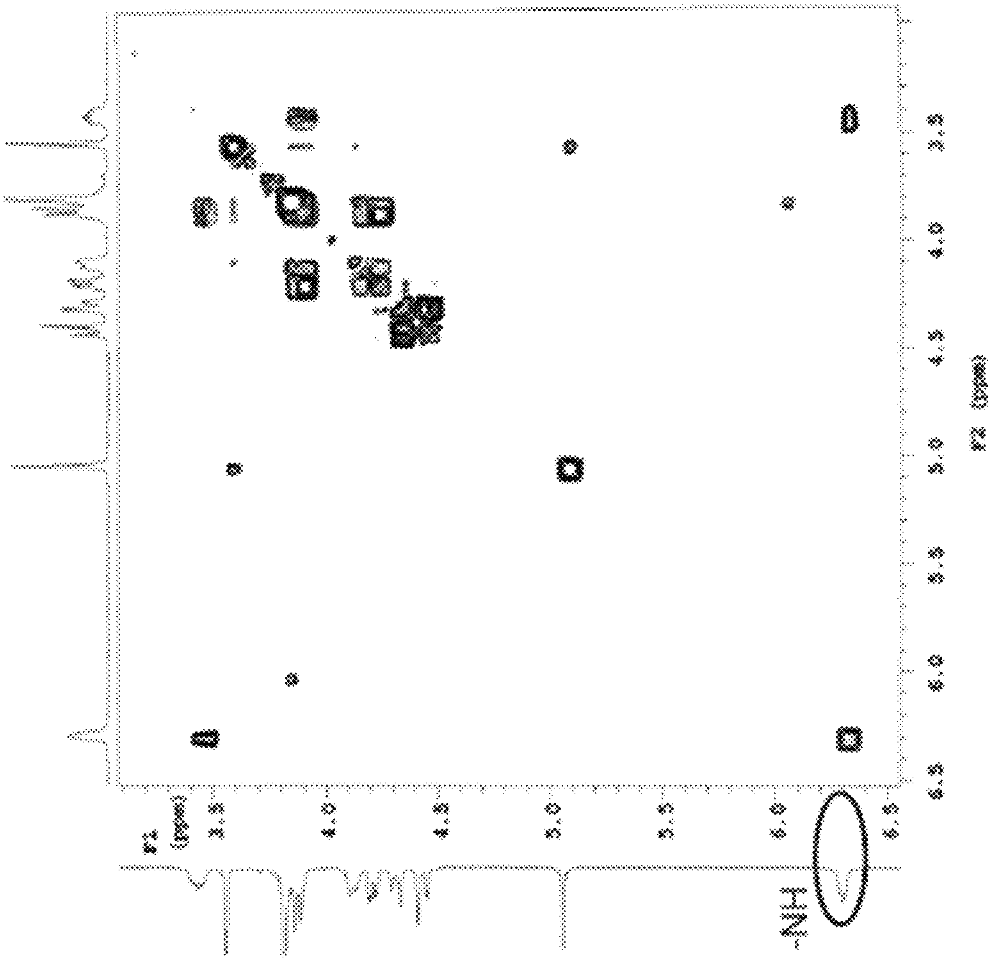

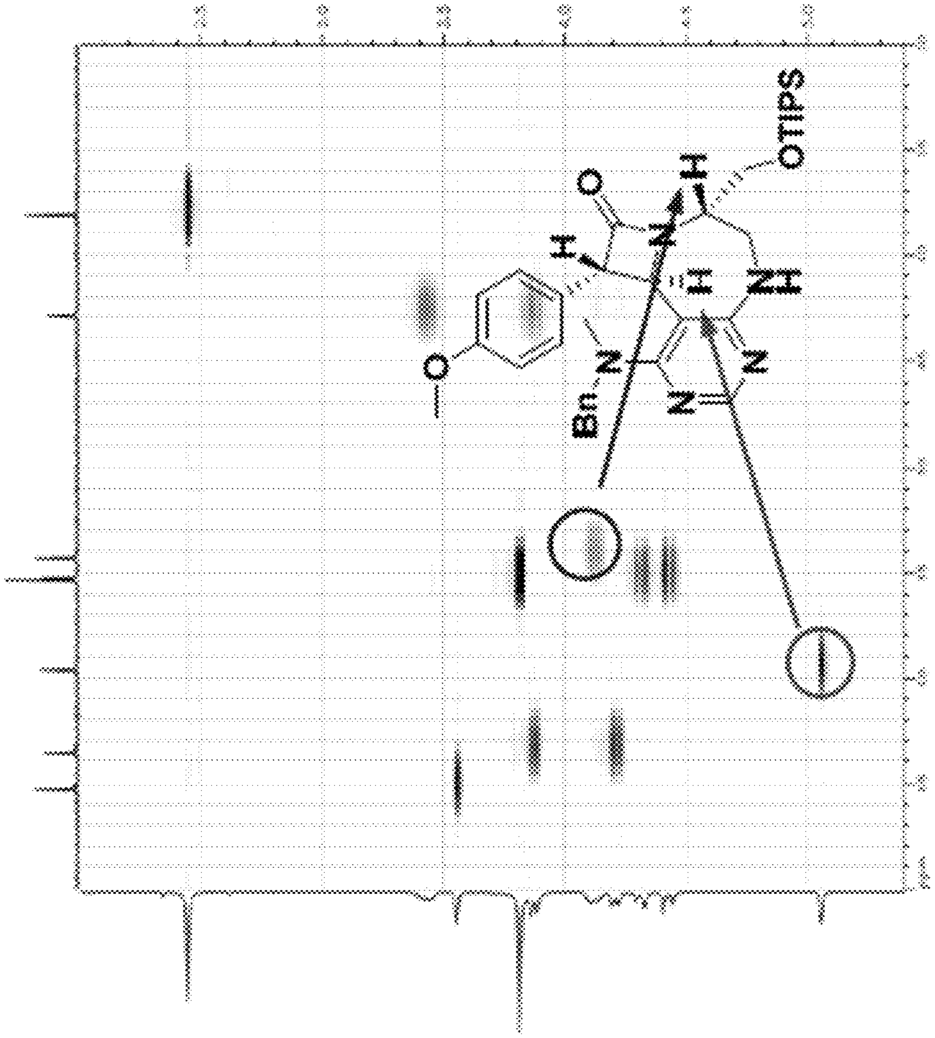
[Figure 9B]

[Figure 9C]
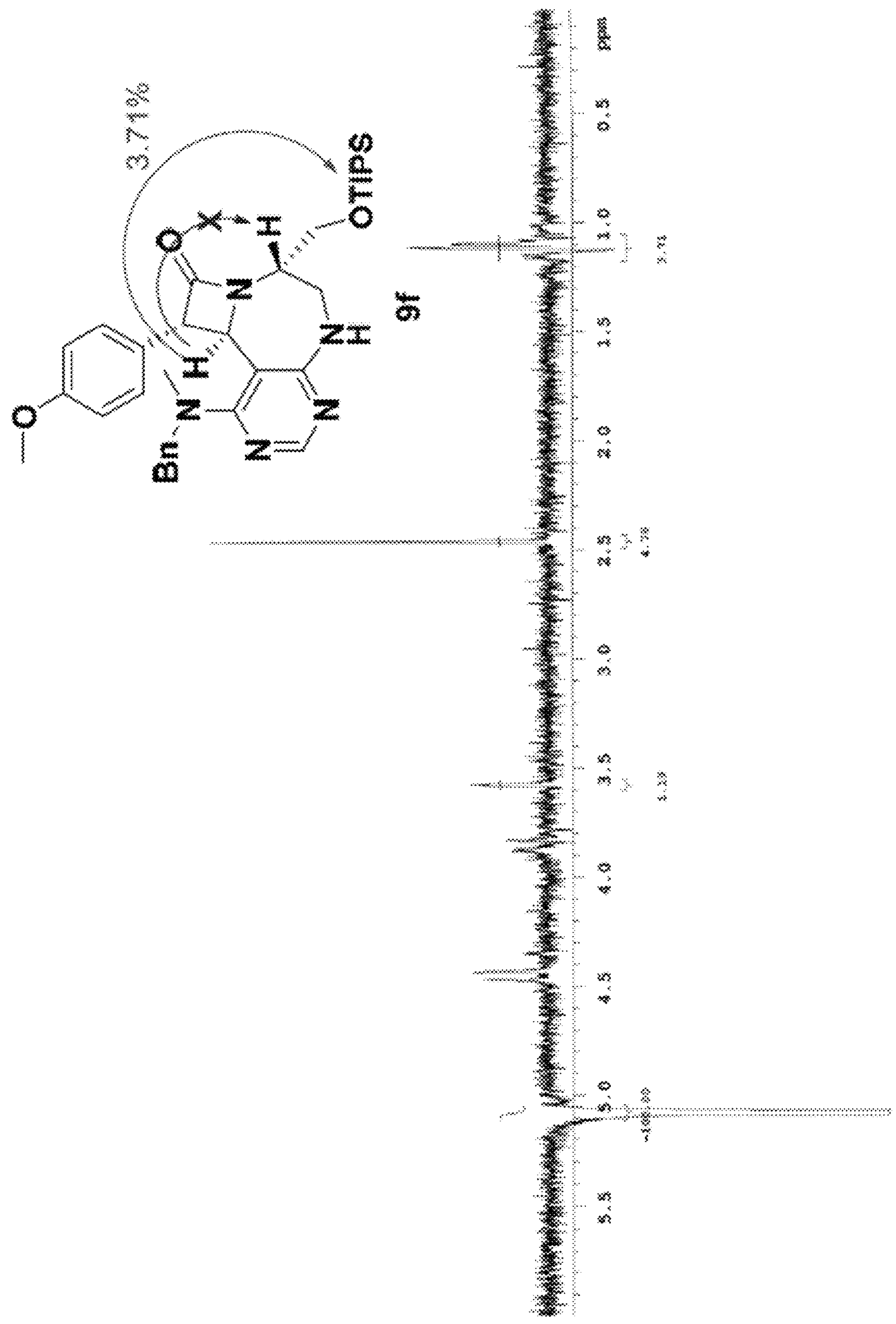
9f

[Figure 10A]
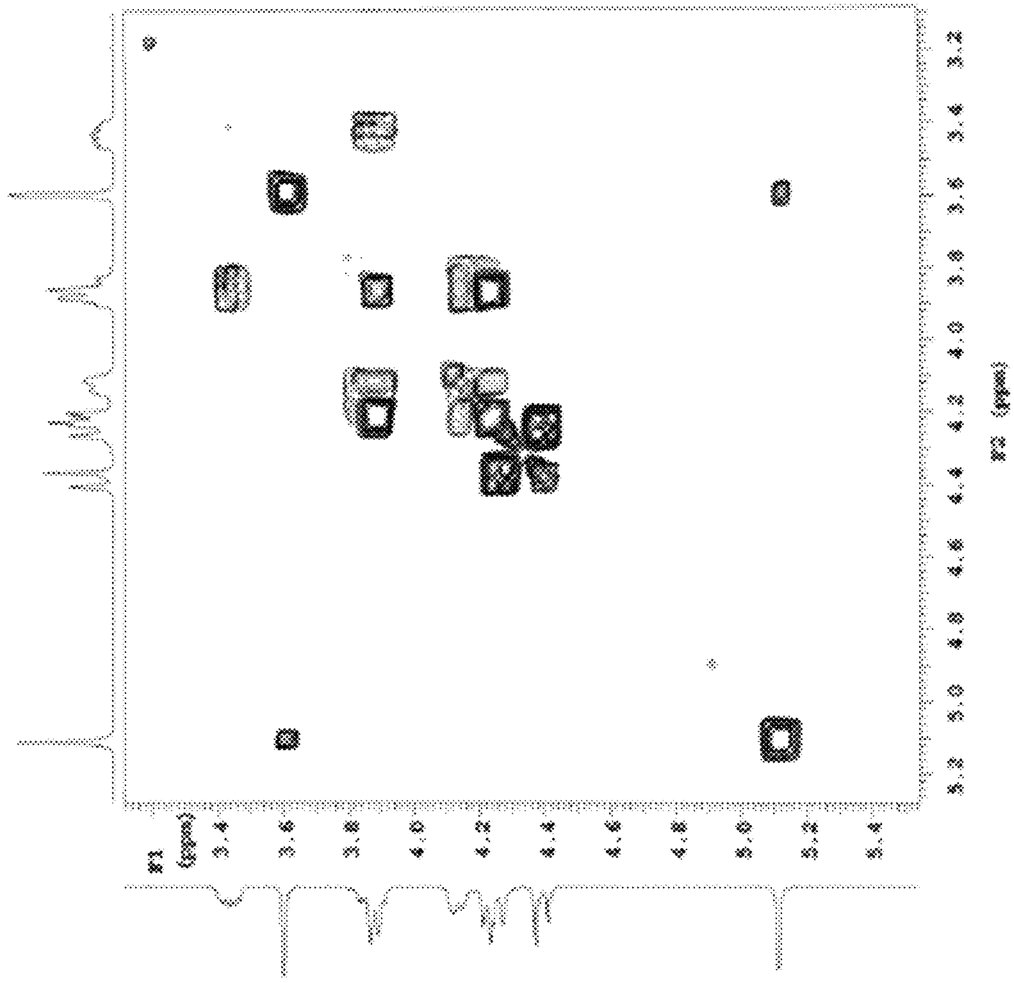

[Figure 10B]
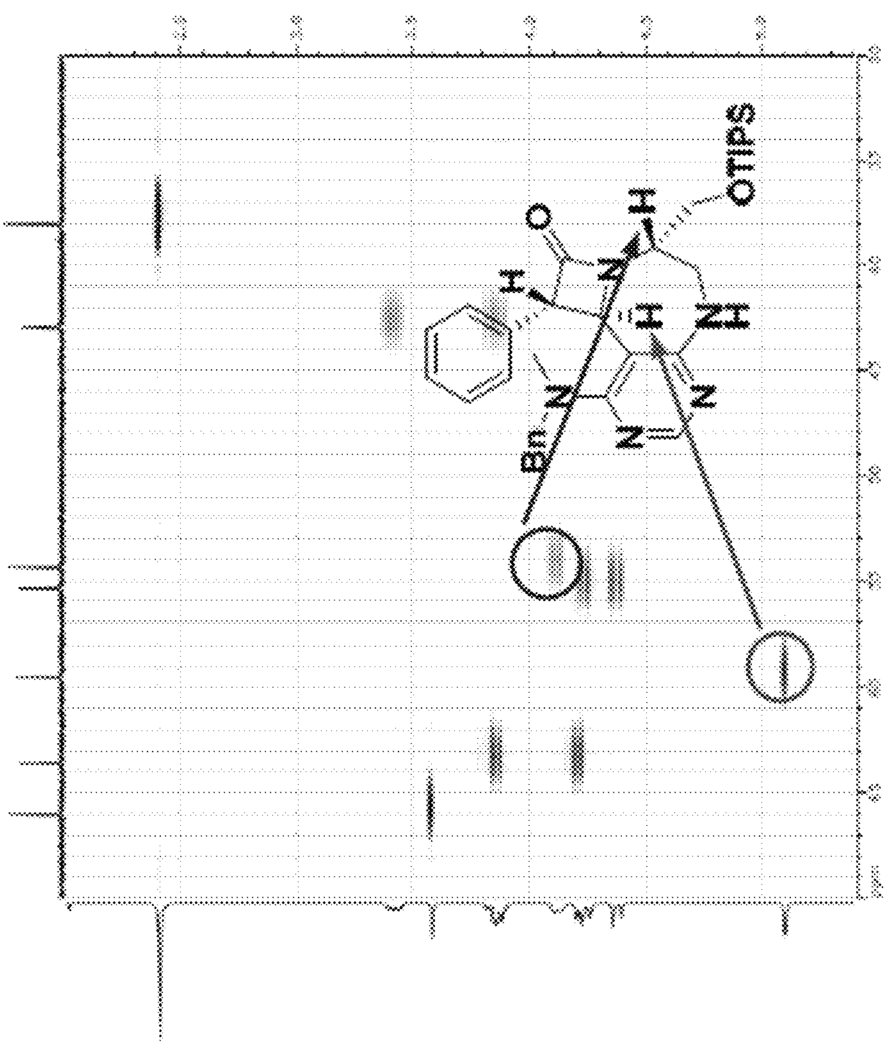

[Figure 10C]
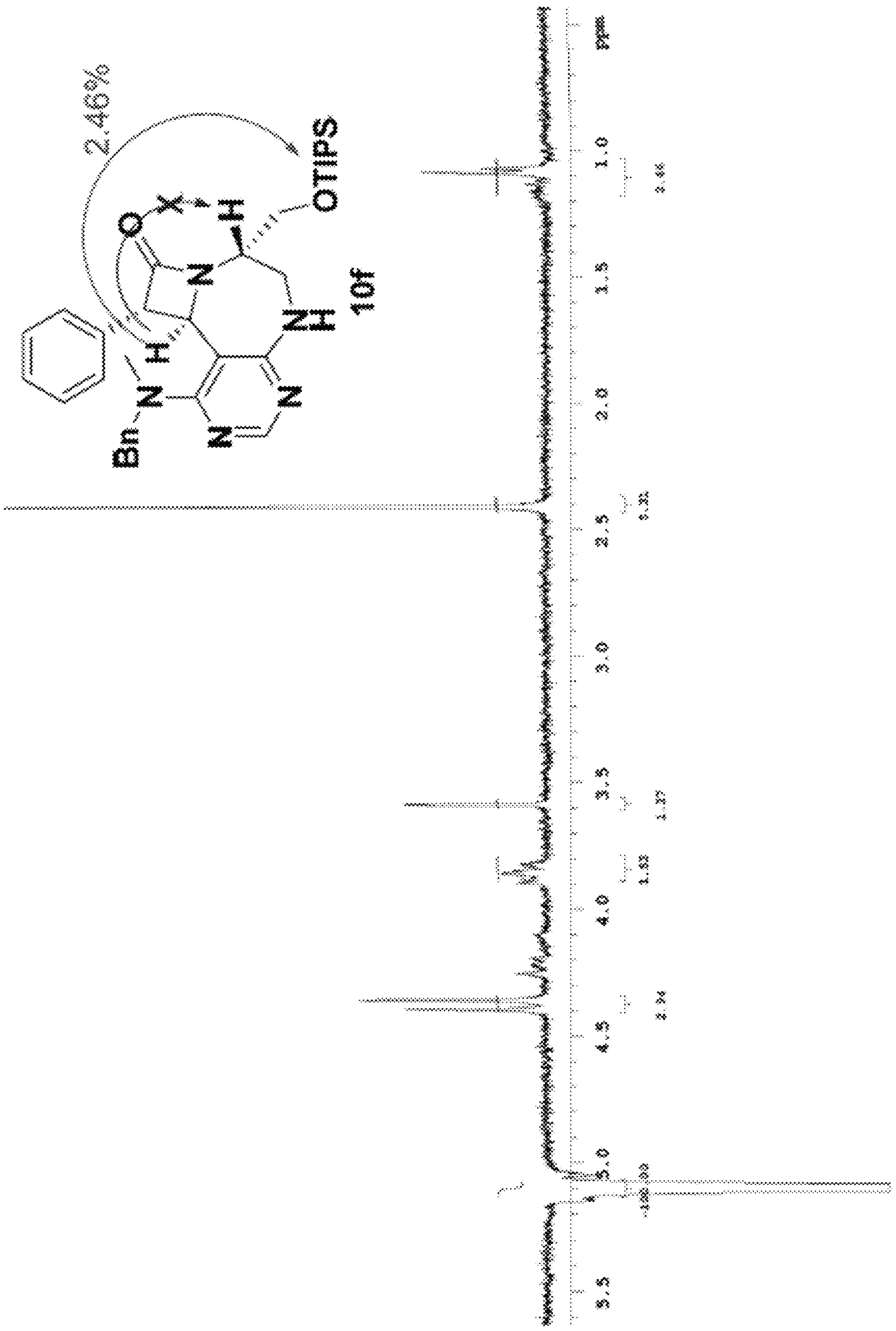
10f

[Figure 11A]
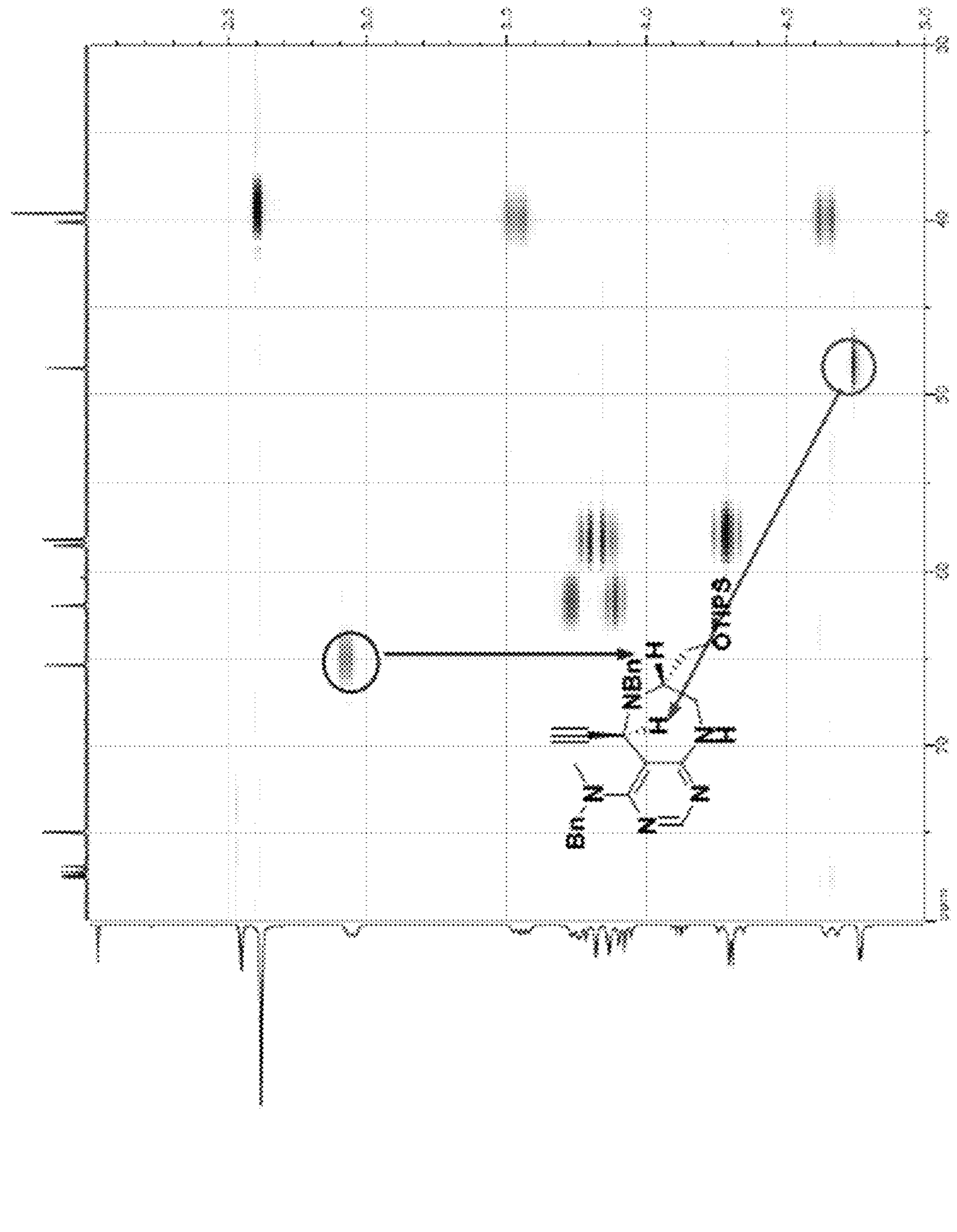

[Figure 11B]
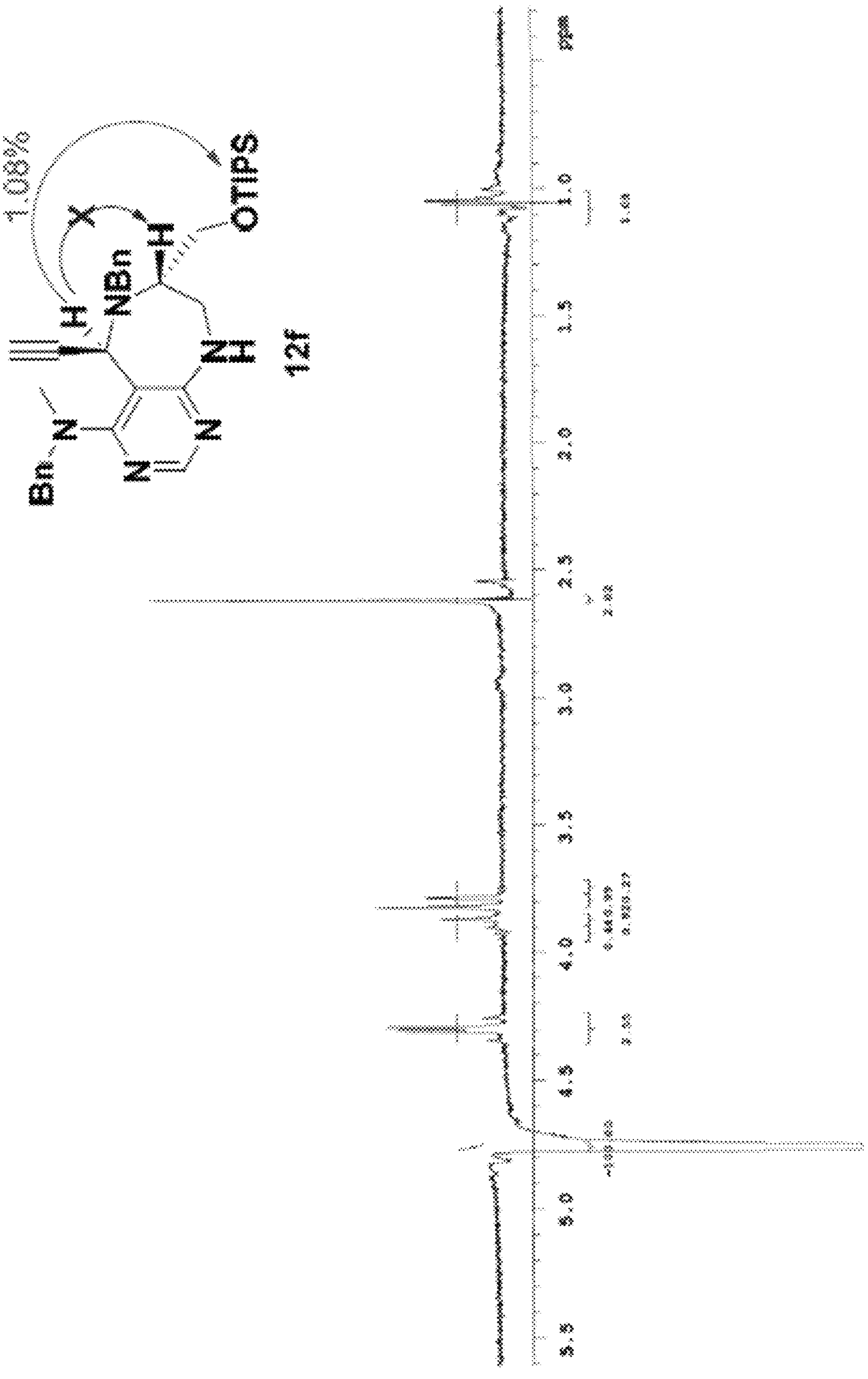
12f

[Figure 12A]
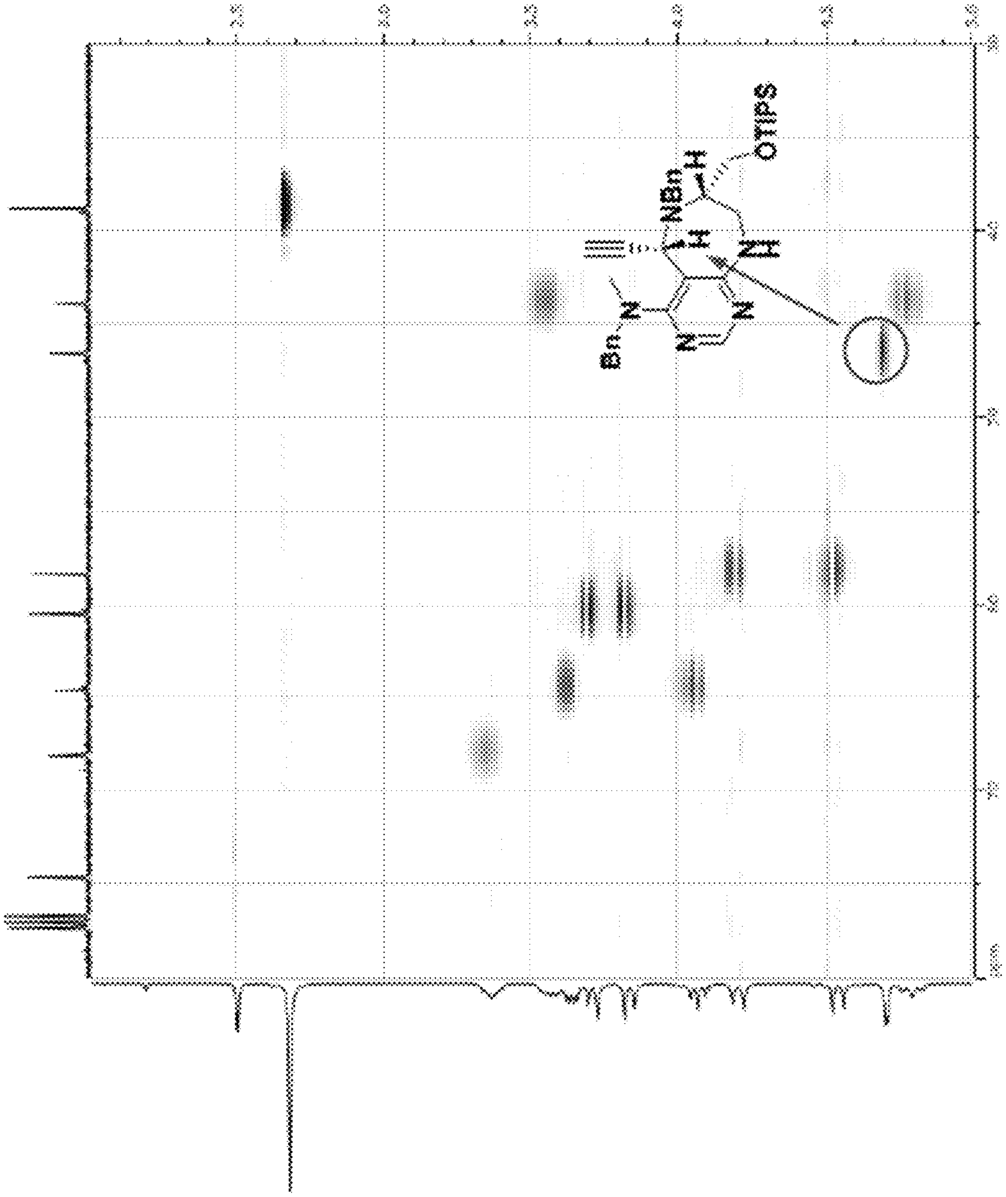

[Figure 12B]
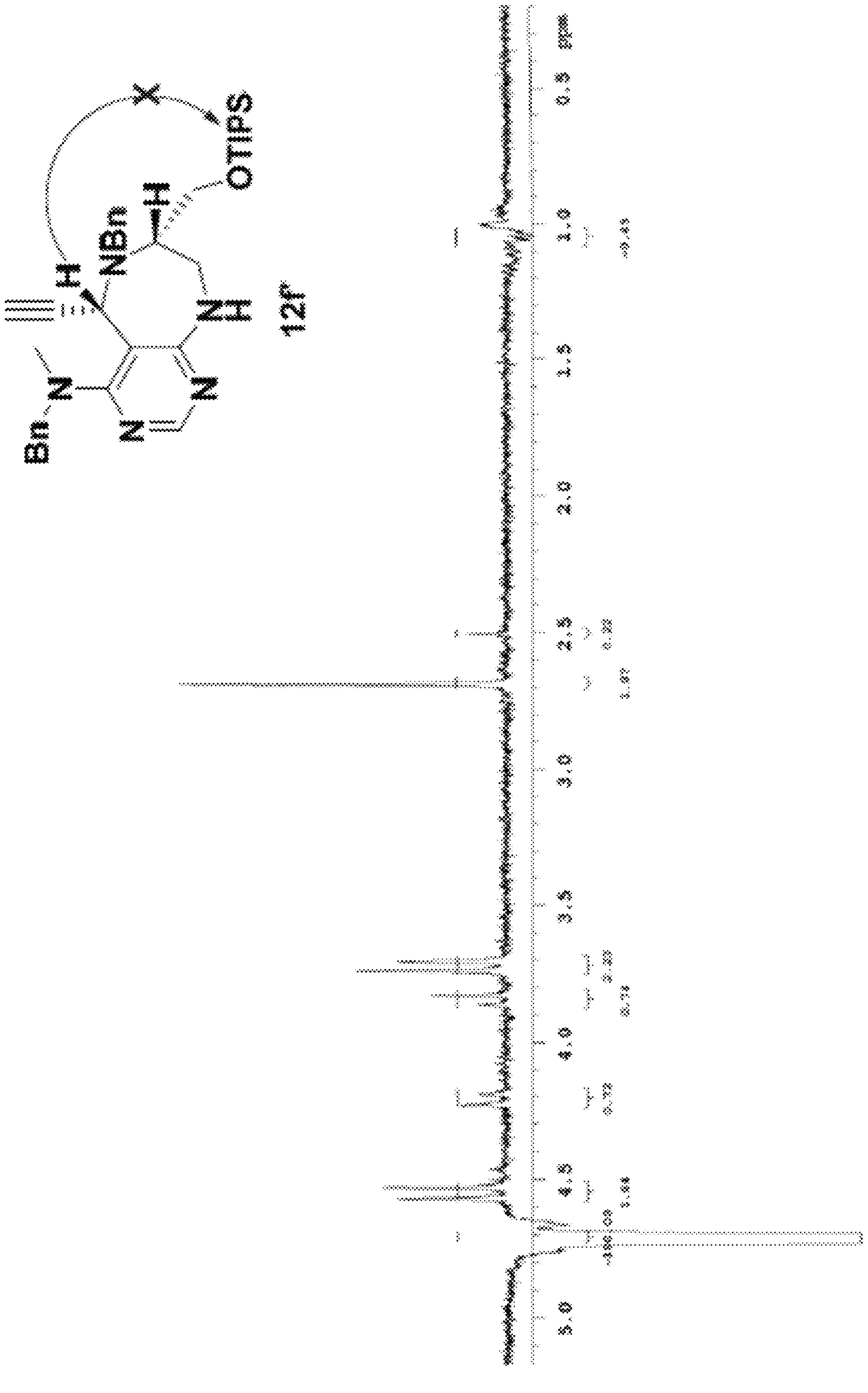
12f'

[Figure 13A]
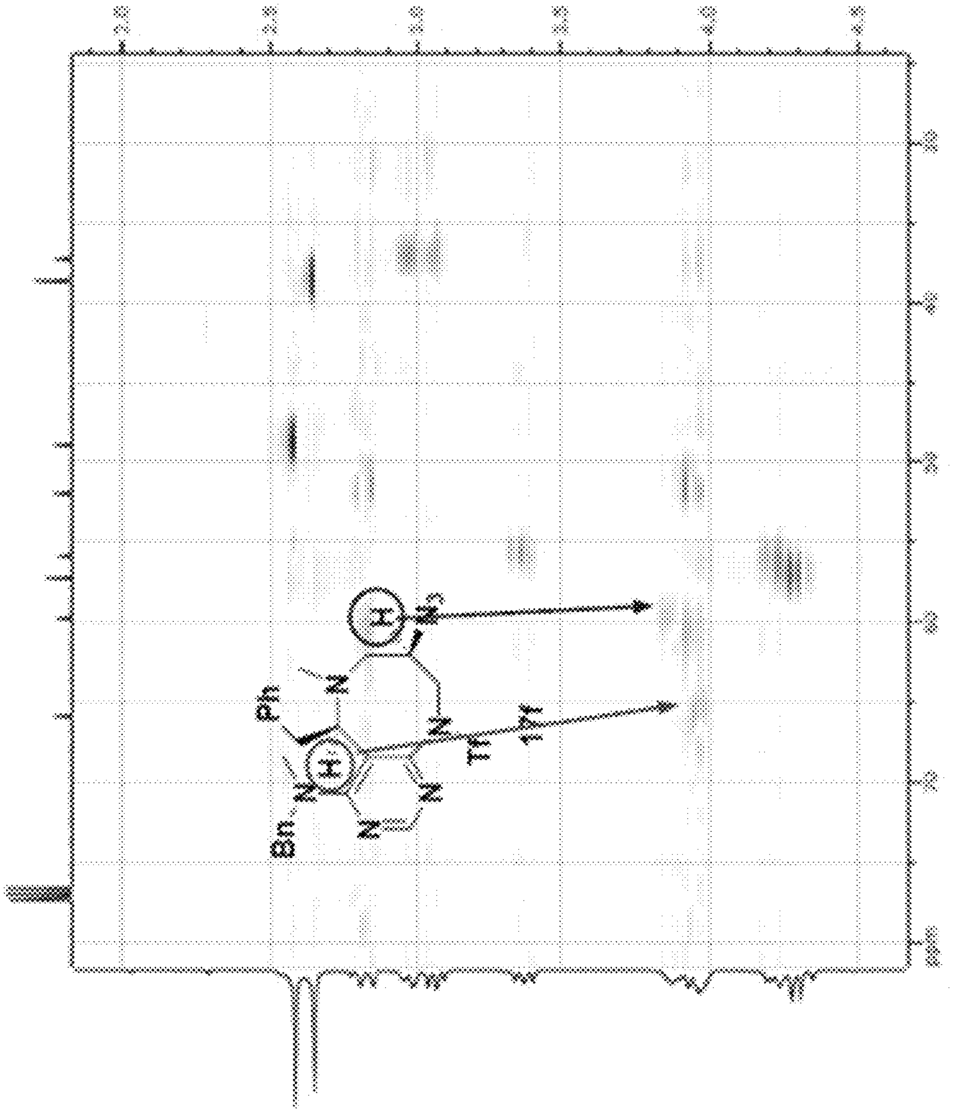

[Figure 13B]
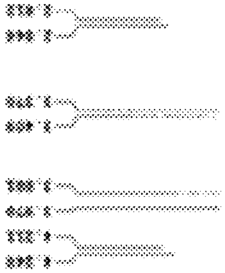
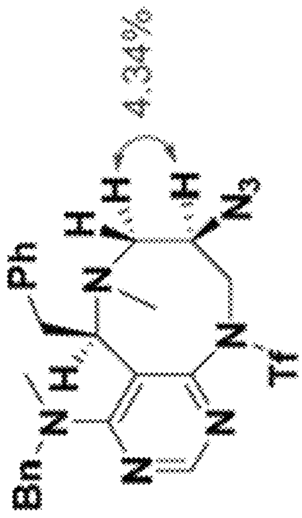
17f
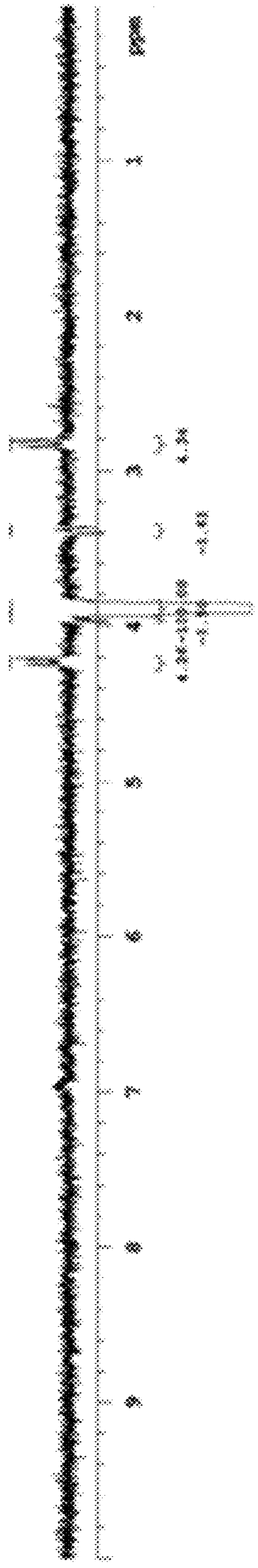

[Figure 13C]
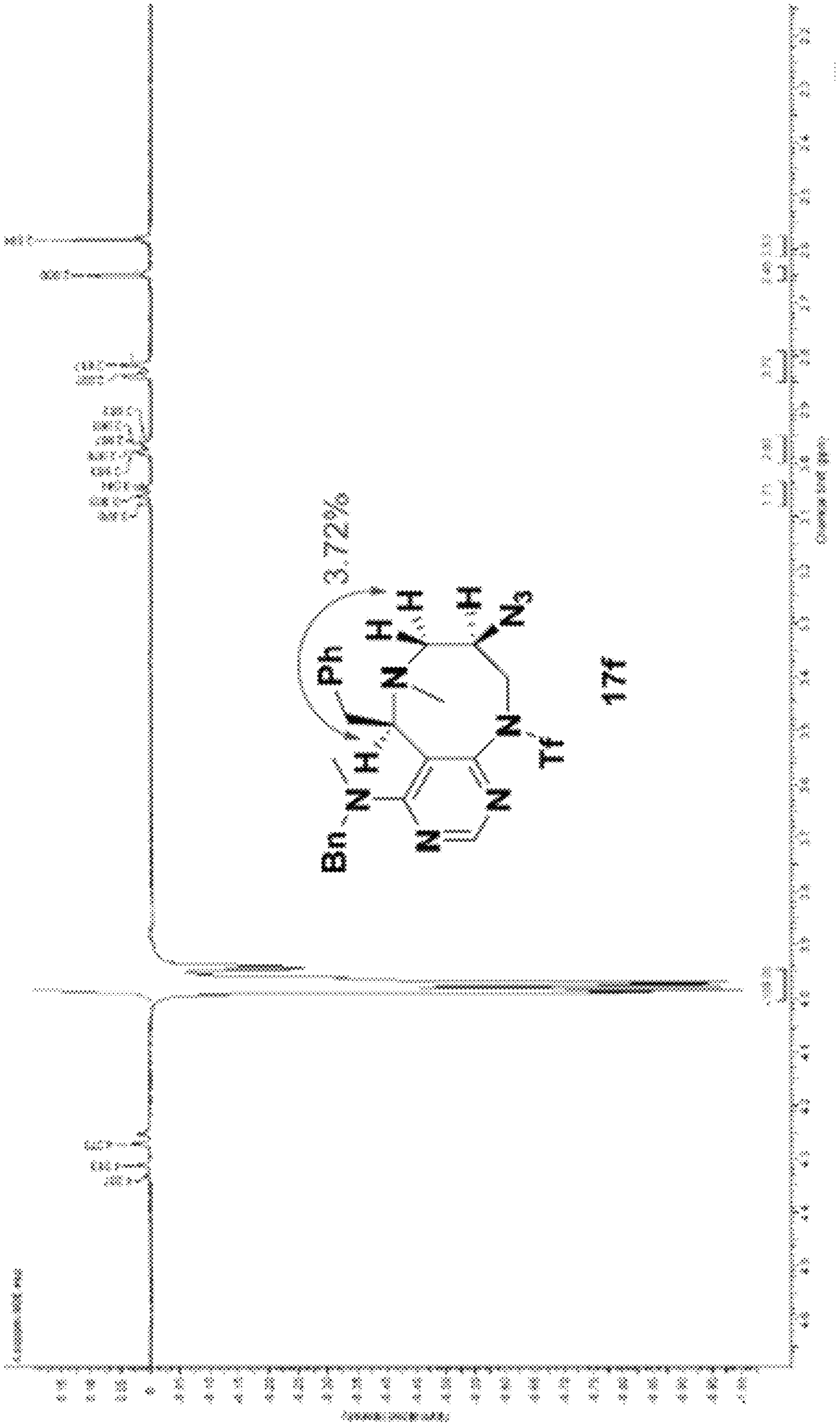
17f

[Figure 14A]
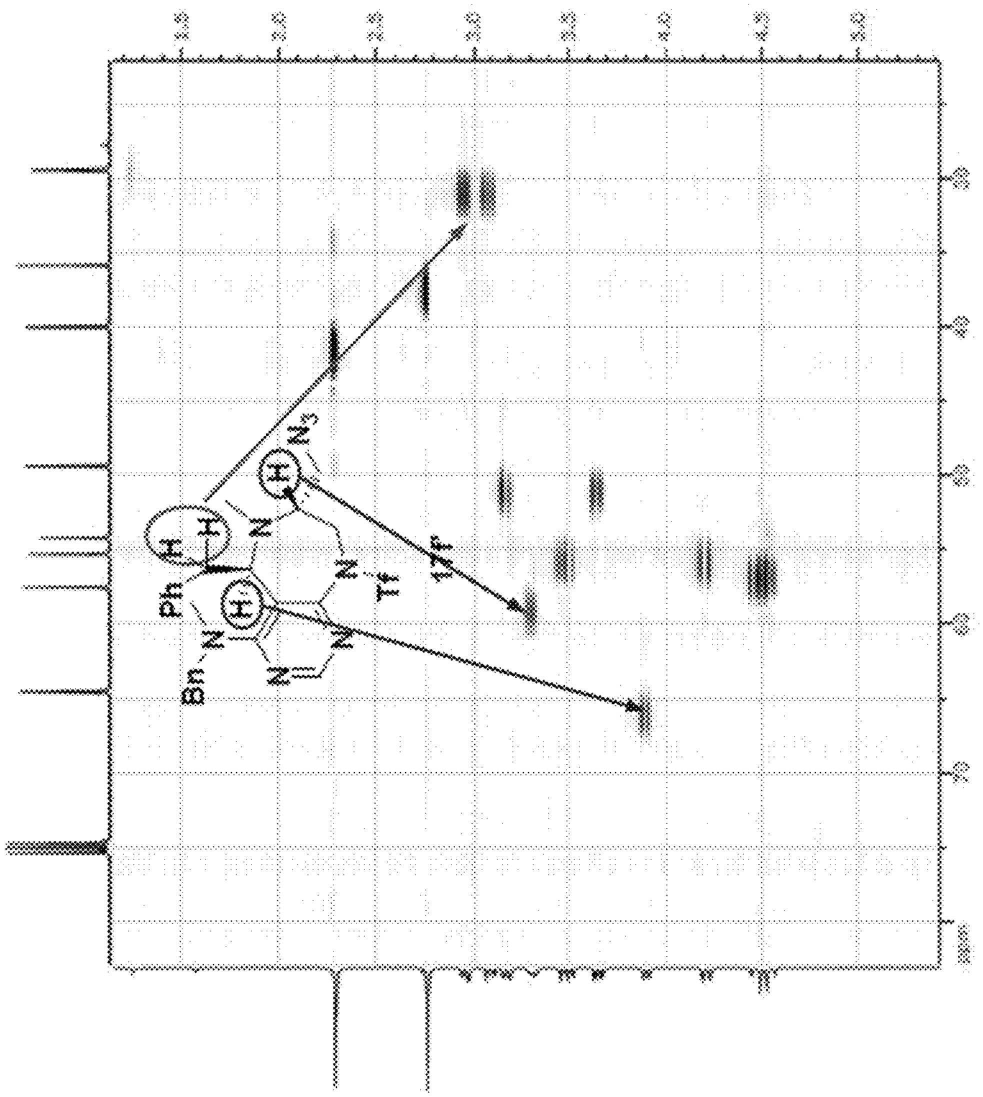

[Figure 14B]
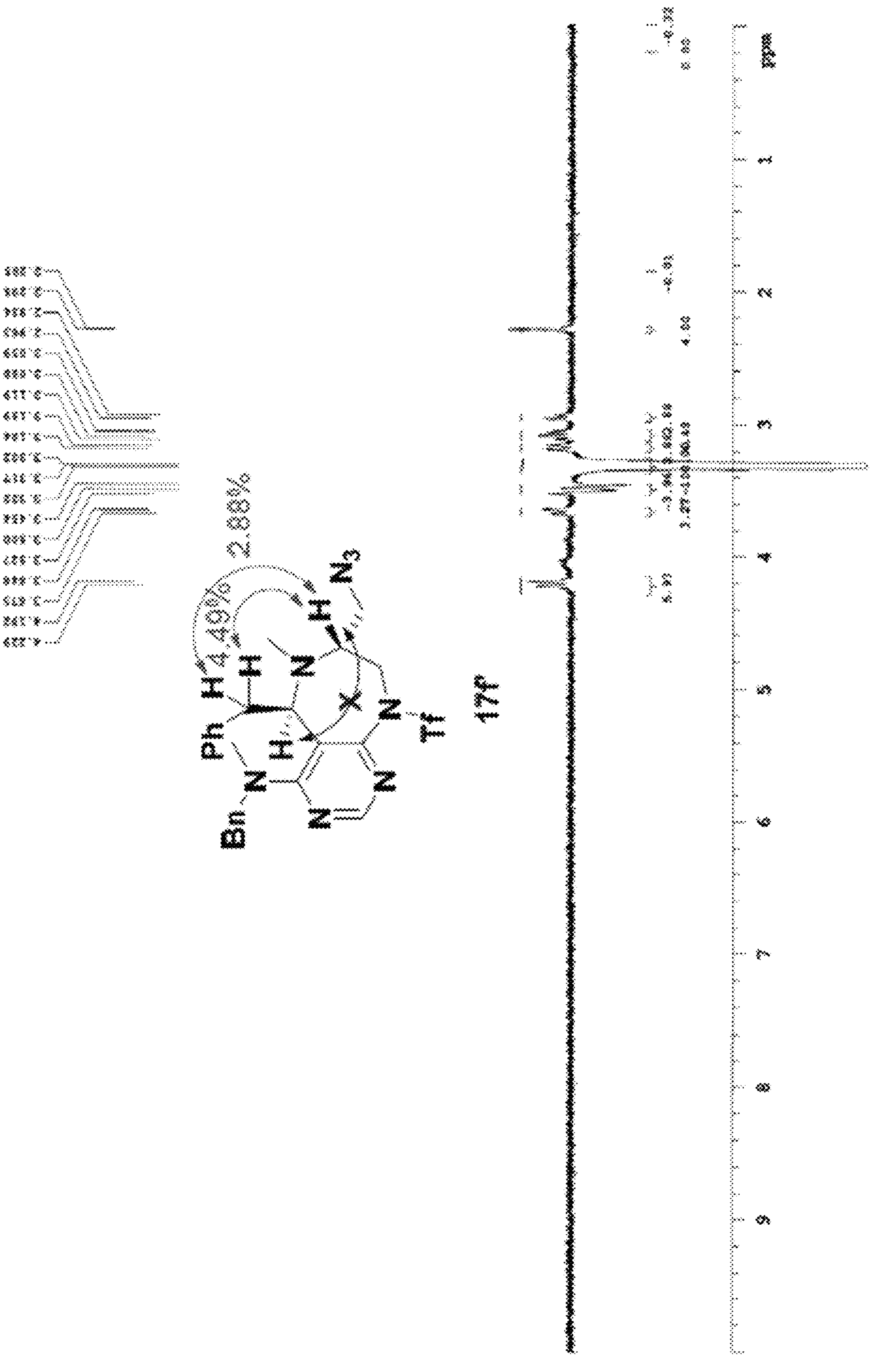
17f

[Figure 15]
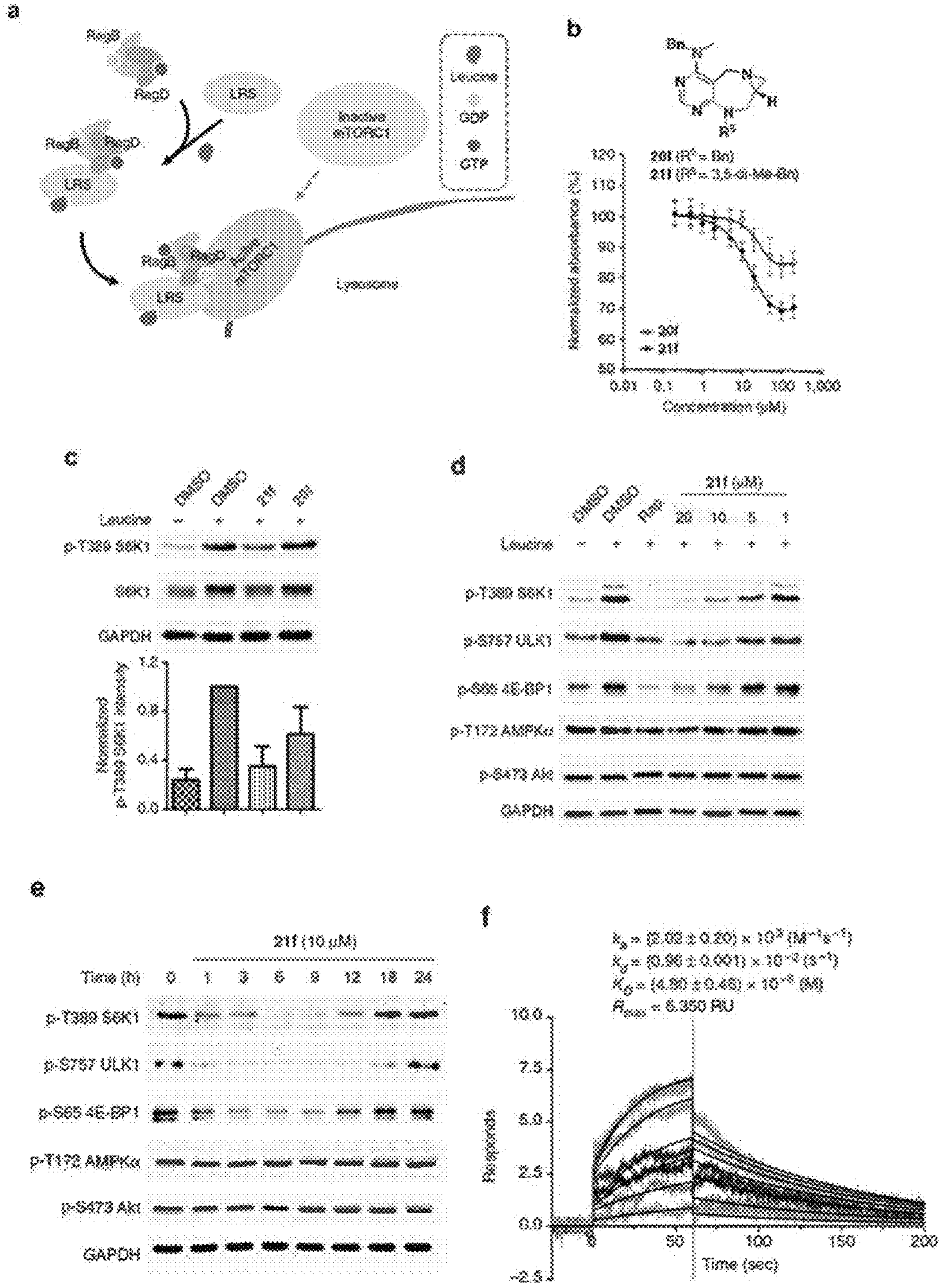

[Figure 16]
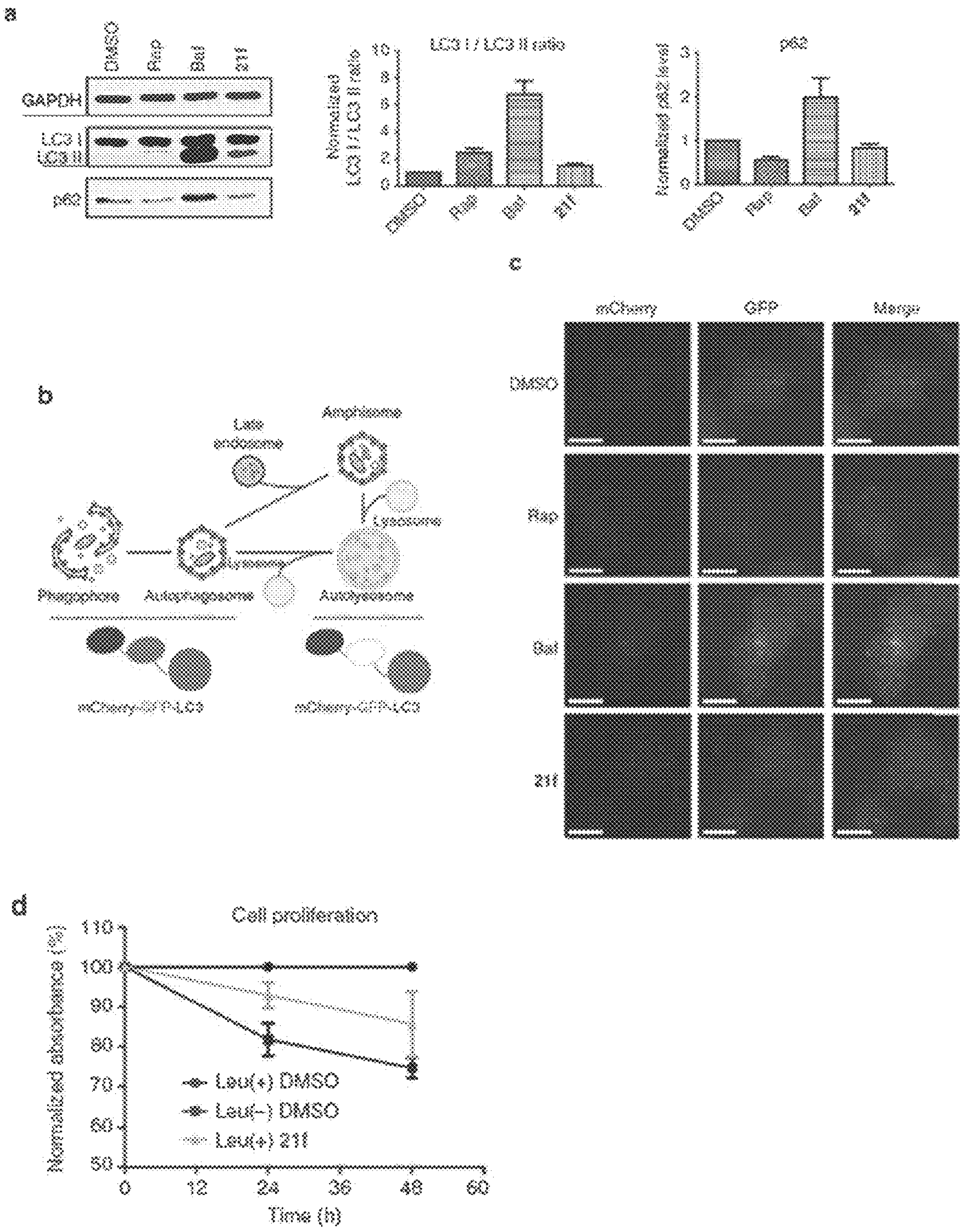

[Figure 17]
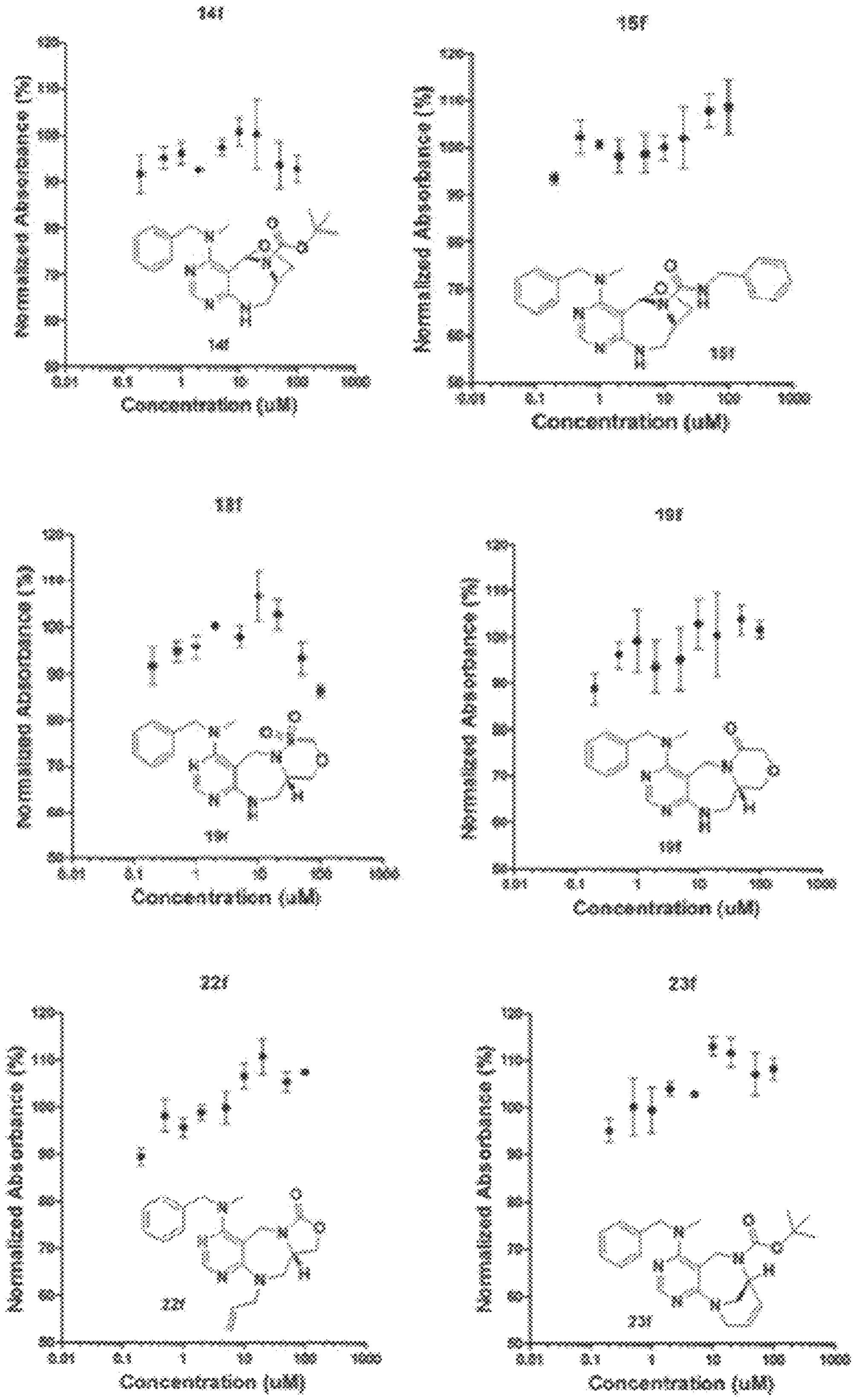

[Figure 18]
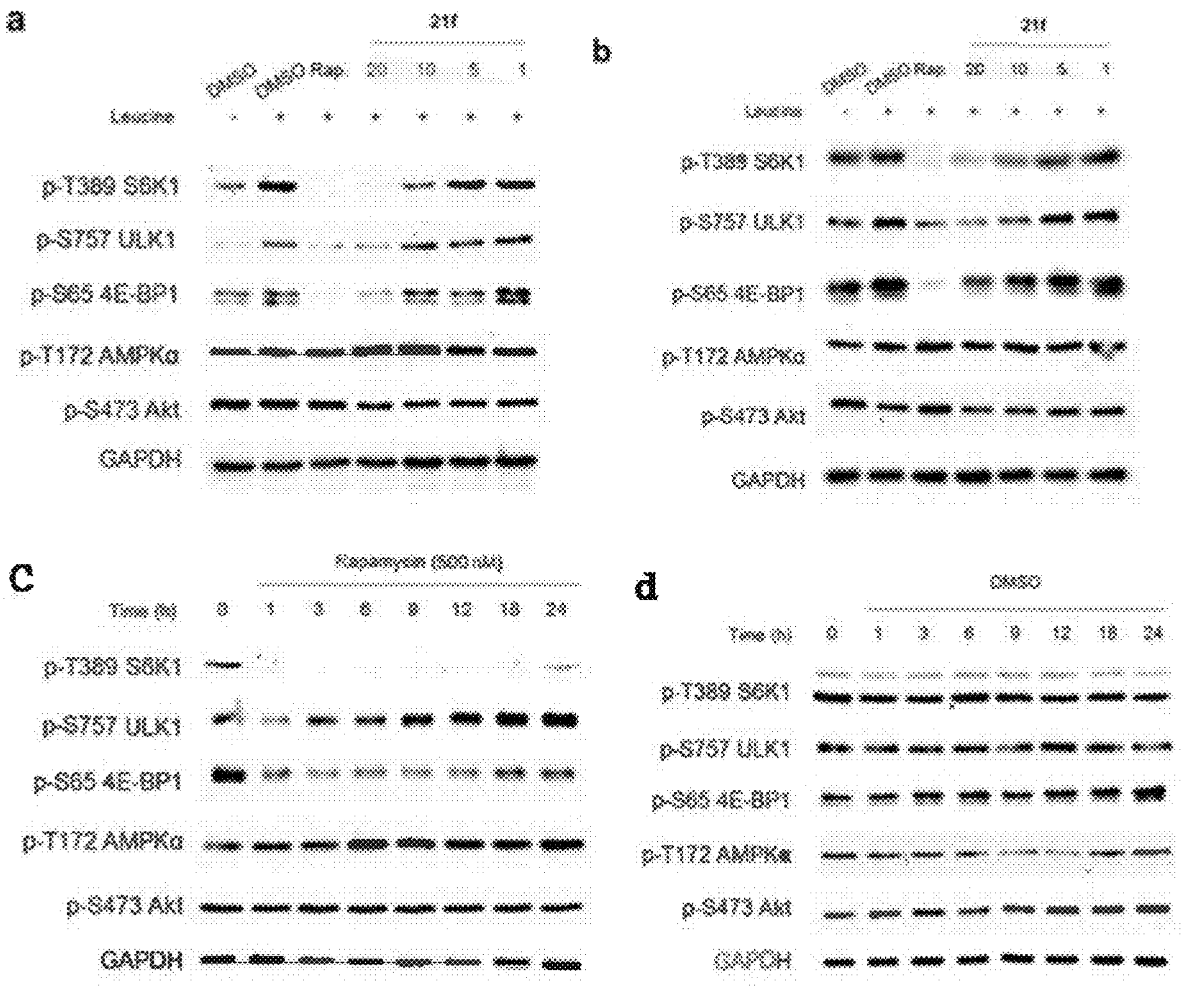

[Figure 19A]
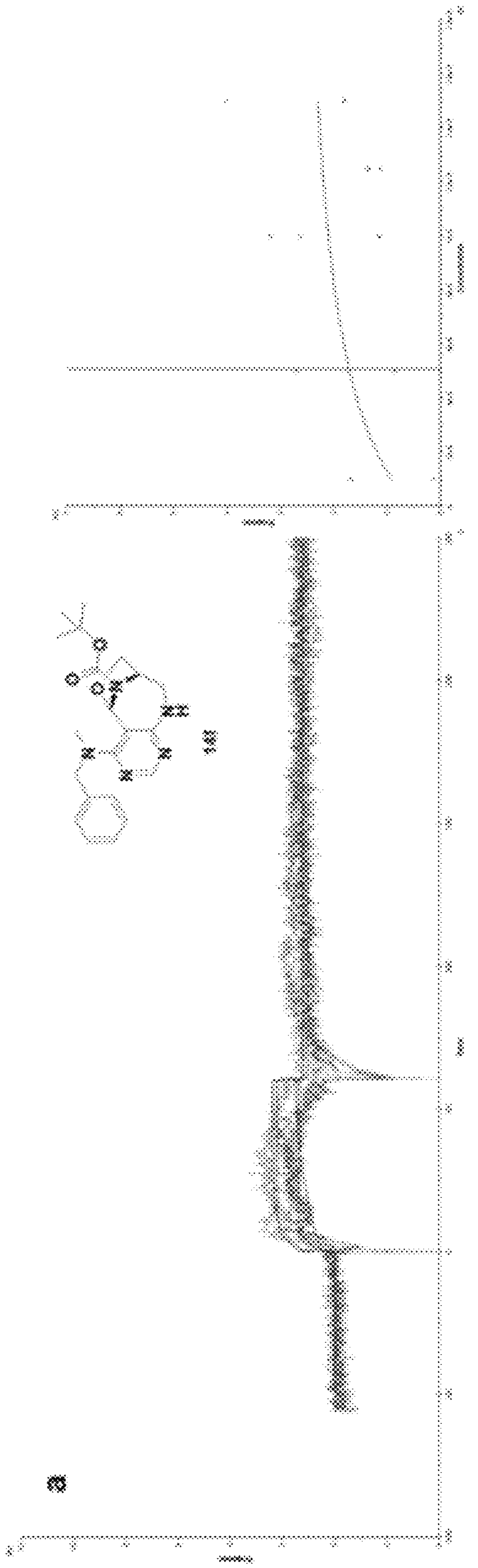

[Figure 19B]
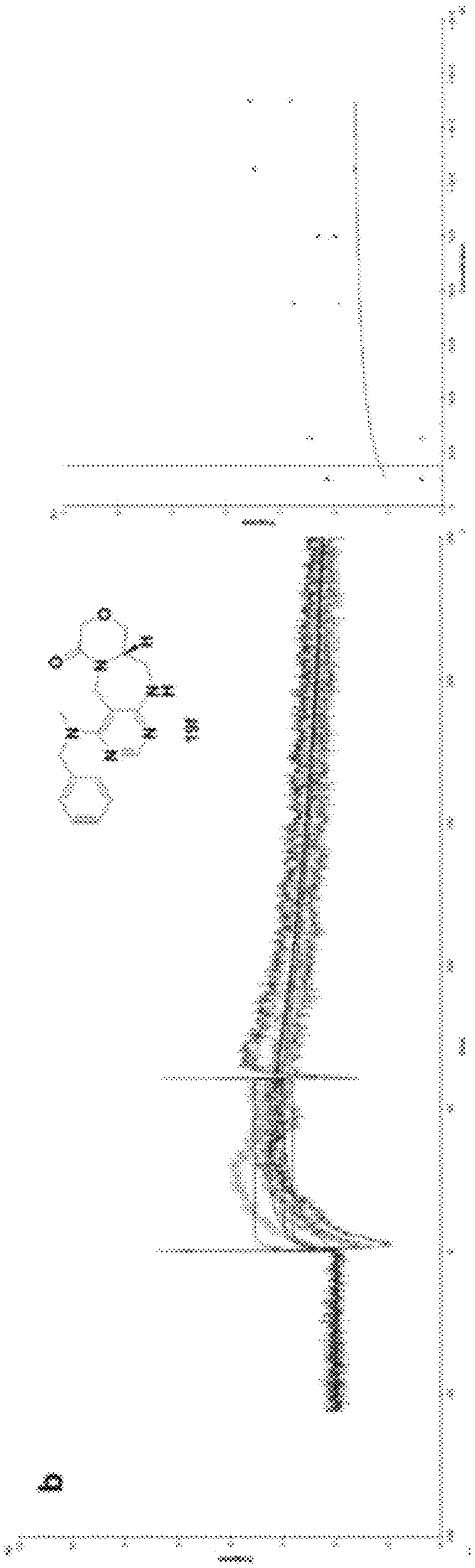

[Figure 19C]
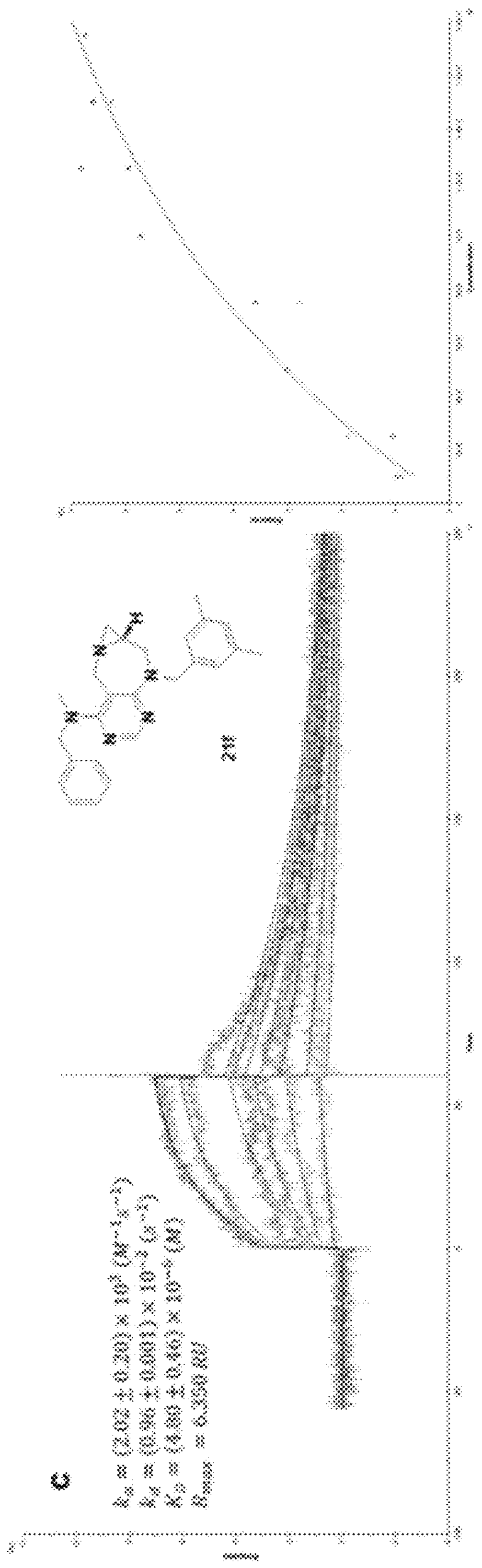

[Figure 20A]
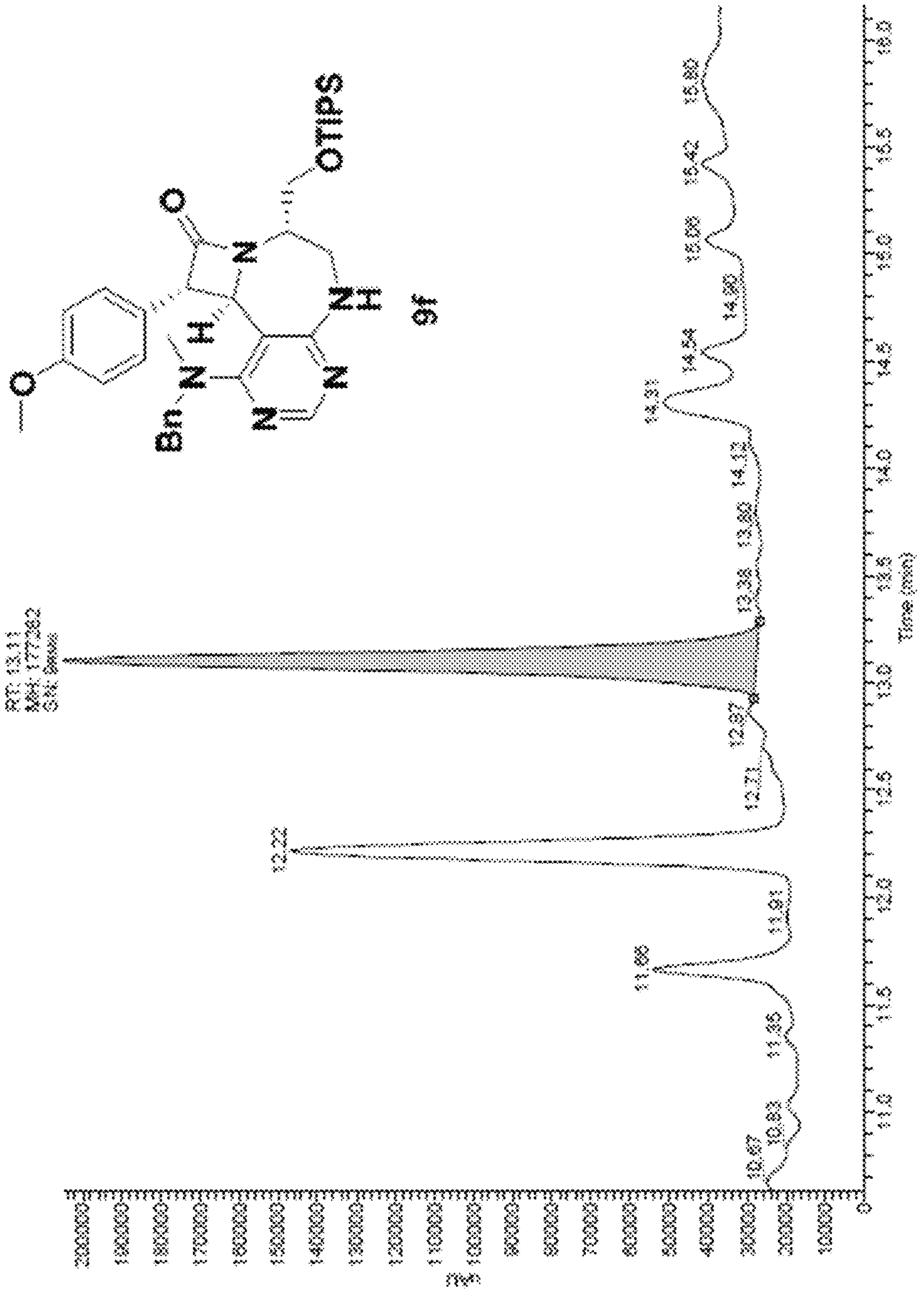
9f

[Figure 20B]
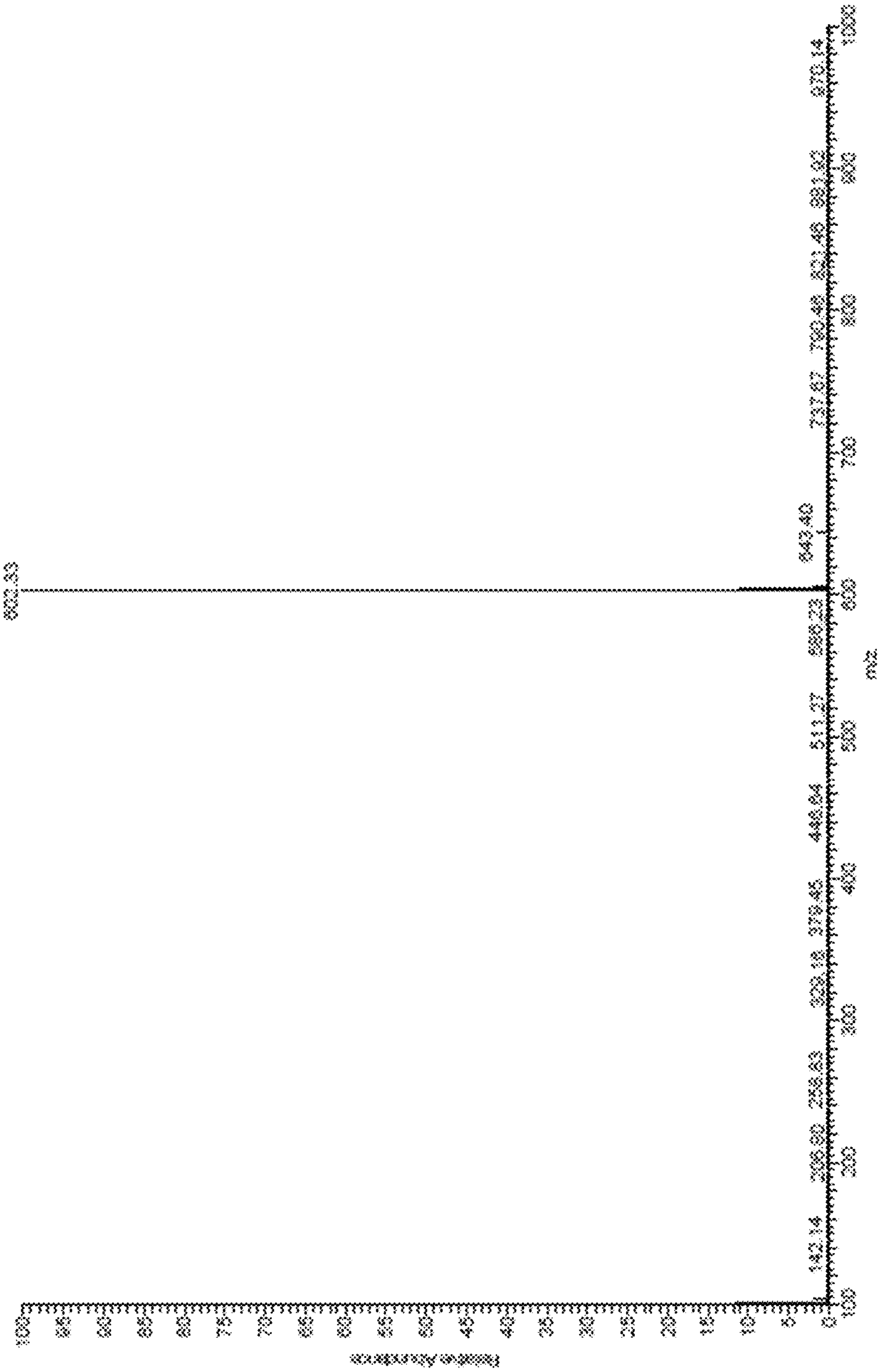

[Figure 21A]
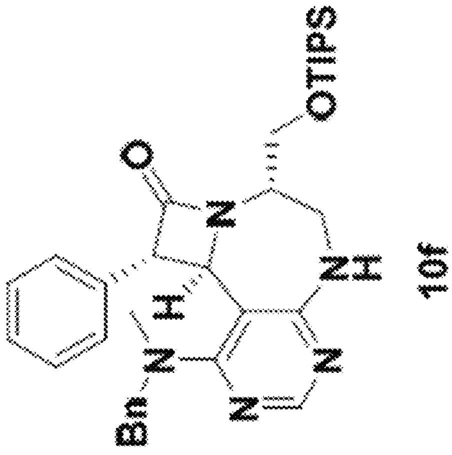
10f
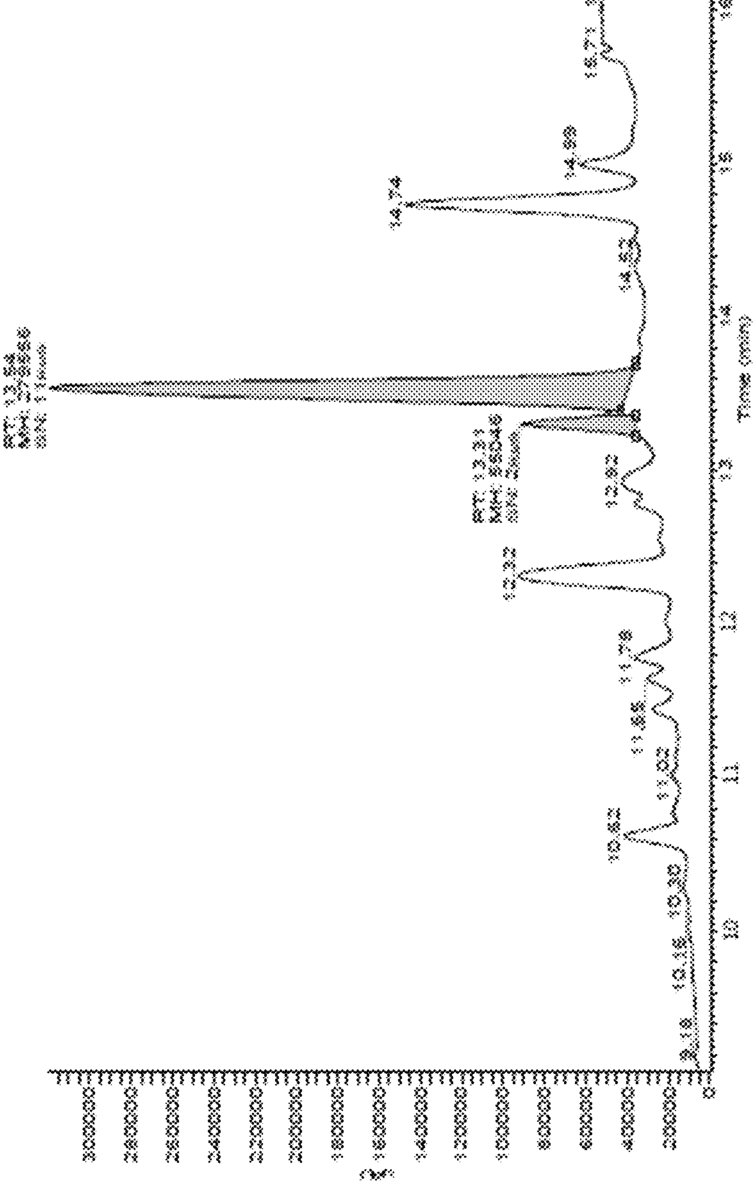

[Figure 21B]
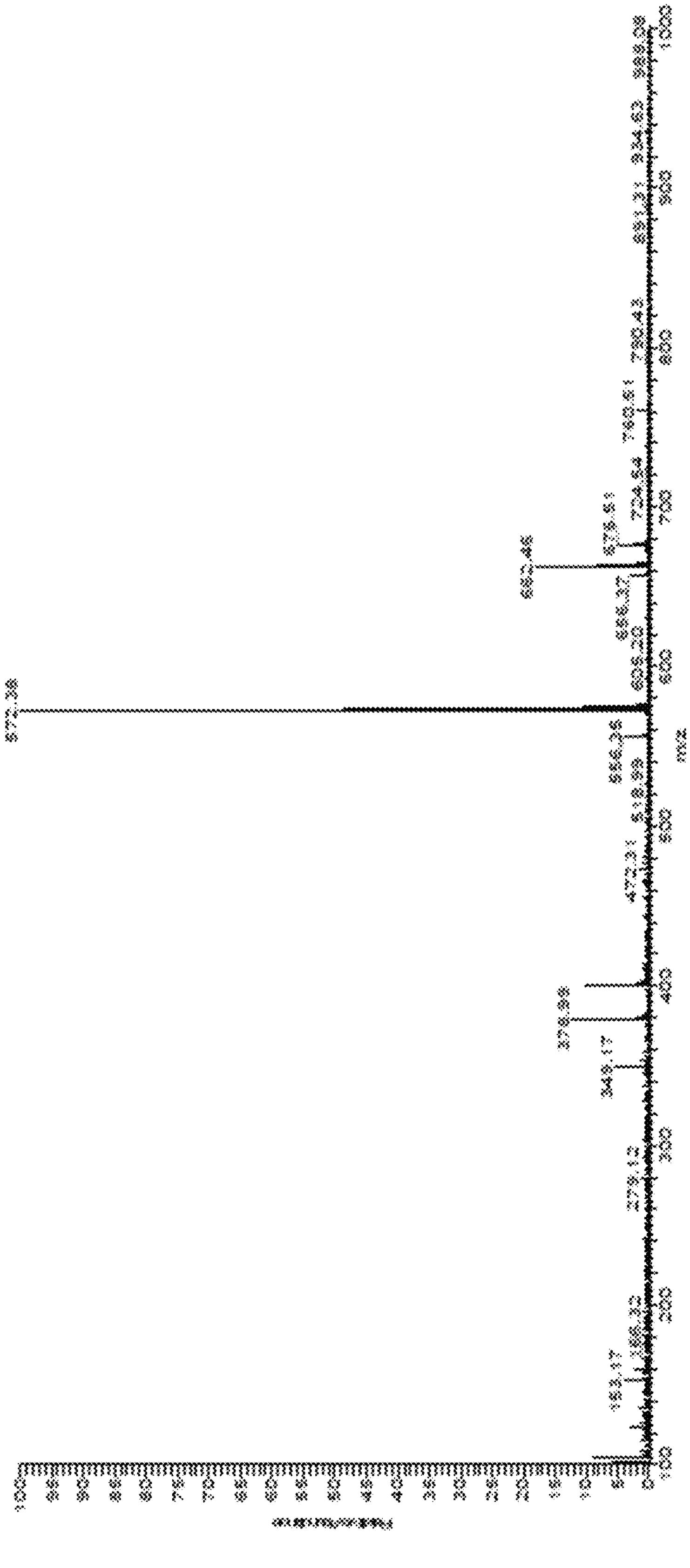

[Figure 21C]
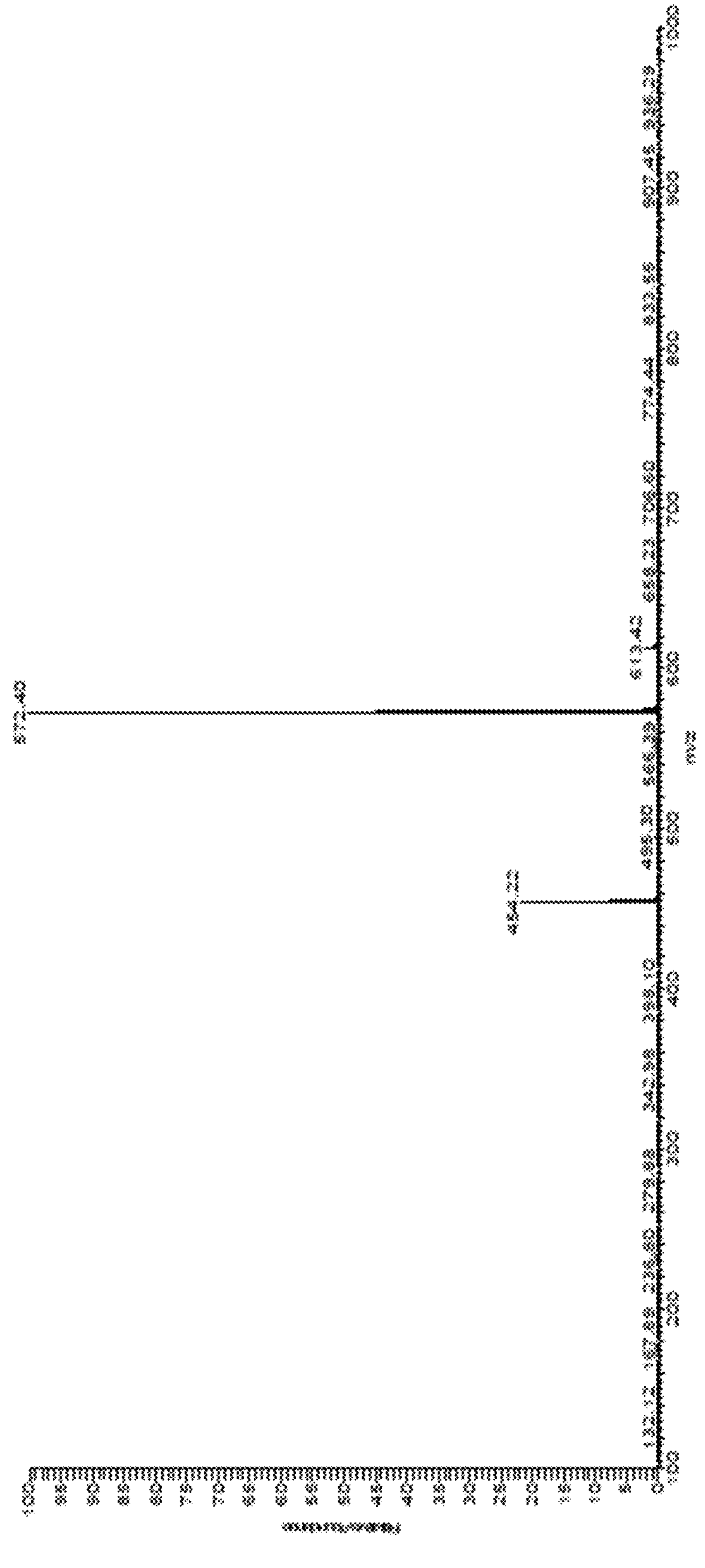

[Figure 22]
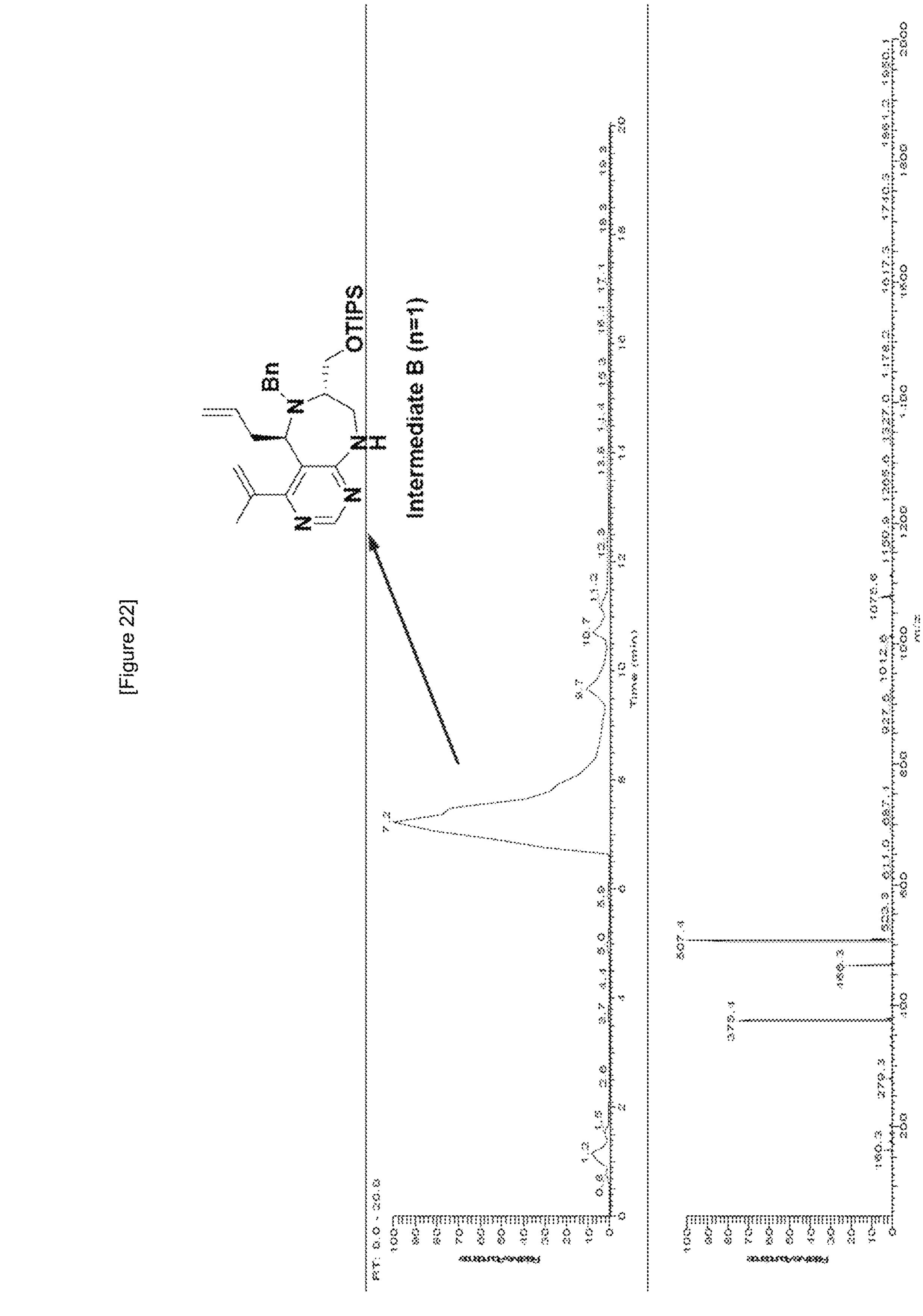

[Figure 23]
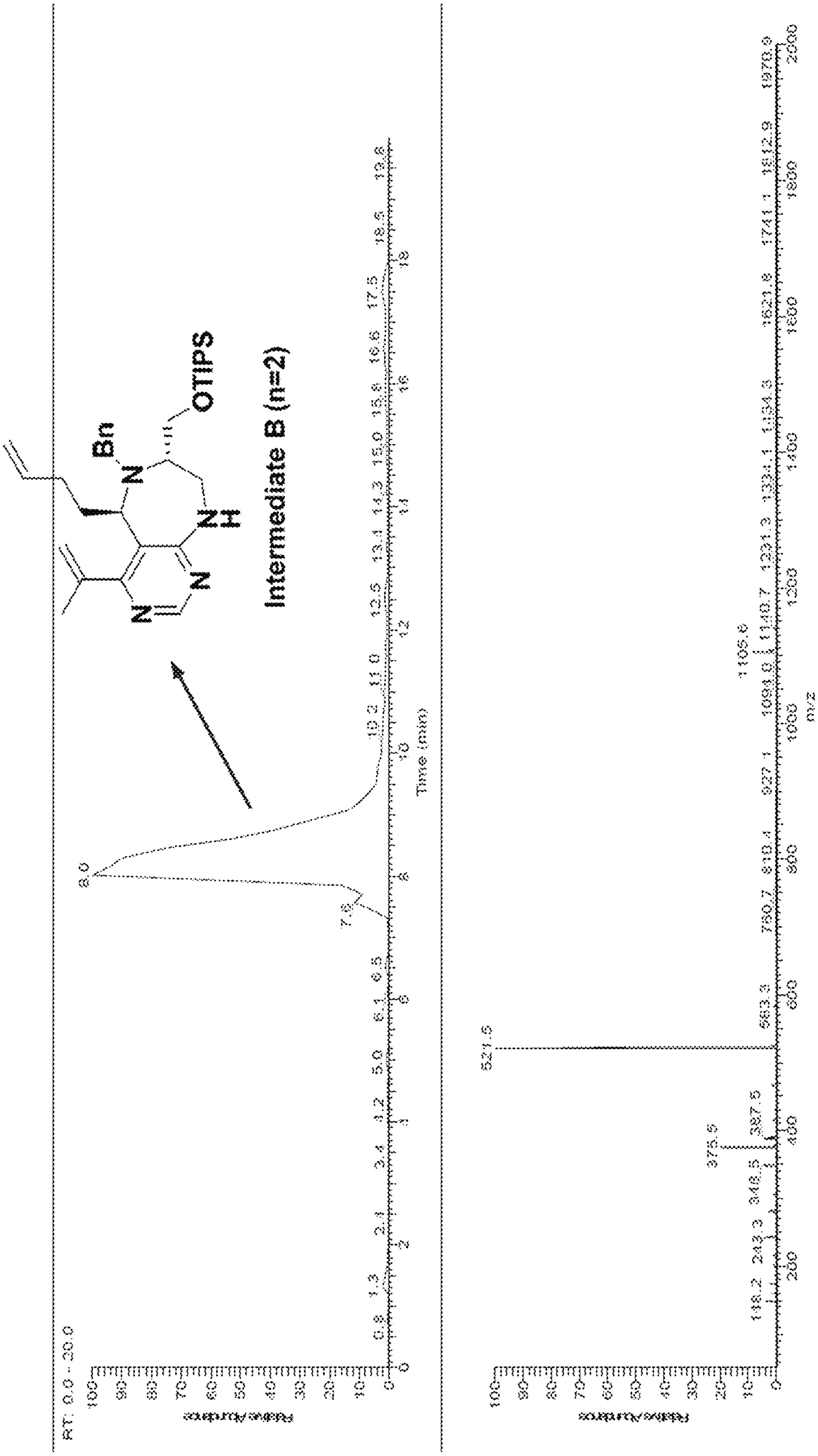
Intermediate B (n=2)

[Figure 24]
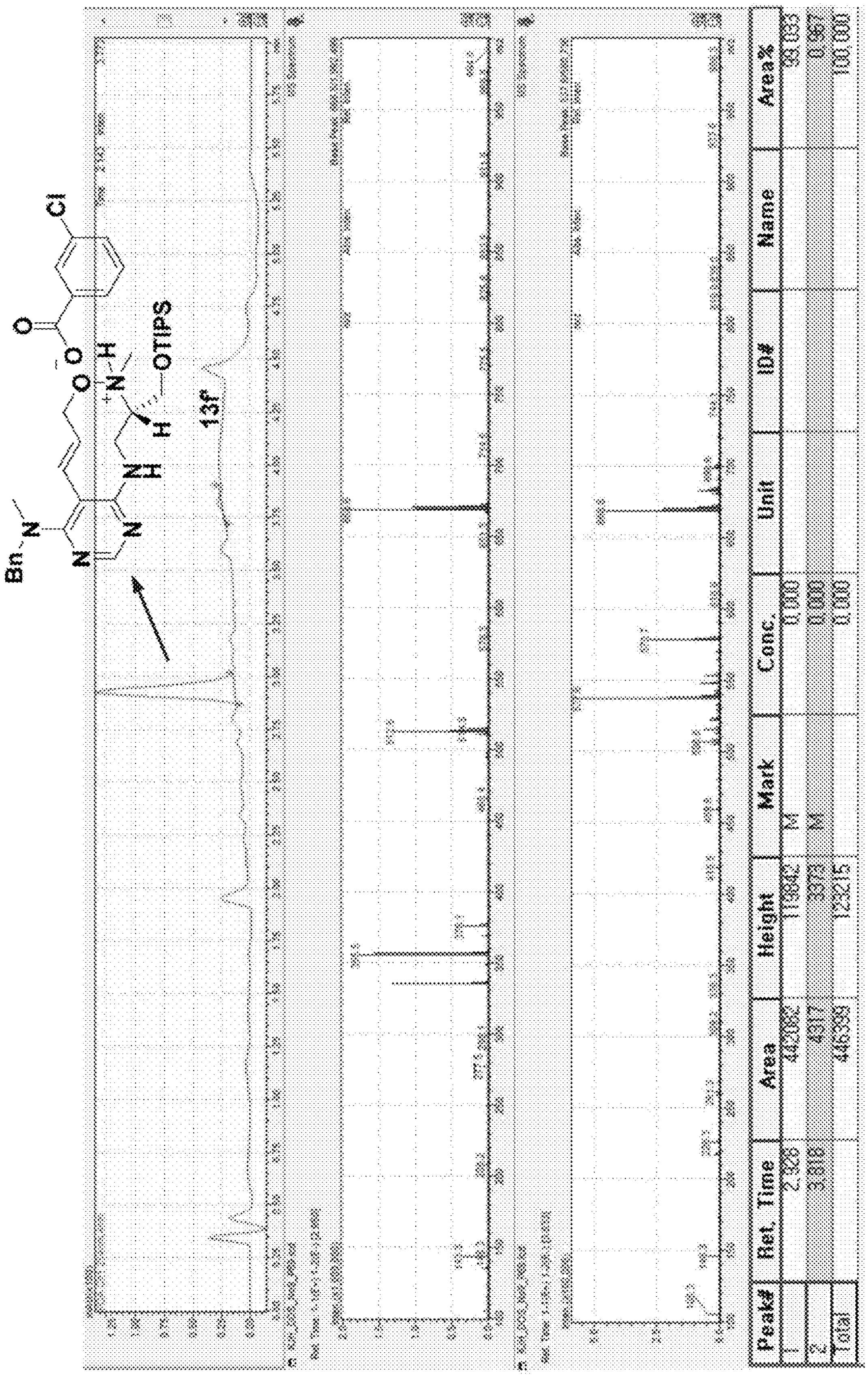
13f
| Peak# | Ret. Time | Area | Height | Mark | Conc. | Unit | ID# | Name | Area% |
|---|---|---|---|---|---|---|---|---|---|
| 1 | 2.326 | 442062 | 119842 | M | 0.000 | | | | 99.033 |
| 2 | 3.818 | 4317 | 3373 | M | 0.000 | | | | 0.967 |
| Total | | 446379 | 123215 | | 0.000 | | | | 100.000 |

[Figure 25A]
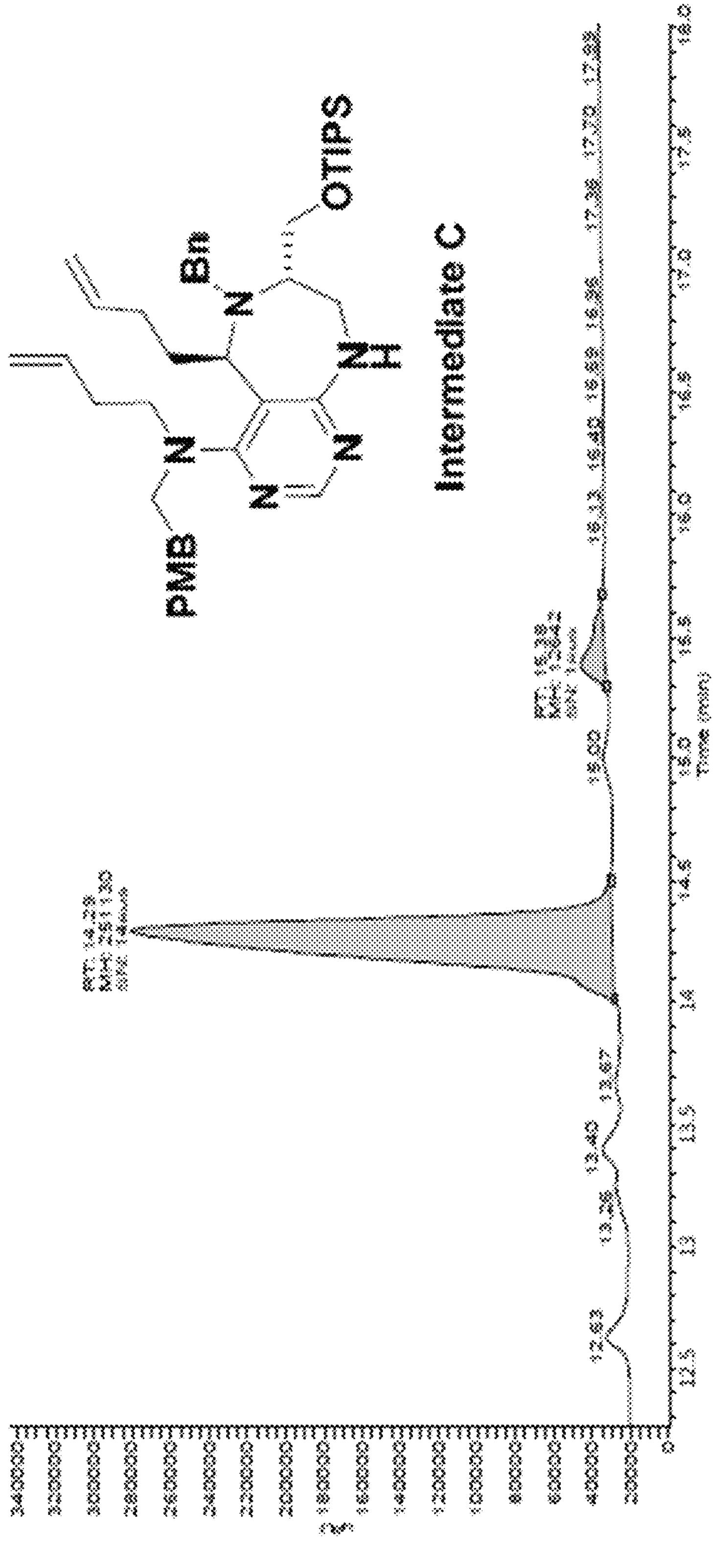

[Figure 25B]
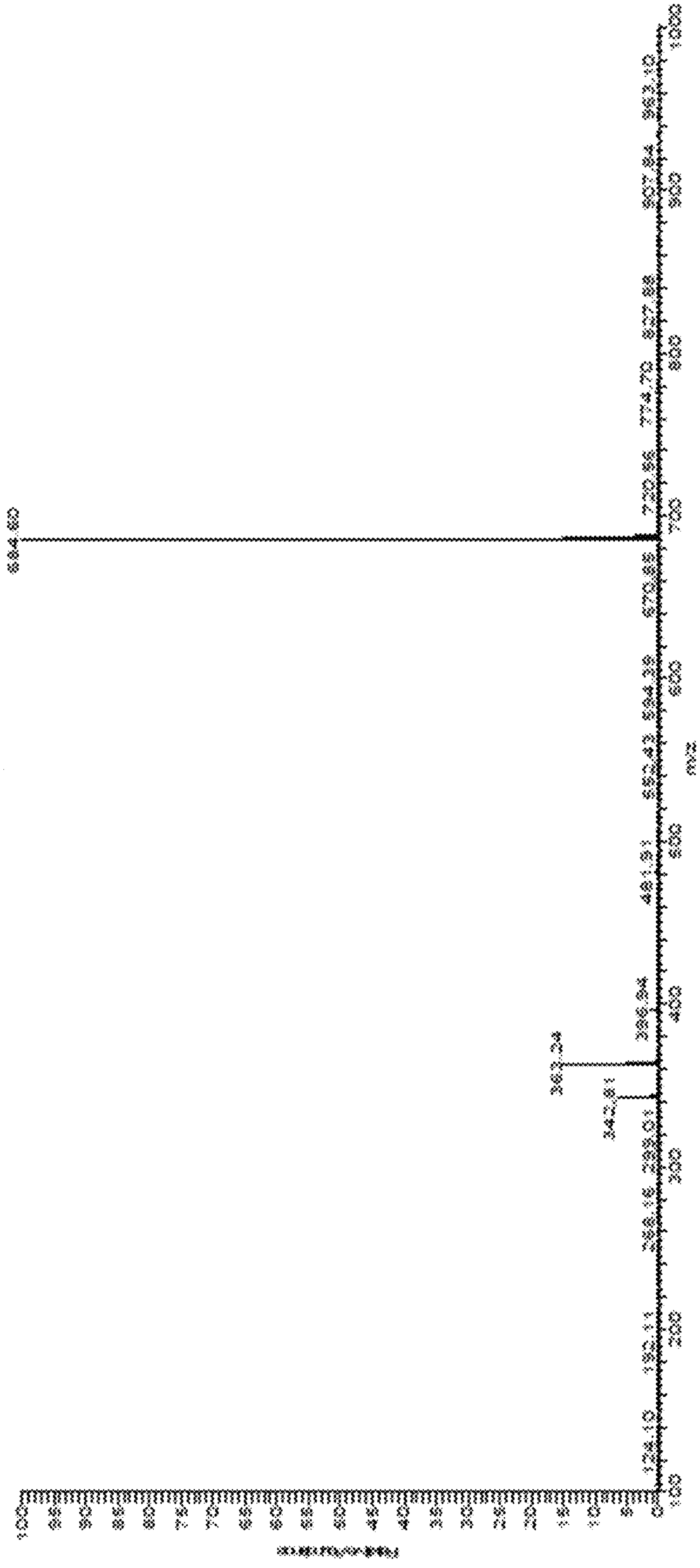

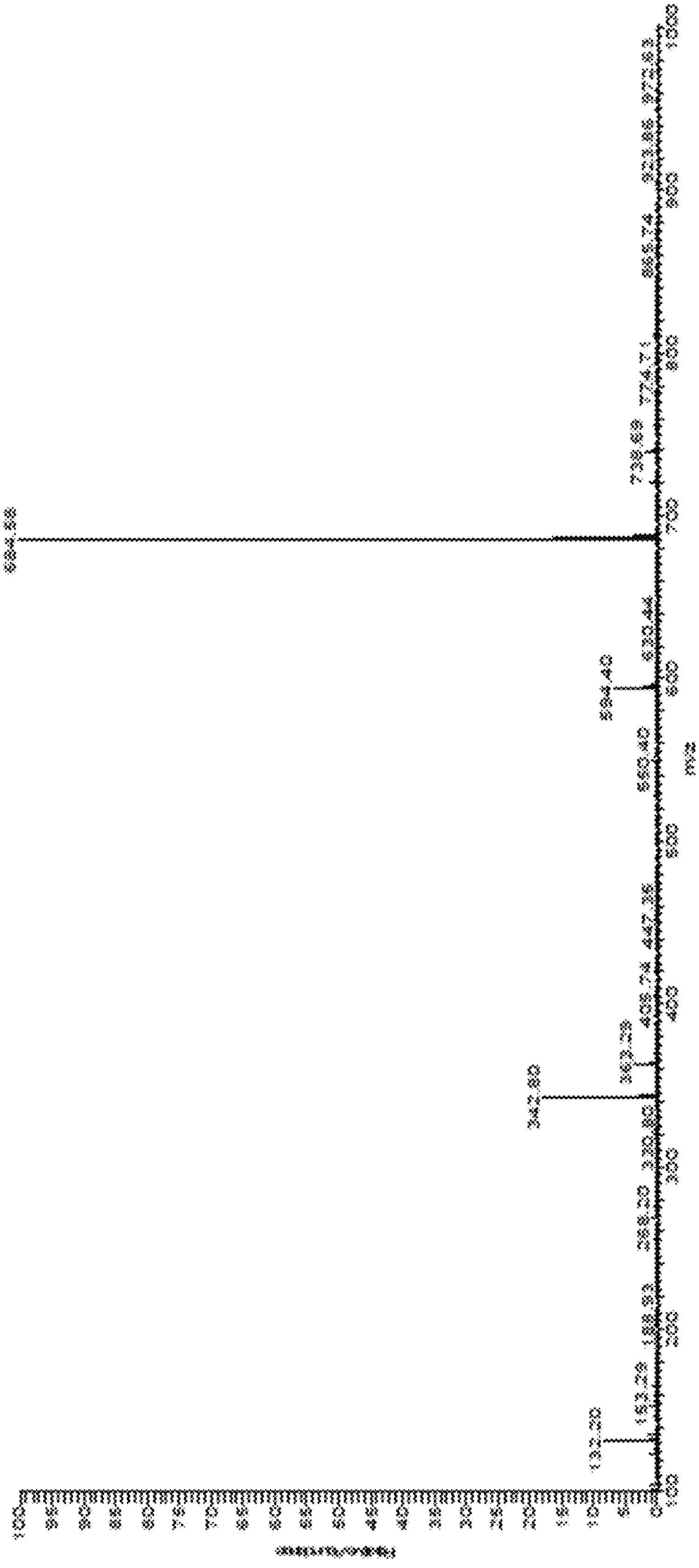
[Figure 25C]

[Figure 26A]
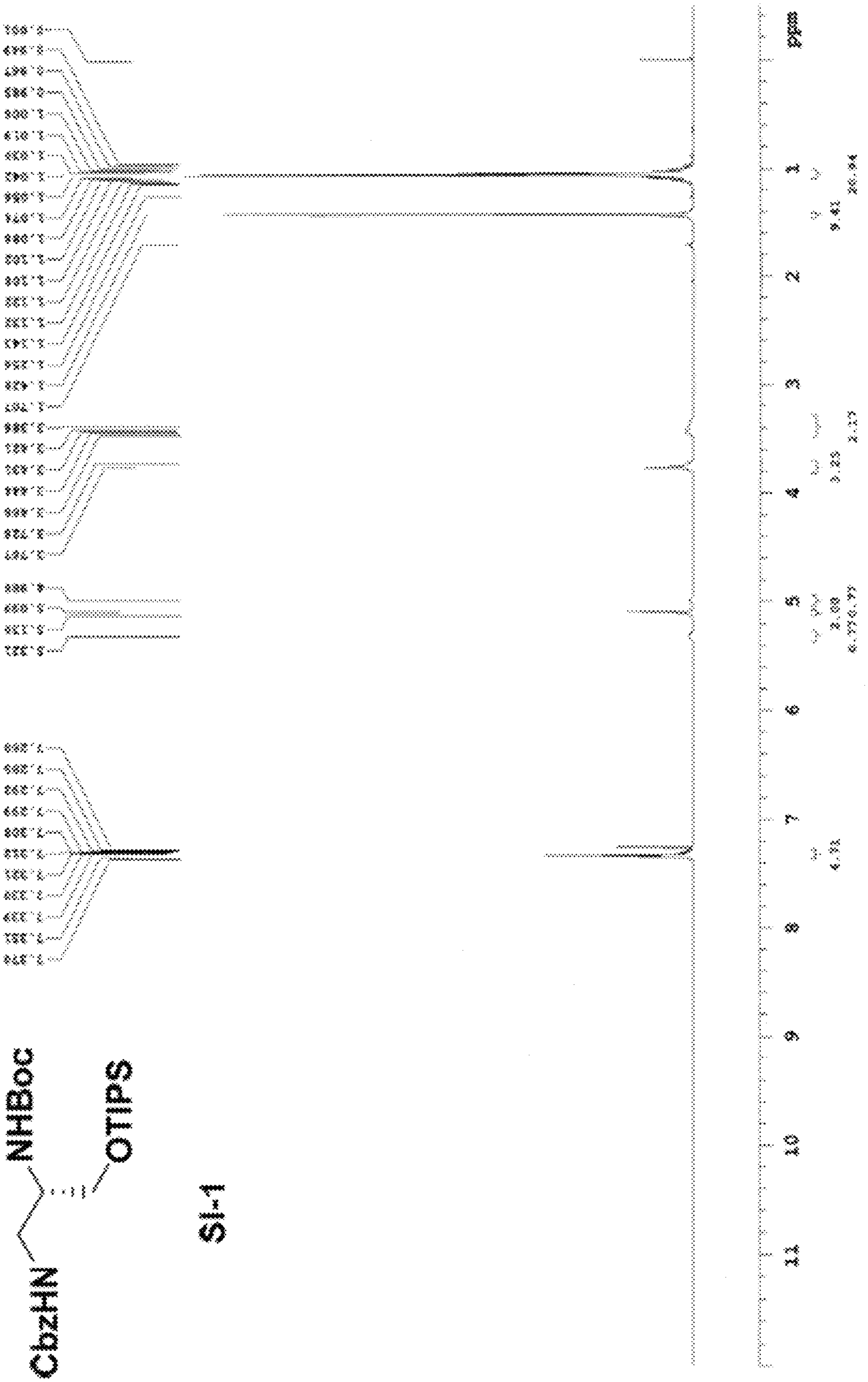
SI-1

[Figure 26B]
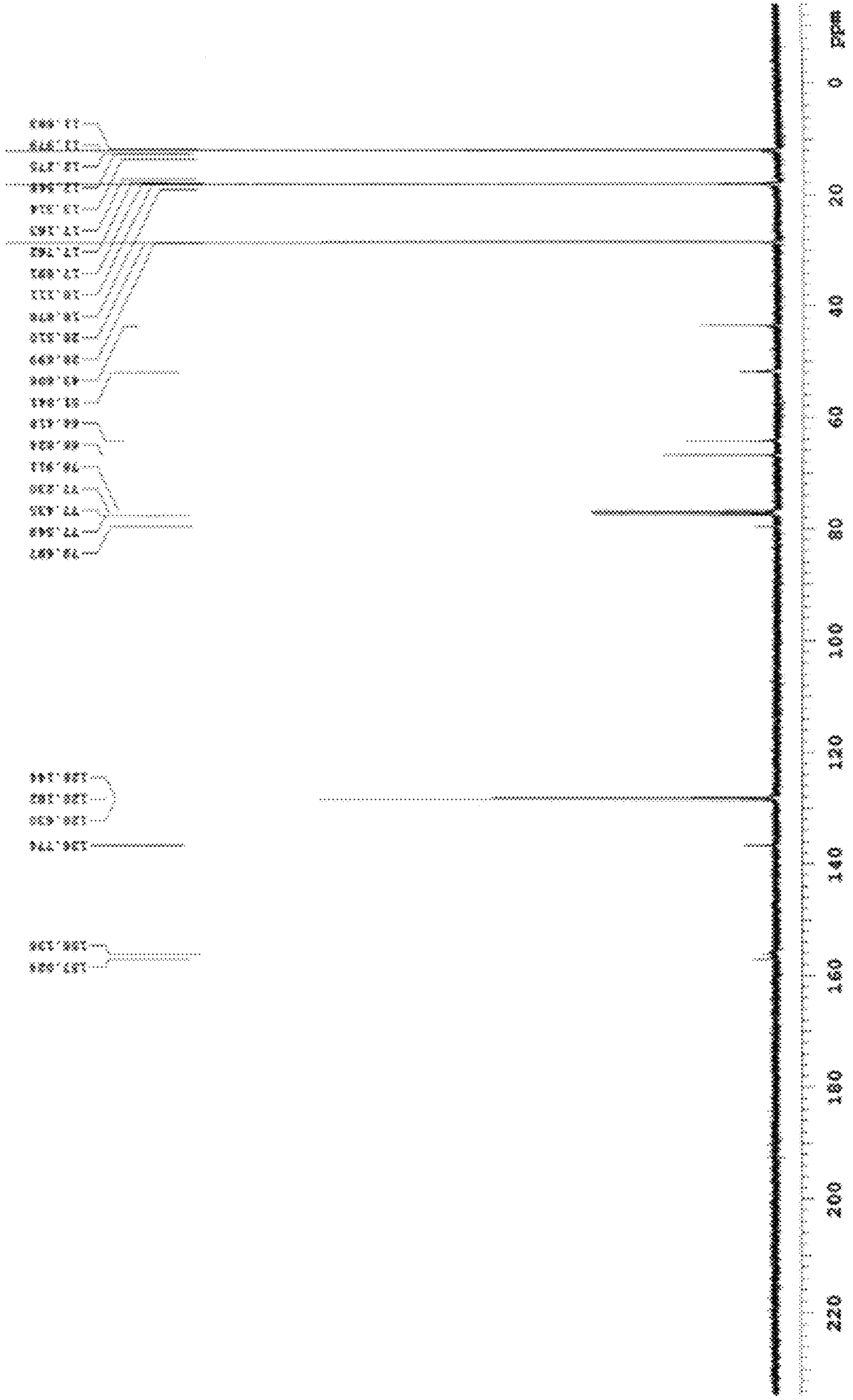

[Figure 27A]
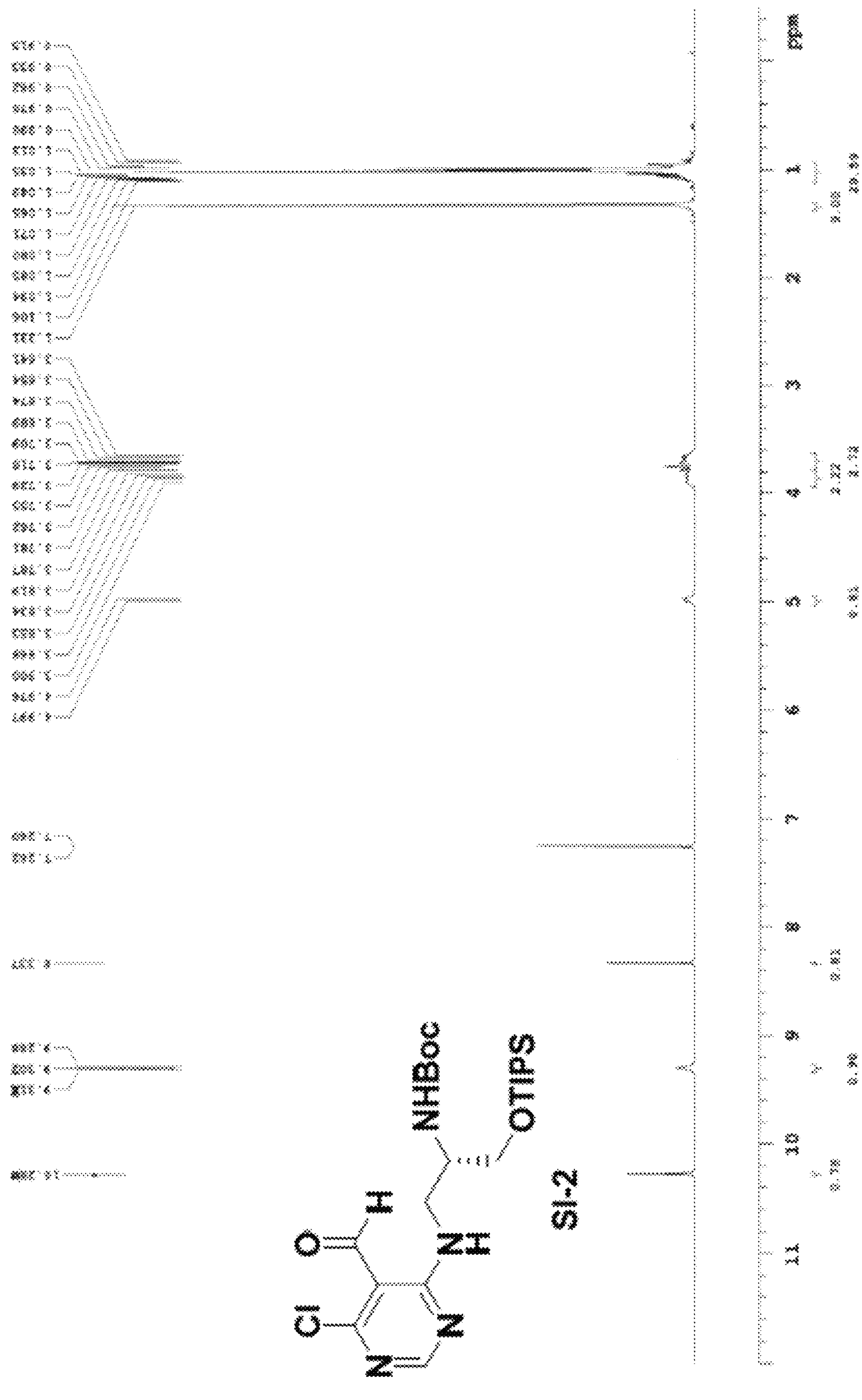
SI-2

[Figure 27B]
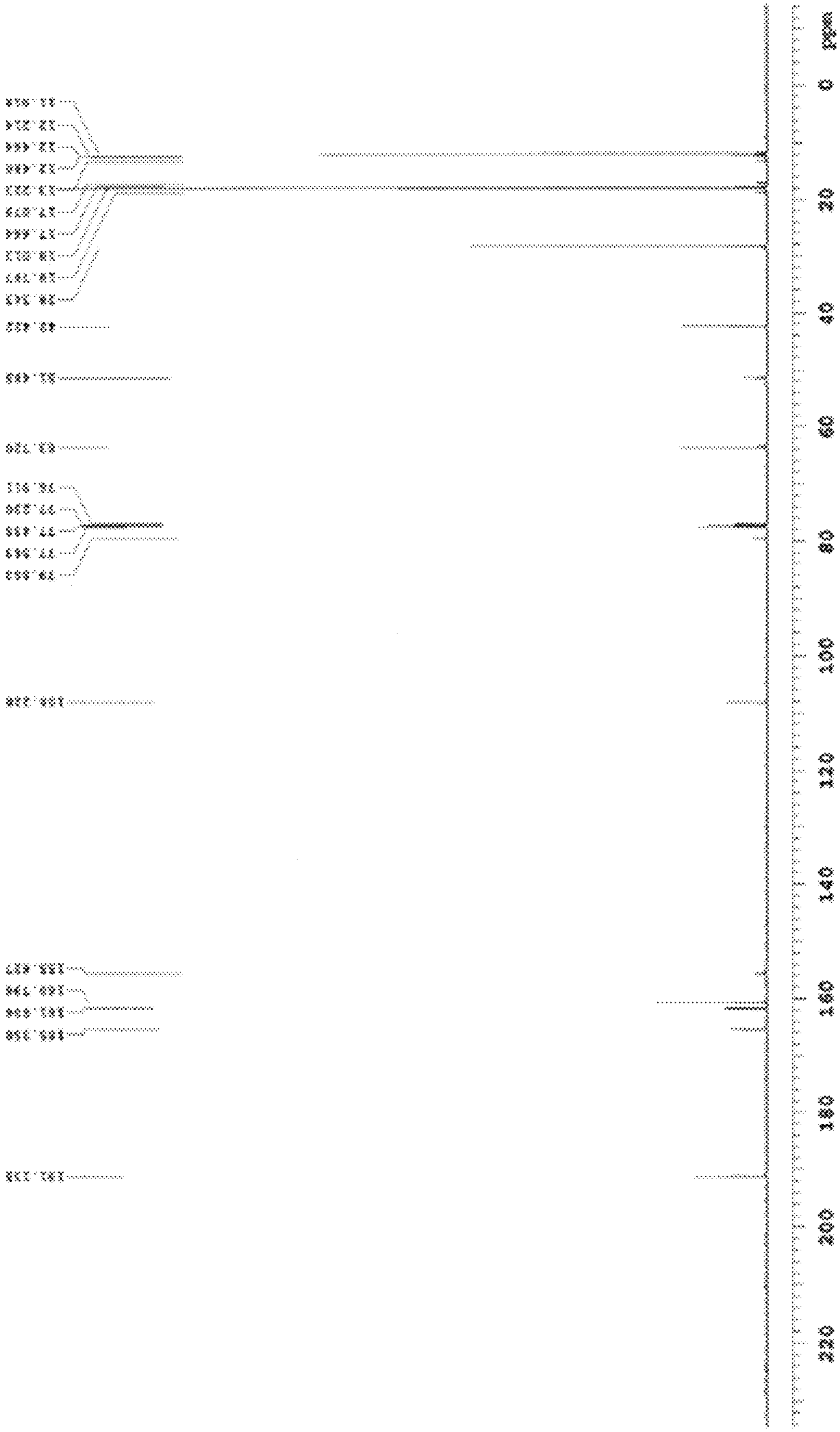

[Figure 28A]
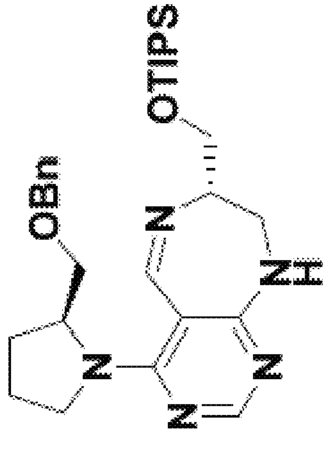
1a
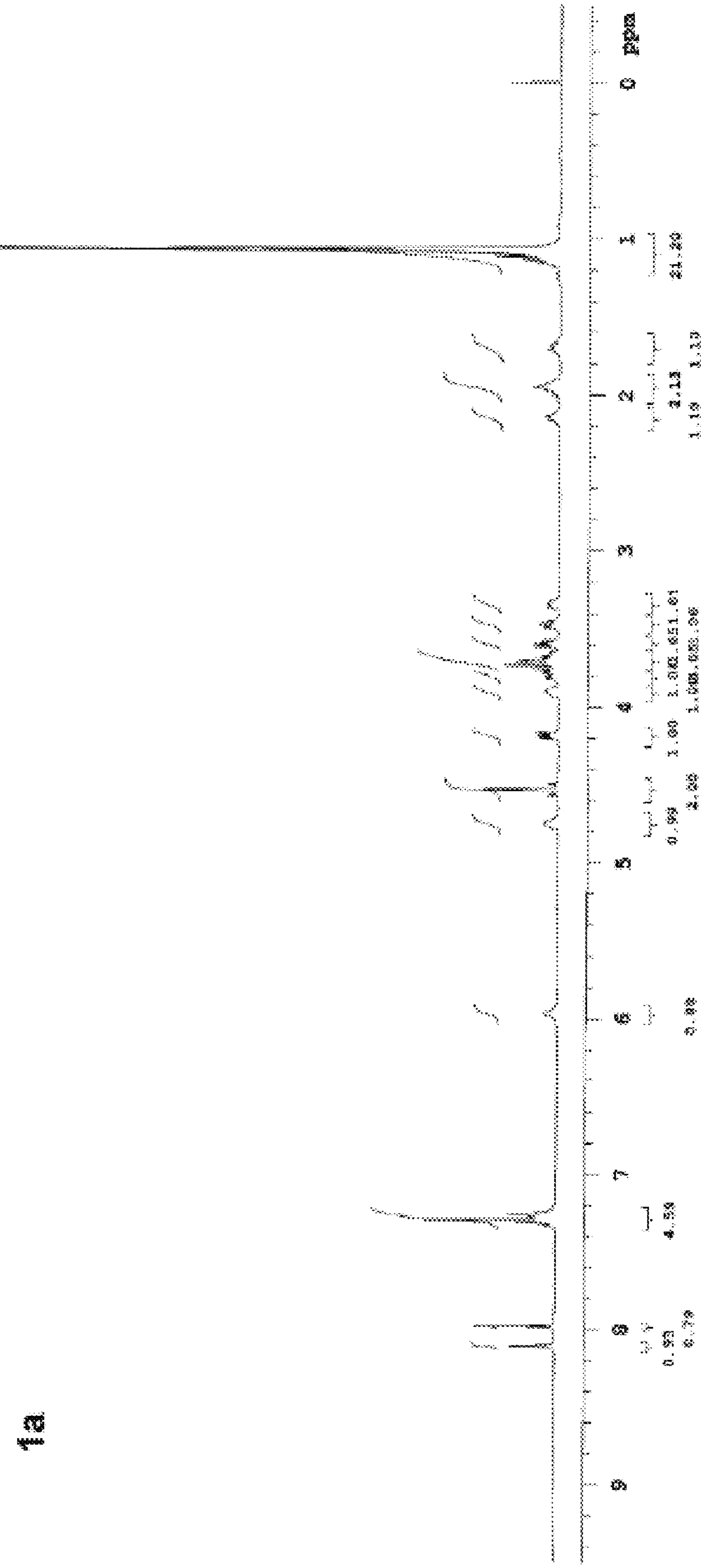

[Figure 28B]
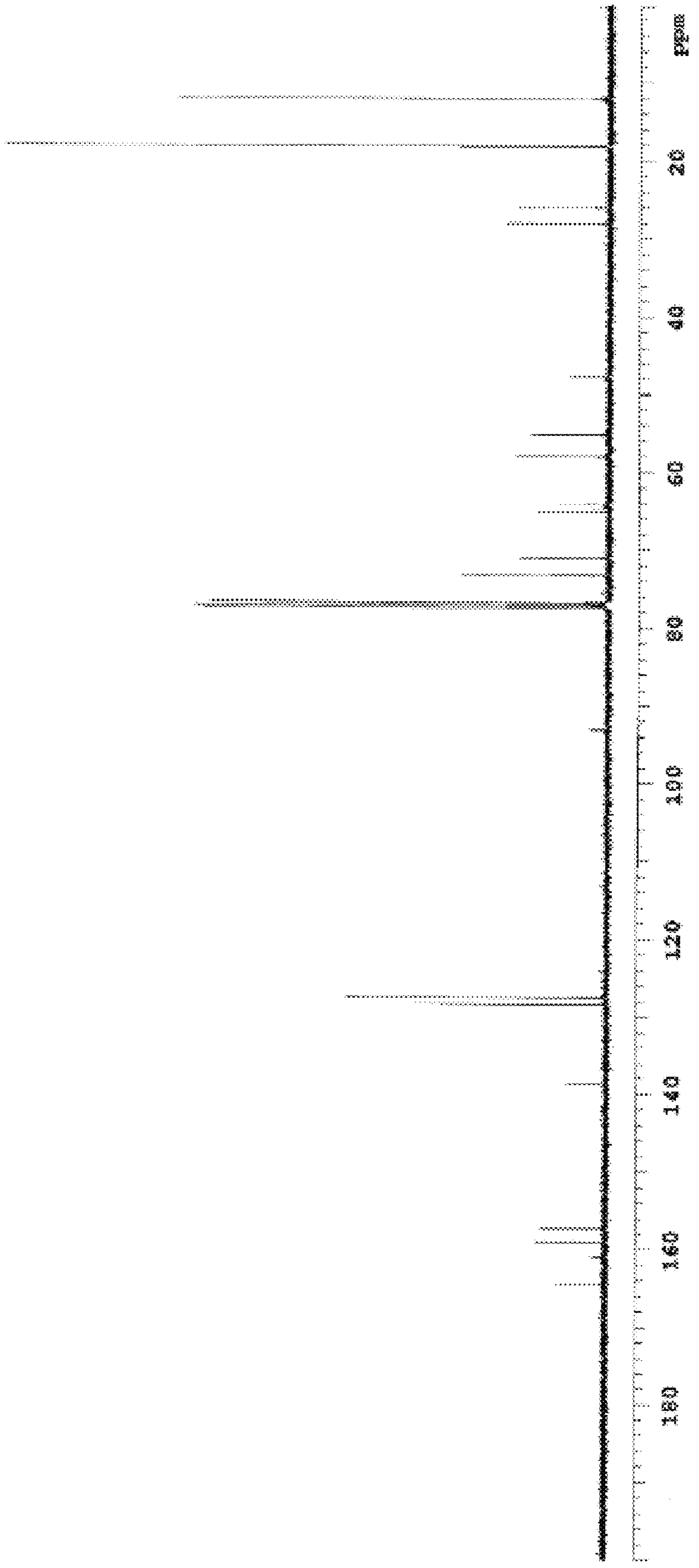

[Figure 29A]
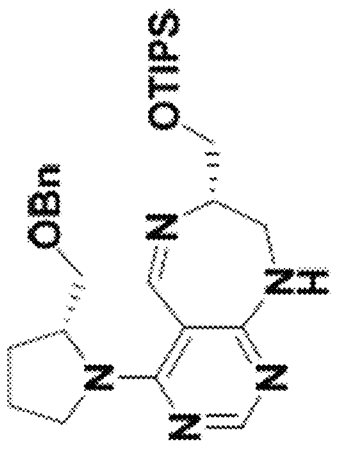
1b
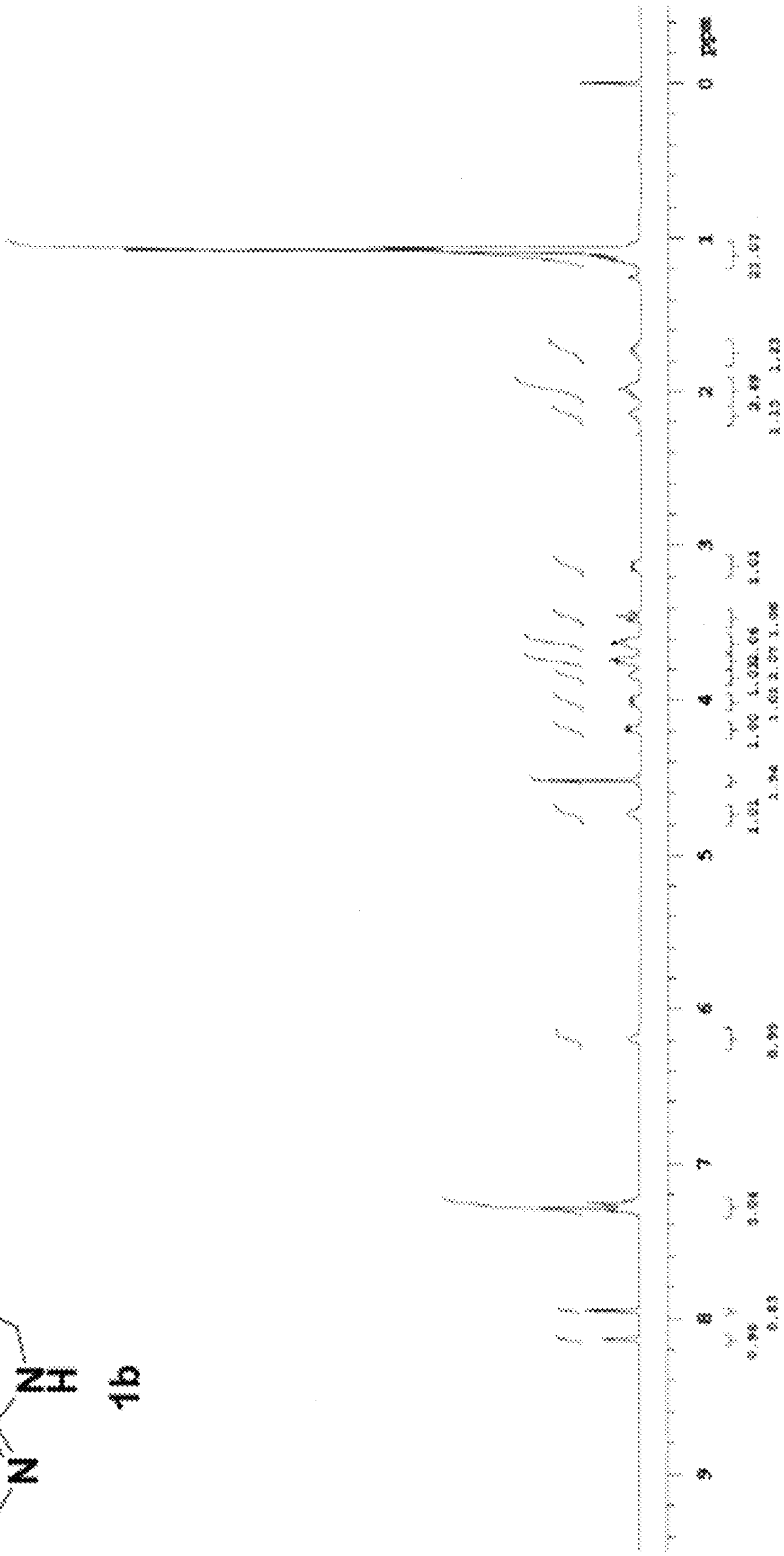

[Figure 29B]
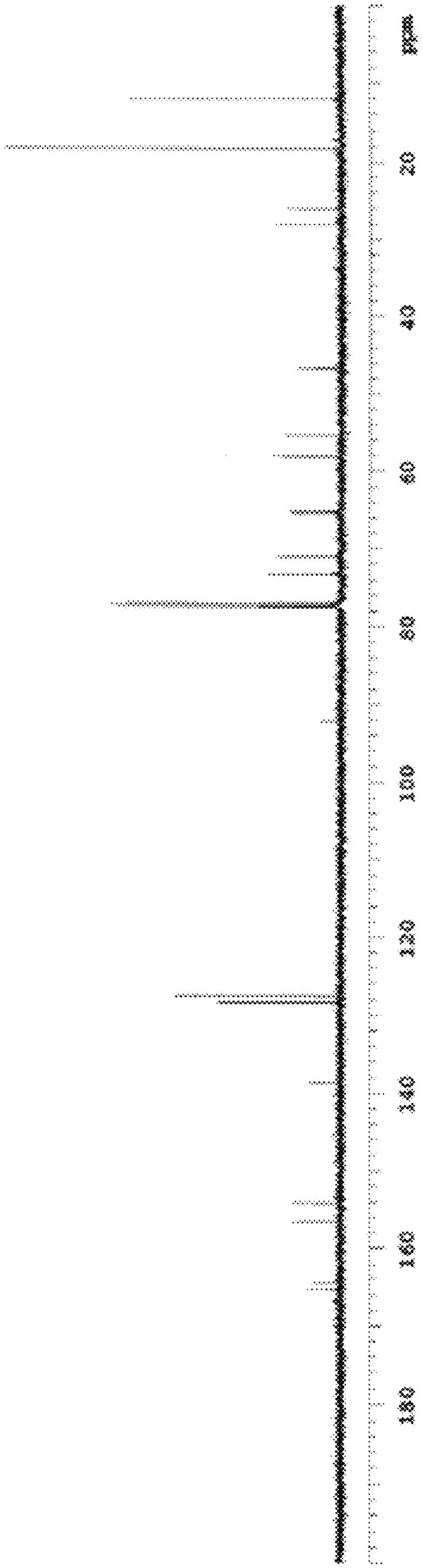

[Figure 30A]
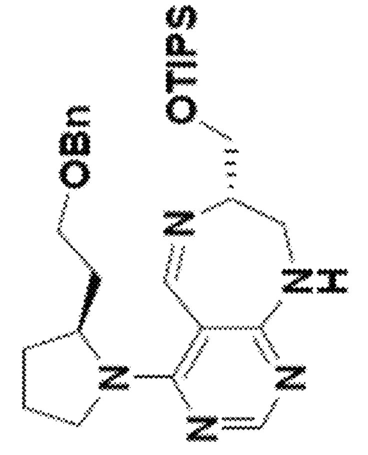
1c
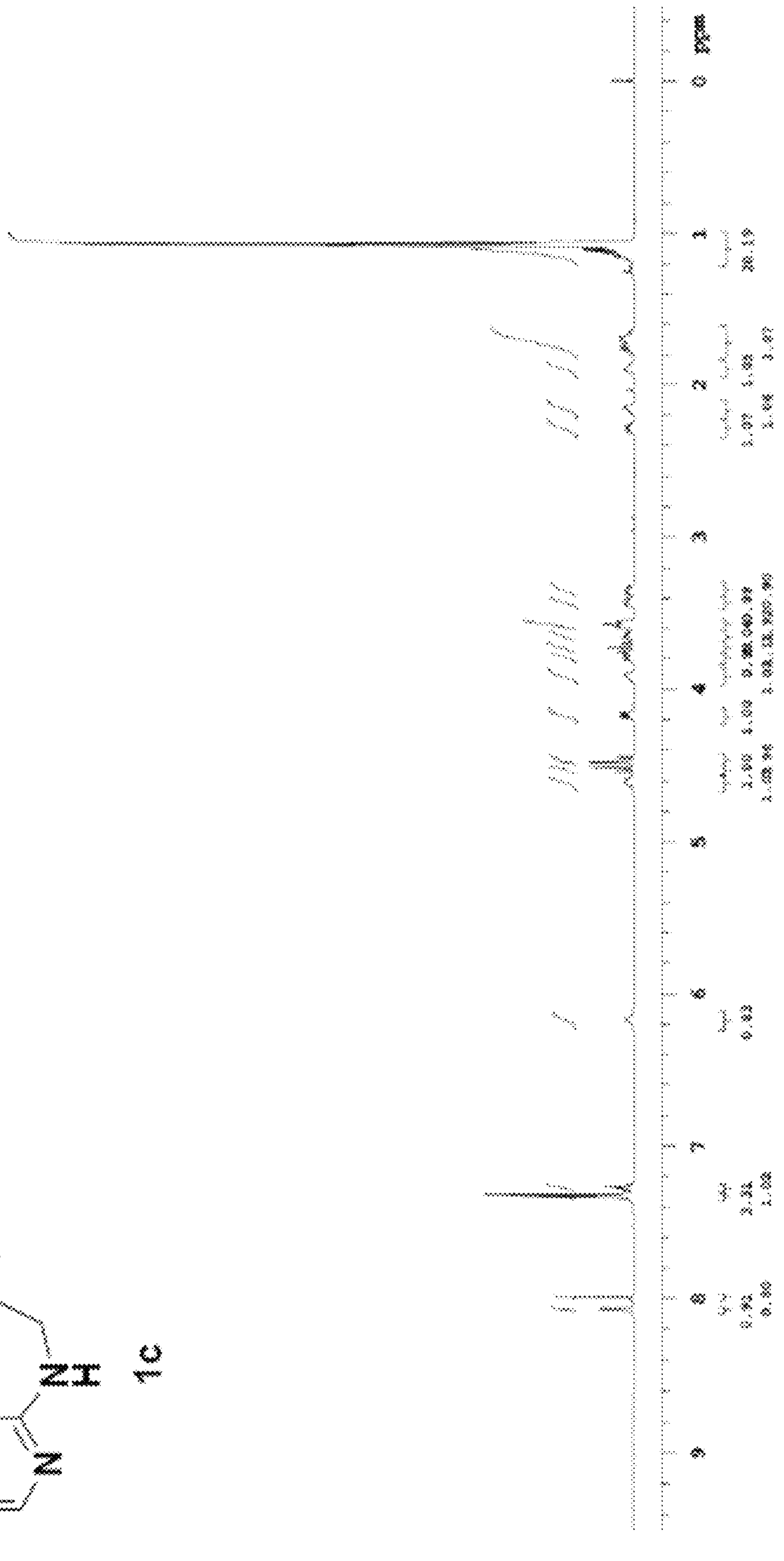

[Figure 30B]
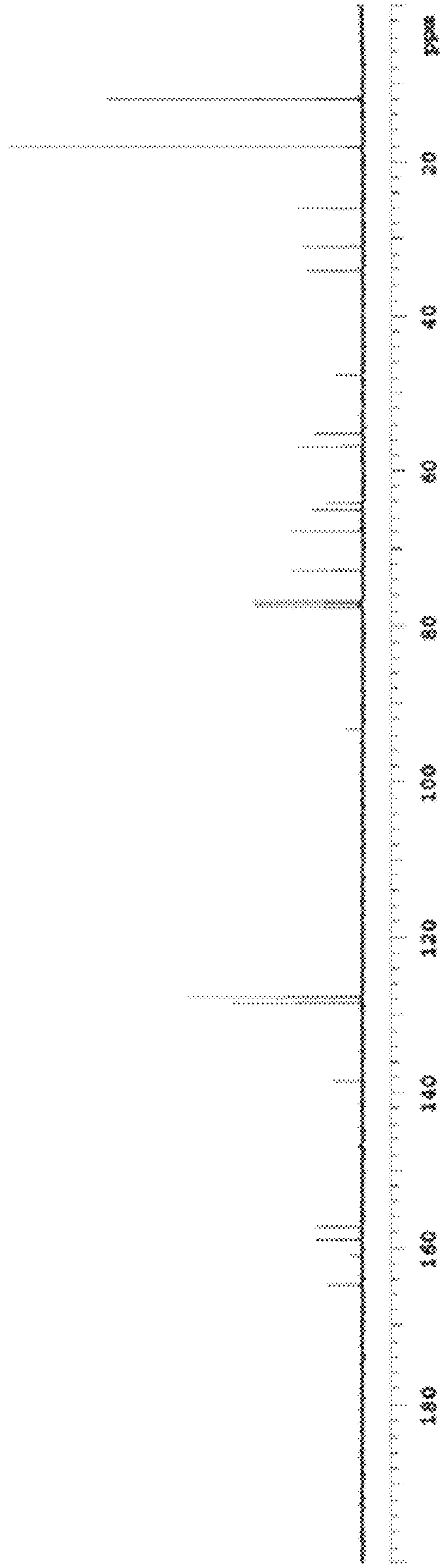

[Figure 31A]
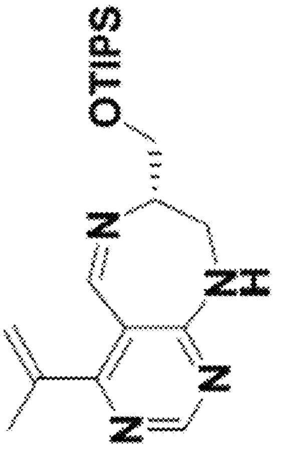
1d
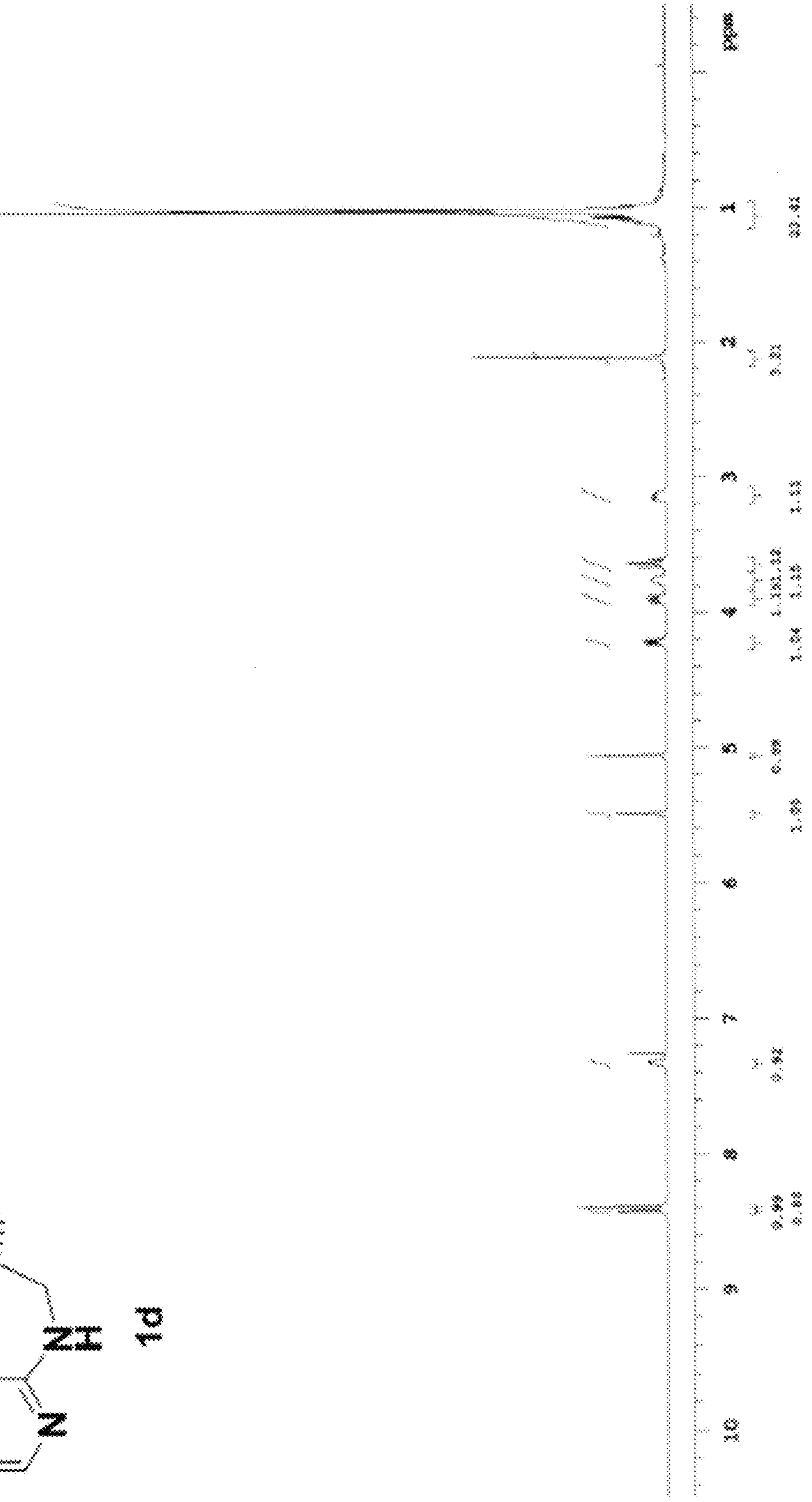

[Figure 31B]
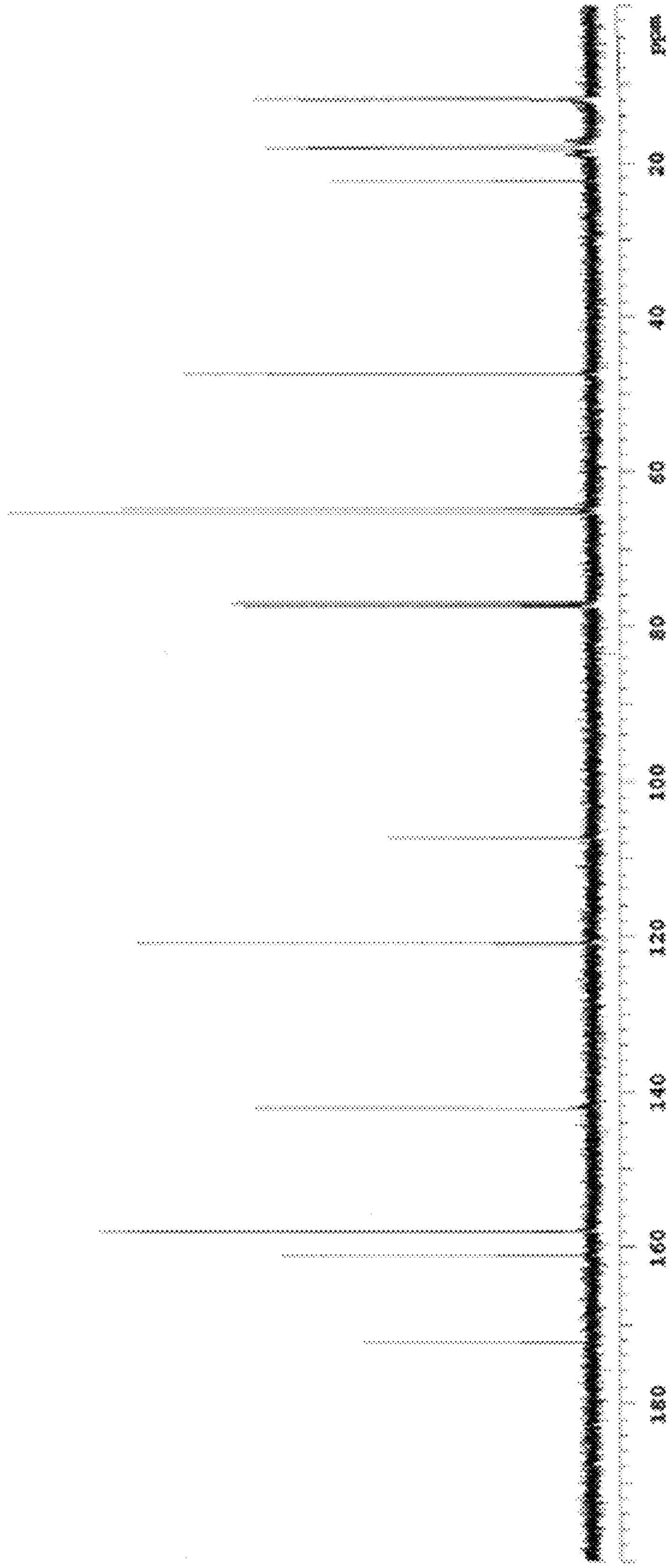

[Figure 32A]
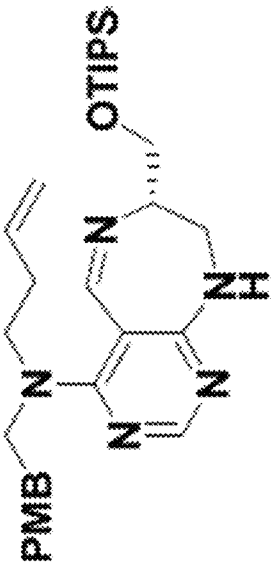
1e
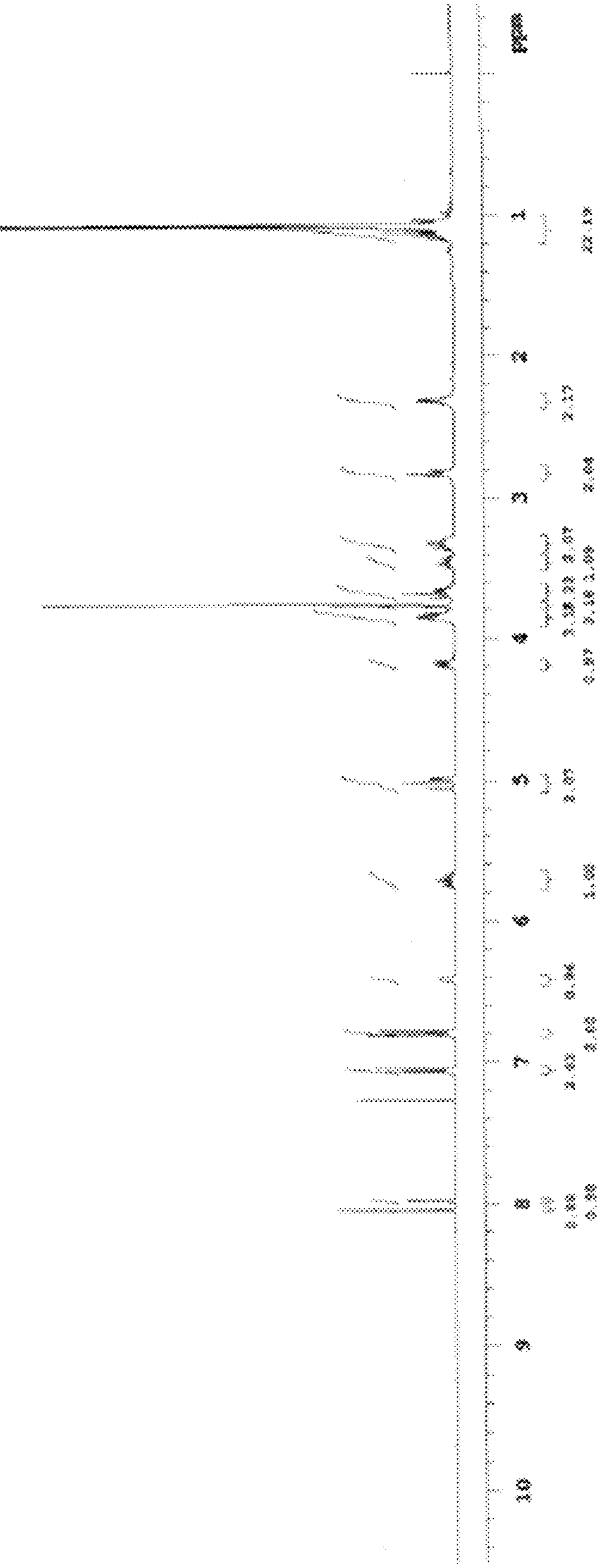

[Figure 32B]
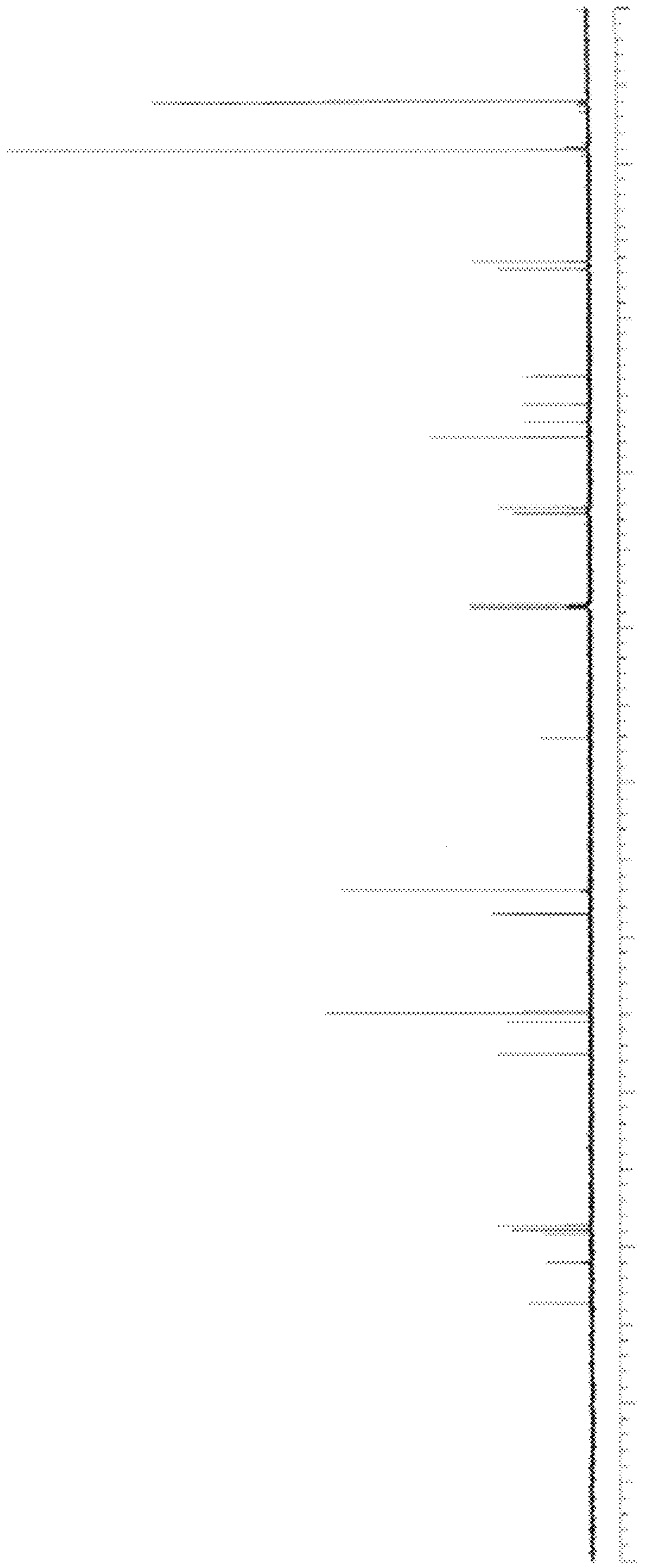

[Figure 33A]
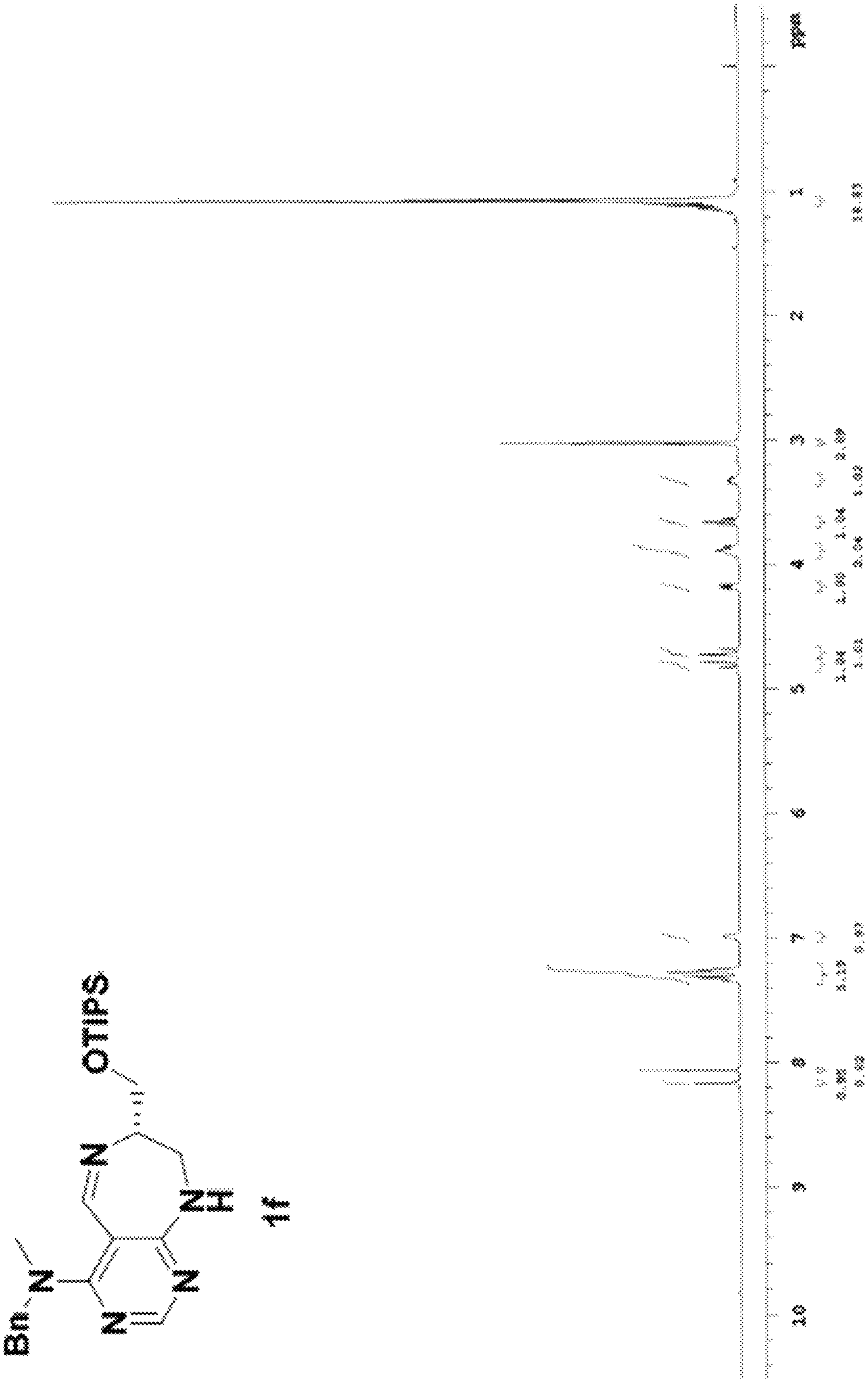
1f

[Figure 33B]
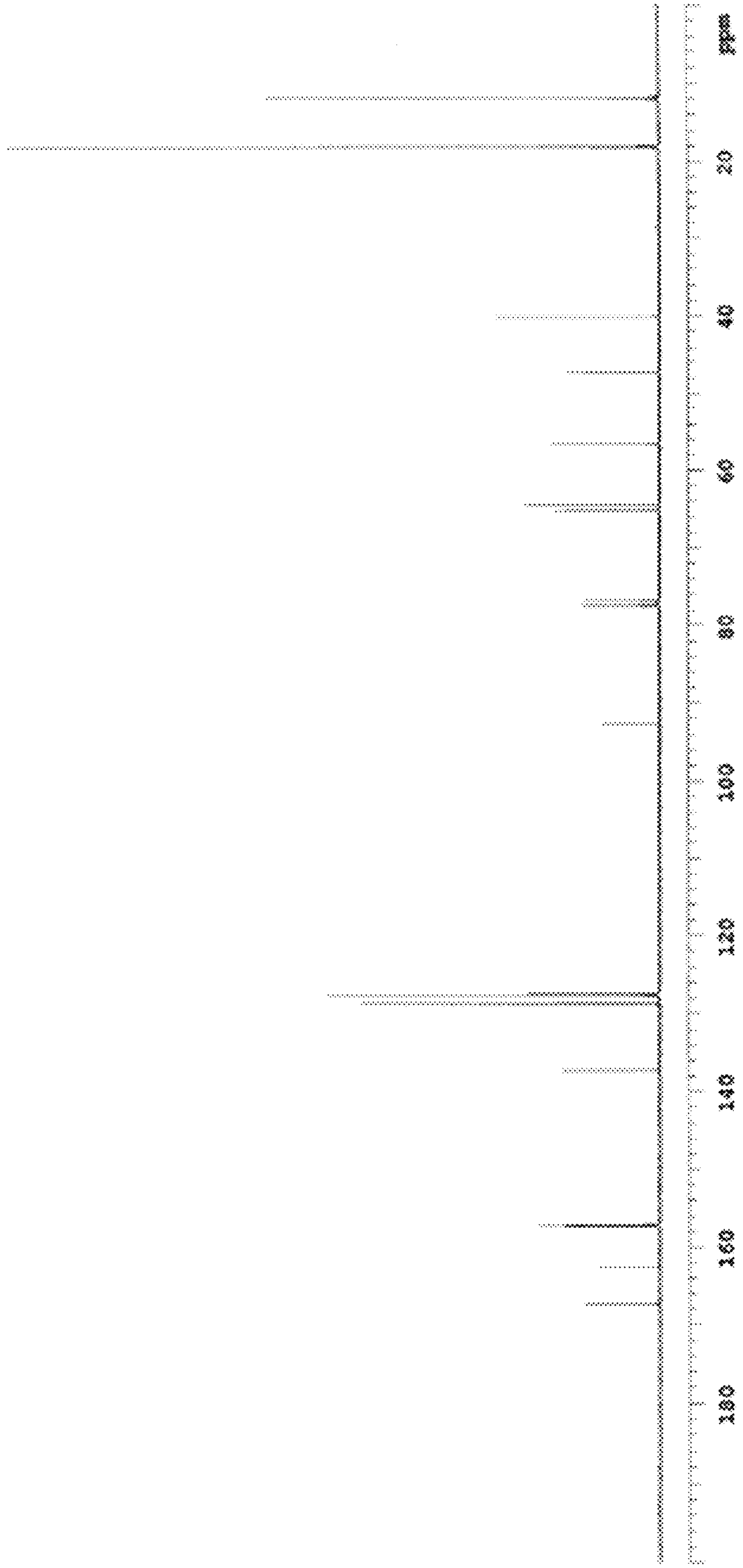

[Figure 34A]
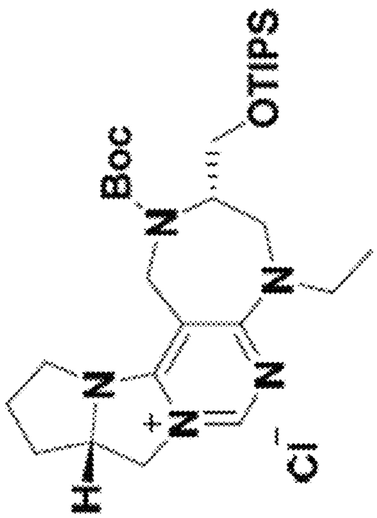
2a
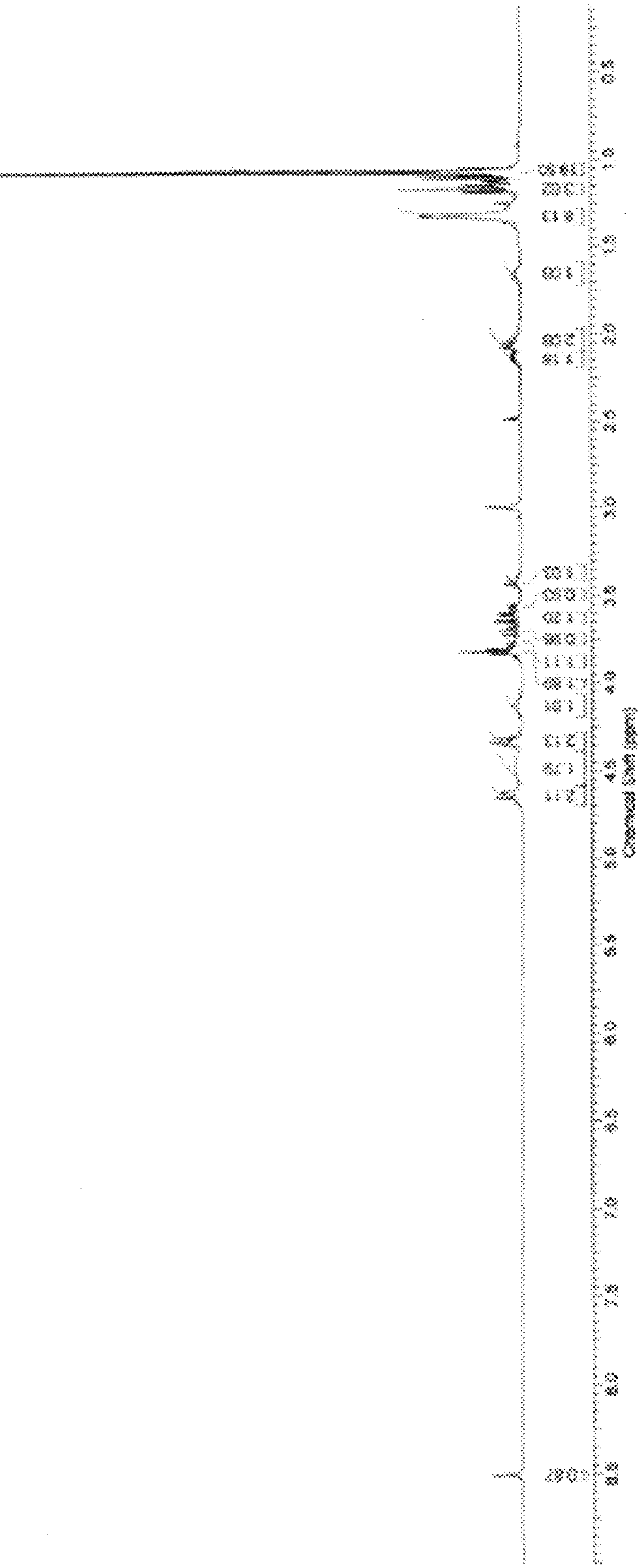

[Figure 34B]
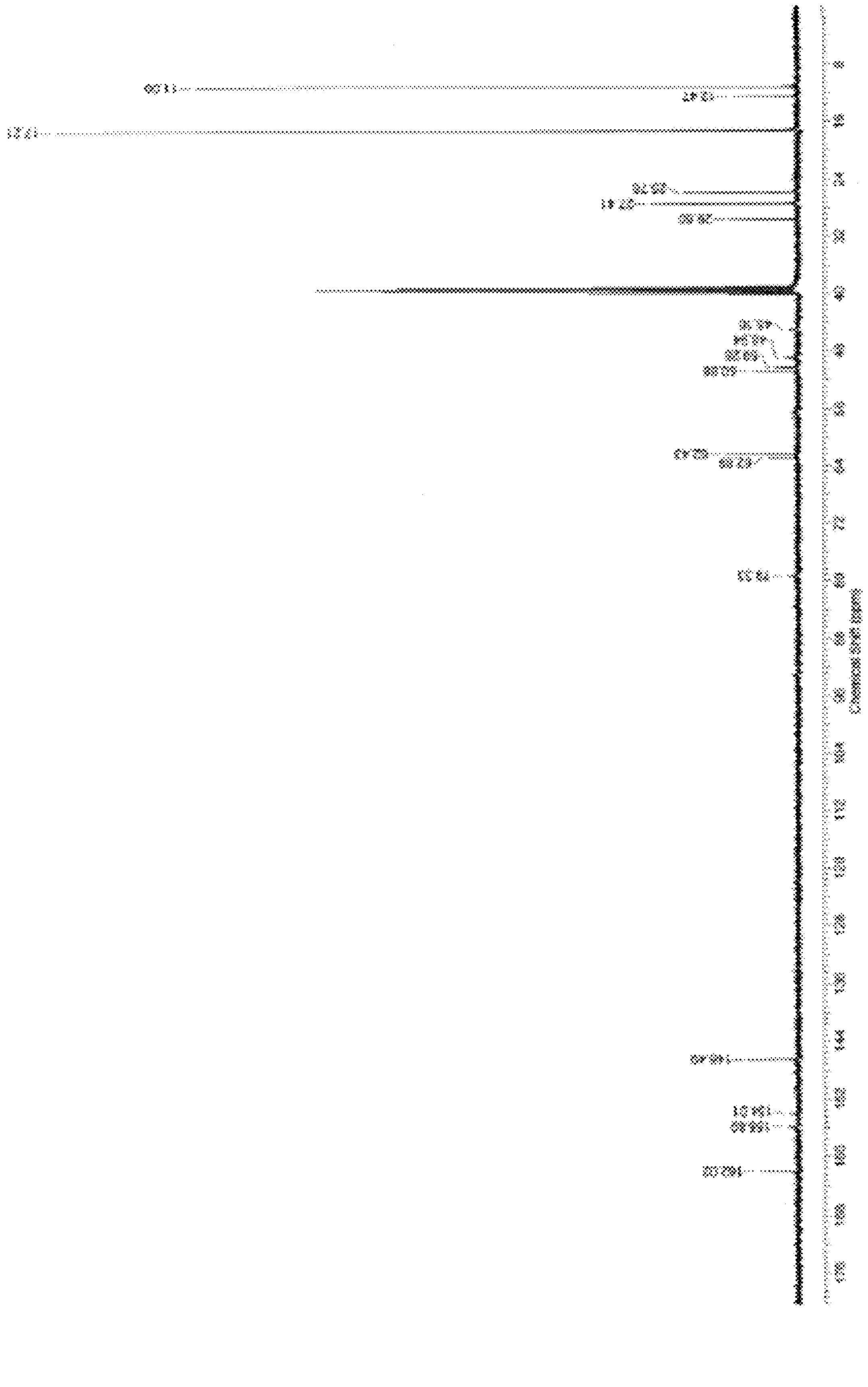

[Figure 35A]
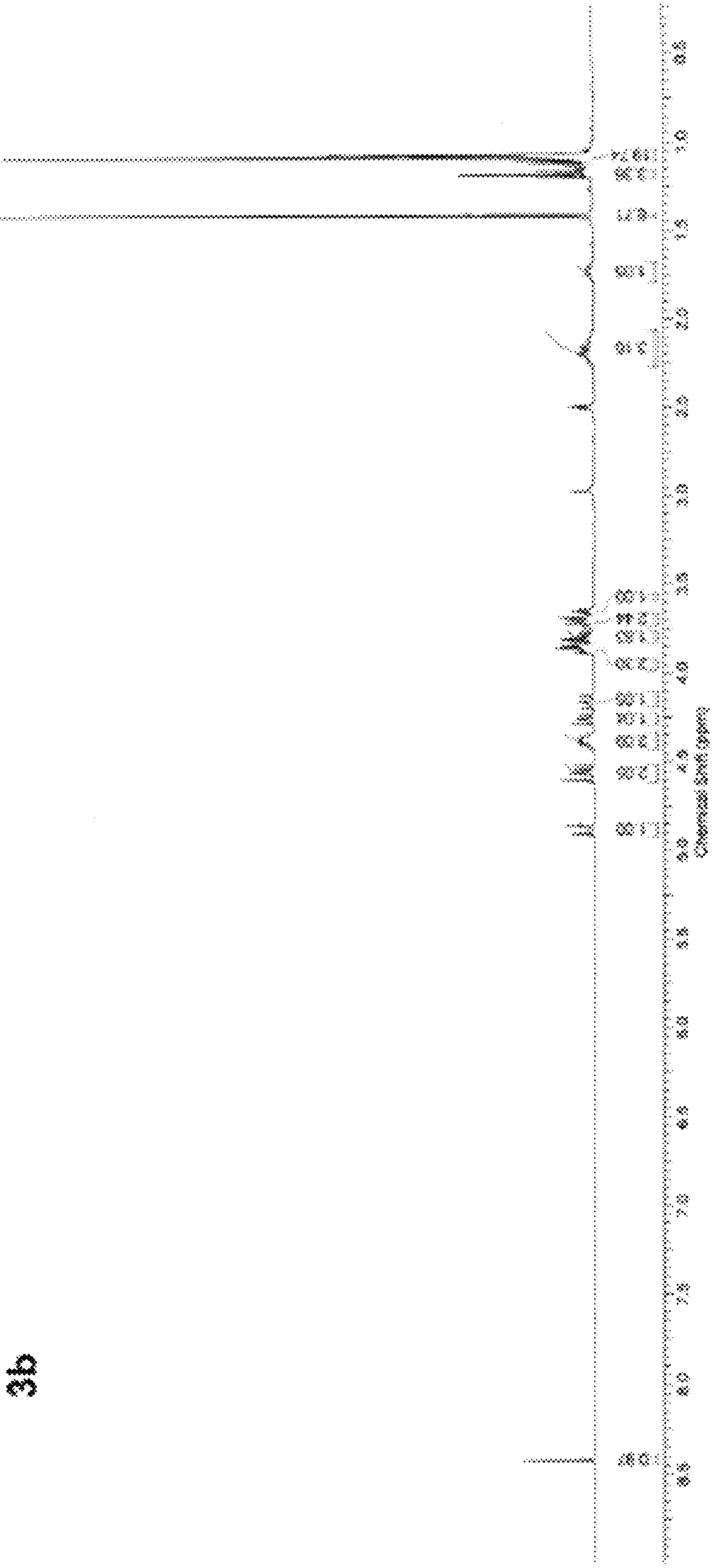
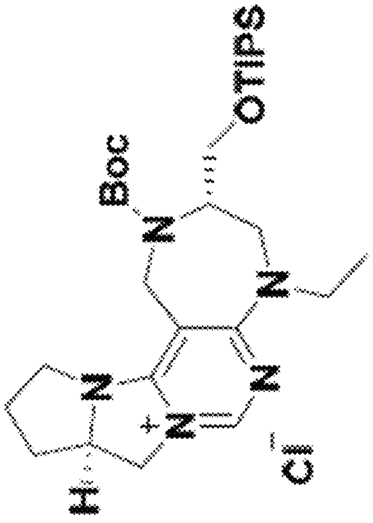
3b

[Figure 35B]
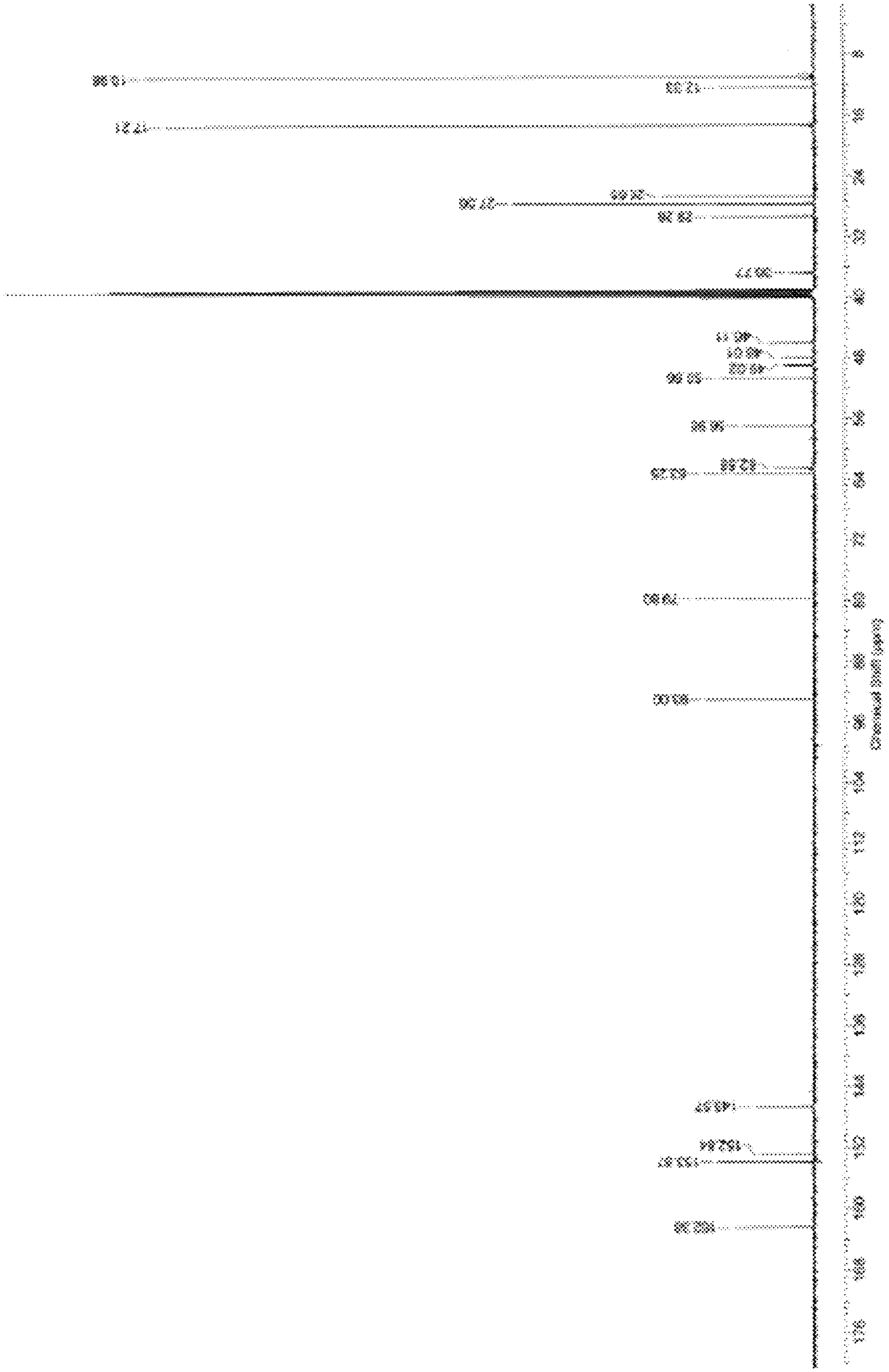

[Figure 36A]
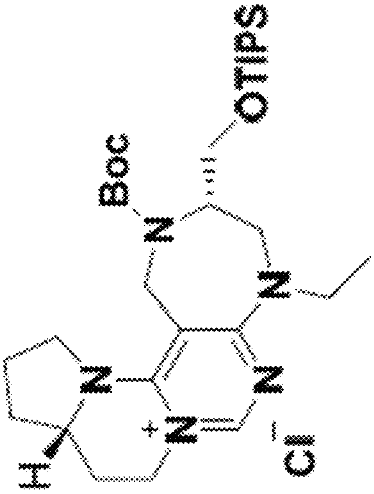
4c
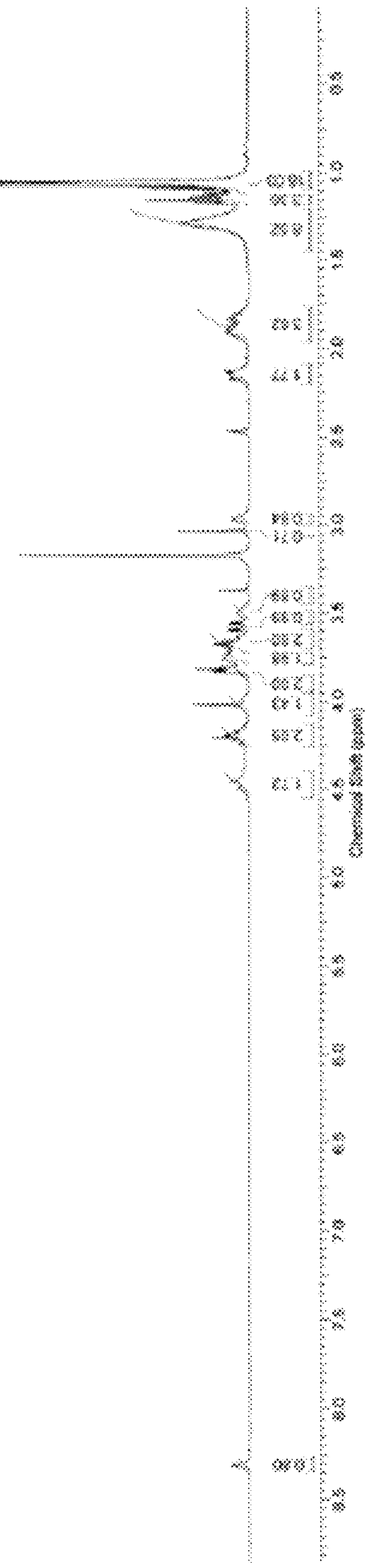

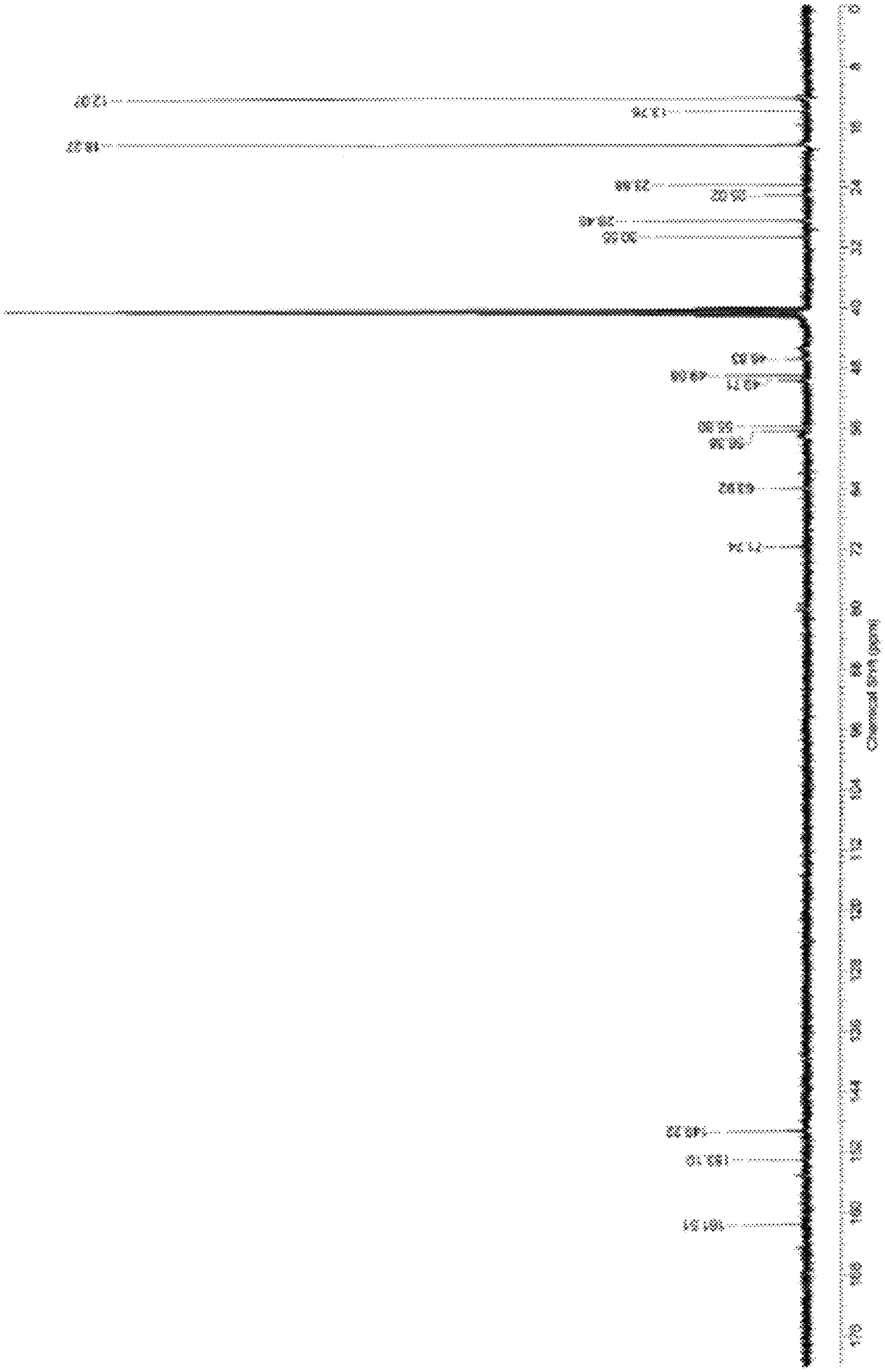
[Figure 36B]

[Figure 37A]
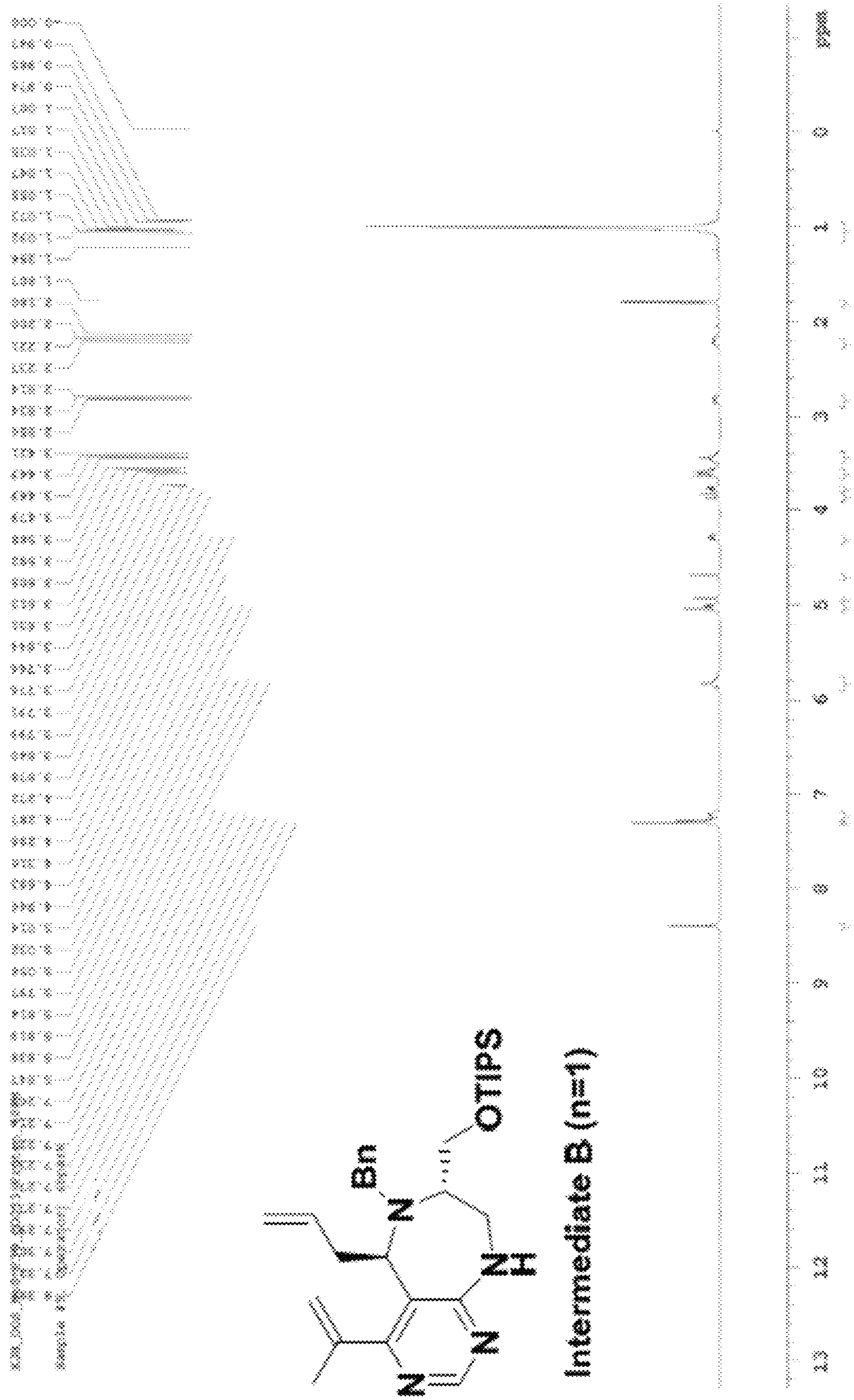
Intermediate B (n=1)

[Figure 37B]
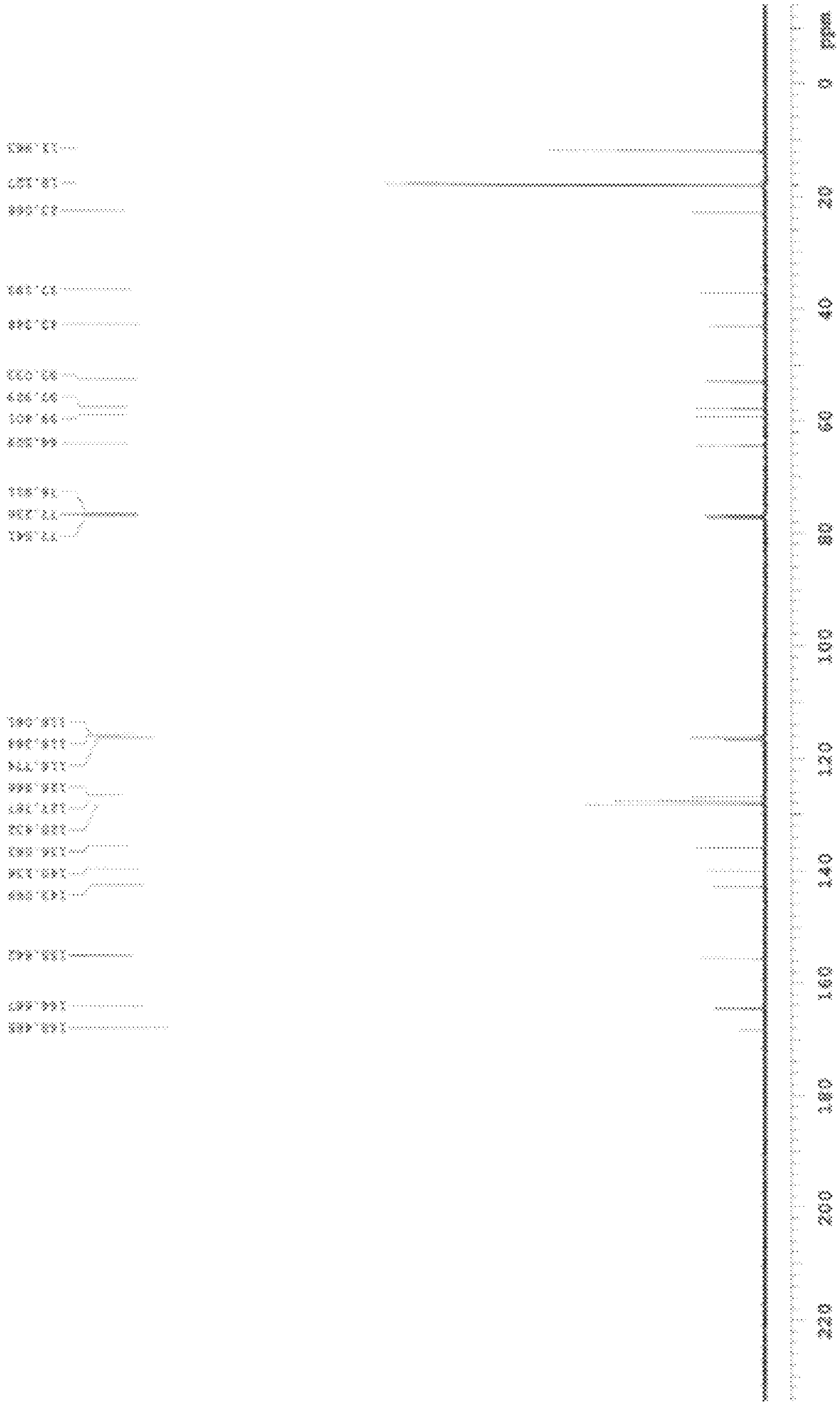

[Figure 38A]
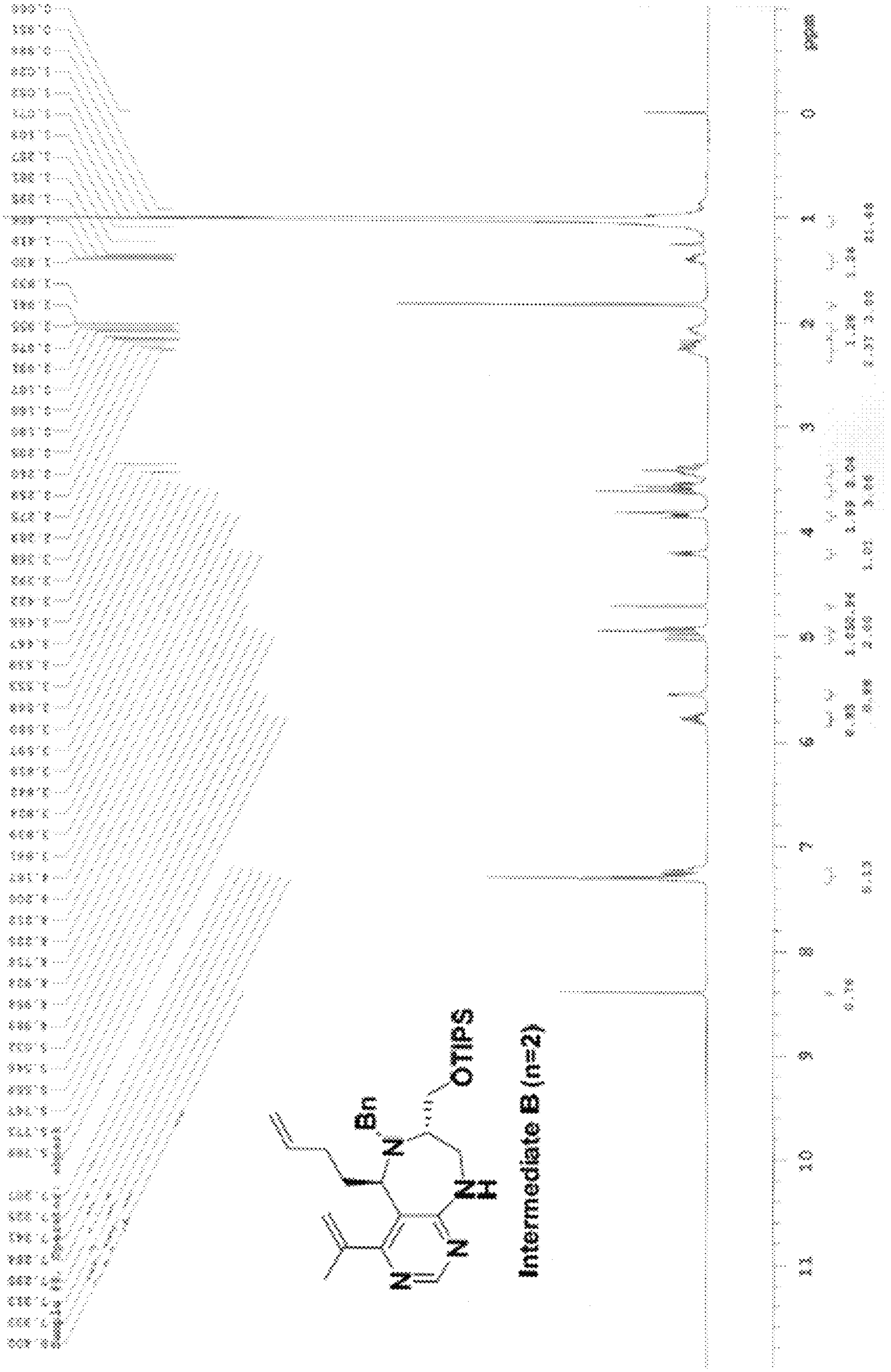
Intermediate B (n=2)

[Figure 38B]
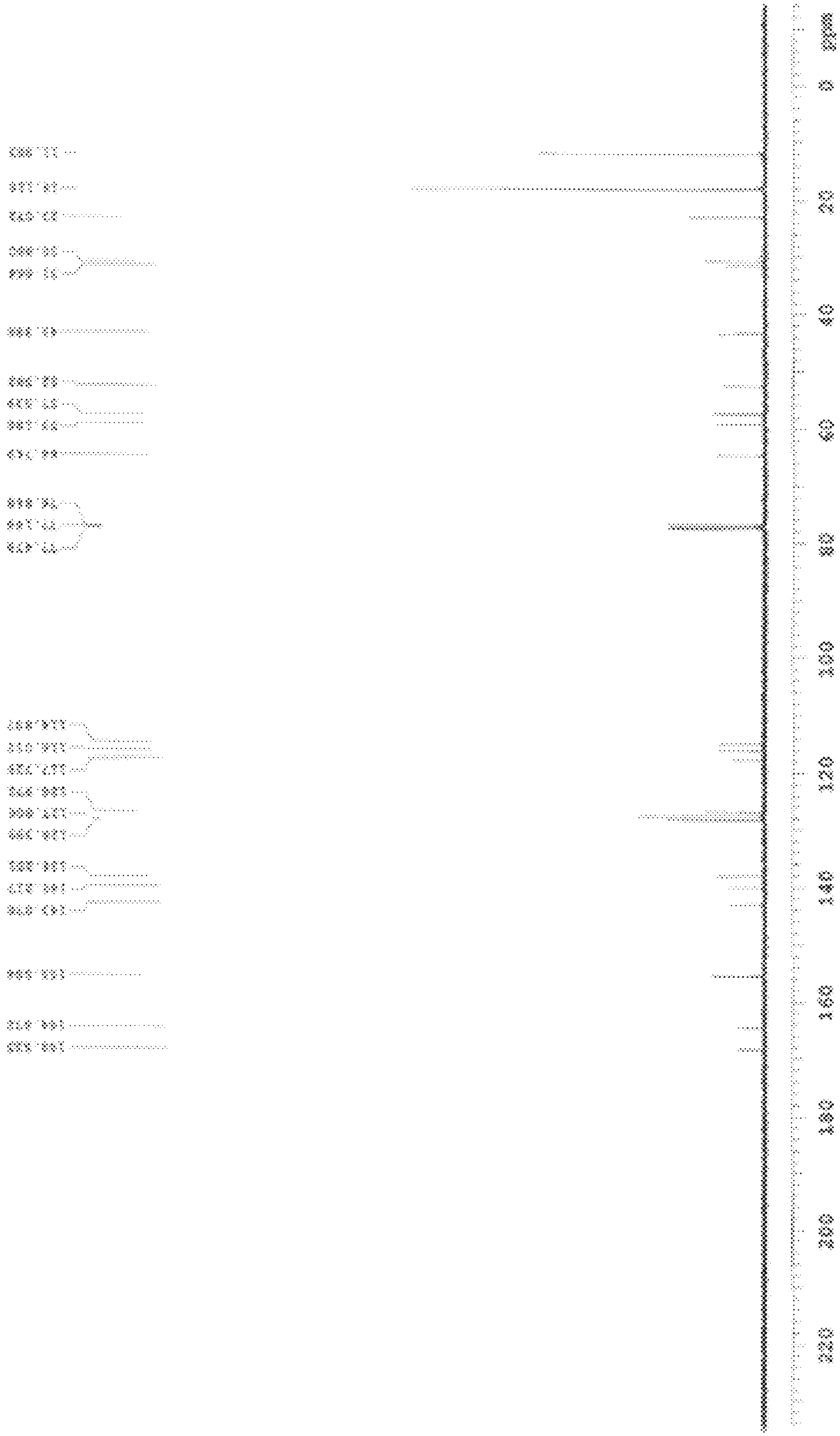

[Figure 39A]
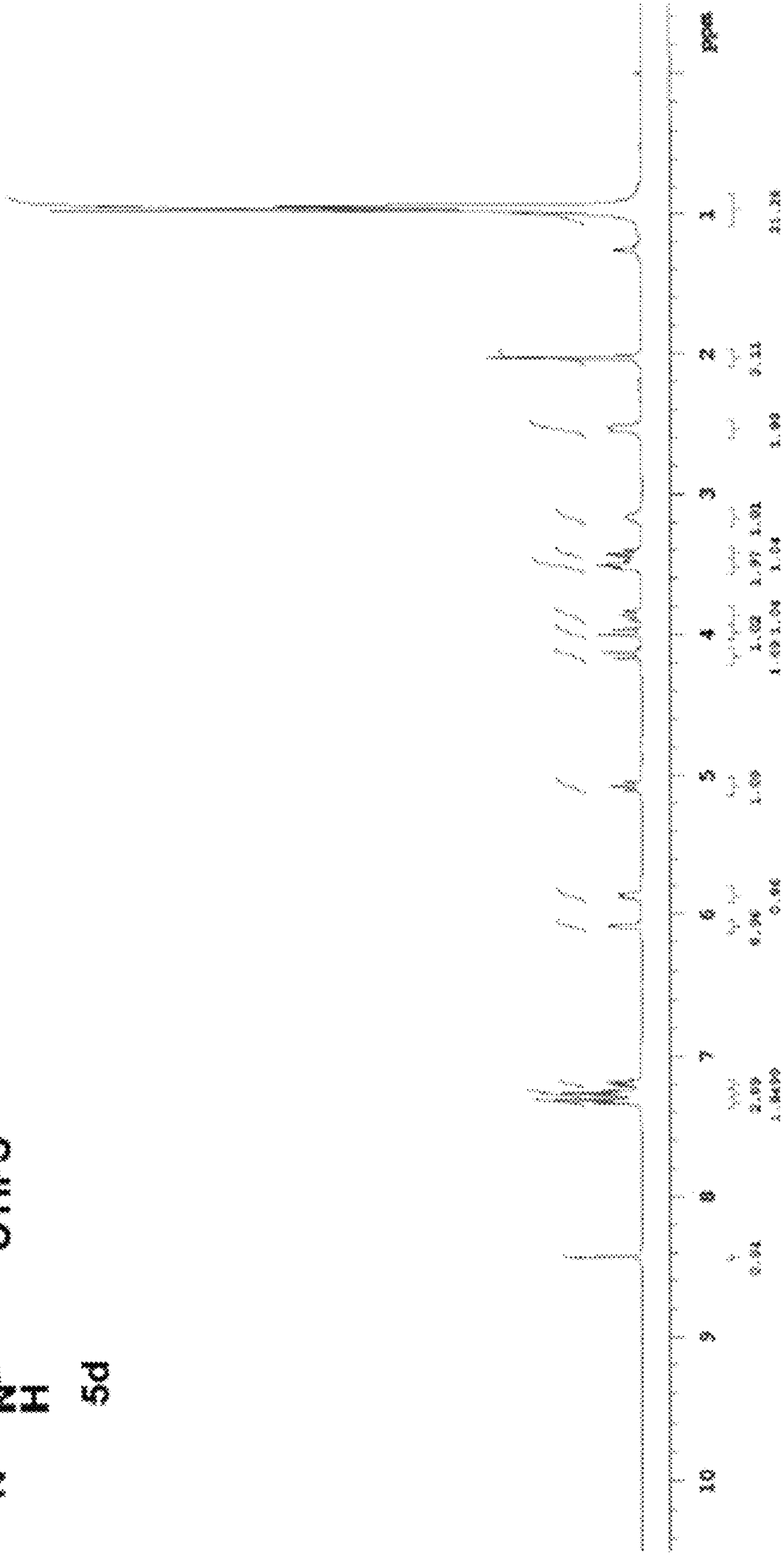
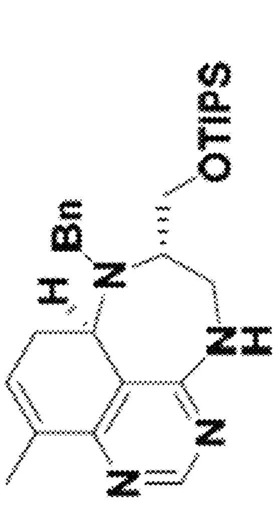
5d

[Figure 39B]
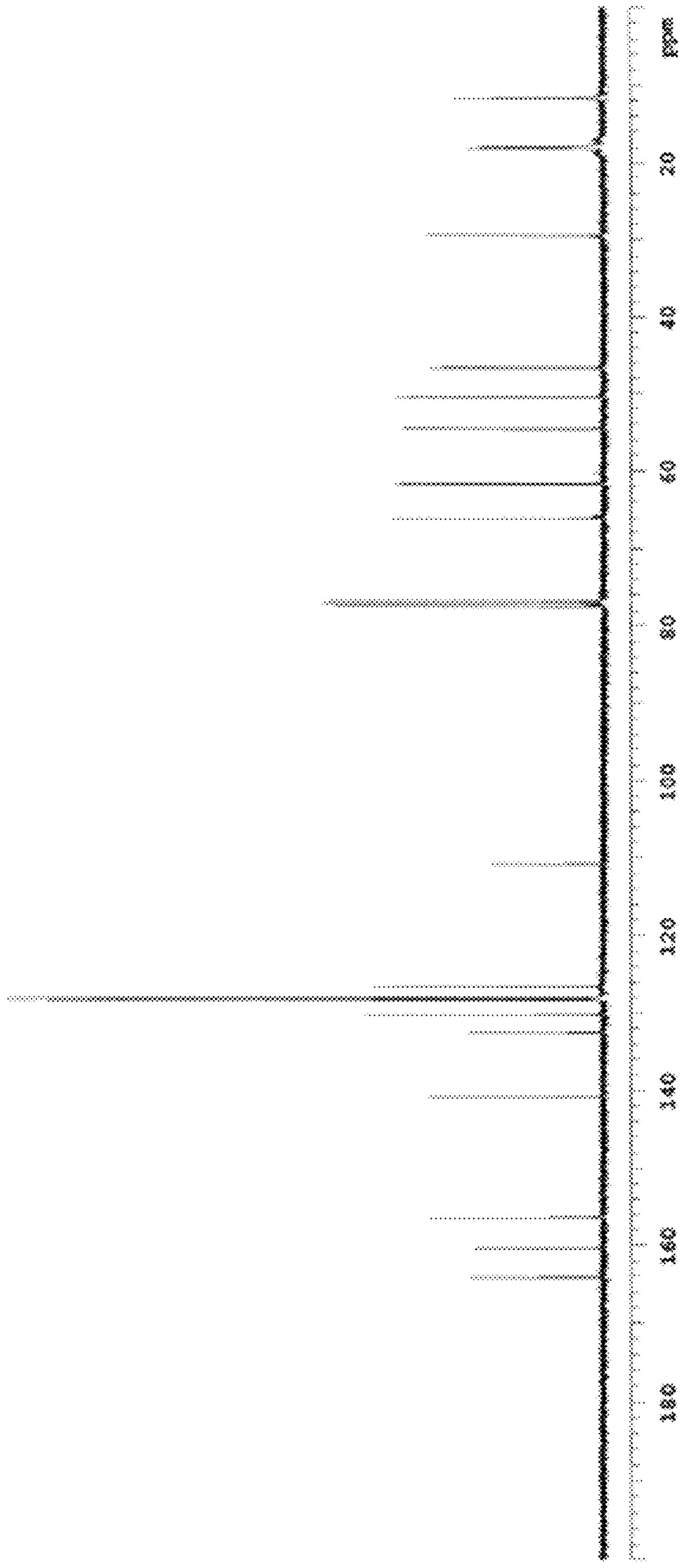

[Figure 40A]
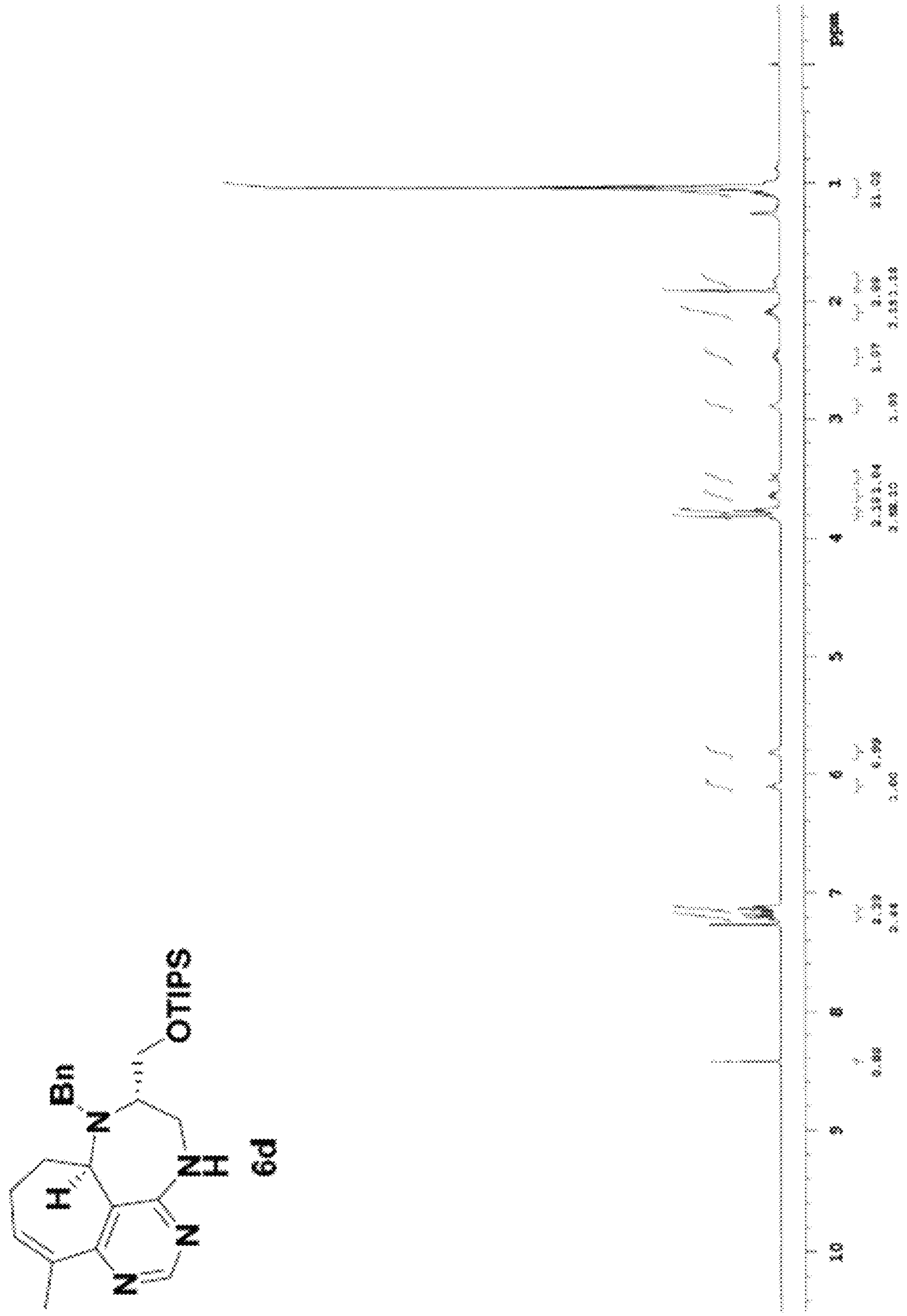
6d

[Figure 40B]
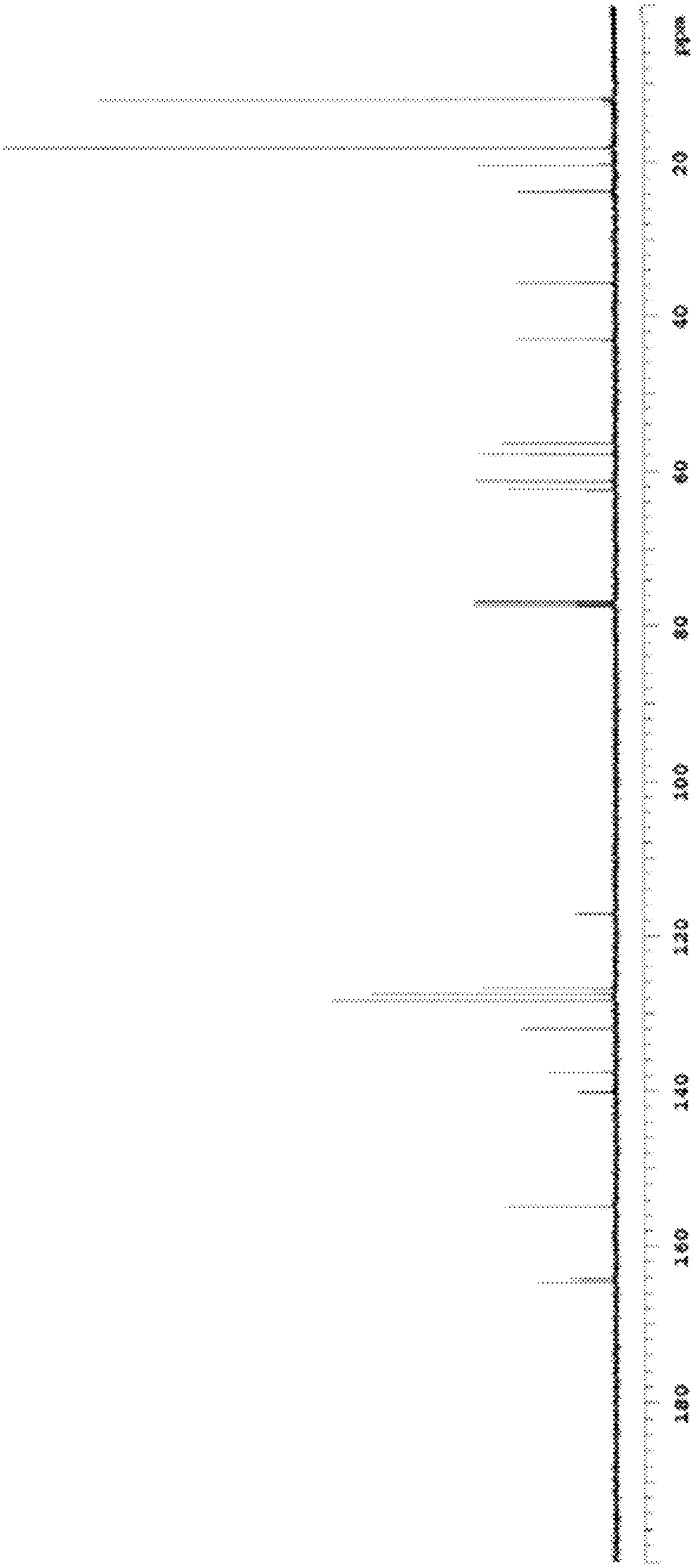

[Figure 41A]
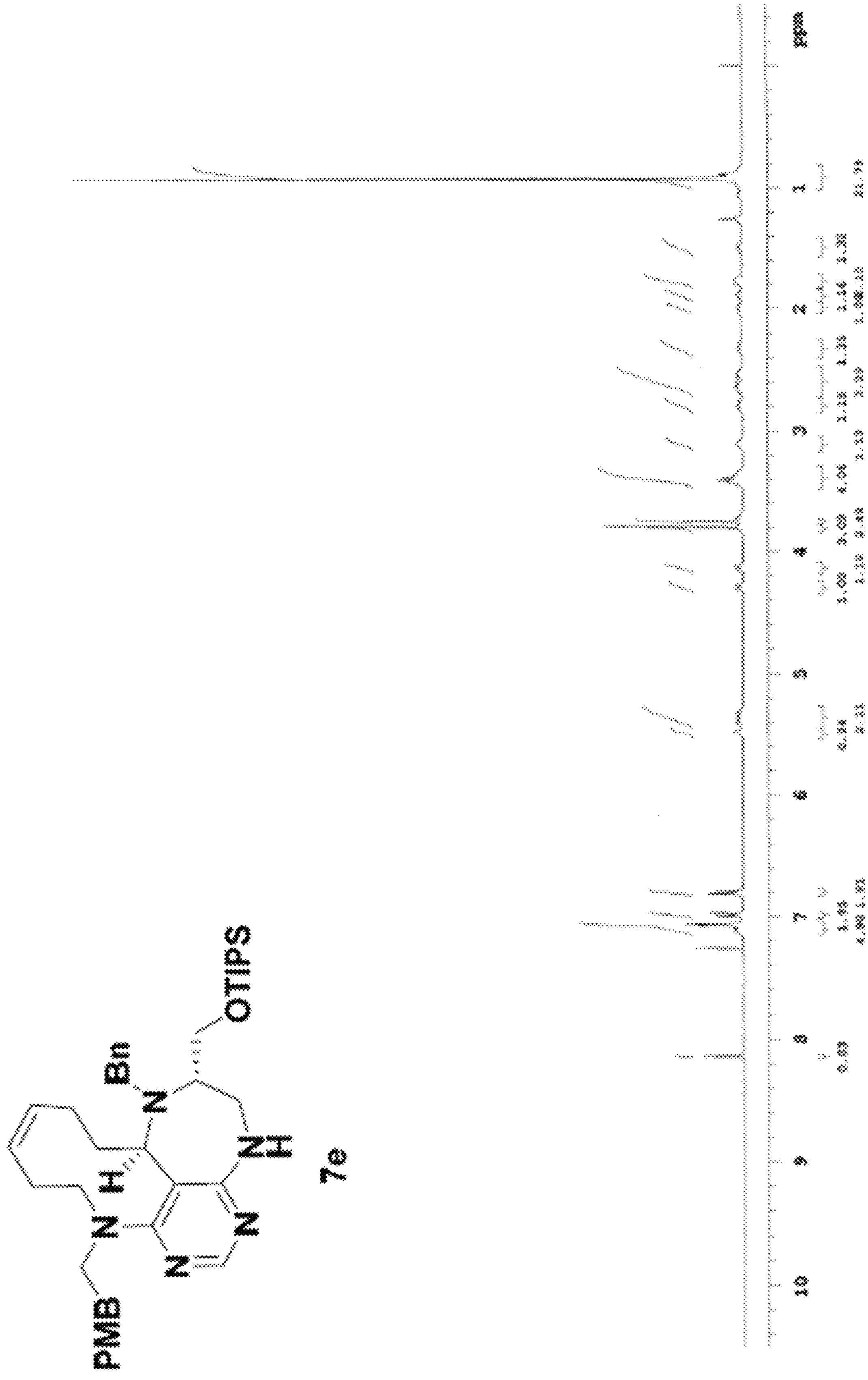
7e

[Figure 41B]
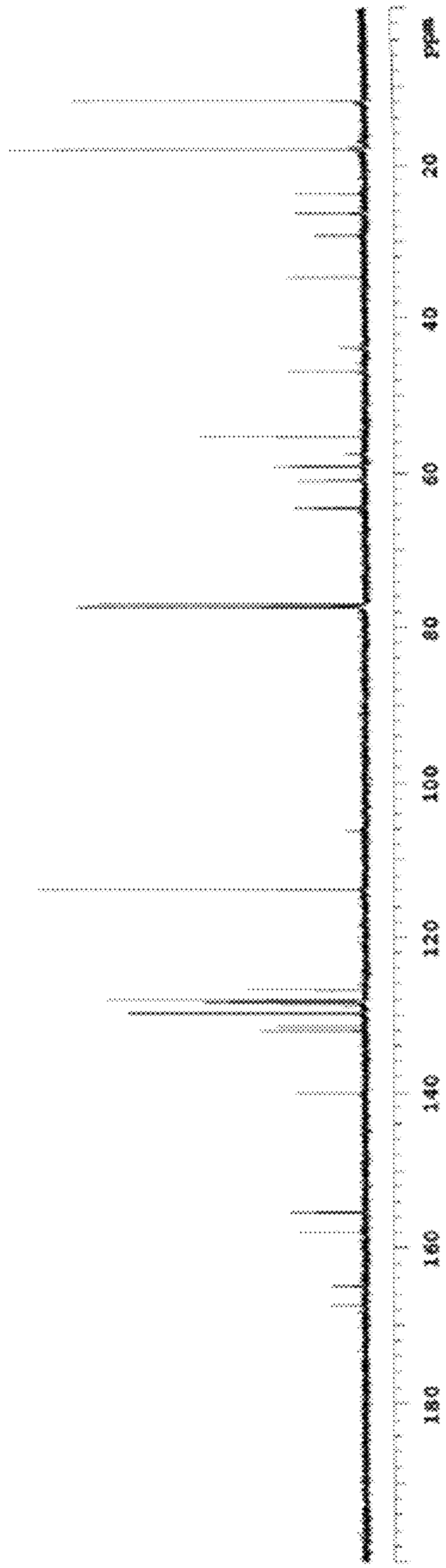

[Figure 42A]
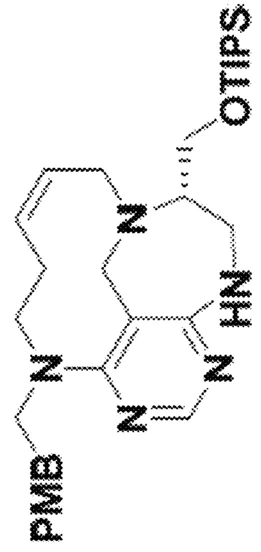
8e
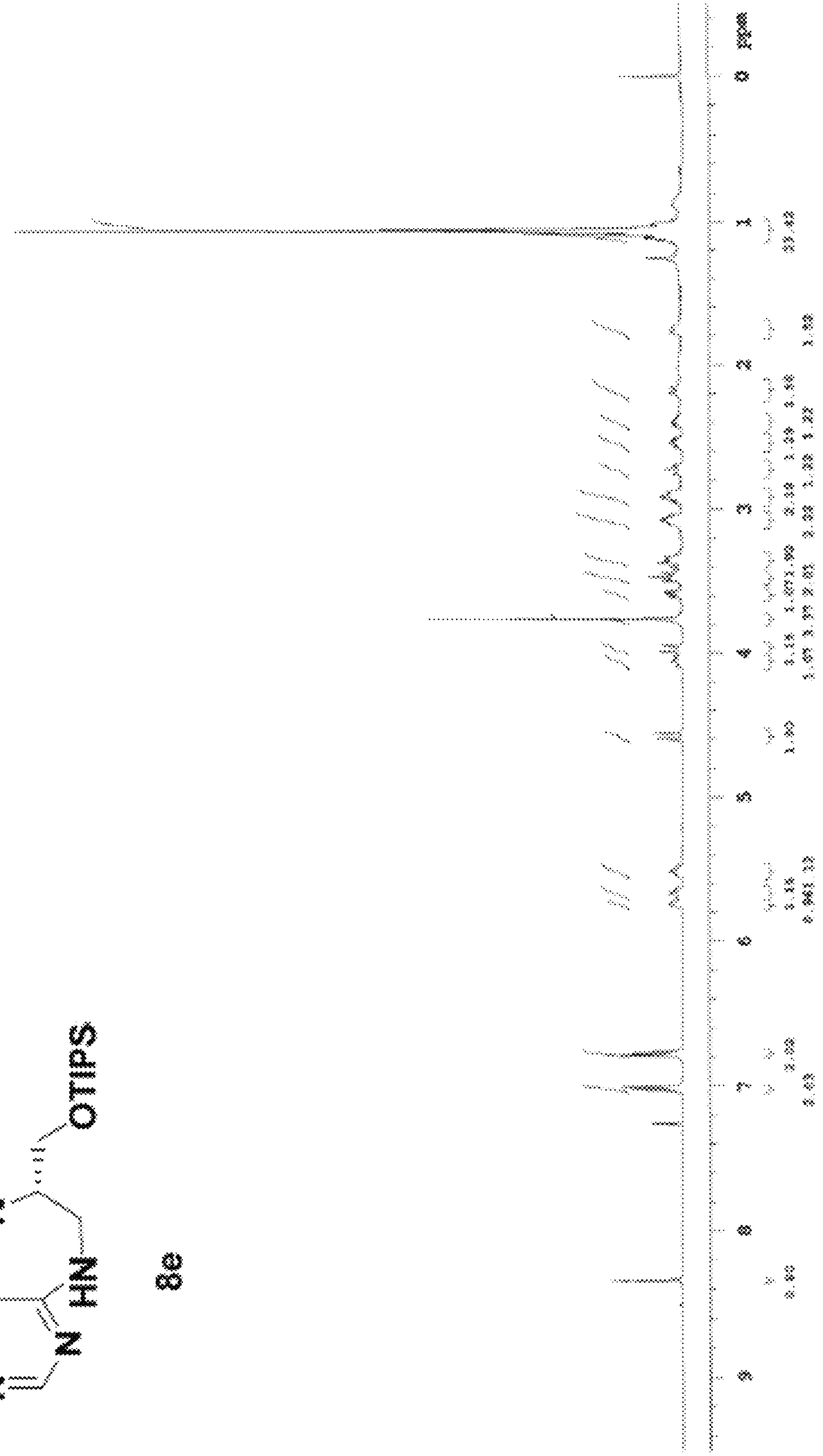

[Figure 42B]
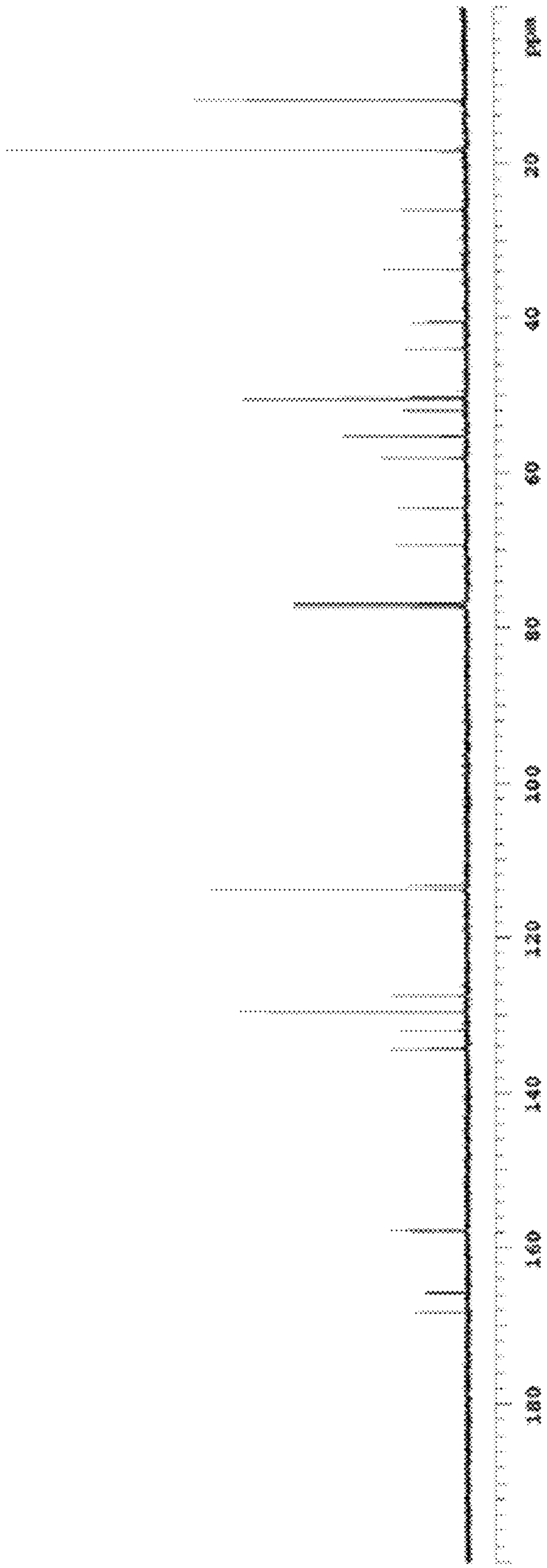

[Figure 43A]
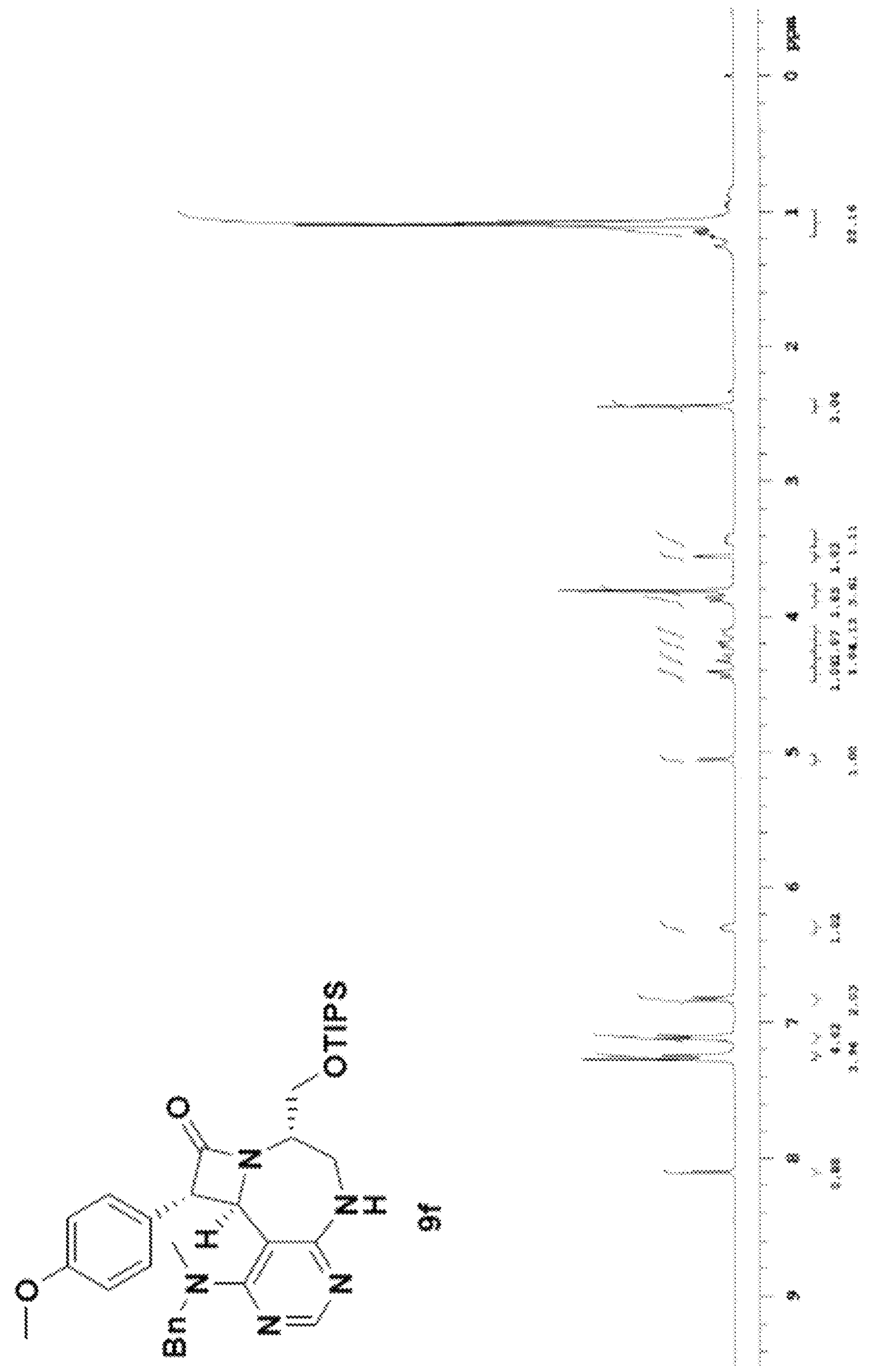
9f

[Figure 43B]
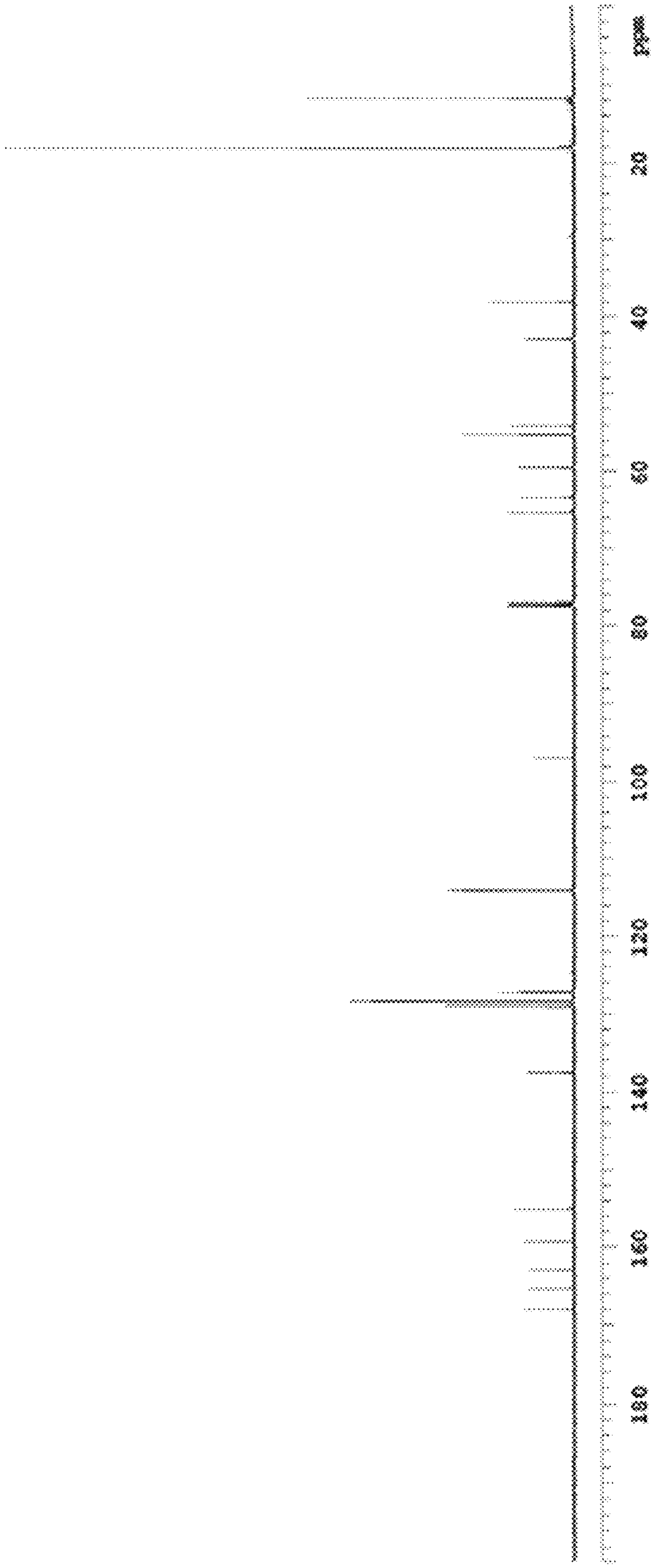

[Figure 44A]
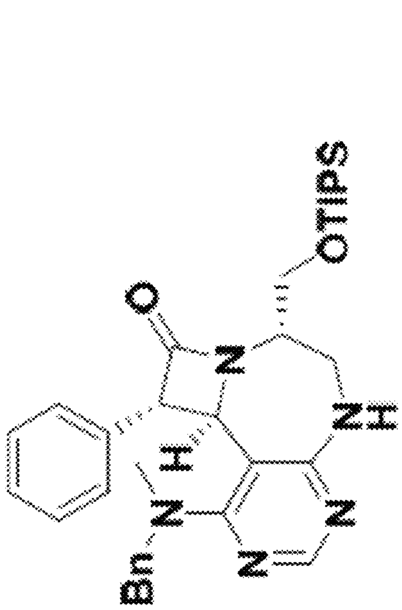
10f
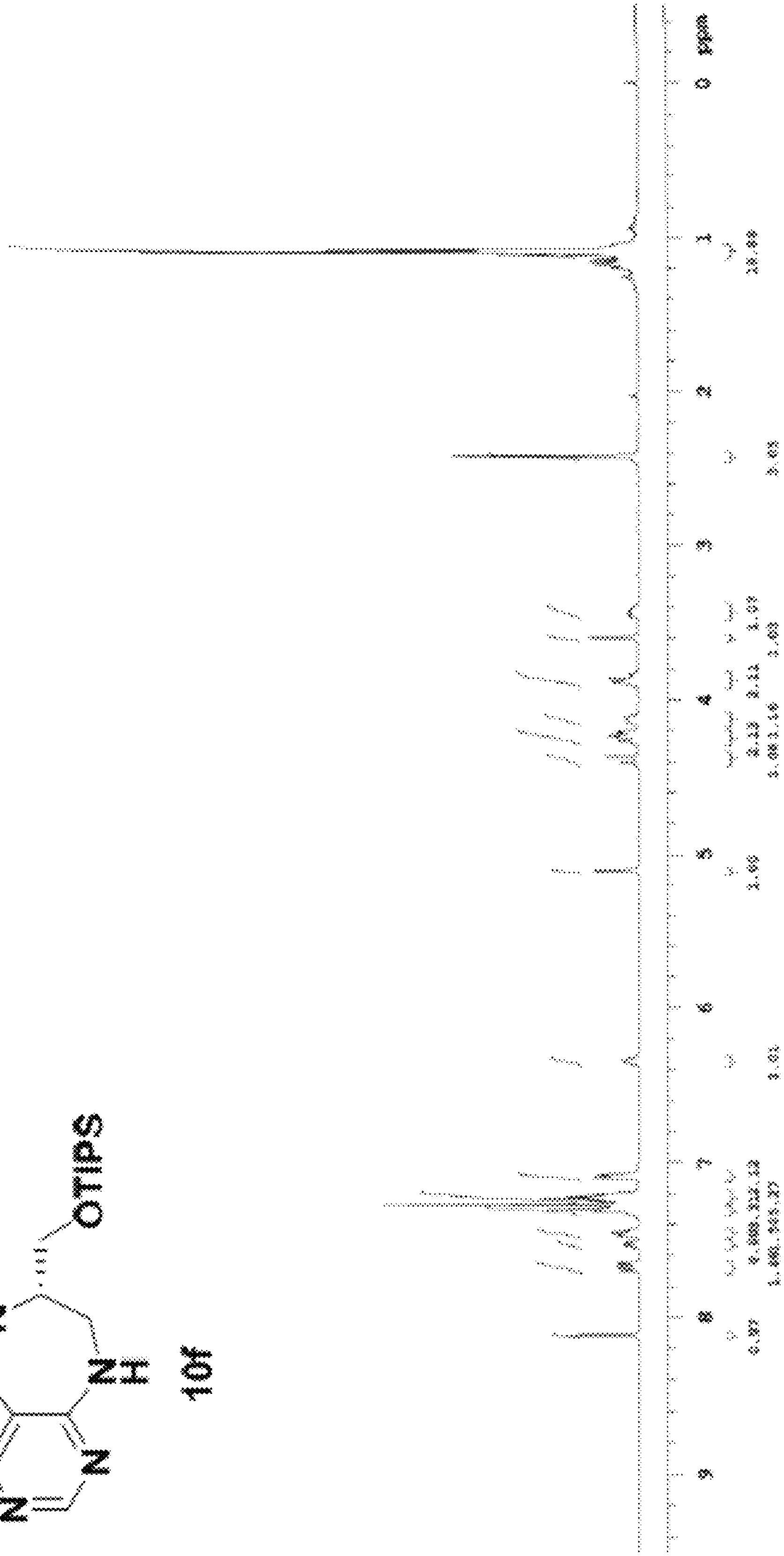

[Figure 44B]
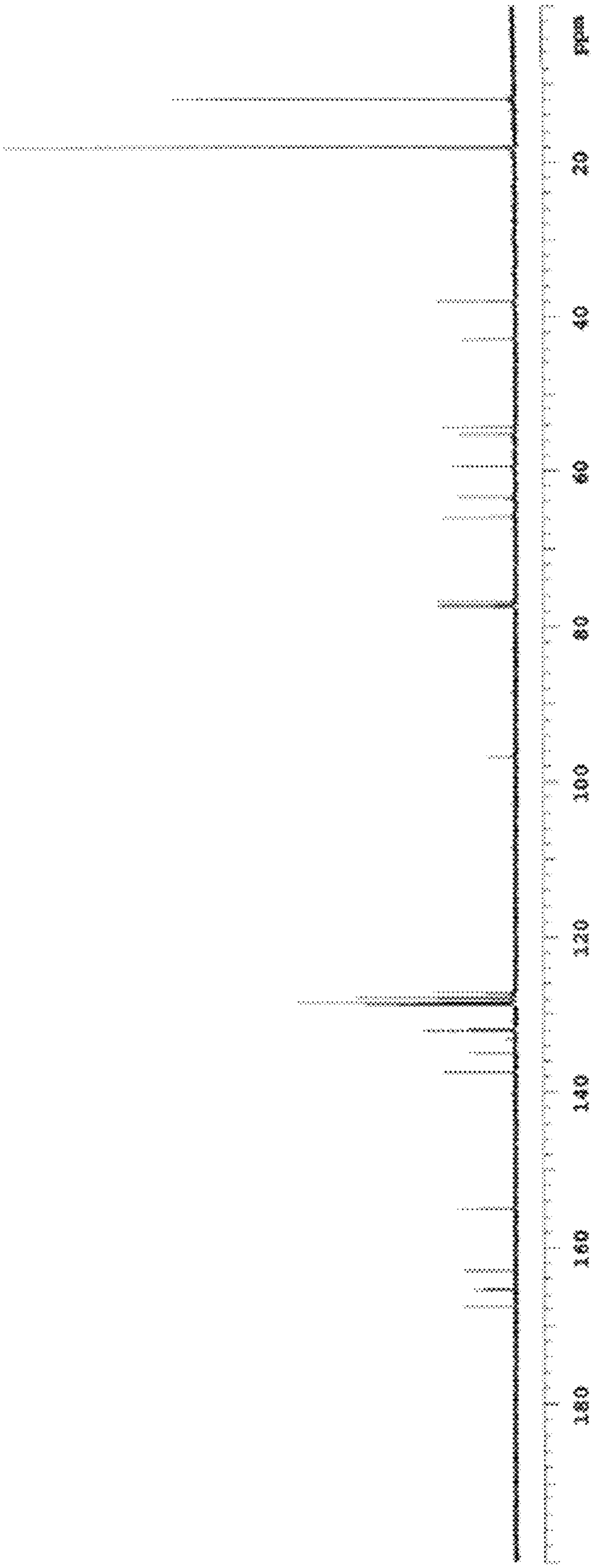

[Figure 45A]
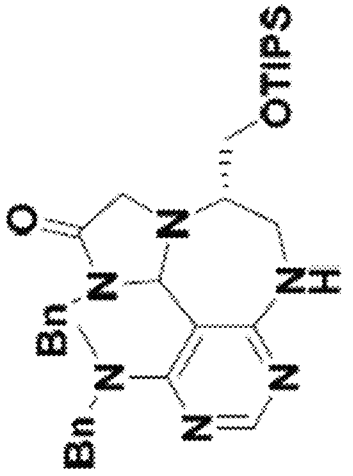
11f
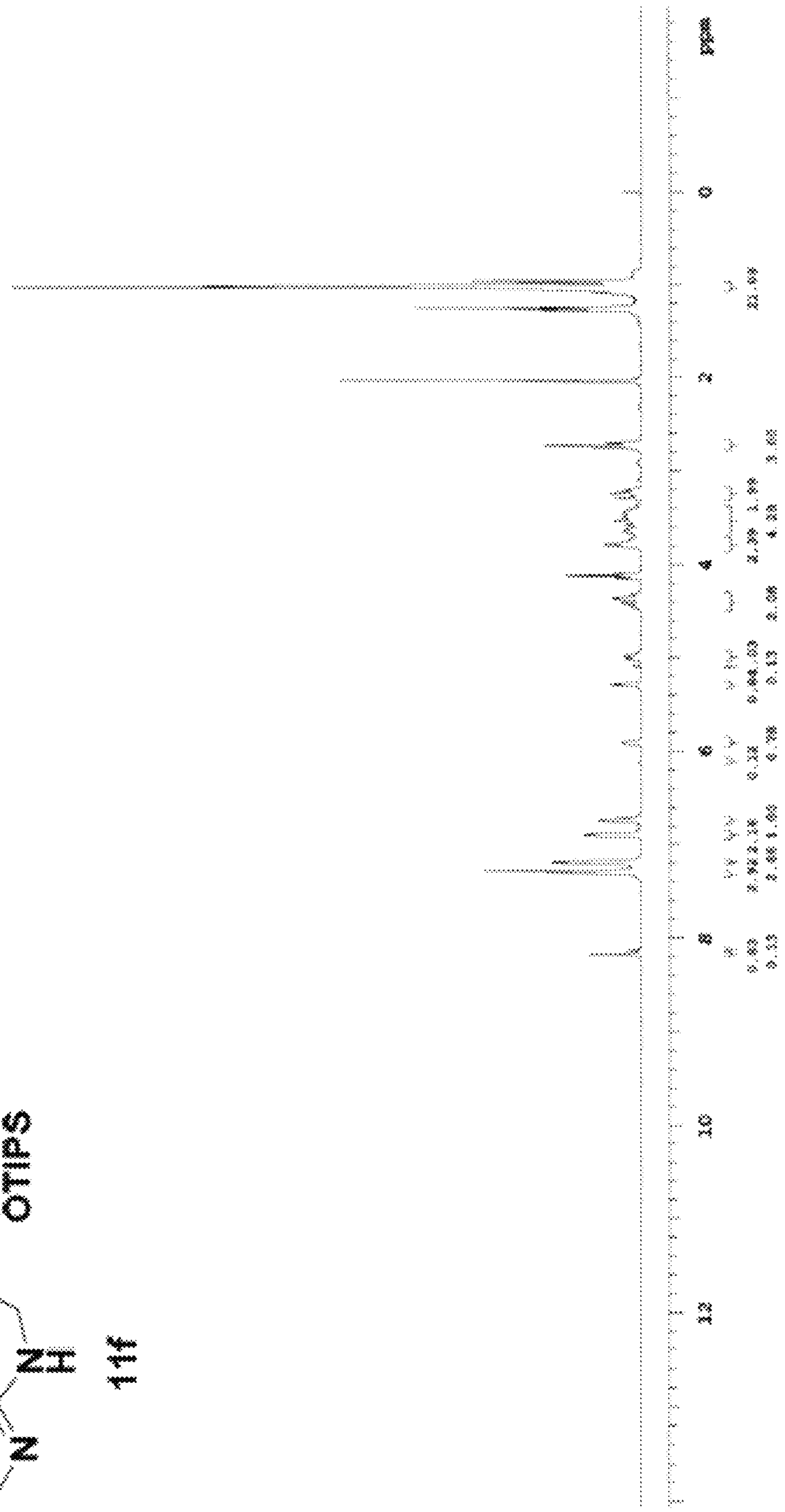

[Figure 45B]
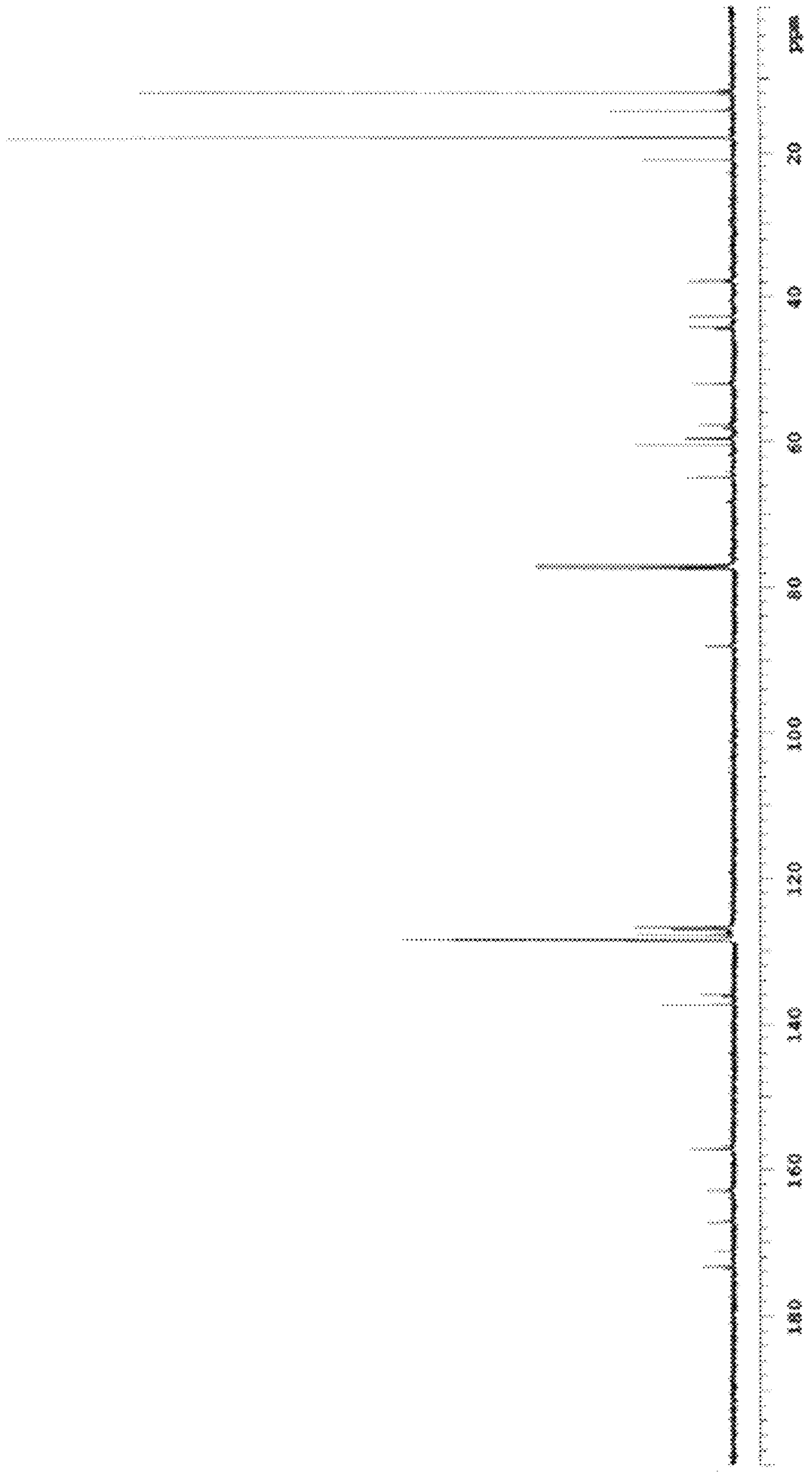

[Figure 46A]
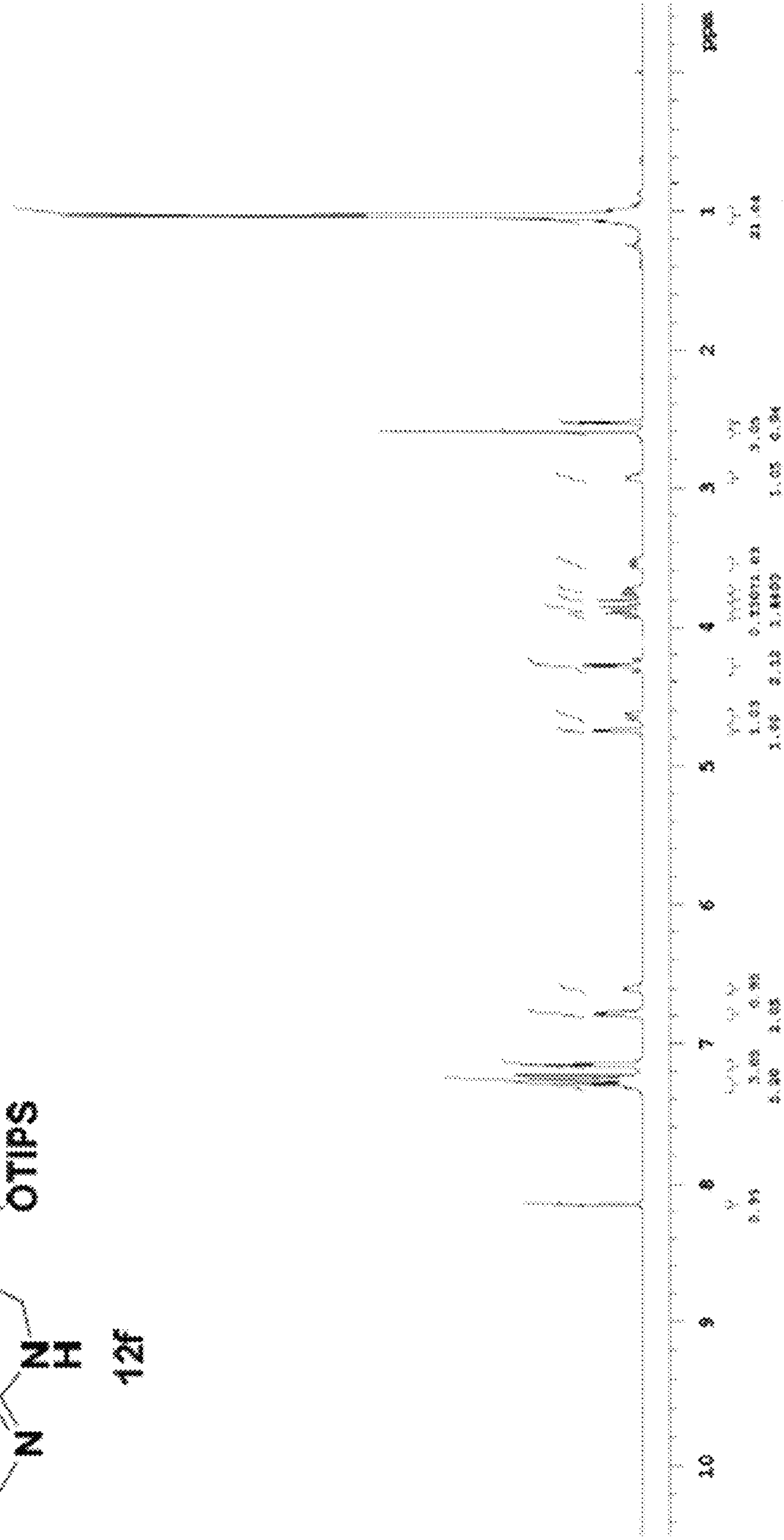
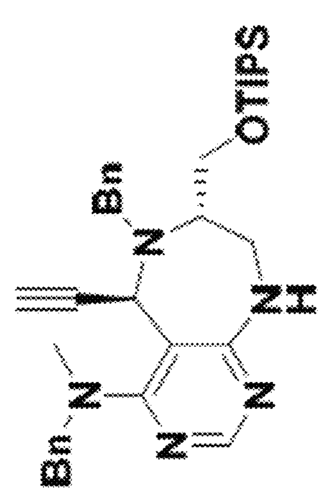
12f

[Figure 46B]
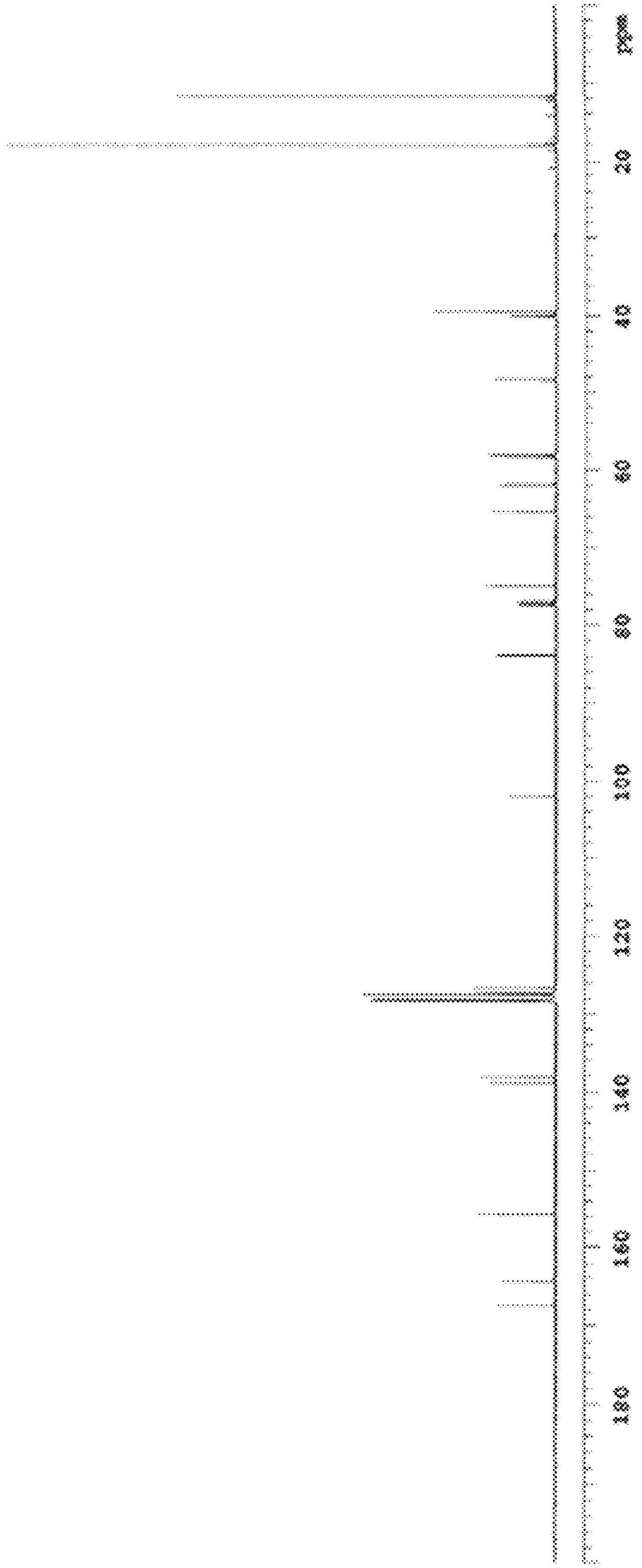

[Figure 47A]
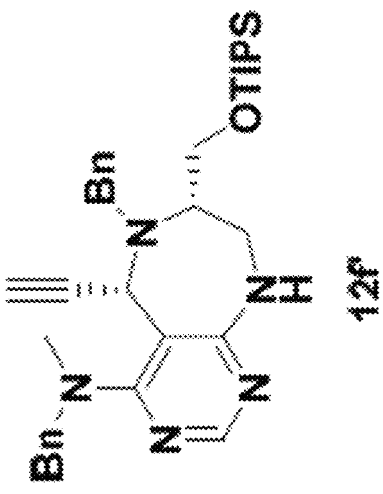
12f
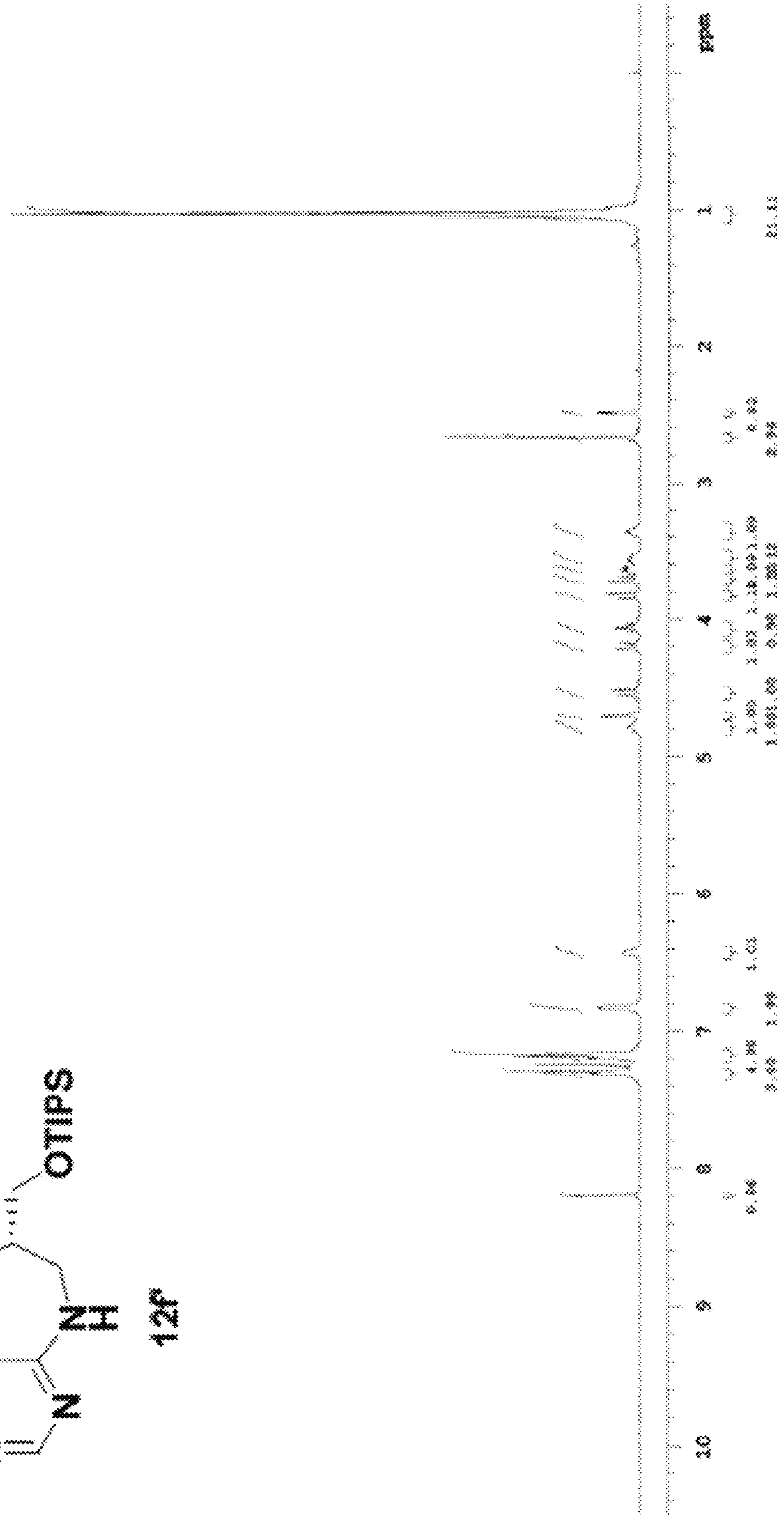

[Figure 47B]
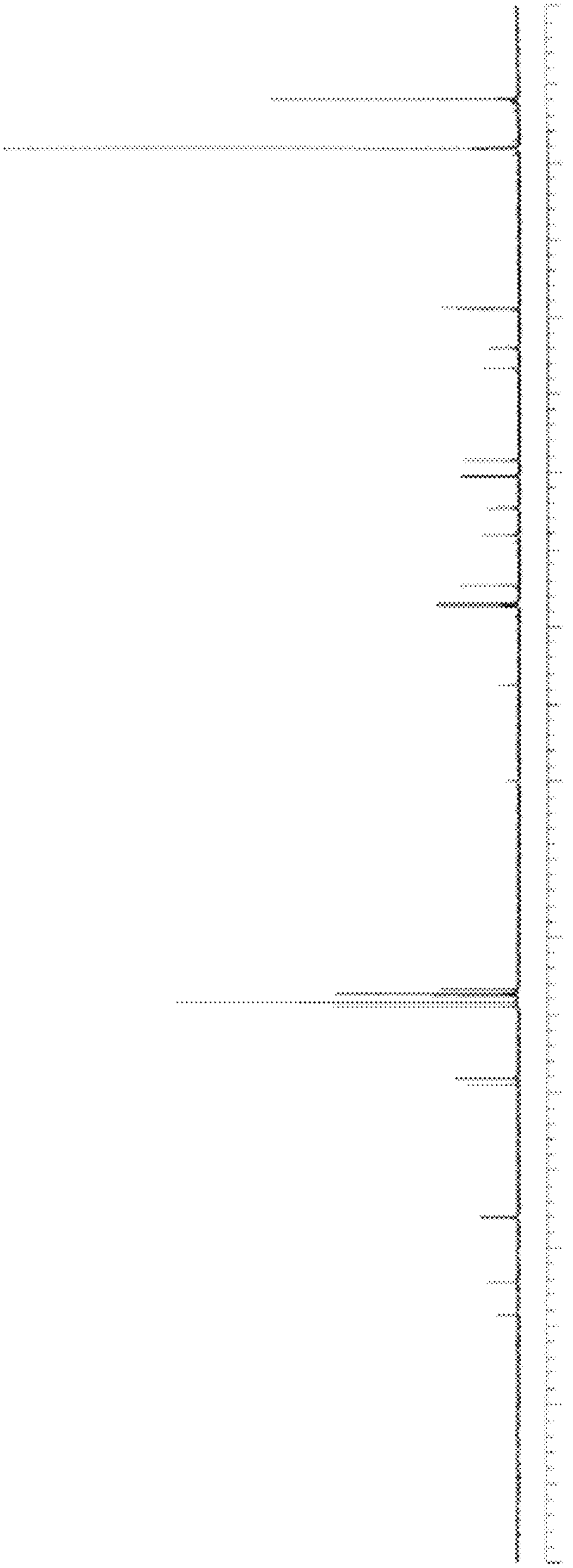

[Figure 48A]
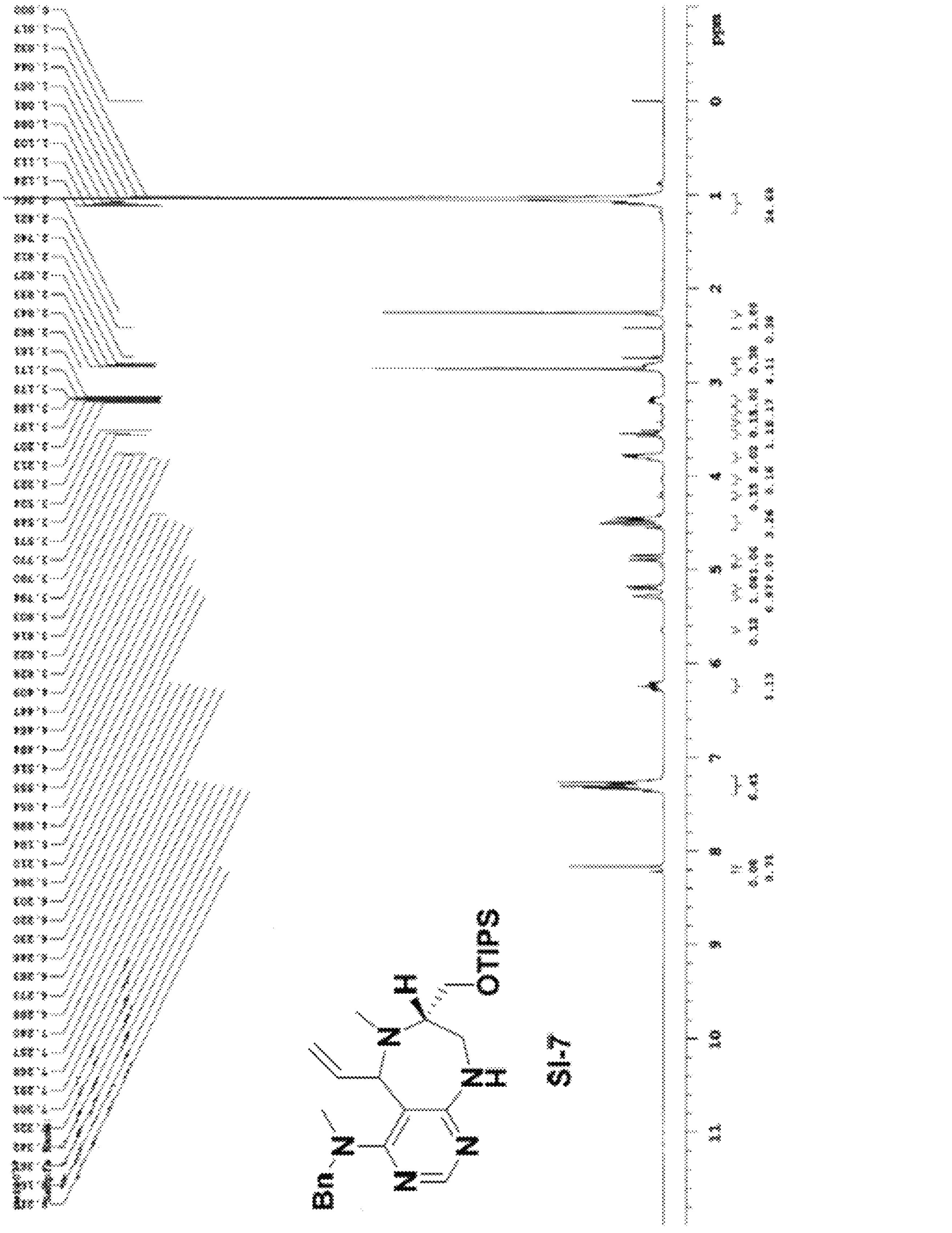
SI-7

[Figure 48B]
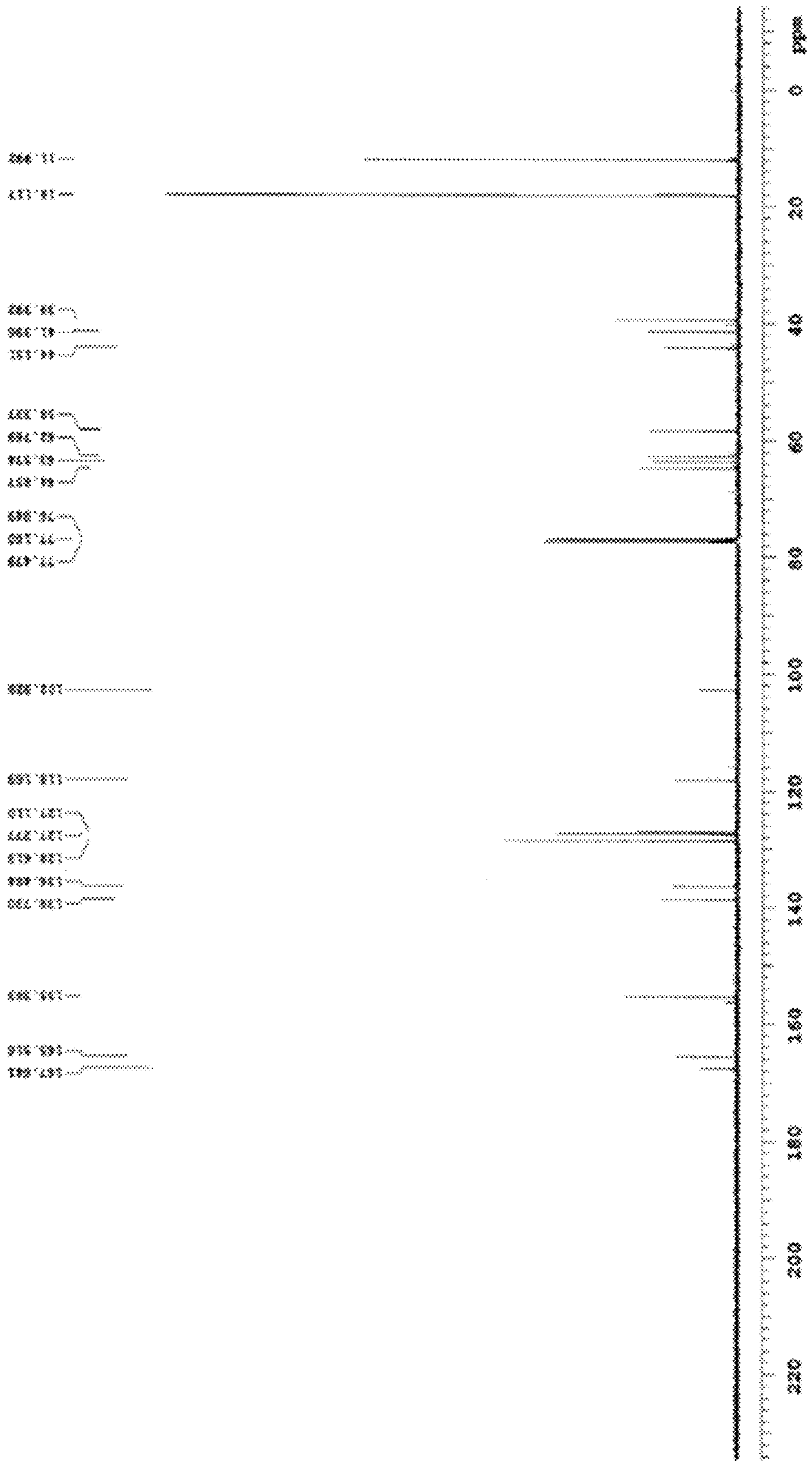

[Figure 49]
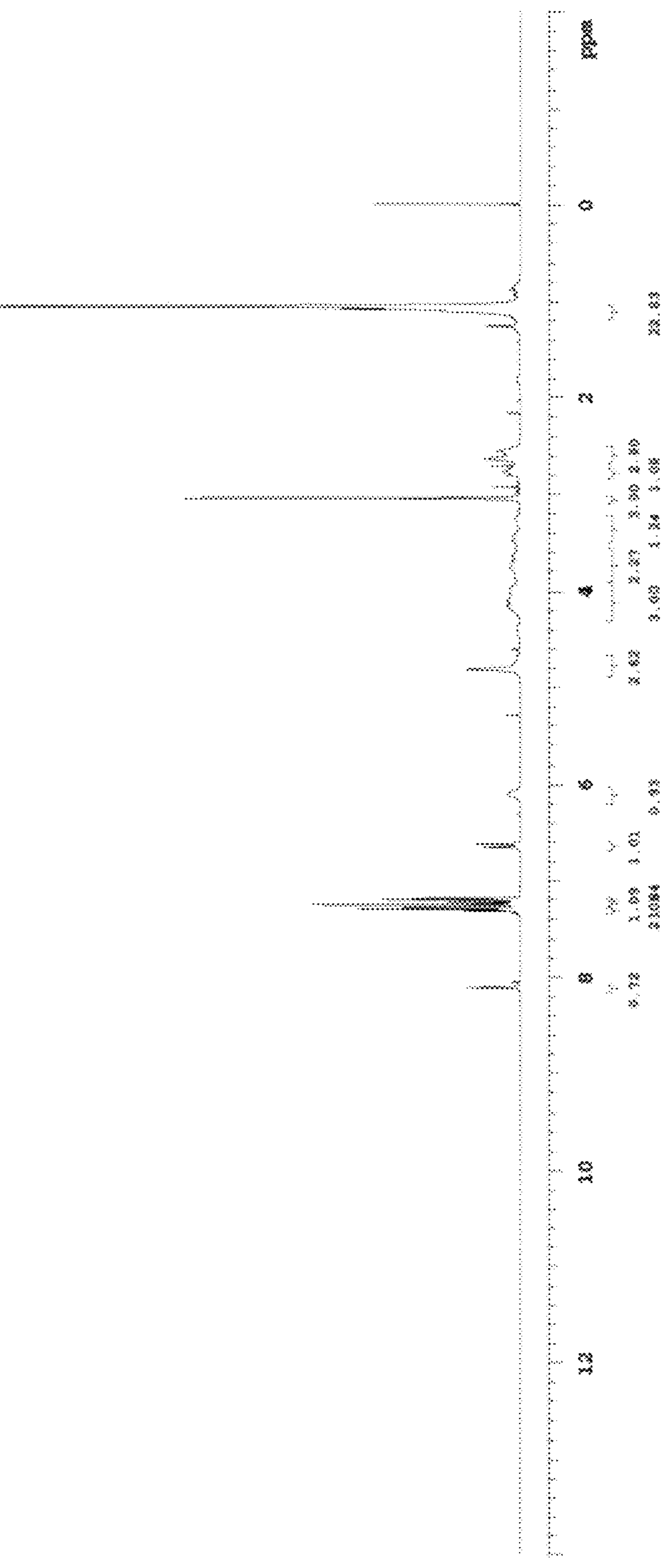
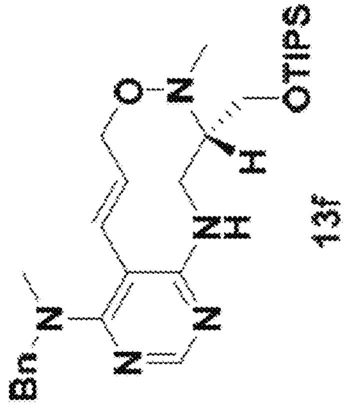
13f

[Figure 50A]
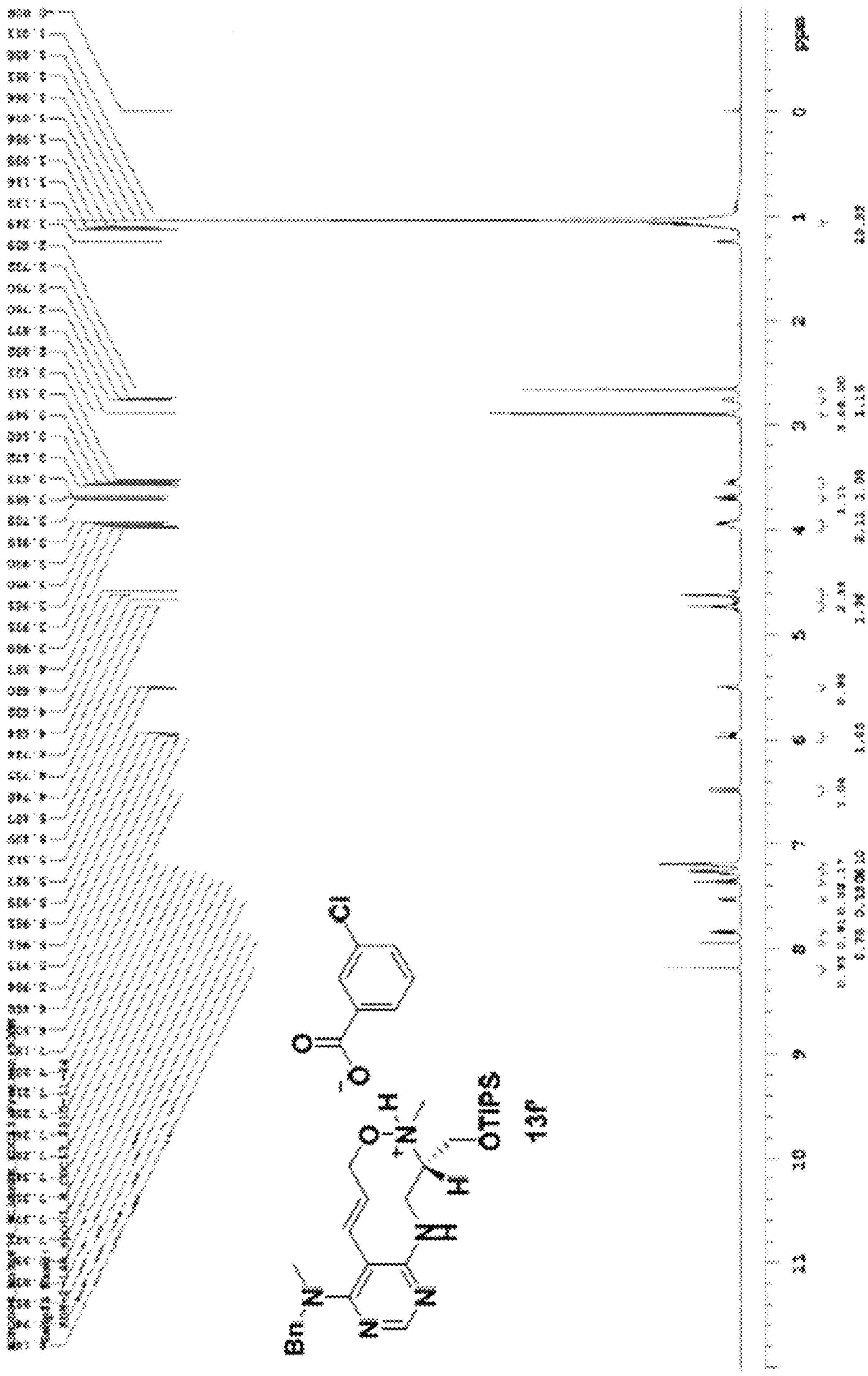
13f

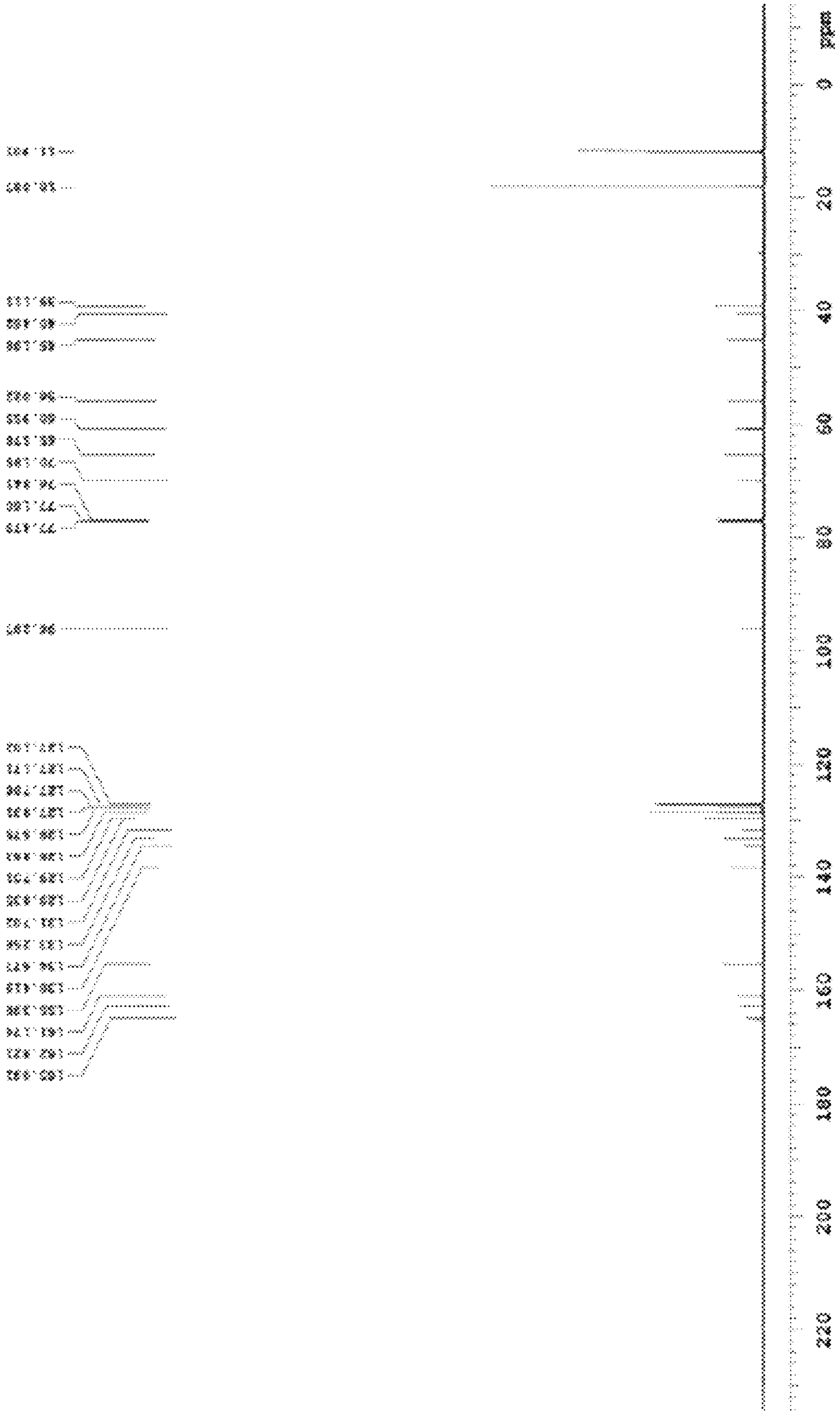
[Figure 50B]

[Figure 51A]
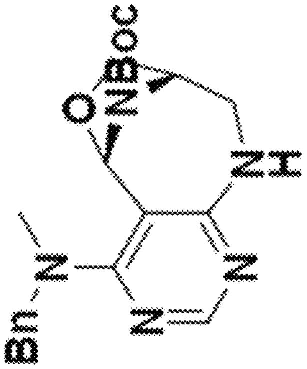
14f
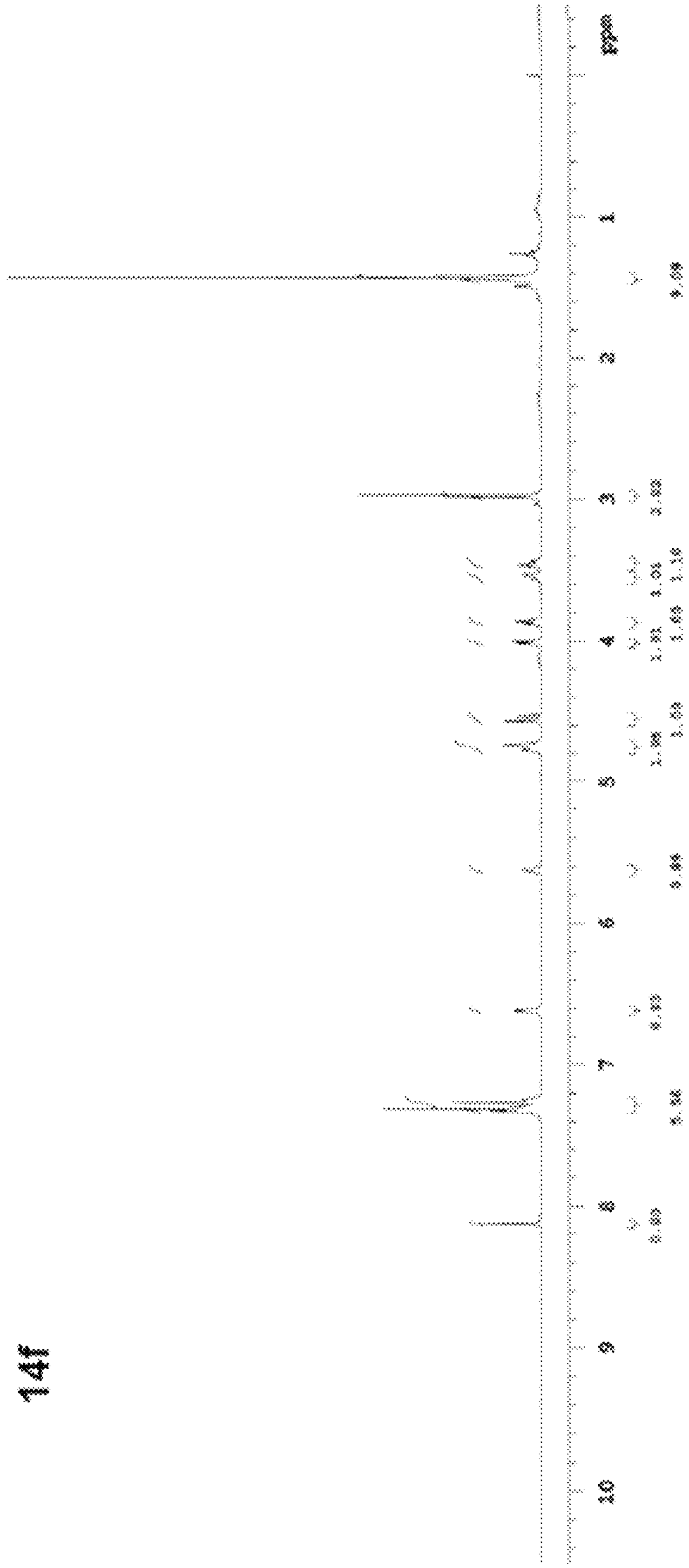

[Figure 51B]
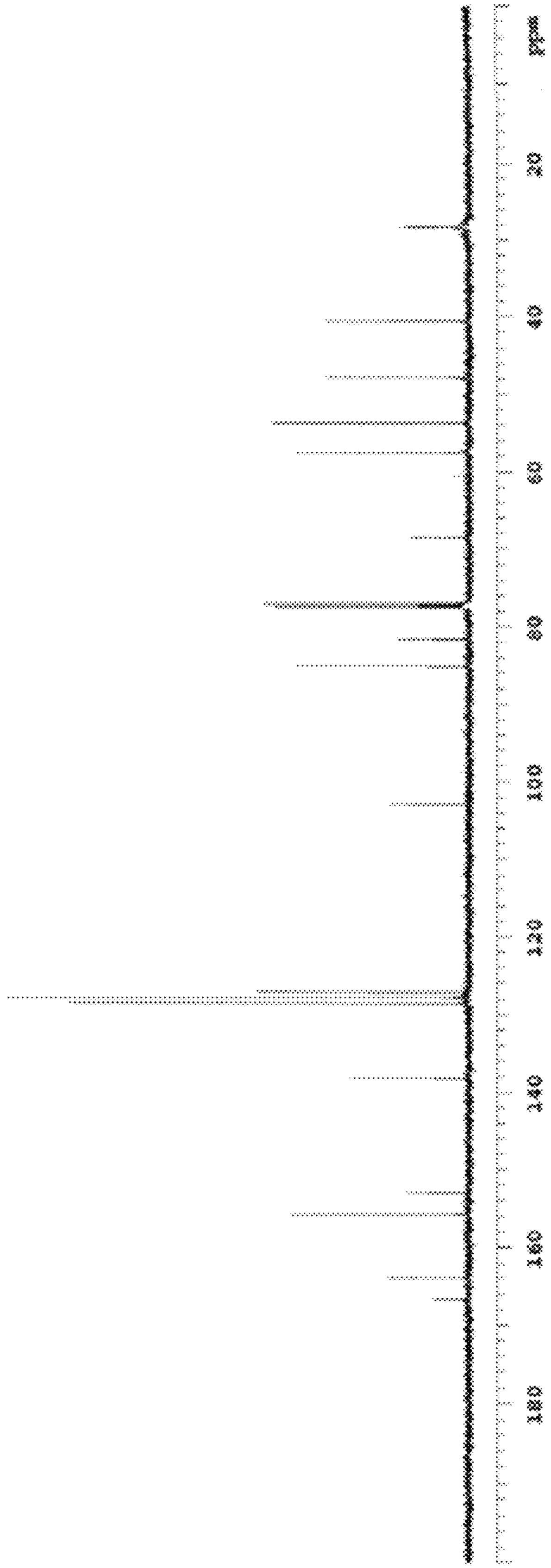

[Figure 52A]
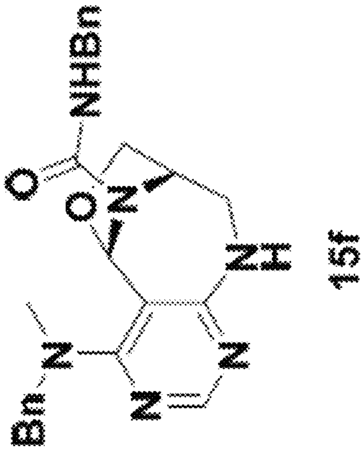
15f
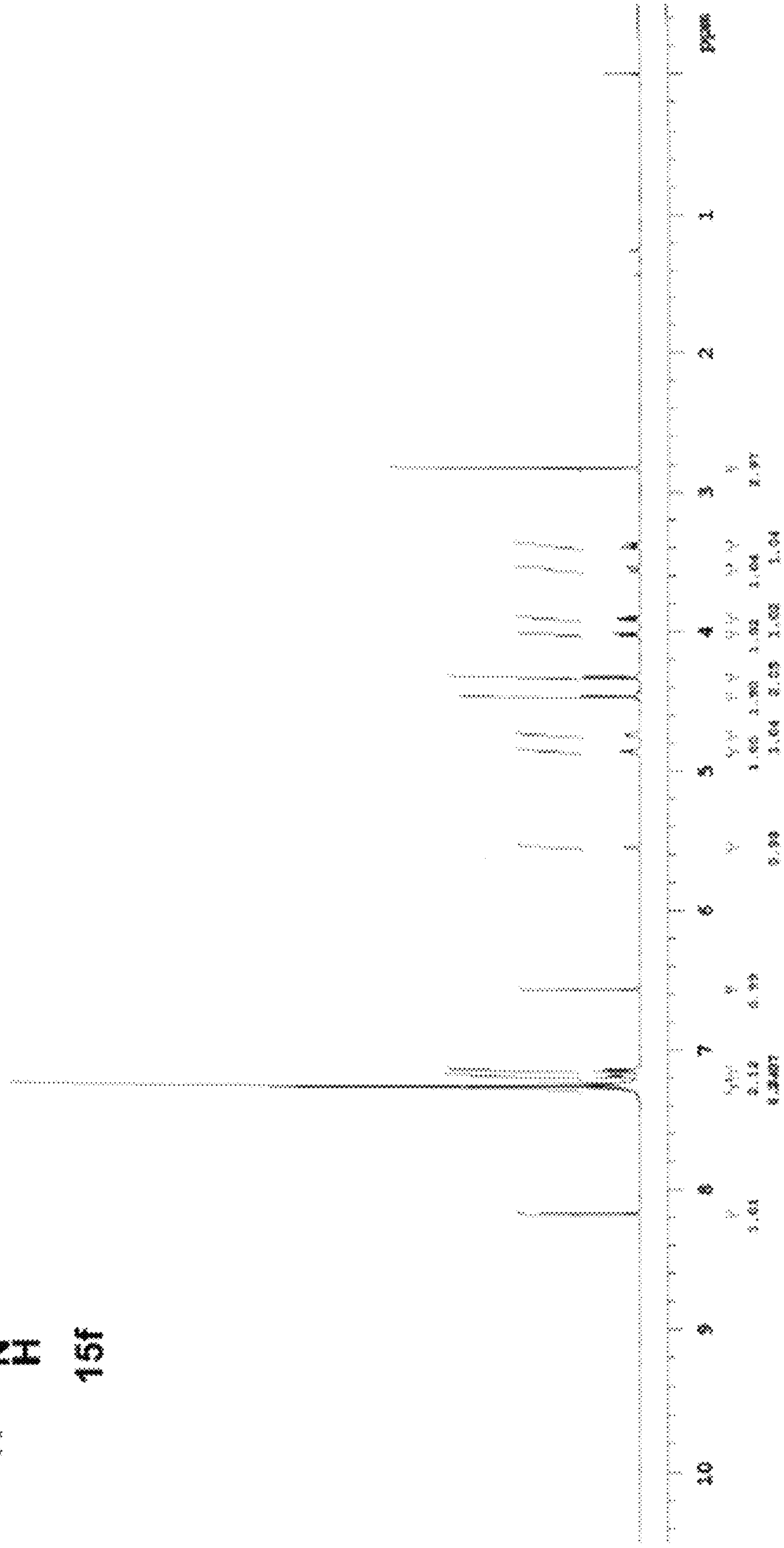

[Figure 52B]
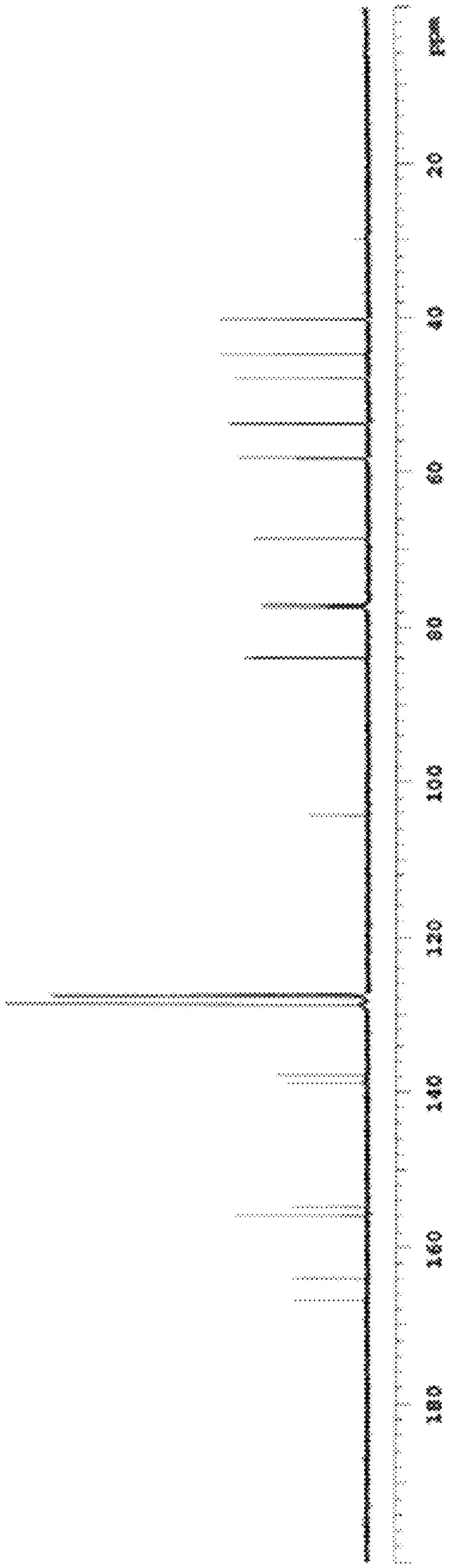

[Figure 53A]
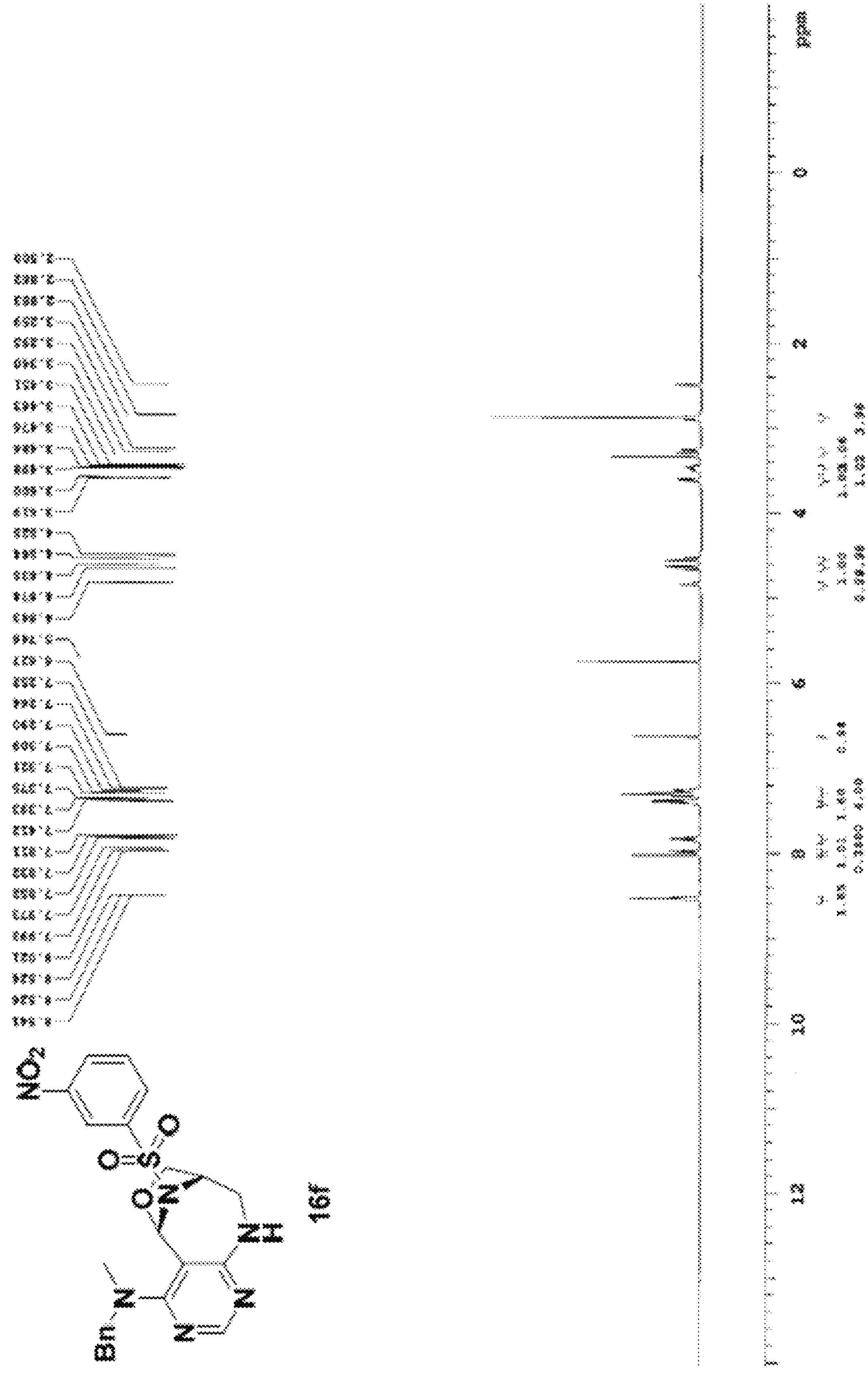
16f

[Figure 53B]
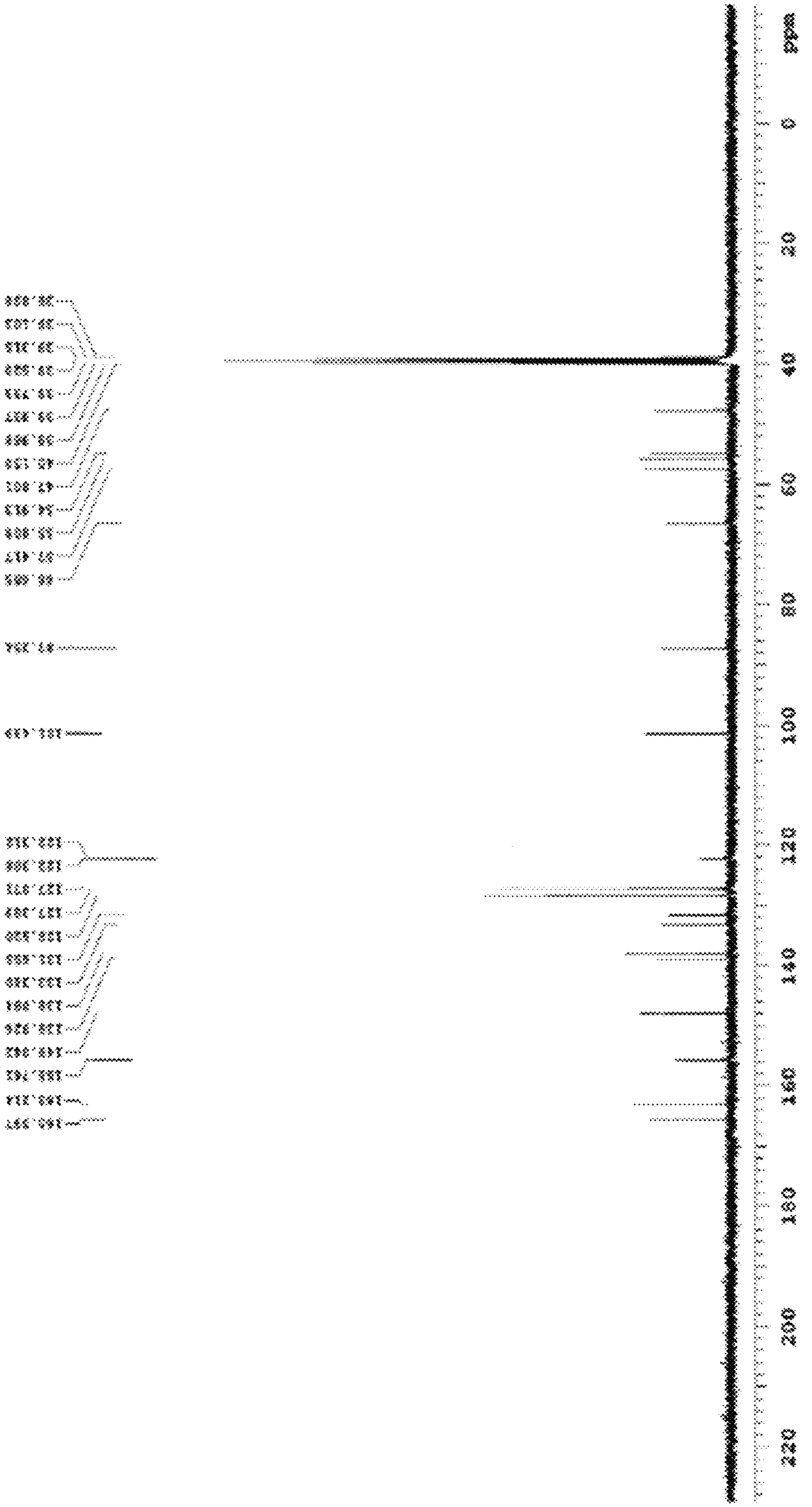

[Figure 54A]
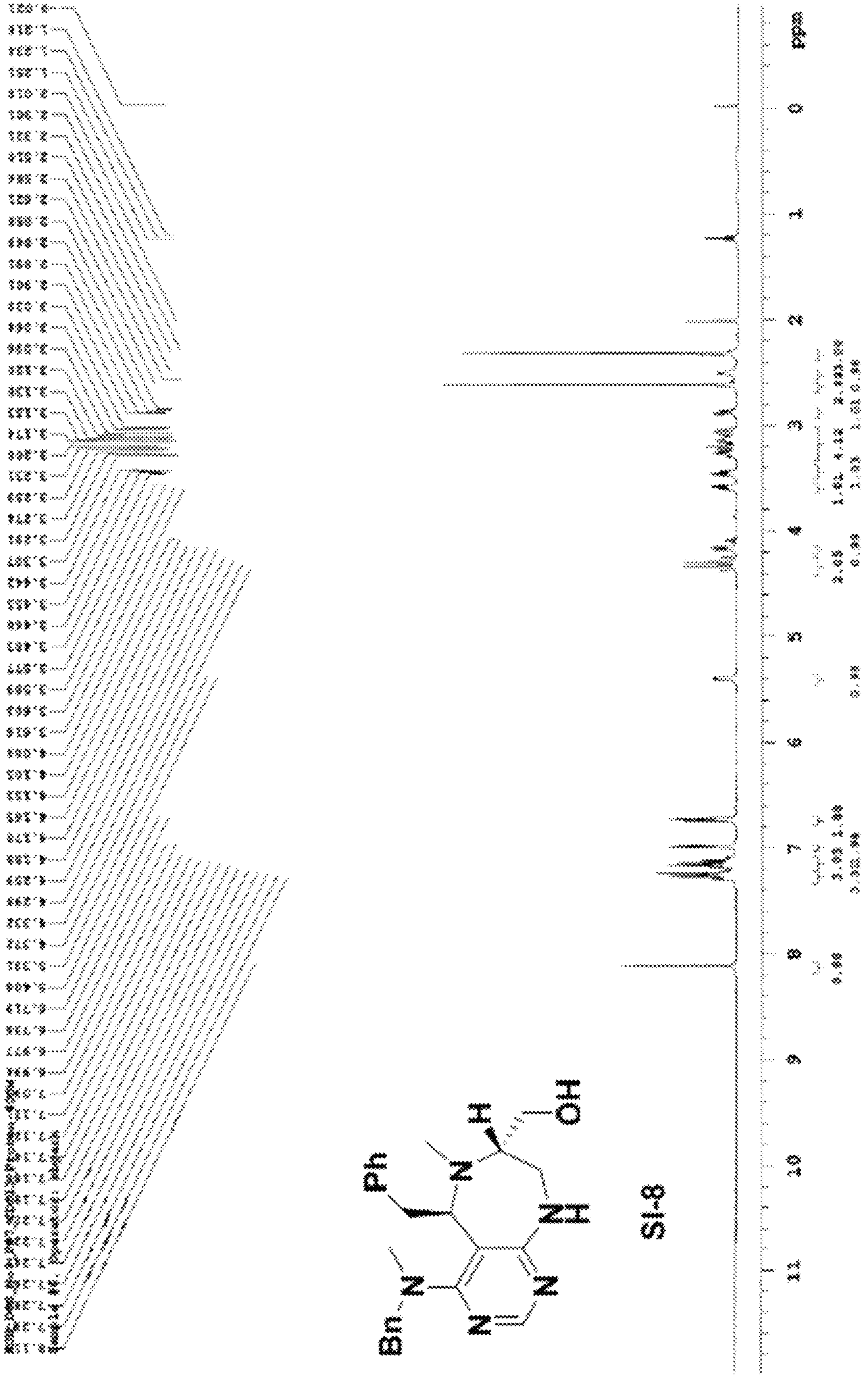
SI-8

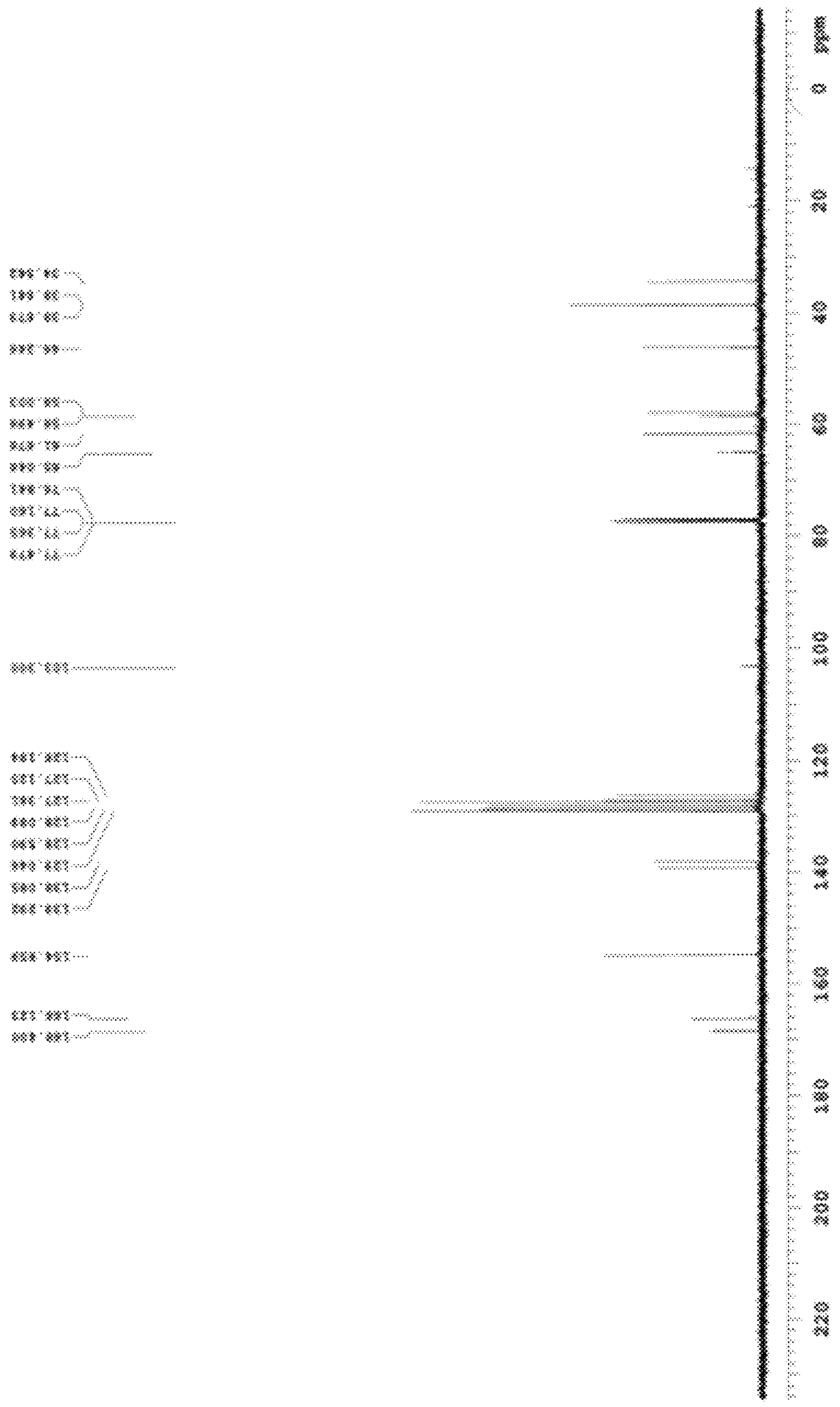
[Figure 54B]

[Figure 55A]
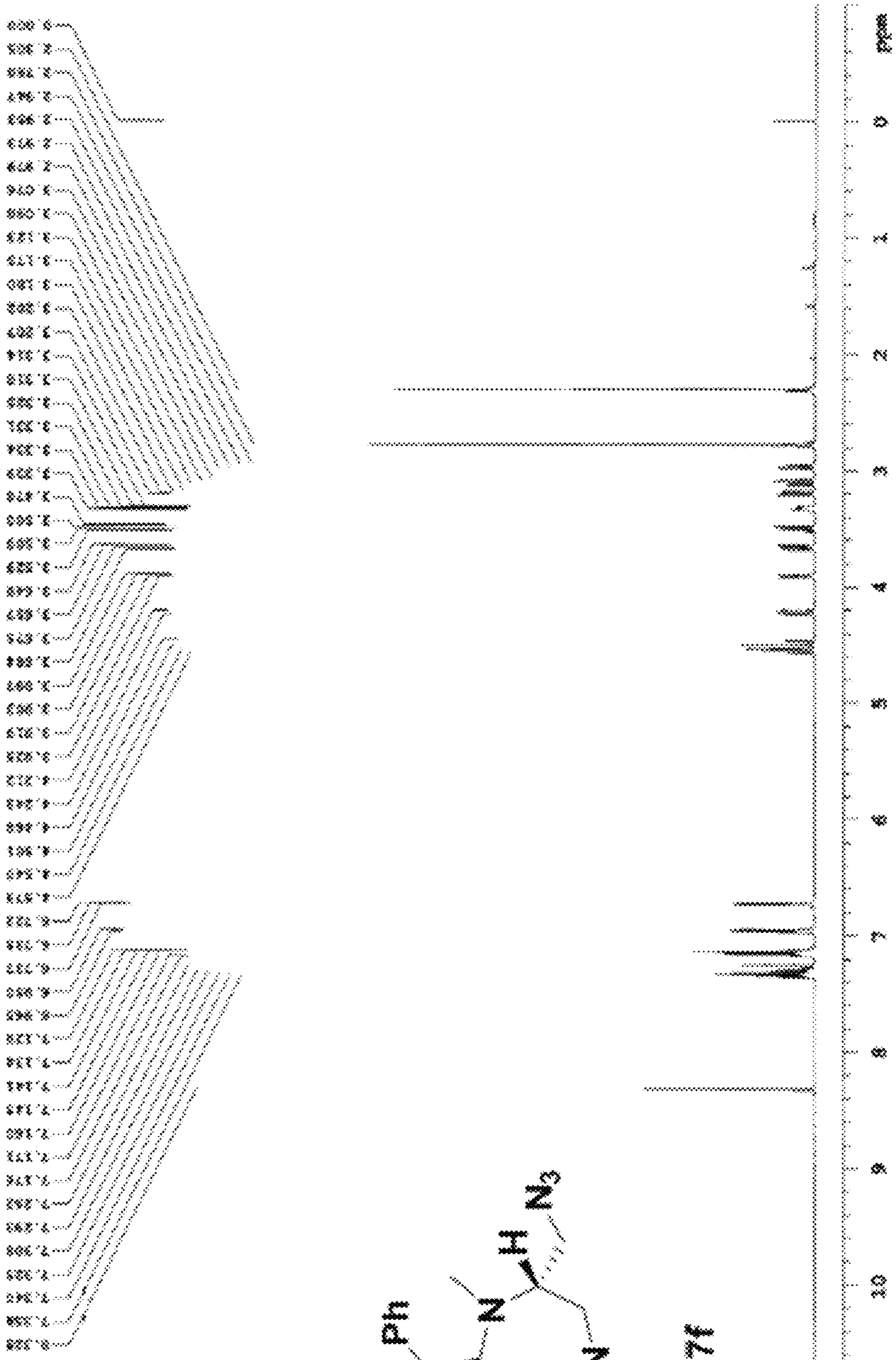
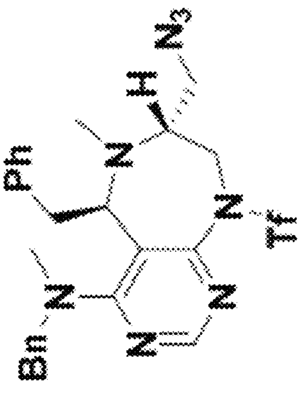
17f

[Figure 55B]
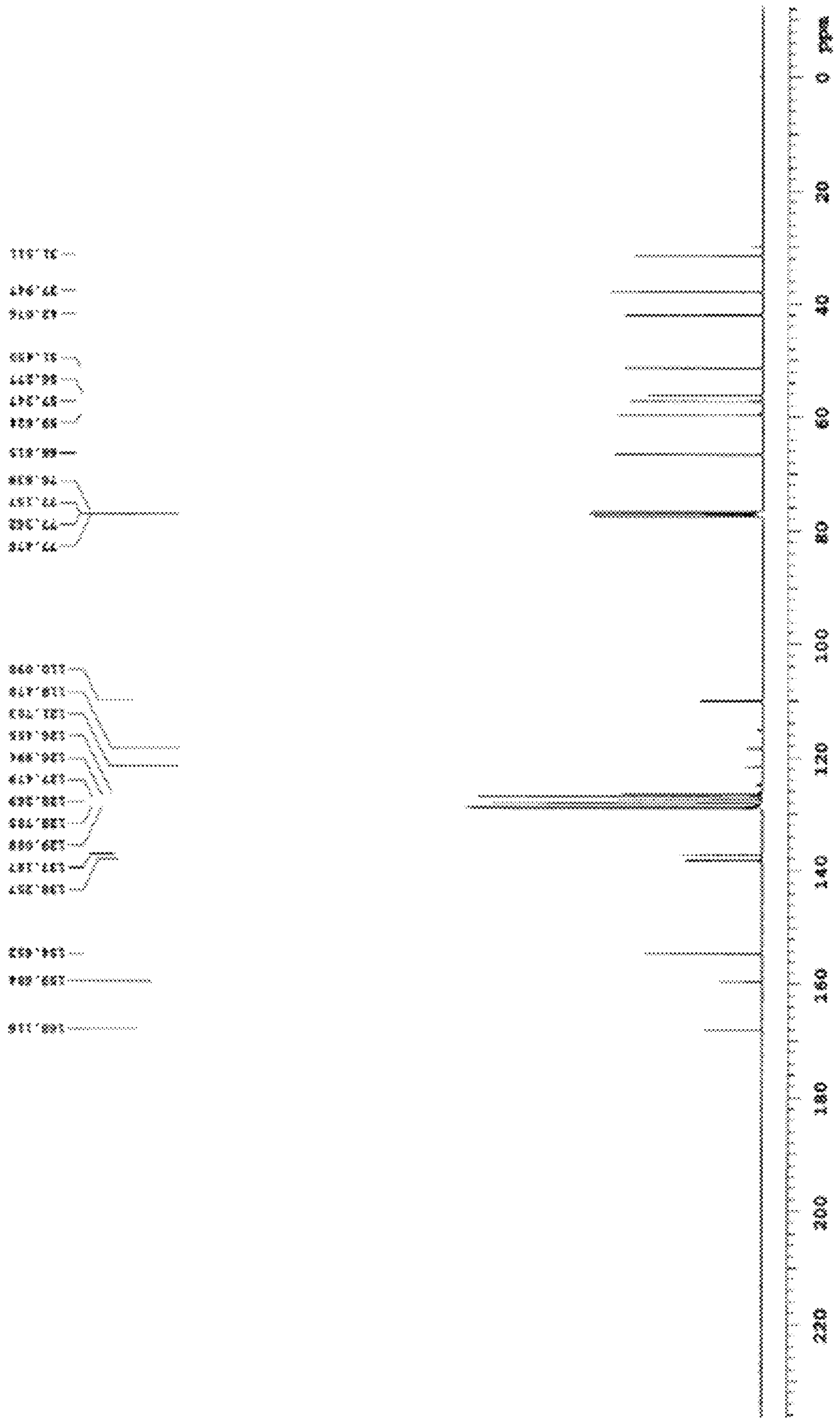

[Figure 56A]
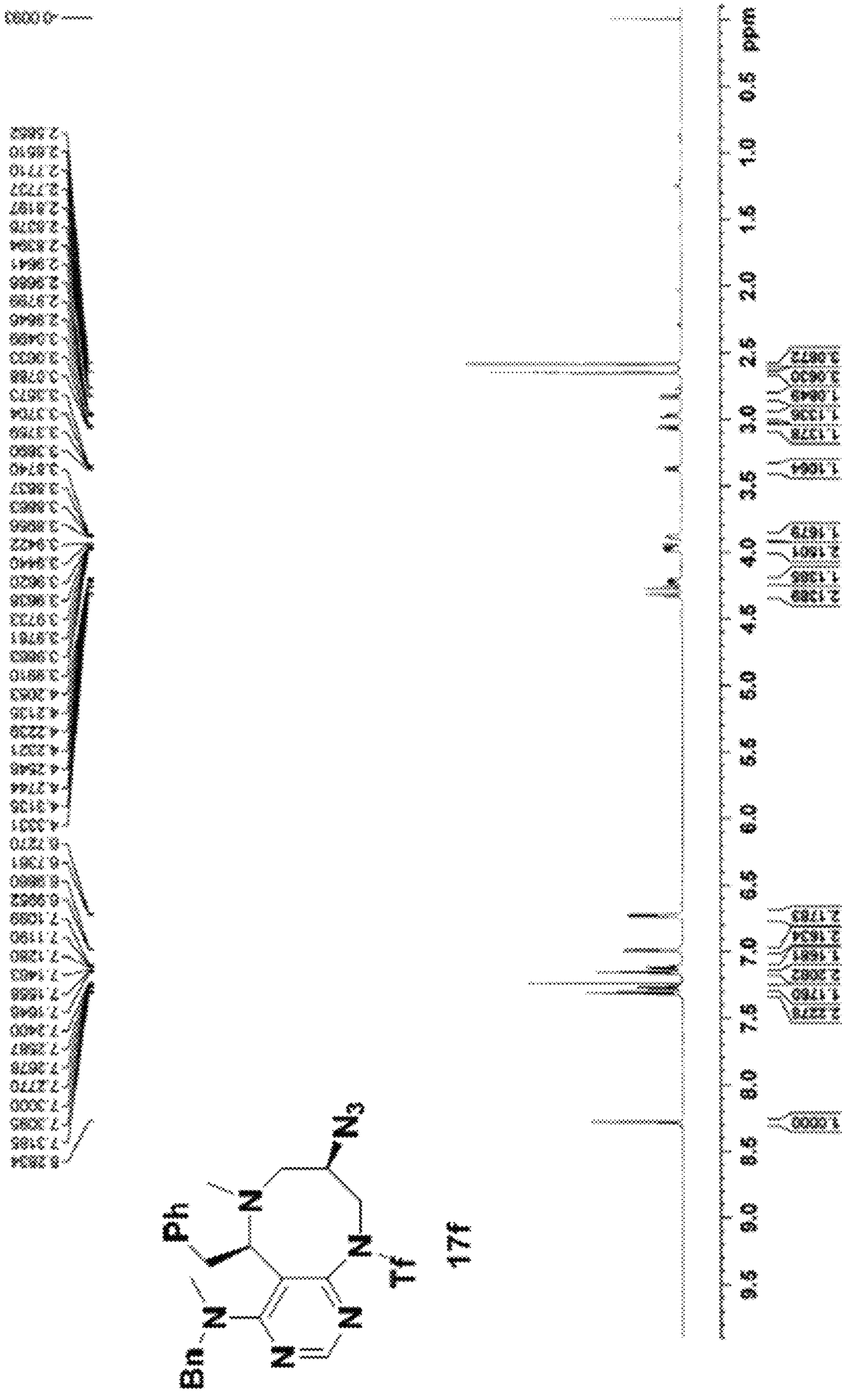
17f

[Figure 56B]
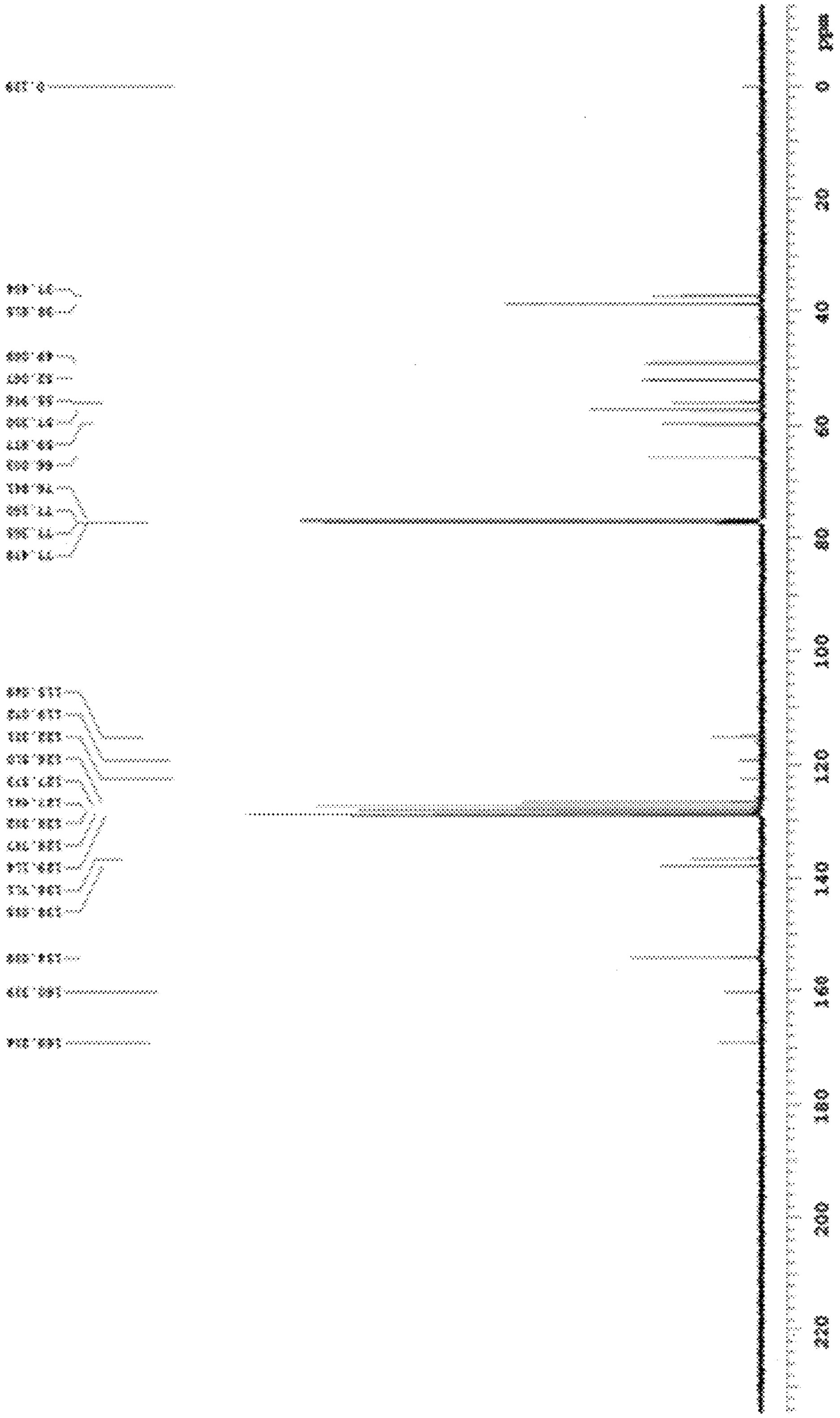

[Figure 57A]
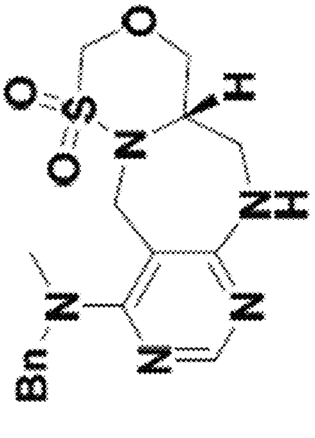
18f
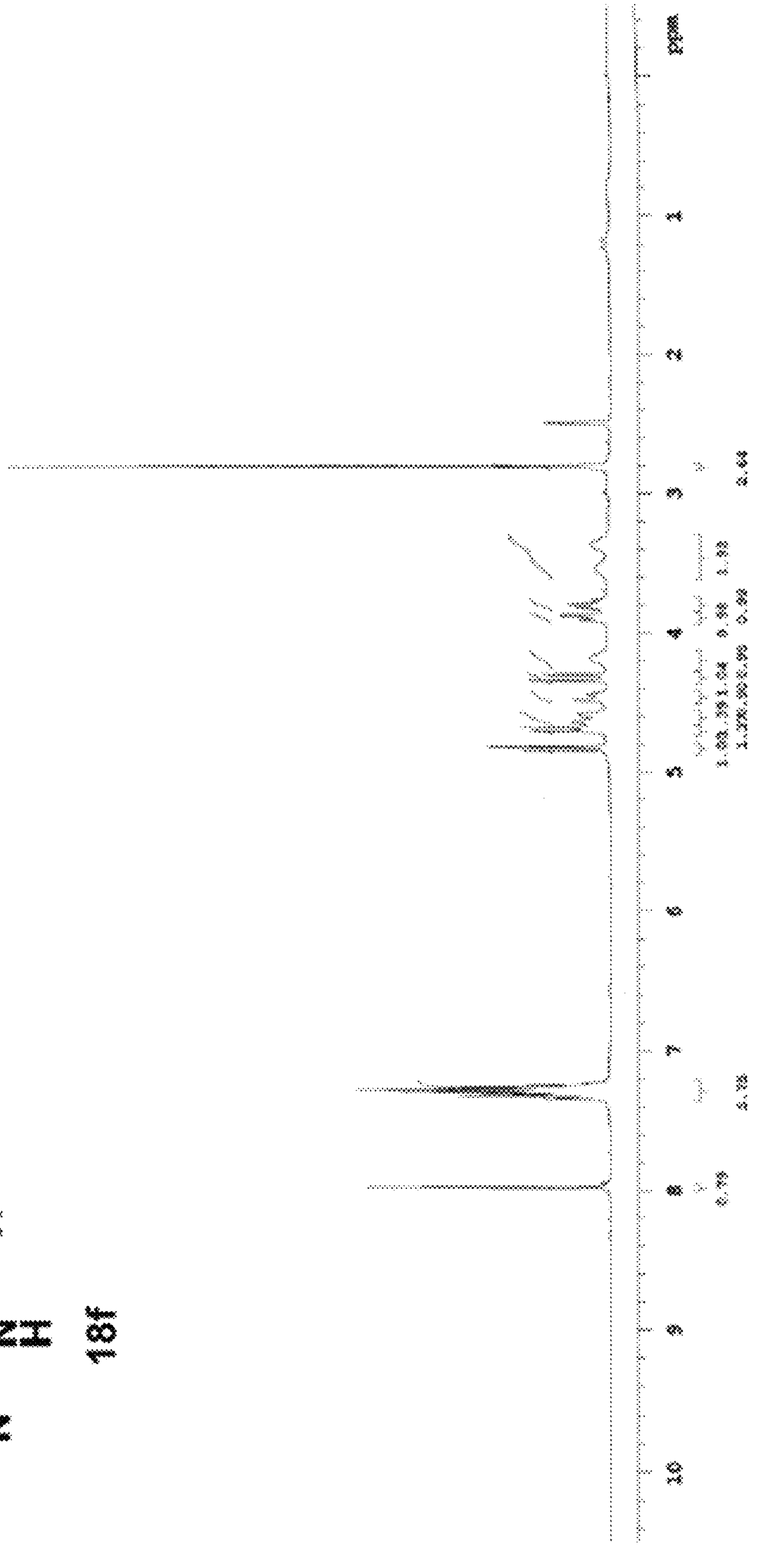

[Figure 57B]
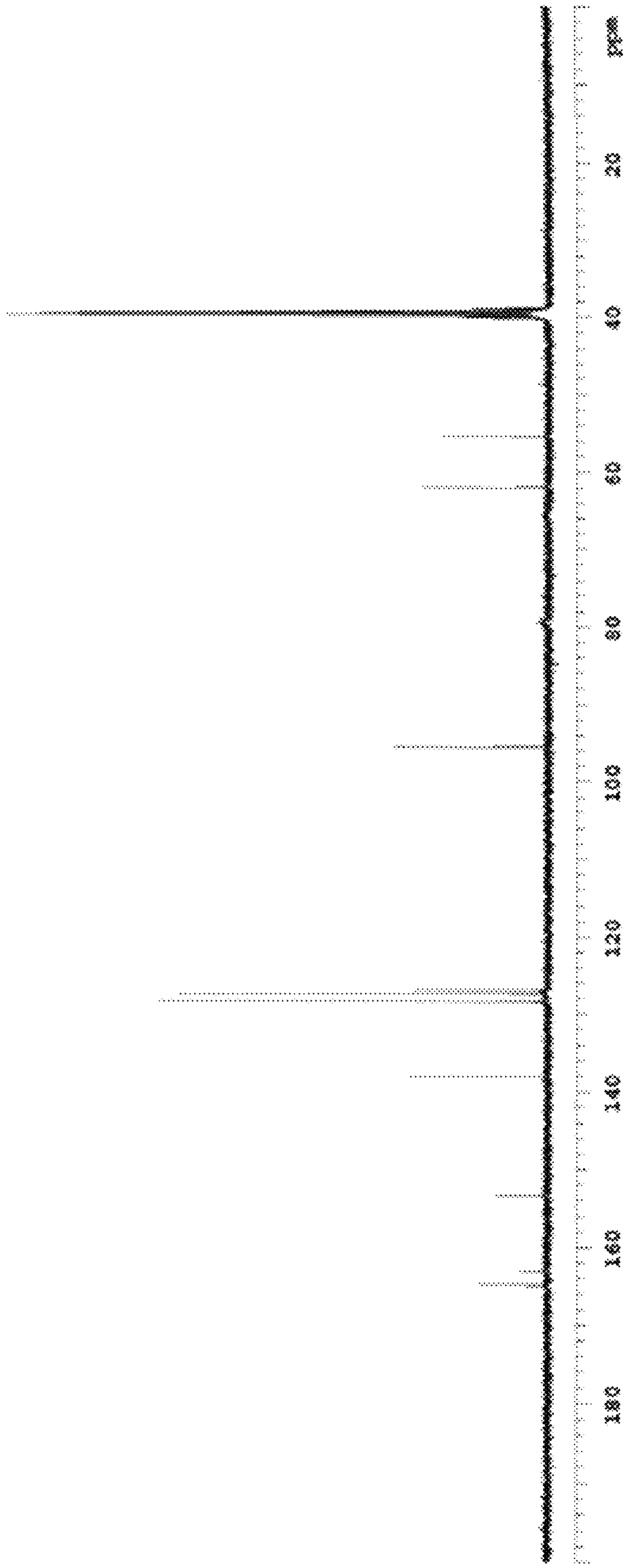

[Figure 58A]
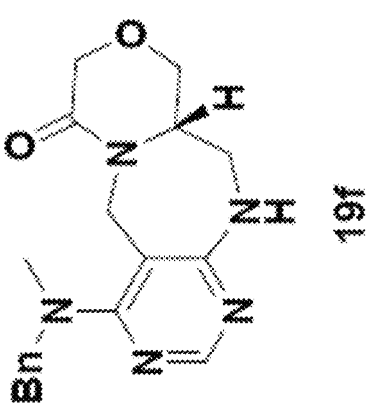
19f
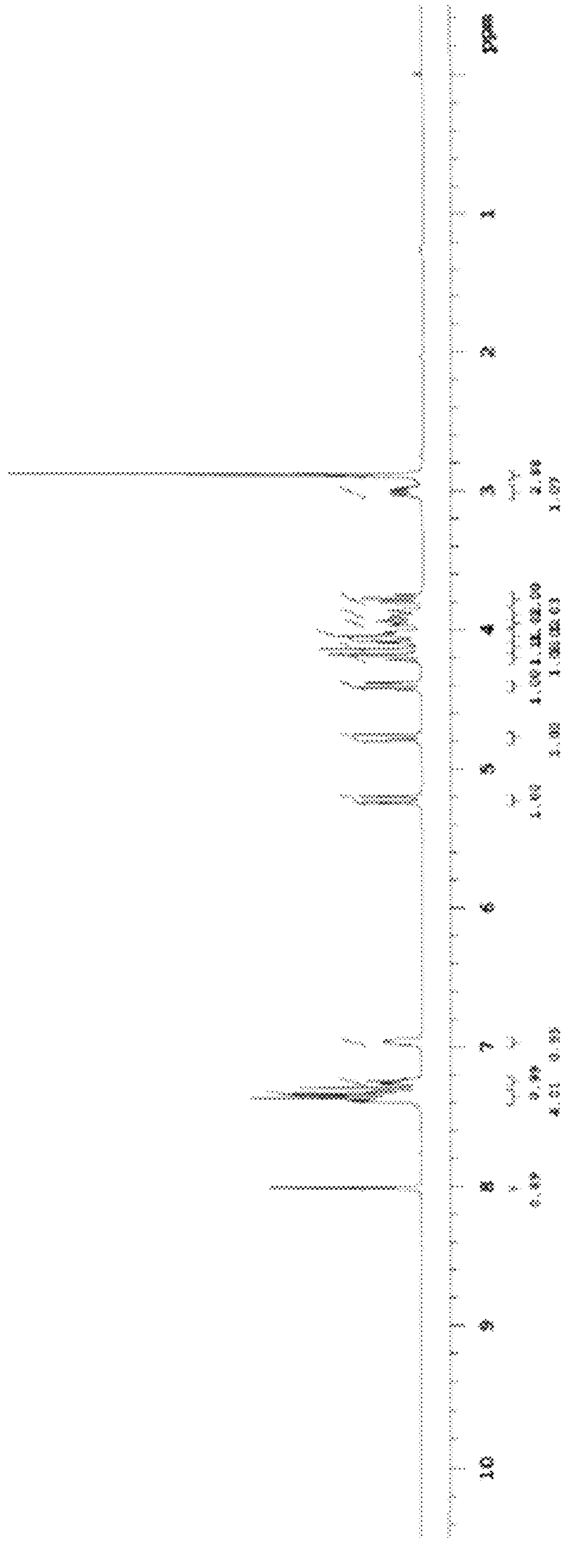

[Figure 58B]
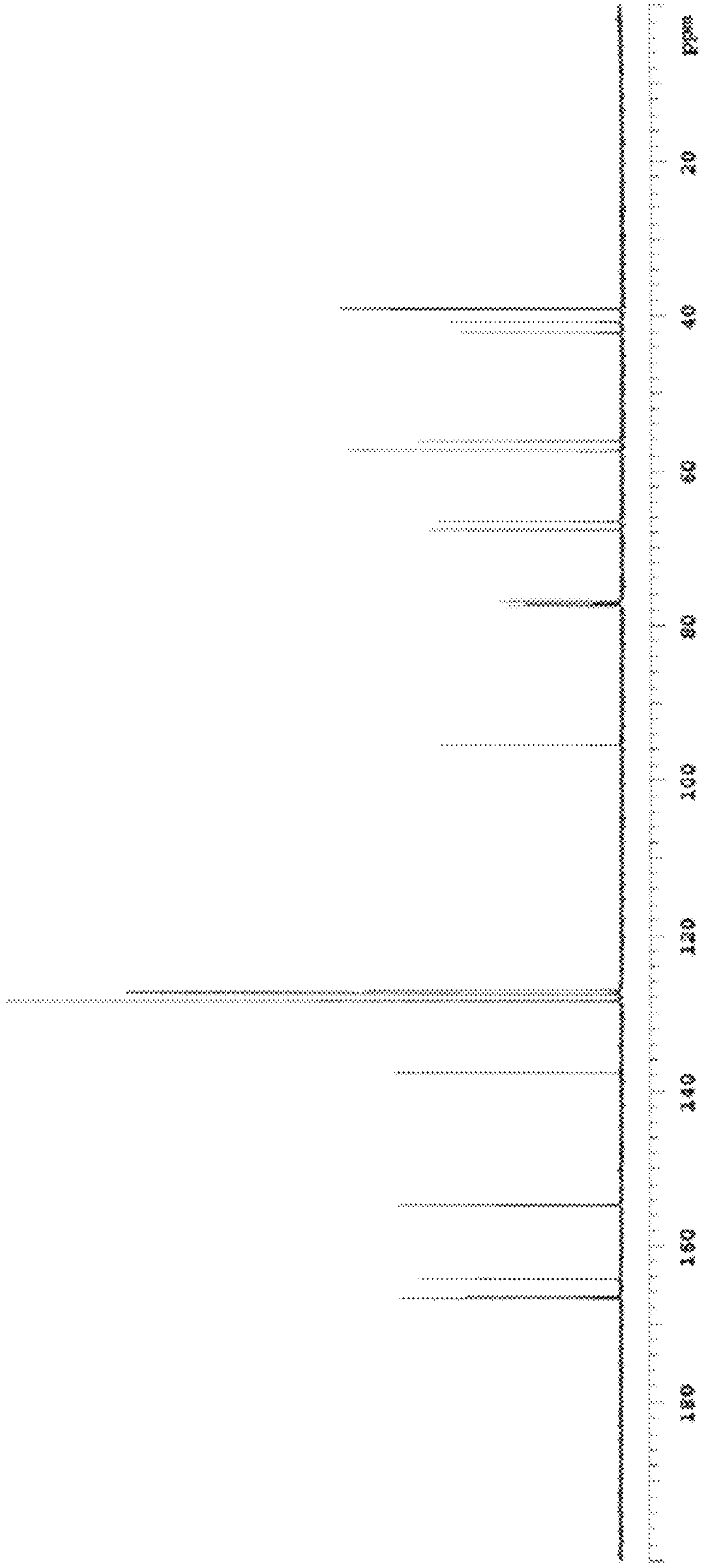

[Figure 59A]
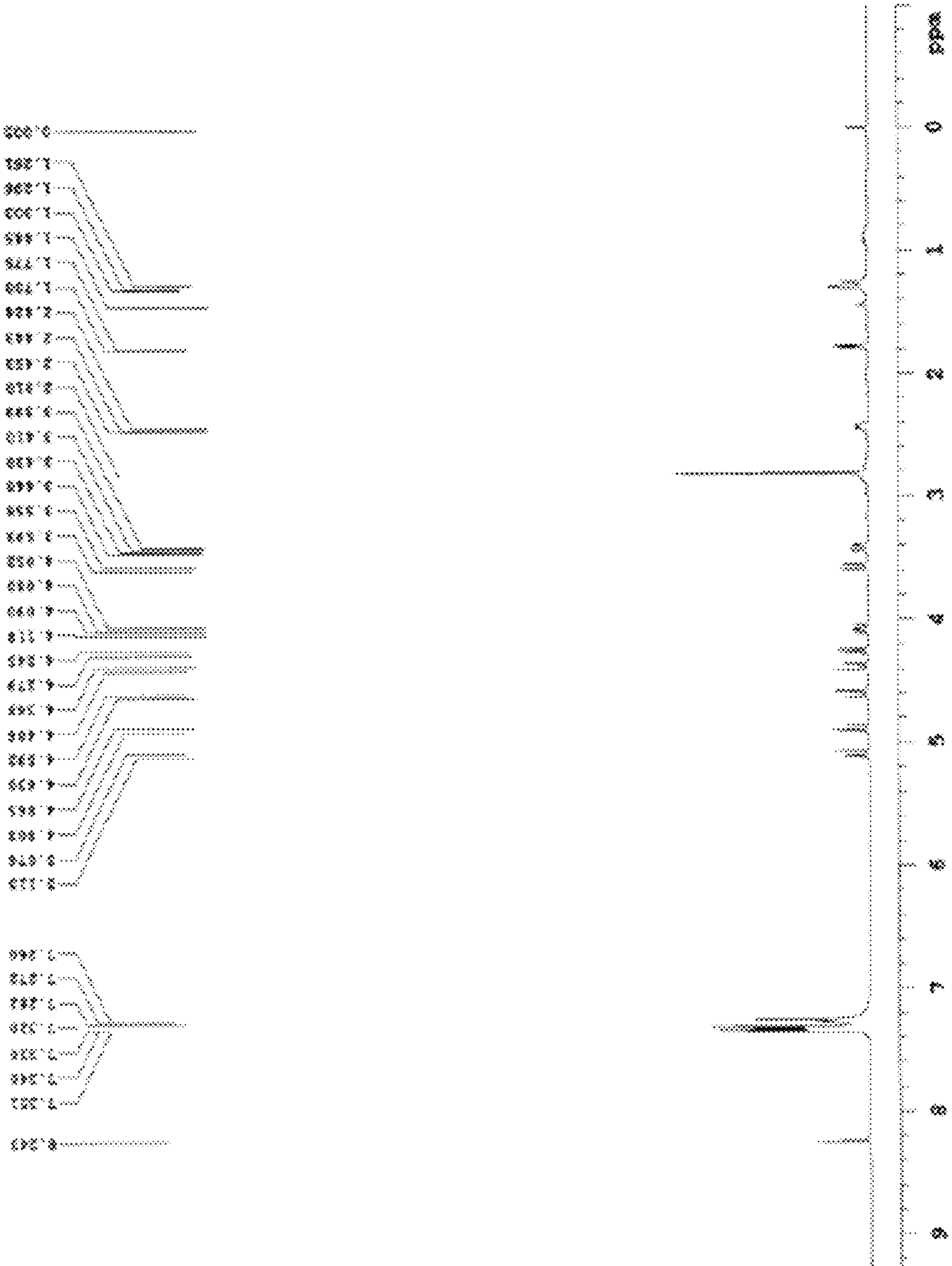
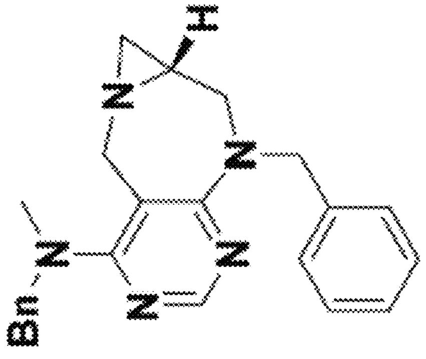
20f

[Figure 59B]
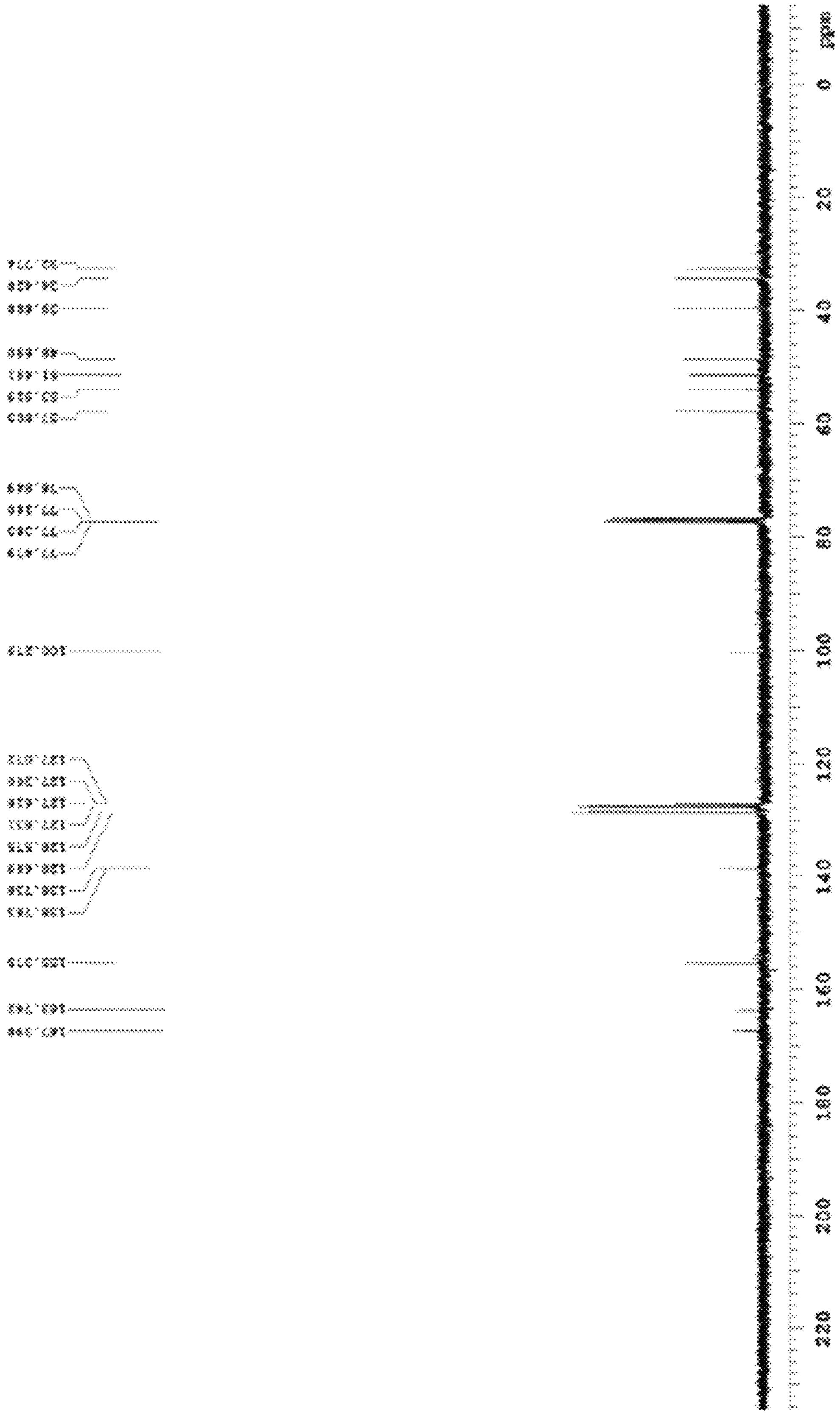

[Figure 60A]
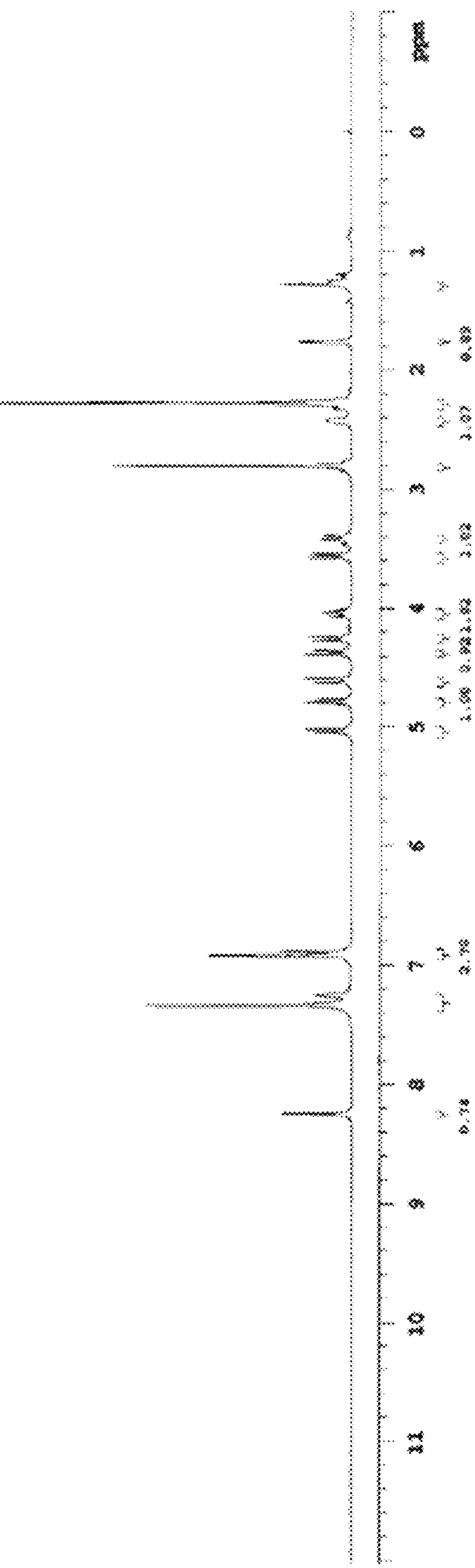
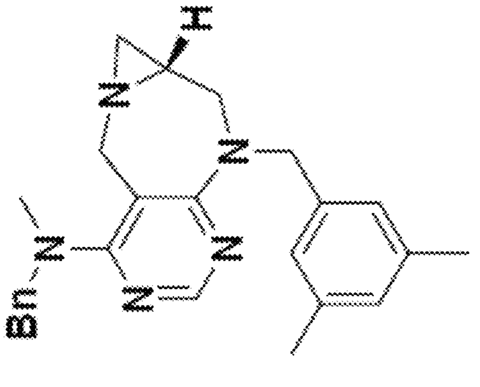
21f

[Figure 60B]
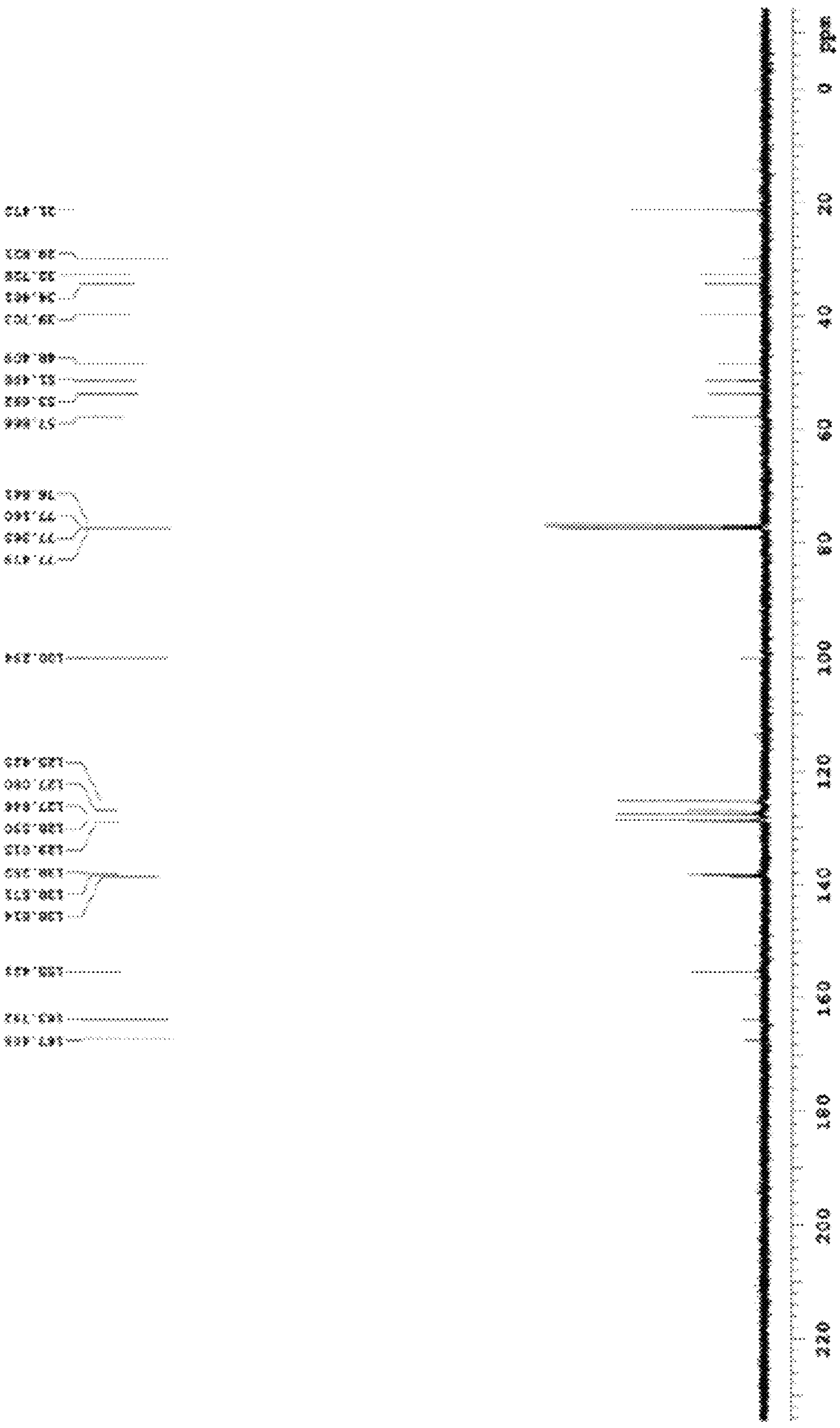

[Figure 61A]
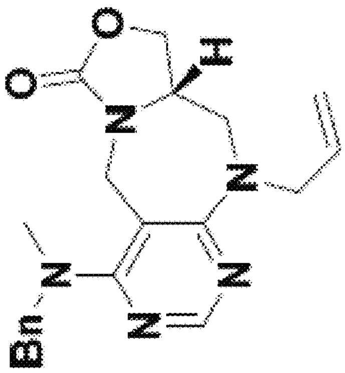
22f
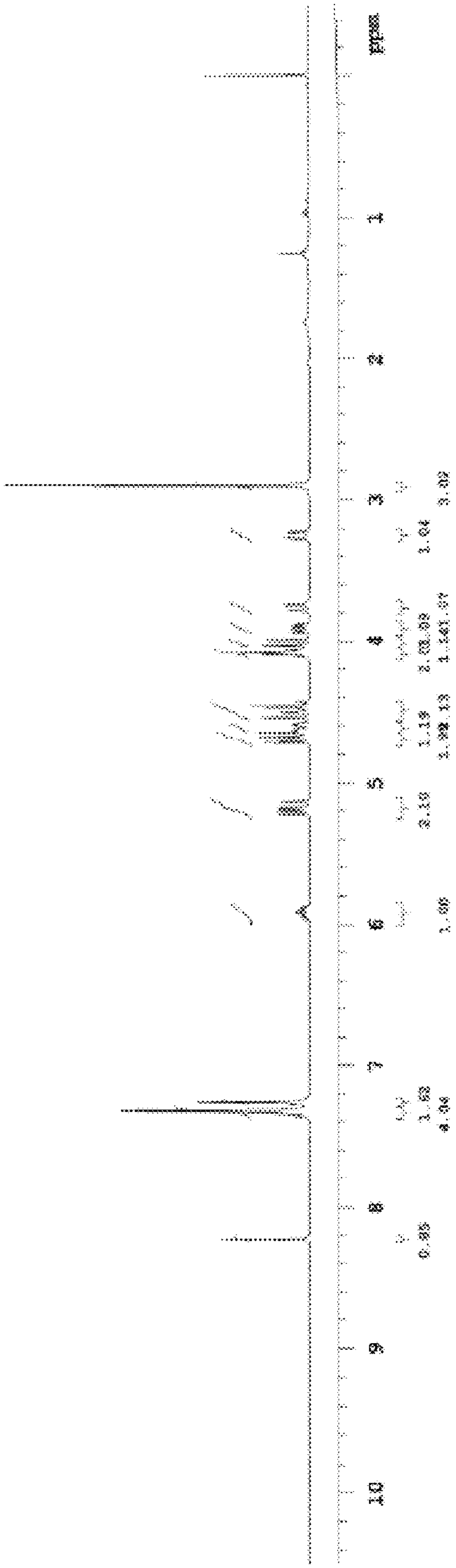

[Figure 61B]
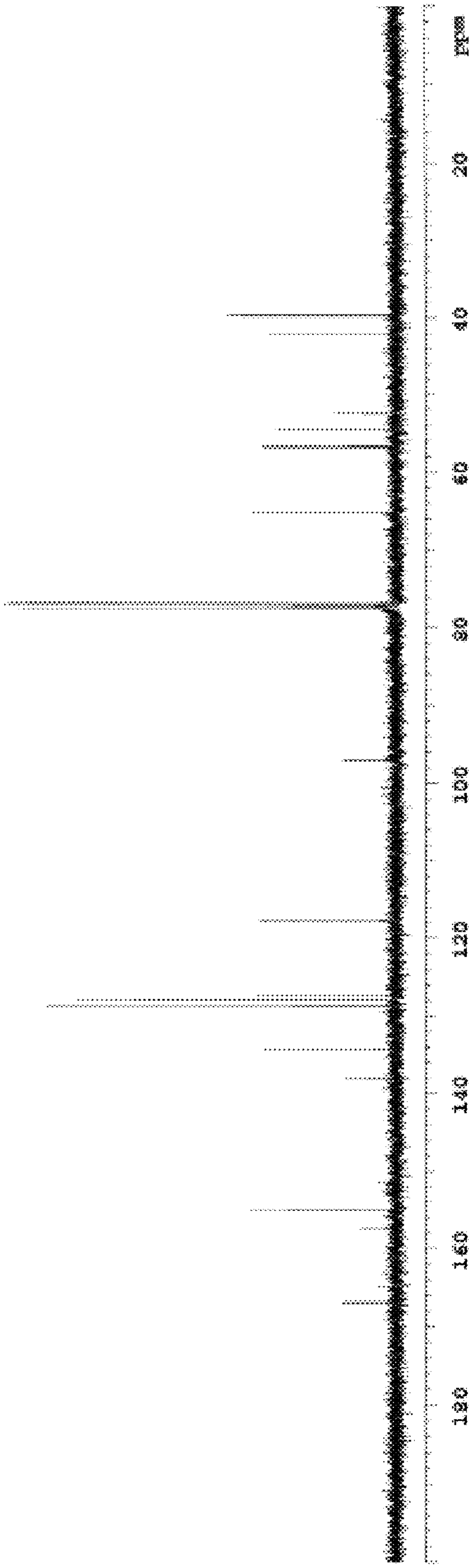

[Figure 62A]
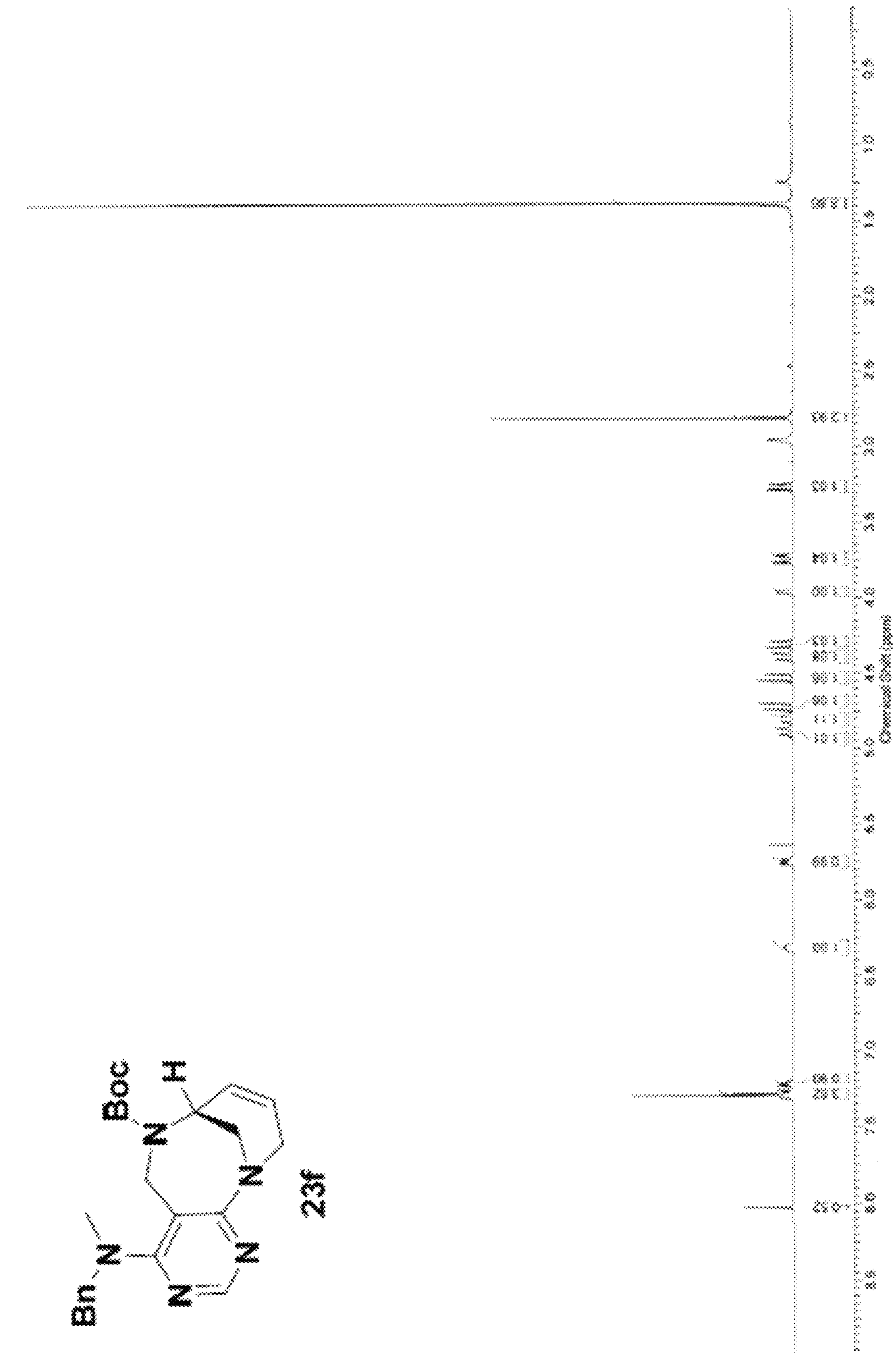
23f

[Figure 62B]
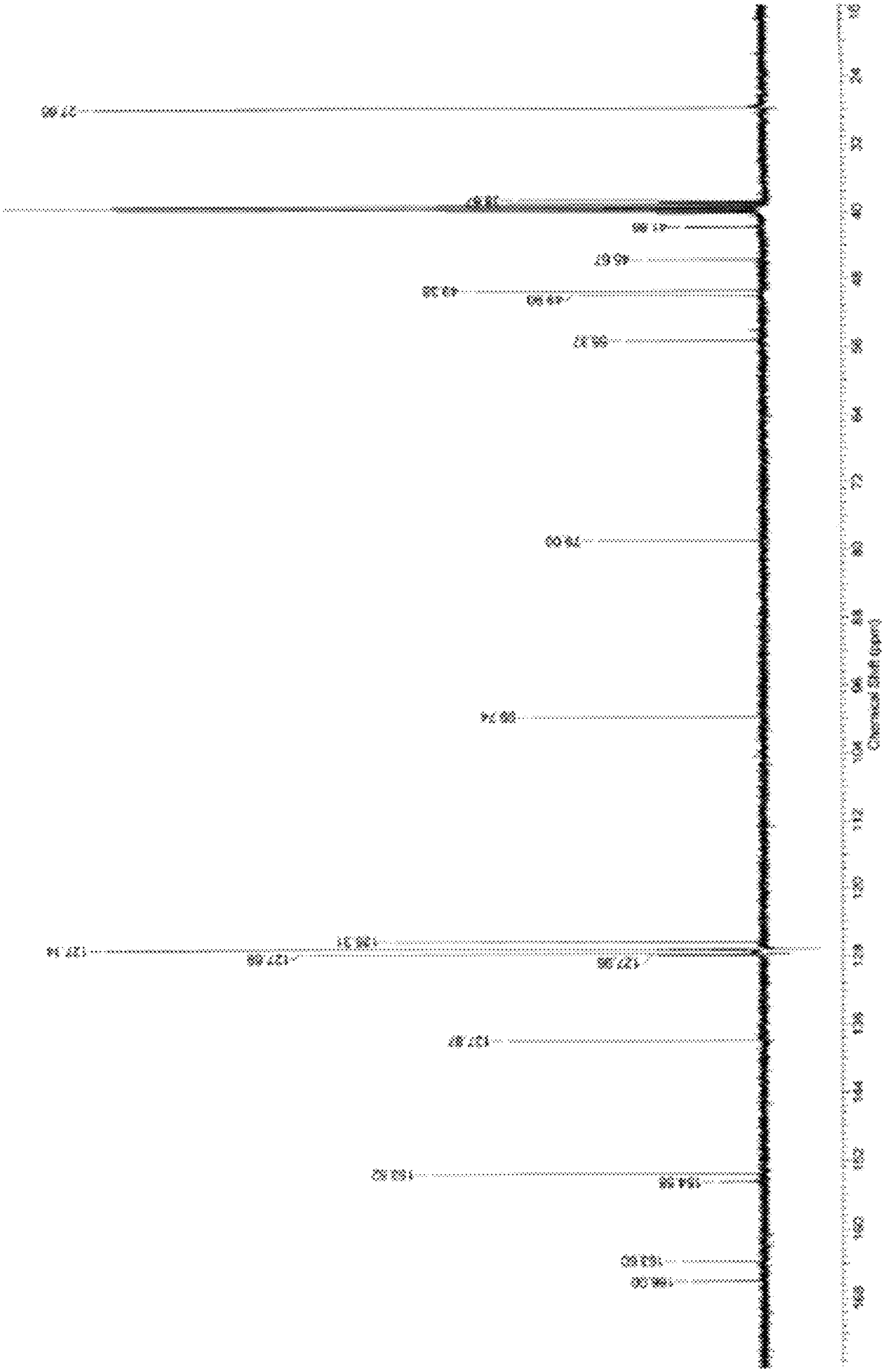

[Figure 63]

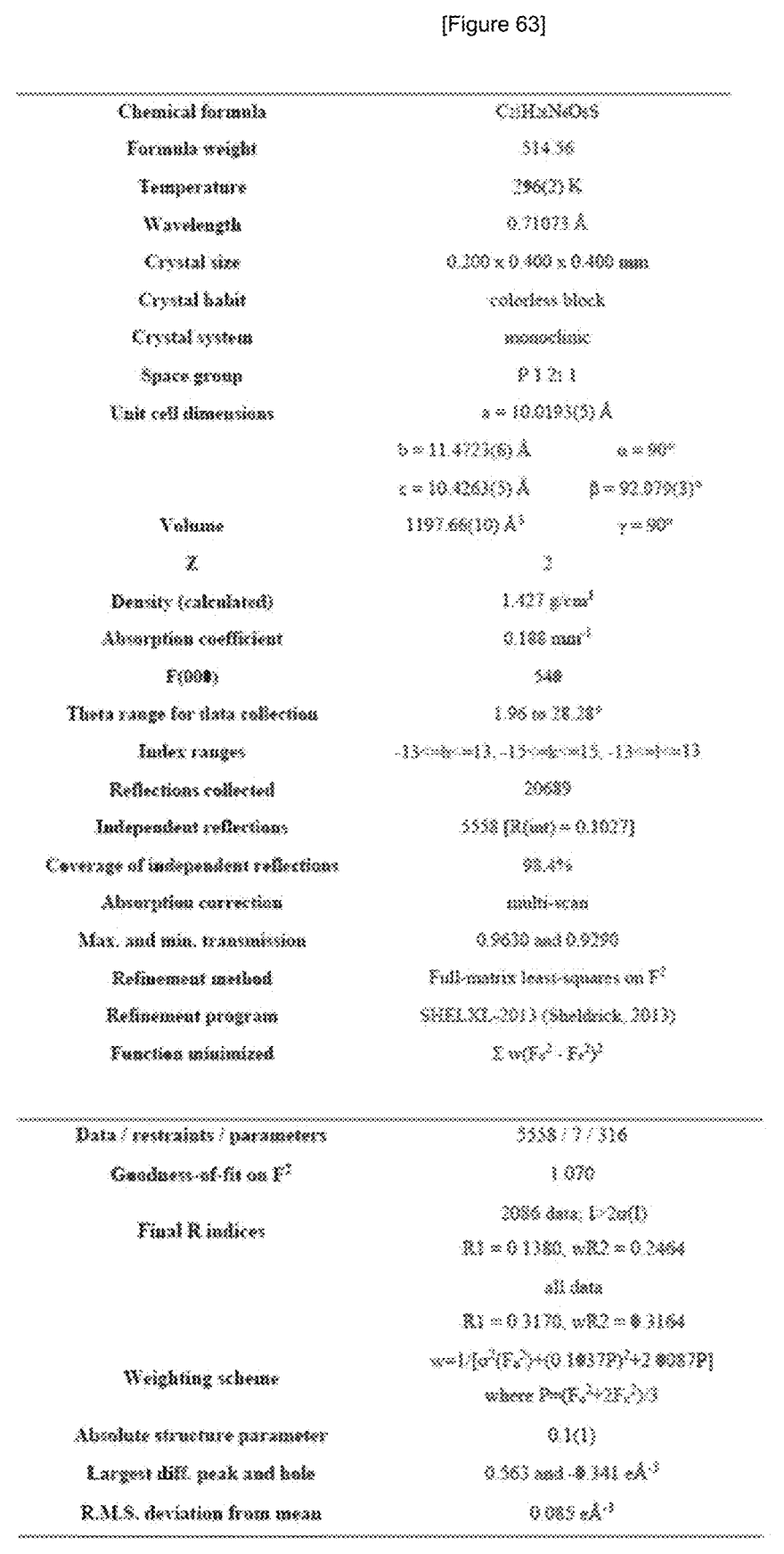

| | | |
|---|---|---|
| **Chemical formula** | [illegible] | |
| **Formula weight** | 514.56 | |
| **Temperature** | 296(2) K | |
| **Wavelength** | 0.71073 Å | |
| **Crystal size** | 0.200 x 0.400 x 0.400 mm | |
| **Crystal habit** | colorless block | |
| **Crystal system** | monoclinic | |
| **Space group** | P 1 2₁ 1 | |
| **Unit cell dimensions** | a = 10.0193(5) Å | |
| | b = 11.4723(6) Å | α = 90° |
| | c = 10.4263(5) Å | β = 92.079(3)° |
| **Volume** | 1197.66(10) $Å^3$ | γ = 90° |
| **Z** | 2 | |
| **Density (calculated)** | 1.427 $g/cm^3$ | |
| **Absorption coefficient** | 0.188 $mm^{-1}$ | |
| **F(000)** | 540 | |
| **Theta range for data collection** | 1.96 to 28.28° | |
| **Index ranges** | -13<=h<=13, -15<=k<=15, -13<=l<=13 | |
| **Reflections collected** | 20689 | |
| **Independent reflections** | 5558 [R(int) = 0.1027] | |
| **Coverage of independent reflections** | 98.4% | |
| **Absorption correction** | multi-scan | |
| **Max. and min. transmission** | 0.9630 and 0.9290 | |
| **Refinement method** | Full-matrix least-squares on $F^2$ | |
| **Refinement program** | SHELXL-2013 (Sheldrick, 2013) | |
| **Function minimized** | $\Sigma w(F_o^2 - F_c^2)^2$ | |
| **Data / restraints / parameters** | 5558 / 7 / 316 | |
| **Goodness-of-fit on $F^2$** | 1.070 | |
| **Final R indices** | 2086 data; I>2σ(I)<br>R1 = 0.1380, wR2 = 0.2464 | |
| | all data<br>R1 = 0.3170, wR2 = 0.3164 | |
| **Weighting scheme** | $w=1/[\sigma^2(F_o^2)+(0.1037P)^2+2.0087P]$<br>where $P=(F_o^2+2F_c^2)/3$ | |
| **Absolute structure parameter** | 0.1(1) | |
| **Largest diff. peak and hole** | 0.563 and -0.341 $eÅ^{-3}$ | |
| **R.M.S. deviation from mean** | 0.085 $eÅ^{-3}$ | |

[Figure 64]

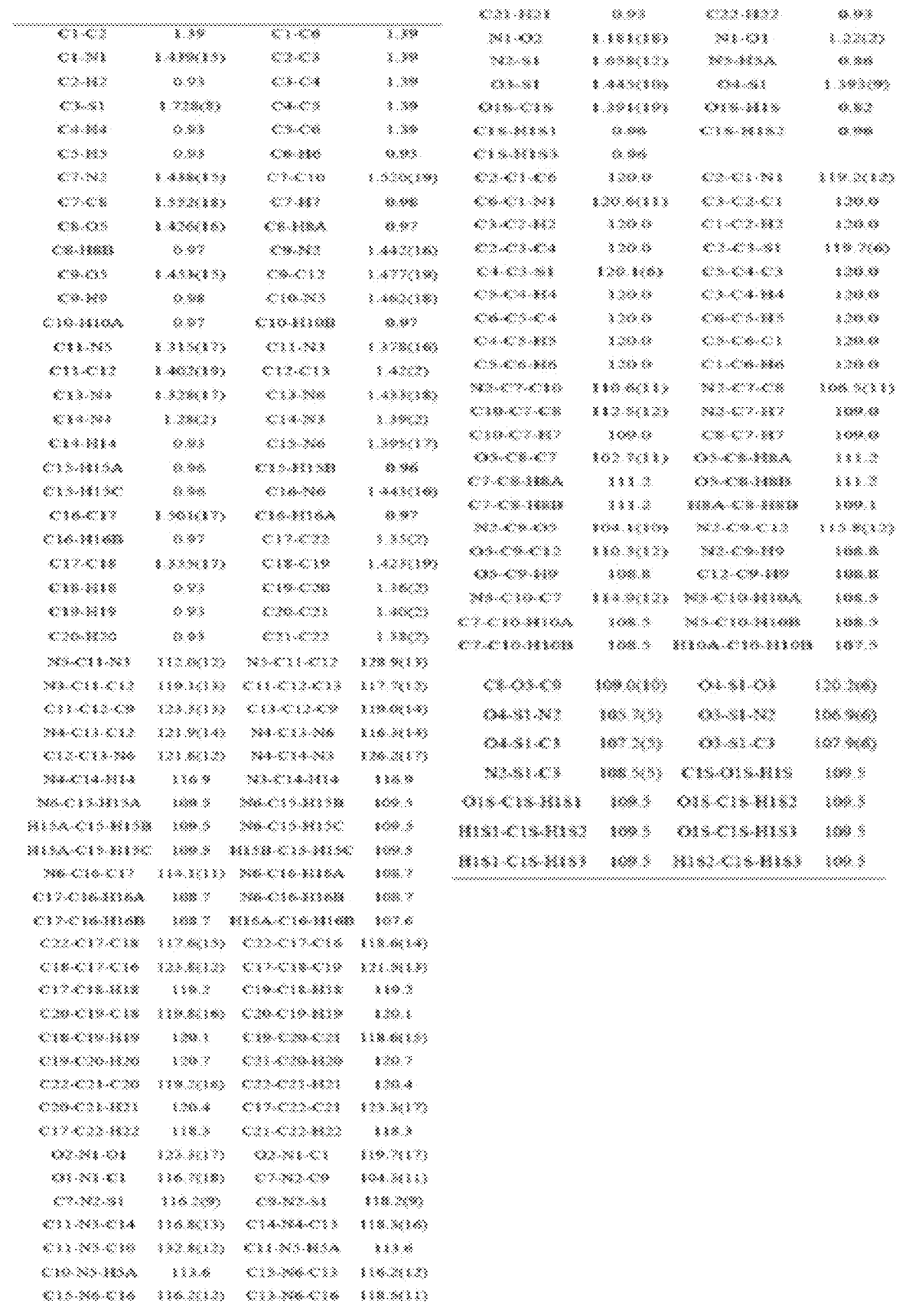

| | | | |
|---|---|---|---|
| C1-C2 | 1.39 | C1-C6 | 1.39 |
| C1-N1 | 1.438(15) | C2-C3 | 1.39 |
| C2-H2 | 0.93 | C3-C4 | 1.39 |
| C3-S1 | 1.728(8) | C4-C5 | 1.39 |
| C4-H4 | 0.93 | C5-C6 | 1.39 |
| C5-H5 | 0.93 | C6-H6 | 0.93 |
| C7-N2 | 1.488(15) | C7-C10 | 1.535(19) |
| C7-C8 | 1.552(18) | C7-H7 | 0.98 |
| C8-O5 | 1.426(16) | C8-H8A | 0.97 |
| C8-H8B | 0.97 | C9-N2 | 1.442(16) |
| C9-O5 | 1.433(15) | C9-C12 | 1.477(19) |
| C9-H9 | 0.98 | C10-N3 | 1.460(18) |
| C10-H10A | 0.97 | C10-H10B | 0.97 |
| C11-N5 | 1.315(17) | C11-N3 | 1.378(16) |
| C11-C12 | 1.402(19) | C12-C13 | 1.42(2) |
| C13-N4 | 1.328(17) | C13-N6 | 1.433(18) |
| C14-N4 | 1.28(2) | C14-N3 | 1.39(2) |
| C14-H14 | 0.93 | C15-N6 | 1.395(17) |
| C15-H15A | 0.96 | C15-H15B | 0.96 |
| C15-H15C | 0.96 | C16-N6 | 1.443(16) |
| C16-C17 | 1.501(17) | C16-H16A | 0.97 |
| C16-H16B | 0.97 | C17-C22 | 1.35(2) |
| C17-C18 | 1.338(17) | C18-C19 | 1.423(19) |
| C18-H18 | 0.93 | C19-C20 | 1.36(2) |
| C19-H19 | 0.93 | C20-C21 | 1.40(2) |
| C20-H20 | 0.93 | C21-C22 | 1.38(2) |
| N5-C11-N3 | 112.8(12) | N5-C11-C12 | 128.9(13) |
| N3-C11-C12 | 119.1(13) | C11-C12-C13 | 117.7(13) |
| C11-C12-C9 | 123.3(13) | C13-C12-C9 | 119.0(14) |
| N4-C13-C12 | 121.9(14) | N4-C13-N6 | 116.3(14) |
| C12-C13-N6 | 121.8(12) | N4-C14-N3 | 126.2(17) |
| N4-C14-H14 | 116.9 | N3-C14-H14 | 116.9 |
| N6-C15-H15A | 109.5 | N6-C15-H15B | 109.5 |
| H15A-C15-H15B | 109.5 | N6-C15-H15C | 109.5 |
| H15A-C15-H15C | 109.5 | H15B-C15-H15C | 109.5 |
| N6-C16-C17 | 114.1(11) | N6-C16-H16A | 108.7 |
| C17-C16-H16A | 108.7 | N6-C16-H16B | 108.7 |
| C17-C16-H16B | 108.7 | H16A-C16-H16B | 107.6 |
| C22-C17-C18 | 117.8(15) | C22-C17-C16 | 118.6(14) |
| C18-C17-C16 | 123.8(12) | C17-C18-C19 | 121.5(13) |
| C17-C18-H18 | 119.2 | C19-C18-H18 | 119.2 |
| C20-C19-C18 | 119.8(16) | C20-C19-H19 | 120.1 |
| C18-C19-H19 | 120.1 | C19-C20-C21 | 118.6(15) |
| C19-C20-H20 | 120.7 | C21-C20-H20 | 120.7 |
| C22-C21-C20 | 119.2(16) | C22-C21-H21 | 120.4 |
| C20-C21-H21 | 120.4 | C17-C22-C21 | 123.3(17) |
| C17-C22-H22 | 118.3 | C21-C22-H22 | 118.3 |
| O2-N1-O1 | 123.3(17) | O2-N1-C1 | 119.7(17) |
| O1-N1-C1 | 116.7(18) | C7-N2-C9 | 104.3(11) |
| C7-N2-S1 | 116.2(9) | C9-N2-S1 | 118.2(9) |
| C11-N3-C14 | 116.8(13) | C14-N4-C13 | 118.3(16) |
| C11-N3-C10 | 132.8(12) | C11-N5-H5A | 113.6 |
| C10-N5-H5A | 113.6 | C15-N6-C13 | 116.2(12) |
| C15-N6-C16 | 116.2(12) | C13-N6-C16 | 118.5(11) |

| | | | |
|---|---|---|---|
| C21-H21 | 0.93 | C22-H22 | 0.93 |
| N1-O2 | 1.181(18) | N1-O1 | 1.22(2) |
| N2-S1 | 1.658(12) | N5-H5A | 0.86 |
| O3-S1 | 1.445(10) | O4-S1 | 1.393(9) |
| O1S-C1S | 1.391(19) | O1S-H1S | 0.82 |
| C1S-H1S1 | 0.96 | C1S-H1S2 | 0.96 |
| C1S-H1S3 | 0.96 | | |
| C2-C1-C6 | 120.0 | C2-C1-N1 | 119.2(12) |
| C6-C1-N1 | 120.6(11) | C3-C2-C1 | 120.0 |
| C3-C2-H2 | 120.0 | C1-C2-H2 | 120.0 |
| C2-C3-C4 | 120.0 | C2-C3-S1 | 119.7(6) |
| C4-C3-S1 | 120.1(6) | C5-C4-C3 | 120.0 |
| C5-C4-H4 | 120.0 | C3-C4-H4 | 120.0 |
| C6-C5-C4 | 120.0 | C6-C5-H5 | 120.0 |
| C4-C5-H5 | 120.0 | C5-C6-C1 | 120.0 |
| C5-C6-H6 | 120.0 | C1-C6-H6 | 120.0 |
| N2-C7-C10 | 110.6(11) | N2-C7-C8 | 106.5(11) |
| C10-C7-C8 | 112.5(12) | N2-C7-H7 | 109.0 |
| C10-C7-H7 | 109.0 | C8-C7-H7 | 109.0 |
| O5-C8-C7 | 102.7(11) | O5-C8-H8A | 111.2 |
| C7-C8-H8A | 111.2 | O5-C8-H8B | 111.2 |
| C7-C8-H8B | 111.2 | H8A-C8-H8B | 109.1 |
| N2-C9-O5 | 104.1(10) | N2-C9-C12 | 113.8(12) |
| O5-C9-C12 | 110.3(12) | N2-C9-H9 | 108.8 |
| O5-C9-H9 | 108.8 | C12-C9-H9 | 108.8 |
| N3-C10-C7 | 114.9(12) | N3-C10-H10A | 108.5 |
| C7-C10-H10A | 108.5 | N3-C10-H10B | 108.5 |
| C7-C10-H10B | 108.5 | H10A-C10-H10B | 107.5 |
| C8-O5-C9 | 109.0(10) | O4-S1-O3 | 120.2(6) |
| O4-S1-N2 | 105.7(5) | O3-S1-N2 | 106.9(6) |
| O4-S1-C3 | 107.2(5) | O3-S1-C3 | 107.9(6) |
| N2-S1-C3 | 108.5(5) | C1S-O1S-H1S | 109.5 |
| O1S-C1S-H1S1 | 109.5 | O1S-C1S-H1S2 | 109.5 |
| H1S1-C1S-H1S2 | 109.5 | O1S-C1S-H1S3 | 109.5 |
| H1S1-C1S-H1S3 | 109.5 | H1S2-C1S-H1S3 | 109.5 |

[Figure 65]

| | $U_{11}$ | $U_{22}$ | $U_{33}$ | $U_{23}$ | $U_{13}$ | $U_{12}$ |
|---|---|---|---|---|---|---|
| C1 | 0.057(11) | 0.085(12) | 0.077(12) | 0.020(10) | -0.010(9) | -0.004(10) |
| C2 | 0.060(10) | 0.077(11) | 0.056(10) | 0.015(8) | -0.007(8) | 0.013(9) |
| C3 | 0.036(8) | 0.089(11) | 0.038(9) | 0.030(8) | -0.012(7) | -0.011(7) |
| C4 | 0.062(9) | 0.083(11) | 0.036(7) | 0.014(7) | -0.009(7) | -0.002(8) |
| C5 | 0.106(13) | 0.108(13) | 0.036(7) | -0.012(8) | 0.030(9) | 0.068(11) |
| C6 | 0.086(13) | 0.120(15) | 0.050(9) | -0.020(10) | -0.060(10) | 0.002(11) |
| C7 | 0.050(8) | 0.044(8) | 0.049(8) | 0.007(7) | 0.003(6) | -0.018(6) |
| C8 | 0.063(10) | 0.062(9) | 0.067(10) | -0.012(8) | 0.003(8) | 0.023(9) |
| C9 | 0.053(9) | 0.066(10) | 0.069(10) | -0.026(8) | 0.016(8) | -0.018(8) |
| C10 | 0.080(12) | 0.041(8) | 0.082(12) | -0.009(8) | 0.028(10) | 0.003(8) |
| C11 | 0.051(8) | 0.050(8) | 0.036(7) | -0.003(7) | 0.003(7) | 0.013(7) |
| C12 | 0.031(7) | 0.089(11) | 0.035(7) | -0.015(7) | -0.027(6) | 0.016(8) |
| C13 | 0.080(11) | 0.059(10) | 0.054(9) | -0.014(9) | -0.012(9) | 0.035(10) |
| C14 | 0.108(15) | 0.070(11) | 0.068(11) | -0.015(10) | 0.021(11) | 0.062(12) |
| C15 | 0.076(5) | 0.078(5) | 0.074(5) | -0.001(3) | 0.000(3) | -0.002(3) |
| C16 | 0.046(7) | 0.050(9) | 0.057(8) | 0.003(7) | -0.006(7) | 0.003(7) |
| C17 | 0.030(7) | 0.076(11) | 0.047(8) | -0.010(8) | -0.012(6) | 0.002(7) |
| C18 | 0.059(9) | 0.047(8) | 0.050(8) | -0.013(7) | -0.013(7) | 0.004(7) |
| C19 | 0.061(10) | 0.069(10) | 0.076(12) | 0.023(9) | -0.022(9) | -0.013(9) |
| C20 | 0.085(13) | 0.113(16) | 0.043(9) | 0.018(10) | -0.013(9) | -0.032(12) |
| C21 | 0.060(11) | 0.109(14) | 0.072(12) | -0.018(11) | 0.023(10) | 0.001(11) |
| C22 | 0.078(12) | 0.074(11) | 0.077(12) | -0.002(11) | -0.021(11) | -0.015(10) |
| N1 | 0.102(13) | 0.137(15) | 0.058(10) | 0.009(10) | -0.020(9) | -0.084(11) |
| N2 | 0.036(7) | 0.045(7) | 0.056(7) | 0.001(5) | 0.027(6) | -0.031(6) |
| N3 | 0.085(9) | 0.060(8) | 0.057(8) | 0.006(7) | -0.009(7) | -0.015(8) |
| N4 | 0.067(8) | 0.057(7) | 0.071(8) | 0.001(7) | -0.004(7) | 0.011(7) |
| N5 | 0.078(10) | 0.064(9) | 0.076(9) | 0.030(7) | -0.013(8) | -0.030(8) |
| N6 | 0.043(7) | 0.034(7) | 0.056(7) | 0.001(6) | -0.027(6) | -0.010(6) |
| O1 | 0.194(18) | 0.175(16) | 0.109(13) | -0.028(12) | -0.075(12) | -0.033(14) |
| O2 | 0.101(11) | 0.178(15) | 0.083(9) | 0.021(9) | 0.006(8) | -0.067(10) |
| O3 | 0.082(7) | 0.055(6) | 0.068(7) | -0.003(5) | 0.007(6) | -0.004(6) |
| O4 | 0.071(6) | 0.071(7) | 0.046(5) | 0.006(5) | 0.023(5) | -0.004(6) |
| O5 | 0.050(6) | 0.058(6) | 0.070(6) | -0.021(5) | 0.003(5) | -0.003(5) |
| S1 | 0.051(2) | 0.062(2) | 0.058(2) | 0.0058(19) | -0.0042(18) | -0.002(2) |
| O1S | 0.099(9) | 0.098(8) | 0.063(7) | -0.019(7) | 0.018(7) | -0.012(8) |
| C1S | 0.114(15) | 0.113(17) | 0.086(13) | 0.038(12) | 0.003(12) | -0.060(14) |

[Figure 66]

|  | x/a | y/b | z/c | U(eq) |
|---|---|---|---|---|
| H2 | 1.1527 | 0.2292 | 1.1155 | 0.077 |
| H4 | 0.7852 | 0.0925 | 1.1397 | 0.075 |
| H5 | 0.7681 | 0.1731 | 1.3426 | 0.099 |
| H6 | 0.9433 | 0.2817 | 1.4319 | 0.104 |
| H7 | 0.9894 | 0.3236 | 0.9126 | 0.057 |
| H8A | 0.8229 | 0.3878 | 1.0293 | 0.077 |
| H8B | 0.7450 | 0.4245 | 0.9011 | 0.077 |
| H9 | 0.7188 | 0.0974 | 0.9027 | 0.075 |
| H10A | 0.9274 | 0.4459 | 0.7425 | 0.081 |
| H10B | 0.9820 | 0.3284 | 0.6890 | 0.081 |
| H14 | 0.4580 | 0.1991 | 0.4507 | 0.098 |
| H15A | 0.3333 | -0.0339 | 0.7582 | 0.114 |
| H15B | 0.4316 | -0.1225 | 0.8264 | 0.114 |
| H15C | 0.4554 | -0.0828 | 0.6852 | 0.114 |
| H16A | 0.3752 | 0.0808 | 0.9442 | 0.061 |
| H16B | 0.5041 | 0.1581 | 0.9453 | 0.061 |
| H18 | 0.6403 | -0.1026 | 0.9528 | 0.063 |
| H19 | 0.7301 | -0.2034 | 1.1314 | 0.083 |
| H20 | 0.6724 | -0.1498 | 1.3344 | 0.097 |
| H21 | 0.5215 | 0.0046 | 1.3575 | 0.096 |
| H22 | 0.4382 | 0.0998 | 1.1788 | 0.092 |
| H5A | 0.7745 | 0.4035 | 0.5976 | 0.088 |
| H1S | 0.2565 | 0.1140 | 0.4756 | 0.13 |
| H1S1 | 0.1324 | 0.0355 | 0.6640 | 0.156 |

|  | x/a | y/b | z/c | U(eq) |
|---|---|---|---|---|
| H1S2 | 0.0391 | 0.0726 | 0.5471 | 0.156 |
| H1S3 | 0.1348 | 0.1642 | 0.6138 | 0.156 |

[Figure 67]

| pDOS Library | | | Natural products[2] | | |
|---|---|---|---|---|---|
| Compound | npr1 | npr2 | Compound | npr1 | npr2 |
| **2a** | 0.431687 | 0.954947 | Actinonin | 0.314978 | 0.841802 |
| **3b** | 0.457578 | 0.764383 | Adriamycin | 0.28322 | 0.800172 |
| **4c** | 0.480318 | 0.950596 | AmphotericinB | 0.215551 | 0.847453 |
| **5d** | 0.425604 | 0.864353 | Apoptolidin | 0.301694 | 0.830875 |
| **6d** | 0.582658 | 0.794739 | Bleomycin | 0.404781 | 0.826205 |
| **7e** | 0.198477 | 0.978871 | BrefeldinA | 0.255142 | 0.817388 |
| **8e** | 0.110591 | 0.946567 | BrevetoxinB | 0.149647 | 0.899486 |
| **9f** | 0.279873 | 0.860449 | CalyculinA | 0.442236 | 0.896401 |
| **10f** | 0.229213 | 0.87778 | Colchicine | 0.395296 | 0.837965 |
| **11f** | 0.65839 | 0.910791 | Colchicine | 0.258193 | 0.846521 |
| **12f** | 0.488957 | 0.808504 | Colchicine | 0.458247 | 0.773003 |
| **12f** | 0.502805 | 0.714443 | Colchicine | 0.513293 | 0.755147 |
| **13f** | 0.323176 | 0.714363 | CytochalasinB | 0.431674 | 0.740608 |
| **14f** | 0.579194 | 0.668807 | Discodermolide | 0.182128 | 0.981632 |
| **15f** | 0.644331 | 0.905114 | DuocarmycinA | 0.104513 | 0.945885 |
| **16f** | 0.529740 | 0.838876 | EpothiloneA | 0.44771 | 0.804309 |
| **17f** | 0.574725 | 0.676289 | ErythromycinA | 0.485996 | 0.81381 |
| **18f** | 0.452583 | 0.828674 | Fumagillin | 0.066479 | 0.974218 |
| **19f** | 0.197015 | 0.944054 | Geldanamycin | 0.369201 | 0.725345 |
| **20f** | 0.476582 | 0.803727 | Geldanamycin | 0.392818 | 0.769442 |
| **21f** | 0.577074 | 0.839108 | GinkgolideB | 0.363537 | 0.879045 |
| **22f** | 0.473966 | 0.836454 | Lactacystin | 0.478299 | 0.938709 |
| **23f** | 0.521283 | 0.939915 | Monensin | 0.221267 | 0.91423 |
| | | | MycobactinS | 0.56741 | 0.787169 |
| | | | PenicillinG | 0.227679 | 0.84074 |
| | | | PhorbolMA | 0.403734 | 0.770927 |
| | | | PhorbolMA | 0.512005 | 0.787906 |

[Figure 68]

Natural products

| Compound | npr1 | npr2 |
|---|---|---|
| RifamycinB | 0.53483 | 0.679088 |
| RifamycinB | 0.544966 | 0.674059 |
| RifamycinB | 0.618686 | 0.762072 |
| RifamycinB | 0.524795 | 0.868426 |
| RifamycinB | 0.648821 | 0.813721 |
| RifamycinB | 0.67808 | 0.844921 |
| RifamycinB | 0.627544 | 0.817624 |
| RifamycinB | 0.60182 | 0.886052 |
| SalicylihalamideA | 0.191225 | 0.84892 |
| Staurosporine | 0.464212 | 0.664055 |
| Streptomycin | 0.335744 | 0.786998 |
| TalaromycinB | 0.186426 | 0.935125 |
| Telomestatin | 0.496427 | 0.509642 |
| TrapoxinB | 0.460215 | 0.680871 |
| Trichostatin | 0.288807 | 0.802339 |
| Vancomycin | 0.516891 | 0.626096 |
| Vincristine | 0.482176 | 0.946784 |
| Quinine | 0.303785 | 0.834042 |
| Spongistatin1 | 0.428667 | 0.817984 |
| ZaragozicAcidA | 0.287707 | 0.92077 |
| Arglabin | 0.402854 | 0.721308 |
| Artemisinin | 0.541282 | 0.644874 |
| Bestatin | 0.29757 | 0.838998 |
| CephamycinC | 0.488698 | 0.85665 |
| Coformycin | 0.298204 | 0.821609 |
| Compactin | 0.430983 | 0.716564 |
| Forskolin | 0.520873 | 0.688349 |
| Mizoribine | 0.239424 | 0.857007 |
| Plaunotol | 0.460051 | 0.90039 |
| Spergualin | 0.541169 | 0.94605 |

Natural products

| Compound | npr1 | npr2 |
|---|---|---|
| SQ26180 | 0.435835 | 0.794101 |
| Thienamycin | 0.47668 | 0.854387 |
| AvermectinB 1a | 0.278083 | 0.812448 |
| Calicheamicin | 0.227585 | 0.92033 |
| CyclosporinA | 0.418415 | 0.935663 |
| Daptomycin | 0.762741 | 0.908347 |
| EchinocandinB | 0.317238 | 0.945521 |
| FK506 | 0.377179 | 0.761235 |
| Lipstatin | 0.462998 | 0.73867 |
| MidecamycinA1 | 0.325184 | 0.904263 |
| PseudomonicAcidA | 0.380836 | 0.748719 |
| Rapamycin | 0.445581 | 0.764618 |
| Taxol | 0.437027 | 0.832107 |
| Validamycin | 0.451444 | 0.807012 |
| MycoleptodisicnA | 0.35082 | 0.758279 |
| SteenkrotinB | 0.634869 | 0.834254 |
| (+)-MuironolideA | 0.627984 | 0.847099 |
| (-)-Morphine | 0.50907 | 0.762043 |
| (-)-Lycoramine | 0.551205 | 0.560635 |
| (-)-Rocaglamide | 0.689462 | 0.890844 |
| SchilancitrilactonesB | 0.242841 | 0.882821 |
| DaphniglaucinC | 0.797208 | 0.883075 |
| DaphnicyclidinA | 0.45685 | 0.651231 |
| (-)-DaphmanidinA | 0.577477 | 0.720988 |
| Anibamine | 0.690921 | 0.808847 |
| Radicicol | 0.490589 | 0.823386 |

[Figure 69]

FDA-approved drugs embedded with pyrimidine moieties[a]

| Compound | npr1 | npr2 |
|---|---|---|
| Lamivudine | 0.245638 | 0.883881 |
| Raltegravir | 0.357692 | 0.772534 |
| Imatinib | 0.670512 | 0.713467 |
| Erlotinib | 0.344318 | 0.888863 |
| Lapatinib | 0.245018 | 0.832311 |
| Rosuvastatin | 0.221782 | 0.838978 |
| Ocinaplon | 0.246698 | 0.771762 |
| Zaleplon | 0.285975 | 0.826159 |
| Indiplon | 0.275805 | 0.767635 |
| Sildenafil | 0.491575 | 0.734667 |
| Avanafil | 0.396445 | 0.784796 |
| Ceritinib | 0.359299 | 0.988453 |
| Pyrimethamine | 0.406723 | 0.697858 |
| Trimethoprim | 0.254044 | 0.862894 |
| Zidovudine | 0.264752 | 0.939218 |

[Figure 70]
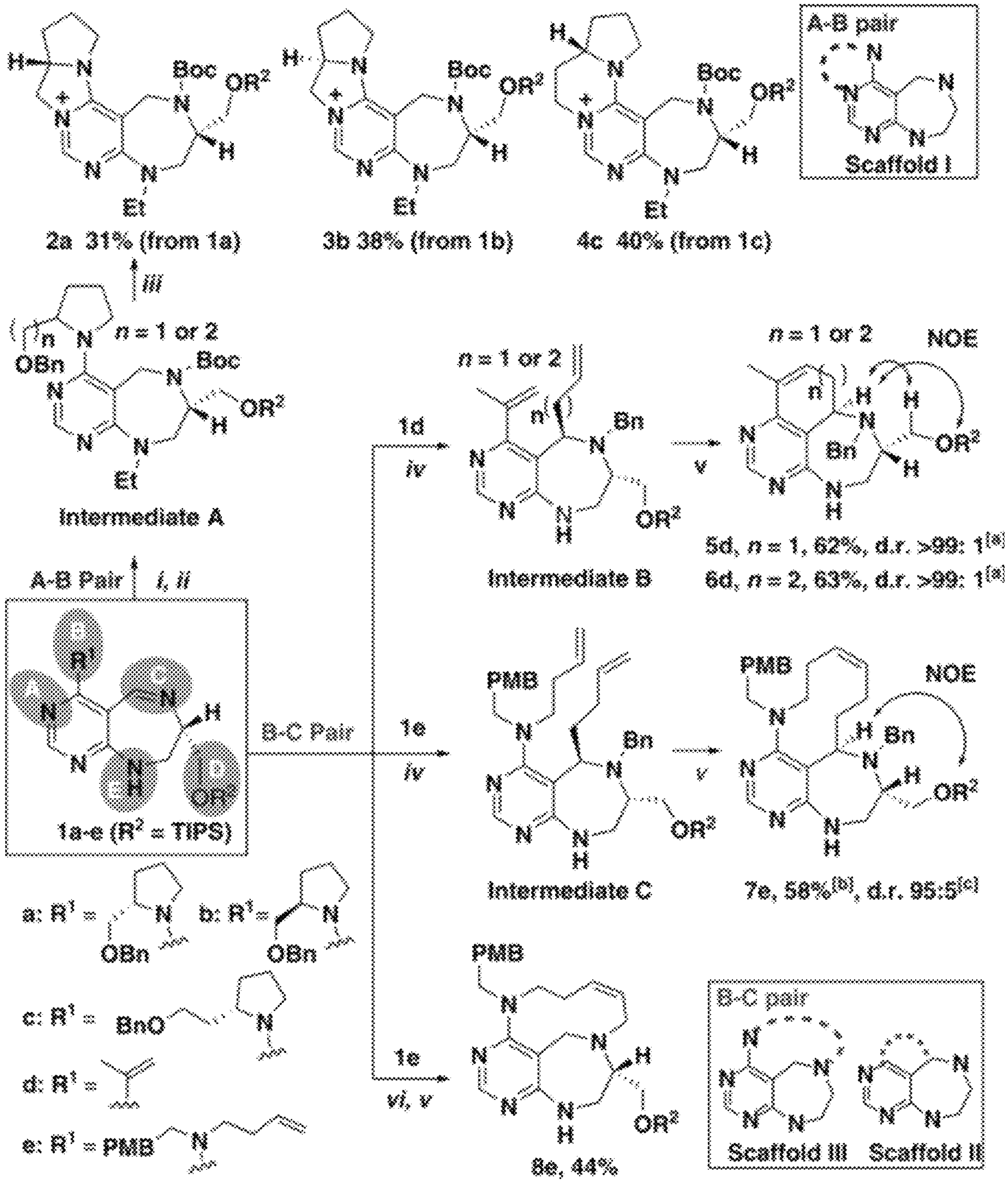

[Figure 71]
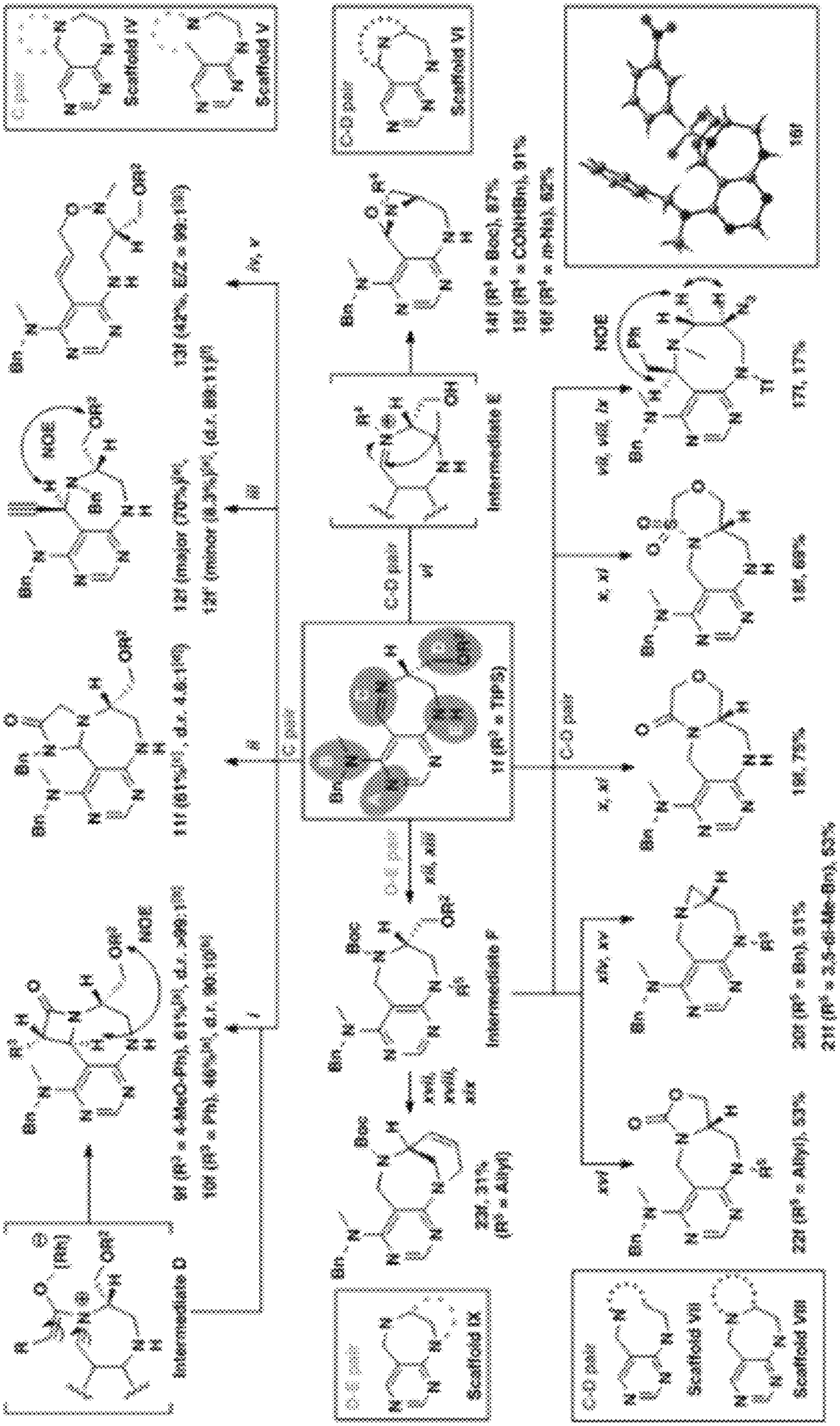

PYRIMIDINE DERIVATIVE COMPOUND, PHARMACEUTICALLY ACCEPTABLE SALT THEREOF, PREPARATION PROCESS THEREOF, AND PHARMACEUTICAL COMPOSITION USING THE SAME

CROSS-REFERENCES TO RELATED APPLICATIONS

This application is a U.S. national phase application, pursuant to 35 U.S.C. § 371, of PCT/KR2017/010120, filed Sep. 15, 2017, designating the United States, which claims priority to Korean Application No. 10-2016-0127045, filed Sep. 30, 2016. The entire contents of the aforementioned patent applications are incorporated herein by this reference.

TECHNICAL FIELD

The present invention is related to a novel pyrimidine derivative compound or a pharmaceutically acceptable salt thereof, a process for preparing the same, and a pharmaceutical composition using the same.

BACKGROUND ART

Leucyl-tRNA synthetase (LRS) catalyses the conjugation of Leucine (Leu) to its cognate tRNA to form an aminoacyl-tRNA, which serves as a precursor for protein biosynthesis. That is, LRS plays a canonical role in protein biosynthesis. Further, it was known that four types of Rag proteins are expressed in human wherein RagD alone is interacted with LRS.

To investigate specific modulators for targets such as protein-protein interaction (hereinafter, 'PPI') based on the mechanism, it was attempted to identify novel chemical inhibitors of the LRS-Ras-related GTP-binding protein D (RagD) interaction for the target regulation of rapamycin complex (mTORC1) pathway—a dominant effector that regulates cellular growth, metabolism, proliferation, and survival. Upon activation of mTORC1 by multiple upstream inputs such as growth factors, energy status, and amino acids, particularly the branched-chain amino acid, leucine (Leu), mTORC1 plays a crucial role in triggering eukaryotic cell growth and proliferation through stimulating protein biosynthesis and other anabolic processes while suppressing a catabolic process, for example, autophagy. Consequently, the dysregulation of mTORC1 accelerates biological pathways that could lead to cancer cell growth, survival, and proliferation. Accordingly, to find a specific and selective inhibitor of mTORC1 is a very important purpose for treating a cancer.

Currently, the LRS-RagD interaction and human LRS and RagD have not yet been fully characterized while neither method nor material for inhibiting the binding between LRS and RagD was known. Given this, the discovery of novel small-molecule PPI inhibitors of LRS and RagD could shed light on the molecular mechanism of mTORC1 activation in a nutrition-dependent manner.

Traditional synthetic organic chemistry has been advanced with the development of target-oriented synthesis. Many organic chemists have conceived and developed various new reactions through the synthesis of diverse natural products. Since the target-oriented synthesis is configured to target and synthesize a specific natural product, the obtained compound may be represented as one point in view of a compound structure space. Thus, target oriented synthesis seems to be very limited in terms of the diversity of compound.

Many efforts have thus been made to track down more physiologically active compounds by improving specific chemical properties of the obtained compound, resulting in the advent and development of combinatorial chemical synthesis.

Combinatorial chemical synthesis is a new synthetic method for the development of new materials. Whereas conventional organic synthesis methods can require a single reaction for the synthesis of one kind of compound, combinatorial chemical synthesis is a highly efficient chemical synthesis to synthesize more various and numerous compounds at the same time or to automate the multi-step synthetic process. With the introduction of combinatorial chemical synthesis, it has become easier to screen biological hit and lead compounds of new structures and to optimize the structure and activity thereof. Combinatorial chemical synthesis has been mainly studied in medicinal chemistry, particularly greatly contributing to the study of structure-activity relationship, and also has allowed for various substitution reactions in a specific skeletal structure, ensuring diversity of compounds.

Developed as a different concept, diversity-oriented synthesis is configured to synthesize a collection of structurally-diverse compounds distributed in a wide range of the compound structure space and then to search for new various physiologically active compounds through high throughput screening (HTS).

In diversity-oriented synthesis, compounds having different core skeletons can be prepared at the same time, and can be constructed into a library, whereby various different active compounds can be identified by various screening methods.

Korean patent publication No. 10-2012-0093940 discloses a compound having a structure of pyrimidodiazepine. However, this is silent on the inhibition activity of the binding between LRS and RagD.

Accordingly, based on diversity-oriented synthesis, the present inventors have synthesized a new pyrimidine derivative compound having an activity inhibiting the binding between LRS and RagD to arrive in the present invention.

DISCLOSURE OF INVENTION

Technical Problem

The purpose of the present invention is to provide a novel pyrimidine derivative compound or a pharmaceutically acceptable salt thereof.

The purpose of the present invention is to provide a process for preparing the novel pyrimidine derivative compound or a pharmaceutically acceptable salt thereof.

The purpose of the present invention is to provide a pharmaceutical composition using the novel pyrimidine derivative compound or a pharmaceutically acceptable salt thereof.

Solution to Problem

The present invention provides a pyrimidine derivative compound represented by any one of formulas I to IX:

[Formula I]

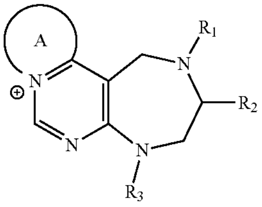

wherein A forms a heterobicyclic ring together with adjacent N and C atoms wherein the heterobicyclic ring is an 8- to 9-membered bicyclic ring which may contain 1 to 3 nitrogen atoms; $R_1$ is -Boc (tert-butyloxycarbonyl) or a benzyl group (Bn); $R_2$ is —$CH_2$—O-TIPS; and $R_3$ is hydrogen, a $C_1$ to $C_3$ alkyl group, an allyl group, -Tf, a $C_1$ to $C_3$ alkyl benzyl, or

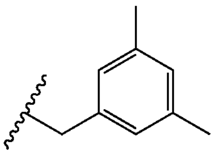

;

[Formula II]

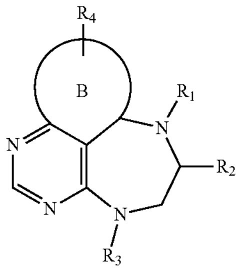

wherein B forms a 6- to 10-membered ring together with adjacent 2 to 3 C atoms wherein the ring may contain 1 to 3 nitrogen atoms; $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl group, or

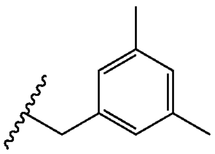

;

and $R_4$ is a $C_1$ to $C_3$ alkyl group or —$CH_2$-PMB;

[Formula III]

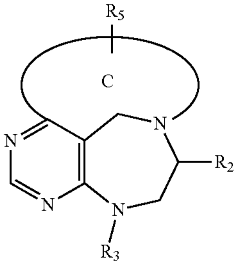

wherein C forms a 10- to 14-membered ring together with adjacent N and C atoms wherein the ring may contain 1 to 3 nitrogen atoms; $R_2$ is —$CH_2$—O-TIPS; $R_3$ is hydrogen, a $C_1$ to $C_3$ alkyl group, an allyl group, -Tf, a $C_1$ to $C_3$ alkyl benzyl group, or

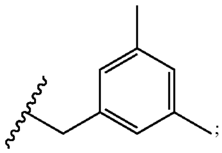 [SMILES: *Cc1cc(C)cc(C)c1]

;

and $R_5$ is a $C_1$ to $C_3$ alkyl group or —$CH_2$-PMB;

[Formula IV]

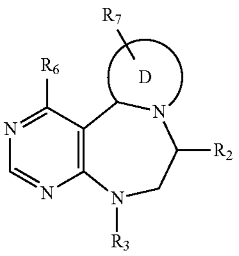

wherein D forms a 4- to 6-membered cyclic imide together with adjacent N and C atoms wherein the cyclic imide is a ring which may contain 1 to 3 nitrogen atoms; $R_2$ is —$CH_2$—O-TIPS; $R_3$ is hydrogen, a —$C_1$ to $C_3$ alkyl group, an allyl group, -Tf, a $C_1$ to $C_3$ alkyl benzyl group, or

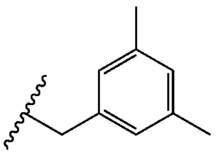

;

$R_6$ is

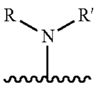

wherein R and R' are each independently a benzyl group or a $C_1$ to $C_3$ alkyl group; and $R_7$ is a benzyl group, a phenyl group, or

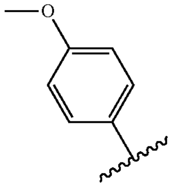

;

[Formula V]

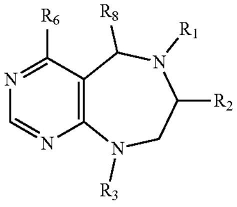

wherein $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl group, or

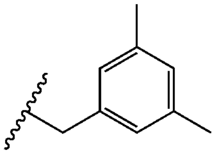

;

$R_6$ is

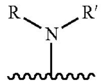

wherein R and R' are each independently a benzyl group or a $C_1$ to $C_3$ alkyl group; and $R_8$ is an acetylene group;

[Formula VI]

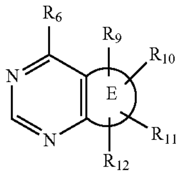

wherein E forms an 8- to 10-membered heterocyclic ring together with adjacent two C atoms wherein the heterocyclic ring is a saturated or unsaturated ring which contains at least two of 2 to 4 nitrogen atoms and 1 to 3 oxygen atoms; $R_6$ is

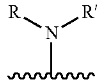

wherein R and R' are each independently a benzyl group or a $C_1$ to $C_3$ alkyl group; and $R_9$ to $R_{12}$ are each independently hydrogen, a methyl group, an azide group, a benzyl group, —$CH_2$—O-TIPS or -Tf;

[Formula VII]

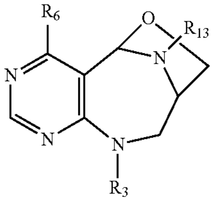

wherein $R_3$ is hydrogen, a —$C_1$ to $C_3$ alkyl group, an allyl group, -Tf, a $C_1$ to $C_3$ alkyl benzyl group, or

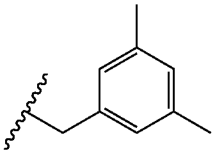

;

$R_6$ is

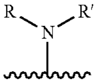

wherein R and R' are each independently a benzyl group or a $C_1$ to $C_3$ alkyl group; and $R_{13}$ is -Boc, —CONHBn, -m-Ns;

[Formula VIII]

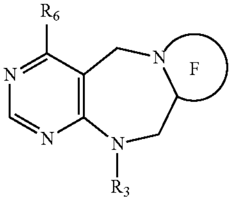

wherein F is —X—$(CH_2)$n-(O—$CH_2$)m- and forms a 3- to 6-membered heterocyclic ring together with adjacent N and C atoms wherein X is

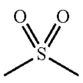

,

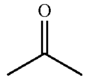

or —$CH_2$—, and n and m are respectively an integer from 0 to 2; $R_3$ is hydrogen, a —$C_1$ to $C_3$ alkyl group, an allyl group, -Tf, a $C_1$ to $C_3$ alkyl benzyl group, or

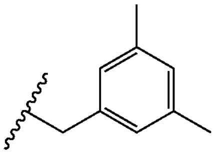

;

and $R_6$ is

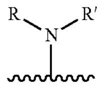

wherein R and R' are each independently a benzyl group or a $C_1$ to $C_3$ alkyl group;

[Formula IX]

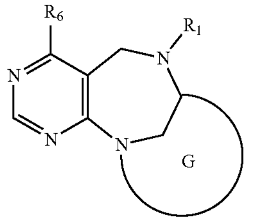

wherein G forms a 6- to 9-membered heterocyclic ring together with adjacent N and C atoms wherein the heterocyclic ring is an unsaturated heterocyclic ring which contains 2 to 3 nitrogen atoms; $R_1$ is -Boc or a benzyl group; and $R_6$ is

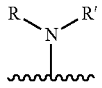

wherein R and R' are each independently a benzyl group or a $C_1$ to $C_3$ alkyl group;

or a pharmaceutically acceptable salt thereof.

The present invention provides a process for preparing the pyrimidine derivative compound of formulas I to IX or a pharmaceutically acceptable salt thereof, characterized in comprising:

step 1 for preparing an intermediate substance, tert-(S)-(1-(6-chloro-5-formylpyrimidin-4-yl)amino)-3-((triisopropylsilyl)oxy)propan-2-yl)carbamate;

step 1a for preparing a starting material represented by formula 1 by reacting the intermediate substance prepared in step 1 with cyclic amine or tetrakis palladium; and

[Formula 1]

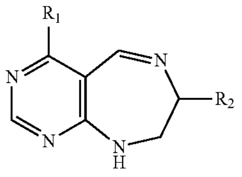

wherein $R_1$ is

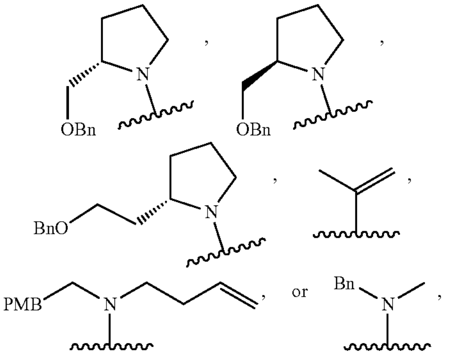

, , , , or , $R_2$ is —$CH_2$—O-TIPS;

step 2 for preparing a desired compound from the starting material prepared in step 1a.

The present invention provides a composition for treating cancer comprising the pyrimidine derivative compound of formulas I to IX or a pharmaceutically acceptable salt thereof as an active ingredient.

Effect of Invention

The novel pyrimidine derivative compound of the present invention exerts excellent toxicity against cancer cells, based on which it can be used as a treating agent for cancer diseases. Further, the compound can be synthesized based on the preparation process according to the present invention in a relatively simple manner.

BRIEF DESCRIPTION OF THE DRAWINGS

FIG. 1 shows diversity-oriented synthetic strategy with pyrimidine as a privileged structure.

a) shows pyrimidine-containing bioactive compounds.

b) shows chemical space occupied by 3-D space structure of pyrimidine and pyrimidine-containing tricyclic 6/6/6 and 6/7/6 systems in terms of diversity and complexity of 3-D space structure.

c) shows synthetic strategy of pyrimidodiazepine- or pyrimidine-containing pyrimidine derivative.

FIG. 2 shows chemoinformatic analysis for structural diversity and complexity of 3D of pDOS library.

a) depicts 16 core skeletons containing pyrimidine- or pyrimidodiazepine.

b) depicts overlay of energy-minimized conformers of 16 core skeletons containing the pyrimidine structure.

c) is a PMI analysis drawing. The 3D structure of pDOS library in red squares was quantitatively compared with that of 15 FDA-approved drugs containing pyrimidine moiety in blue squares and bioactive natural products in grey dots.

FIG. 3 shows X-ray structure of compound 16f (Deposition number in Cambridge Structural Database: CCDC1500586).

FIG. 4 shows pyrimidine diversity-oriented synthesis (pDOS) library used in PMI analysis.

FIG. 5 shows FDA-approved drugs embedded with pyrimidine moieties.

FIGS. 6A, 6B, 6C, 7A, 7B, 8A, 8B, 9A, 9B, 9C, 10A, 10B, 10C, 11A, 11B, 12A, 12B, 13A, 13B, 13C, 14A, and 14B depict analysis on COSY, HSQC and NOE spectra for some of desired compounds (i.e., compounds 5d, 6d, 7e, 9f, 10f, 12f, 12f, 17f, 17f).

FIG. 15 relate to experiments on discovery of chemical modulator for LRS-RagD interaction a) is a diagram relevant to experiments on discovery of chemical modulator for LRS-RagD interaction. It shows noncanonical role of LRS and Leucine-loaded LRS binds to RagD, which promotes the translocation of mTORC1 to lysosomal surface and subsequent activation.

b) displays how LRS-RagD interaction affects mTORC1, showing the dose-response curves in ELISA of 20f and 21f wherein the results represent the mean of three replicates. This means that 20f and 21f inhibit the LRS-RagD interaction in a dose-dependent manner.

c) Effects of 20f and 21f on mTORC1 signalling pathway. HEK293T cells were treated with 20 μM of 20f and 21f for 3 h, followed by western blotting to obtain the result as depicted. Cells deprived of leucine for 3 h was used as a control. The graph shows a relative level of phospho-T389 S6K1 to a DMSO-treated experimental group. The result represents the mean of five replicates. It was found that the cells treated with 21f showed a reduced amount of phospho-T389 S6K1, similarly to cells deprived of leucine, to inactivate mTORC1. The reduction degree of 20f is less than that of 21f.

d) Effects of 21f on mTORC1 signalling pathway. HEK293Tcells were treated with 20, 10, 5 and 1 μM of compound 21f for 3 h. Cells deprived of leucine for 3 h and cells treated with 200 nM of rapamycin for 3 h were used as a control. Phospho-T389 S6K1, phospho-S757 ULK1, and phospho-S65 4E-BP1 were reduced in cells treated with 21f in a dose-dependent manner, which shows that 21f well inhibits mTORC1. Contrary to this, no effects were found on phospho-T172 AMPKα and phospho-S473 Akt, from which it was confirmed that the compound selectively affects only mTORC1, without any effects on AMPK signaling pathways or mTORC2 signaling pathways.

e) Effects of 21f on mTORC1 within cells were analyzed for 0-24 h. HEK293T cells were treated with 10 μM of 21f. Phospho-T389 S6K1, phospho-S757 ULK1, and phospho-S65 4E-BP1 were reduced in cells treated with 21f as time passed. The effect lasted for at least about 12 h. Further, no effects were found on phospho-T172 AMPKα and phospho-S473 Akt, from which it was confirmed that the compound selectively affects only mTORC1, without any effects on AMPK signaling pathways or mTORC2 signaling pathways.

f) Analysis results of surface plasmon resonance (SPR) spectroscopy. 21f showed its concentration-dependent binding to LRS. The concentration of 21f as experimented were 1, 2.5, 5, 10, 12.5, 15, 17.5 and 20 μM. The curve fittings are shown in black. The results represent the mean of two replicates.

FIG. 16 shows autophagic activation of compound 21f and its inhibition activity of cell division.

a) Western blot analysis of LC3 and p62. HeLa cells were treated with 200 nM of rapamycin (Rap), 10 nM of bafilomycin (Baf), or 20 μM of 21f for 6 h, followed by western blotting. The graph shows analysis results of western blotting of experimental and control groups based on LC3 I/LC3 II ratio and p62 level of the DMSO group. The results represent the mean of at least three replicates. Comparing with the DMSO group, rapamycin activates autophagic activity, lowering LC3 I/LC3 II ratio and reducing p62 level. Bafilomycin is a compound inhibiting autophagic activity by preventing formation of autolysosome. Similarly to rapamycin, 21f activates autophagic activity, lowering LC3 I/LC3 II ratio and reducing p62 level.

b) Schematic depiction of mCherry-GFP-LC3 fluorescence image system. The pH decreases with lysosome fusion to autophagosome, thereby quenching GFP fluorescence while mCherry fluorescence not sensitive to pH is maintained.

c) depicts mCherry and GFP fluorescence images. mCherry-GFP-LC3 genes are expressed in HeLa cells, treated with 200 nM of Rap, 10 nM of Baf, or 20 μM of 21f for 6 h, followed by obtaining an image through fluorescence microscope. Scale bar is 15 mm. Rapamycin activates autophagic activity, which results in combining lysosome with autophagosome to lower pH and lose GFP fluorescence, whereby red fluorescence of mCherry fluorescence alone remained. Bafilomycin inhibits combining lysosome with autophagosome, which results in maintaining pH and then GFP fluorescence, whereby mCherry fluorescence overlaps with GFP fluorescence to exert yellow color. Similarly to rapamycin, 21f exerts red fluorescence.

d) shows the results where cellular division level in HEK293T cells was measured by BrdU assay. The Leu-deprived cells were used as a control. In an experimental group treated with 21f, cellular division was inhibited as treatment time passed.

FIG. 17 shows dose-dependent graphs in ELISA with compounds 14f, 15f, 18f, 19f, 22f and 23f. Compounds embedded with pyrimidodiazepine skeleton other than 20f and 21f did not inhibit the LRS-RagD interaction in a dose-dependent manner.

FIG. 18 shows the results of western blotting of DMSO and Rapamycin (Rap) as a control and compound 21f.

a) shows the results based on the experiment procedure of FIG. 15*d*, provided that it was carried out in Ca Ski cells.

b) shows the results based on the experiment procedure of FIG. 15*d*, provided that it was carried out in DU145 cells.

The results from the two cancer cell lines were same as those from HEK293T cells.

c) shows the results based on the experiment procedure of FIG. 15*e*, provided that being treated with 500 nM of rapamycin.

d) shows the results based on the experiment procedure of FIG. 15*e*, provided that being treated with DMSO.

FIGS. 19A, 19B, and 19C depict SPR analysis results showing concentration-dependent binding of compounds 14f, 19f, and 21f to purified LRS. 14f and 19f did not bind to LRS in a concentration-dependent manner, which is different from 21f.

FIGS. 20A, 20B, 21A, 21B, 21C, 22, 23, 24, 25A, 25B, and 25C depict LC-MS analysis results on compounds 9f and 10f, intermediate B (n=1 or 2), 13f, intermediate C.

FIGS. 26A, 26B, 27A, 27B, 28A, 28B, 29A, 29B, 30A, 30B, 31A, 31B, 32A, 32B, 33A, 33B, 34A, 34B, 35A, 35B, 36A, 36B, 37A, 37B, 38A, 38B, 39A, 39B, 40A, 40B, 41A, 41B, 42A, 42B, 43A, 43B, 44A, 44B, 45A, 45B, 46A, 46B, 47A, 47B, 48A, 48B, 49, 50A, 50B, 51A, 51B, 52A, 52B, 53A, 53B, 54A, 54B, 55A, 55B, 56A, 56B, 57A, 57B, 58A, 58B, 59A, 59B, 60A, 60B, 61A, 61B, 62A, and 62B depict $^{1}H$ and $^{13}C$ NMR analysis results on desired compounds of the present invention (i.e., compound 2a to 23f), intermediate substance, or intermediate.

FIG. 63 shows crystal structure data of compound 16f.

FIG. 64 shows bond lengths (Å) and bond angles)(°) for compound 16f.

FIG. 65 shows anisotropic atomic displacement parameters ($Å^2$) for compound 16f. The anisotropic atomic displacement factor was applied for the function: $-2\pi^2[h^2 a^{*2} U_{11} + \ldots + 2 h k a^* b^* U_{12}]$.

FIG. 66 shows hydrogen atomic coordinates and isotropic atomic displacement parameters ($Å^2$) for compound 16f.

FIGS. 67, 68, and 69 show normalized PMI ratios of pDOS library, natural products and FDA-approved drugs embedded with pyrimidine moieties.

FIGS. 70 and 71 depict a reaction scheme (Scheme 1) and another reaction scheme (Scheme 2), respectively, of a preparation process of an embodiment of the present invention.

DETAILED DESCRIPTION OF THE INVENTION

The present invention is related to a novel pyrimidine derivative compound, a process for preparing the novel pyrimidine derivative compound, and a pharmaceutical composition using the novel pyrimidine derivative compound.

Specifically, a pyrimidine derivative compound of the present invention comprises a pyrimidine derivative compound represented by any one of formulas I to IX:

[Formula I]

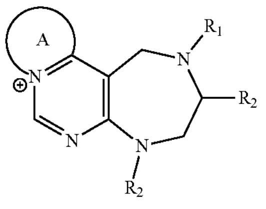

wherein A forms a heterobicyclic ring together with adjacent N and C atoms wherein the heterobicyclic ring is an 8- to 9-membered bicyclic ring which may contain 1 to 3 nitrogen atoms; $R_1$ is -Boc (tert-butyloxycarbonyl) or a benzyl group (Bn); $R_2$ is —$CH_2$—O-TIPS; and $R_3$ is hydrogen, a $C_1$ to $C_3$ alkyl group, an allyl group, -Tf, a $C_1$ to $C_3$ alkyl benzyl, or

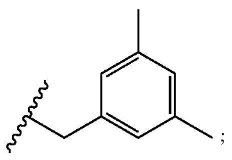 [SMILES: *Cc1cc(C)cc(C)c1]

-continued

[Formula II]

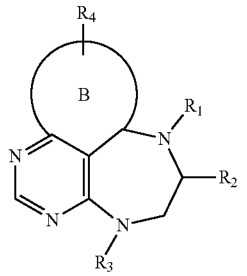

wherein B forms a 6- to 10-membered ring together with adjacent 2 to 3 C atoms wherein the ring may contain 1 to 3 nitrogen atoms; $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl group, or

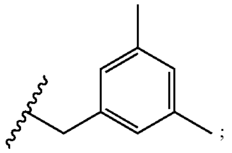 [SMILES: *Cc1cc(C)cc(C)c1]

and $R_4$ is a $C_1$ to $C_3$ alkyl group or —$CH_2$-PMB;

[Formula III]

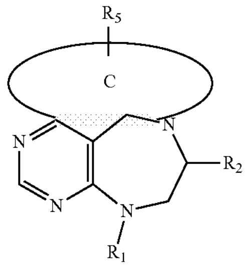

wherein C forms a 10- to 14-membered ring together with adjacent N and C atoms wherein the ring may contain 1 to 3 nitrogen atoms; $R_2$ is —$CH_2$—O-TIPS; $R_3$ is hydrogen, a $C_1$ to $C_3$ alkyl group, an allyl group, -Tf, a $C_1$ to $C_3$ alkyl benzyl group, or

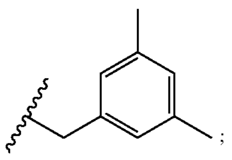 [SMILES: *Cc1cc(C)cc(C)c1]

and $R_5$ is a $C_1$ to $C_3$ alkyl group or —$CH_2$-PMB;

[Formula IV]

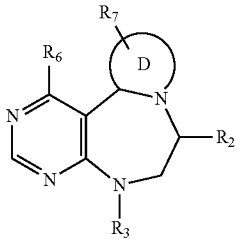

wherein D forms a 4- to 6-membered cyclic imide together with adjacent N and C atoms wherein the cyclic imide is a ring which may contain 1 to 3 nitrogen atoms; $R_2$ is —$CH_2$—O-TIPS; $R_3$ is hydrogen, a —$C_1$ to $C_3$ alkyl group, an allyl group, -Tf, a $C_1$ to $C_3$ alkyl benzyl group, or

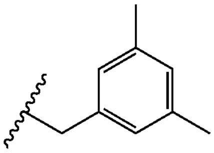 ;

$R_6$ is

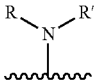

wherein R and R' are each independently a benzyl group or a $C_1$ to $C_3$ alkyl group; and $R_7$ is a benzyl group, a phenyl group, or

[Formula V]

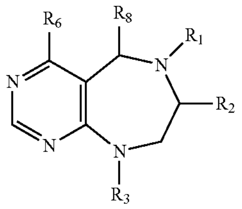

wherein $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl group, or

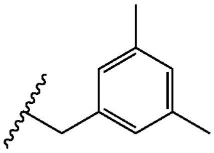 ;

$R_6$ is

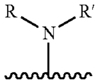

wherein R and R' are each independently a benzyl group or a $C_1$ to $C_3$ alkyl group; and $R_8$ is an acetylene group;

[Formula VI]

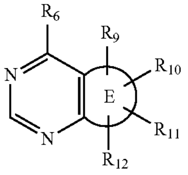

wherein E forms an 8- to 10-membered heterocyclic ring together with adjacent two C atoms wherein the heterocyclic ring is a saturated or unsaturated ring which contains at least two of 2 to 4 nitrogen atoms and 1 to 3 oxygen atoms; $R_6$ is

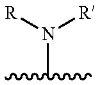

wherein R and R' are each independently a benzyl group or a $C_1$ to $C_3$ alkyl group; and $R_9$ to $R_{12}$ are each independently hydrogen, a methyl group, an azide group, a benzyl group, —$CH_2$—O-TIPS or -Tf;

[Formula VII]

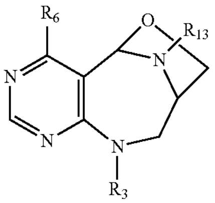

wherein $R_3$ is hydrogen, a —$C_1$ to $C_3$ alkyl group, an allyl group, -Tf, a $C_1$ to $C_3$ alkyl benzyl group, or

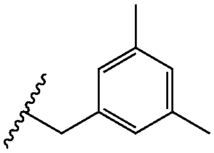 ;

$R_6$ is

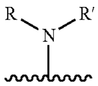

wherein R and R' are each independently a benzyl group or a $C_1$ to $C_3$ alkyl group; and $R_{13}$ is -Boc, —CONHBn, -m-Ns;

[Formula VIII]

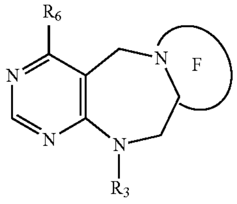

wherein F is —X—$(CH_2)$n-(O—$CH_2$)m- and forms a 3- to 6-membered heterocyclic ring together with adjacent N and C atoms wherein X is

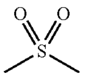 , 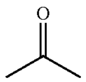

or —$CH_2$—, and n and m are respectively an integer from 0 to 2; $R_3$ is hydrogen, a —$C_1$ to $C_3$ alkyl group, an allyl group, -Tf, a $C_1$ to $C_3$ alkyl benzyl group, or

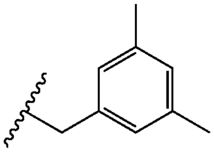 ;

and $R_6$ is

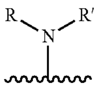

wherein R and R' are each independently a benzyl group or a $C_1$ to $C_3$ alkyl group;

[Formula IX]

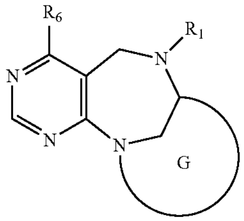

wherein G forms a 6- to 9-membered heterocyclic ring together with adjacent N and C atoms wherein the heterocyclic ring is an unsaturated heterocyclic ring which contains 2 to 3 nitrogen atoms; $R_1$ is -Boc or a benzyl group; and $R_6$ is

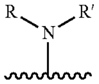

wherein R and R' are each independently a benzyl group or a $C_1$ to $C_3$ alkyl group;

or a pharmaceutically acceptable salt thereof.

Further, the present invention comprises a compound represented by any one of formulas I-1 to IX-1:

[Formula I-1]

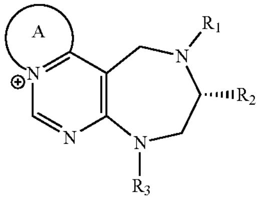

wherein A forms a heterobicyclic ring together with adjacent N and C atoms wherein the heterobicyclic ring is an 8- to 9-membered bicyclic ring which may contain 1 to 3 nitrogen atoms; $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl, or

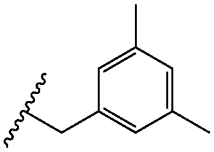 ;

[Formula II-1]

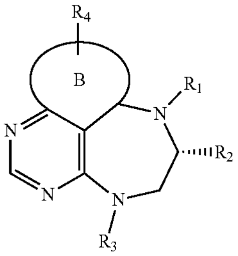

wherein B forms a 6- to 10-membered ring together with adjacent 2 to 3 C atoms wherein the ring may contain 1 to 3 nitrogen atoms; $R_1$ is -Boc or a benzyl group; $R_2$ is —$CH_2$—O-TIPS; and $R_3$ is hydrogen, a $C_1$ to $C_3$ alkyl group, an allyl group, -Tf, a $C_1$ to $C_3$ alkyl benzyl group, or

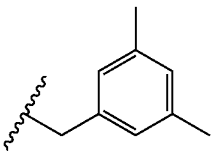 ;

and $R_4$ is $C_1$ to $C_3$ alkyl group or —$CH_2$-PMB;

[Formula III-1]

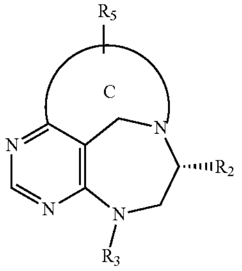

wherein a C forms a 10- to 14-membered ring together with adjacent N and C atoms wherein the ring may contain 1 to 3 nitrogen atoms; $R_2$ is —$CH_2$—O-TIPS; $R_3$ is hydrogen, a $C_1$ to $C_3$ alkyl group, an allyl group, -Tf, a $C_1$ to $C_3$ alkyl benzyl group, or

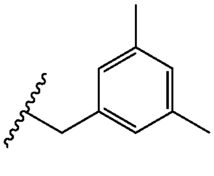

;

and $R_5$ is $C_1$ to $C_3$ alkyl group or —$CH_2$-PMB;

[Formula IV-1]

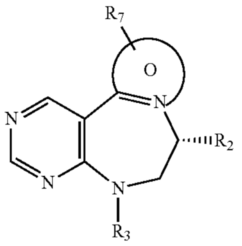

wherein D forms a 4- to 6-membered cyclic imide together with adjacent N and C atoms wherein the cyclic imide is a ring which may contain 1 to 3 nitrogen atoms; $R_2$ is —$CH_2$—O-TIPS; $R_3$ is hydrogen, a —$C_1$ to $C_3$ alkyl group, an allyl group, -Tf, a $C_1$ to $C_3$ alkyl benzyl group, or

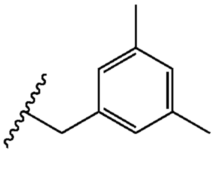

;

$R_6$ is

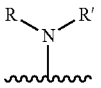

wherein R and R' are each independently a benzyl group or a $C_1$ to $C_3$ alkyl group; $R_7$ is a benzyl group, a phenyl group, or

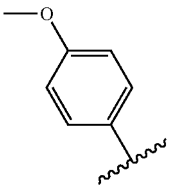

;

[Formula V-1]

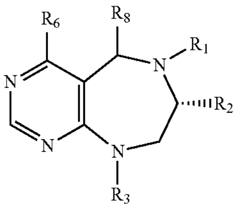

wherein $R_1$ is -Boc or a benzyl group; $R_2$ is —$CH_2$—O-TIPS; and $R_3$ is hydrogen, a —$C_1$ to $C_3$ alkyl group, an allyl group, -Tf, a $C_1$ to $C_3$ alkyl benzyl group, or

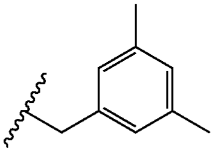

;

$R_6$ is

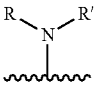

wherein R and R' are each independently a benzyl group or a $C_1$ to $C_3$ alkyl group; and $R_8$ is an acetylene group;

[Formula VII-1]

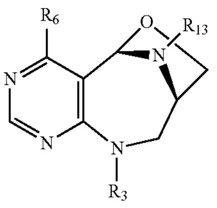

wherein $R_3$ is hydrogen, a —$C_1$ to $C_3$ alkyl group, an allyl group, -Tf, a $C_1$ to $C_3$ alkyl benzyl group, or

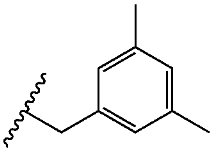

;

$R_6$ is

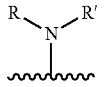

wherein R and R' are each independently a benzyl group or a $C_1$ to $C_3$ alkyl group; and $R_{13}$ is -Boc, —CONHBn, -m-Ns;

[Formula VIII-1]

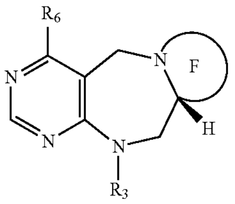

wherein F is —X—$(CH_2)$n-(O—$CH_2$)m- and forms a 3- to 6-membered heterocyclic ring together with adjacent N and C atoms wherein X is

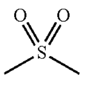
,
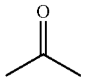

or —$CH_2$—, and n and m are respectively an integer from 0 to 2; $R_3$ is hydrogen, a —$C_1$ to $C_3$ alkyl group, an allyl group, -Tf, a $C_1$ to $C_3$ alkyl benzyl group, or

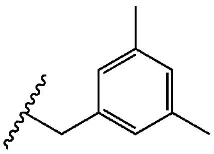
;

and $R_6$ is

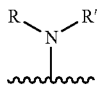

wherein R and R' are each independently a benzyl group or a $C_1$ to $C_3$ alkyl group;

[Formula IX-1]

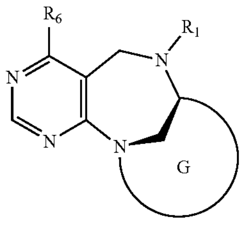

wherein G forms a 6- to 9-membered heterocyclic ring together with adjacent N and C atoms wherein the heterocyclic ring is an unsaturated heterocyclic ring which contains 2 to 3 nitrogen atoms; $R_1$ is -Boc or a benzyl group; and $R_6$ is

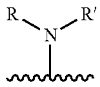

wherein R and R' are each independently a benzyl group or a $C_1$ to $C_3$ alkyl group;

or a pharmaceutically acceptable salt thereof.

Specifically, the compound of the present invention comprises a compound represented by any one of the formulas:

2a

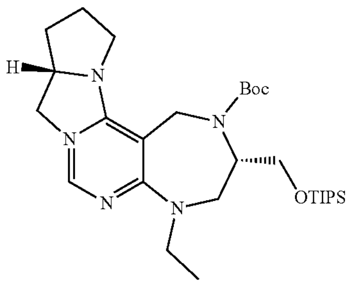

3b

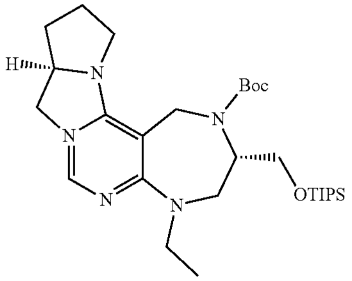

4c

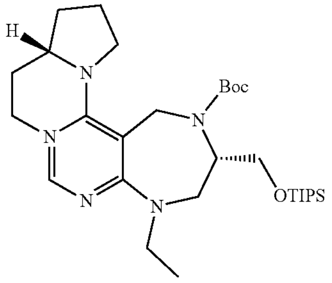

5d

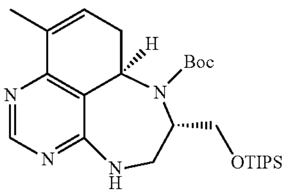

-continued
6d
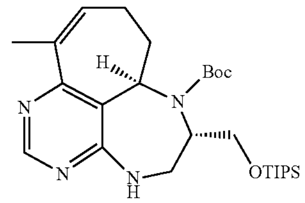
7e
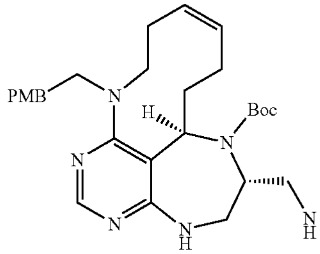
8e
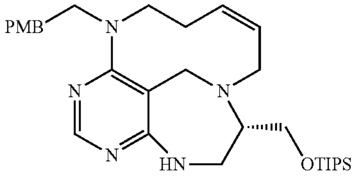
9f
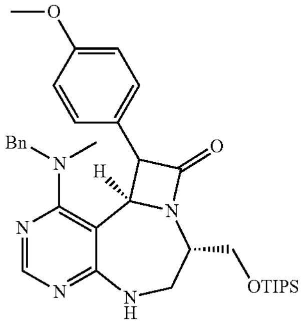
10f
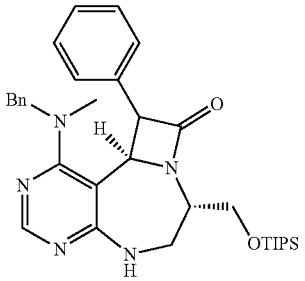
11f
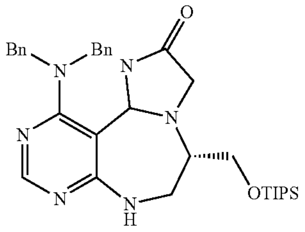
-continued
12f
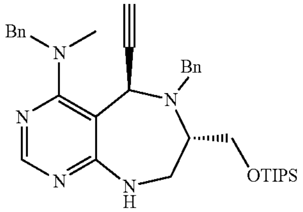
12f
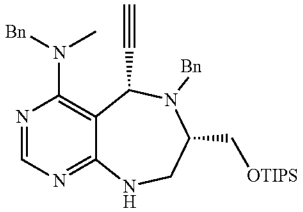
13f
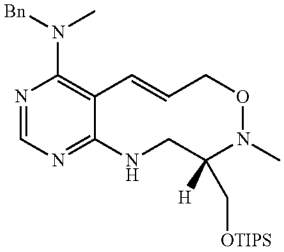
14f
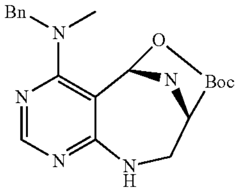
15f
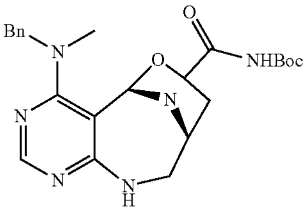
16f
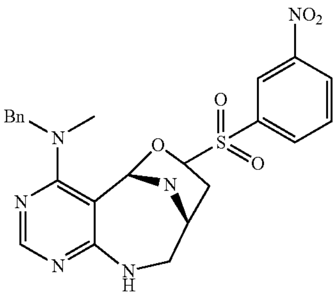

-continued

17f

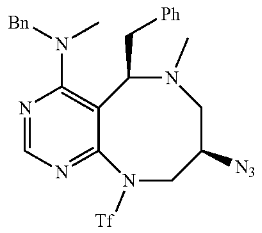

18f

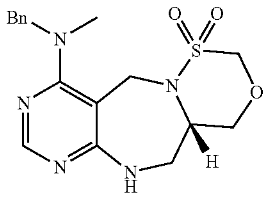

19f

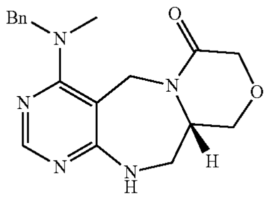

20f

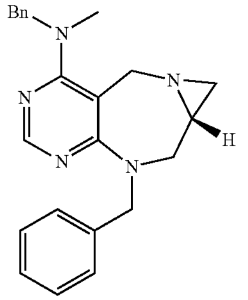

21f

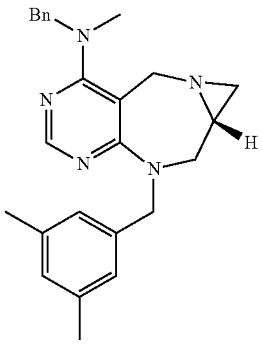

22f

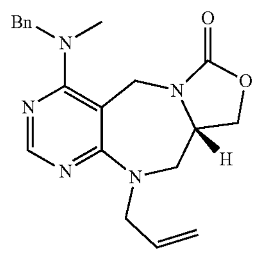

-continued

23f

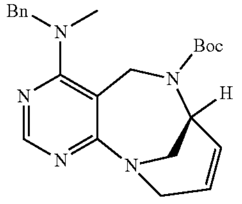

or a pharmaceutically acceptable salt thereof.

In the formulas of the present invention, A to G comprise at least one atom selected from C, N, S and O, and comprise all substituents to form a structure of a compound of formulas I to IX. Specifically, they comprise all substituents to form a structure of compounds 2a, 3b, 4c, 5d to 6d, 7e to 8e, and/or 9f to 23f.

In the present invention, the pyrimidine moiety is commonly present in various bioactive small molecules (FIGS. 5 and 67), and it plays a critical role as a nucleoside analogue in various kinase inhibitors or adenosine receptor modulators due to its hydrogen bonding ability (FIG. 1*a*). Therefore, many synthetic efforts towards pyrimidine-containing species have been focused on aromatic monocyclic or bicyclic skeletons, which limits the structural diversity of the pyrimidine-containing core skeletons. In addition, the 3D structural complexity of the core skeletons (FIG. 2) became important because planar frameworks less frequently constitute FDA-approved chemical entities, especially in regard to undruggable targets.

Based on the above, to expand the molecular diversity beyond monocyclic and bicyclic pyrimidine skeletons, the present invention developed a new pDOS strategy towards the divergent synthesis of natural product-like polyheterocycles containing pyrimidodiazepine or pyrimidine. Diazepine is also often found in complex natural products that exhibit a wide range of biological activities, and is known to be a prominent privileged structure that can improve the bioavailability and bioactivity of compounds. In addition, seven-membered rings that are fused to aromatic rings generally have higher conformational flexibility and a greater number of reactive sites than five- or six-membered fused ring systems, as confirmed by the direct comparison of pyrimidine-embedded tricyclic 6/6/6 and 6/7/6 systems by overlaying the energy-minimized conformational isomers aligned along the pyrimidine substructure (FIG. 1*b*). Thus, pyrimidodiazepine can serve as a versatile intermediate to access highly diverse and complex polyheterocycles through the incorporation of additional ring systems, which forms the basis of a new pyrimidodiazepine-based pDOS pathway. To establish the pDOS pathway, we first designed and synthesized, as a starting material, formula 1 comprising highly functionalized pyrimidodiazepine containing five reactive sites (A-E). In the pDOS strategy of the present invention, the compound of formula 1 as a starting material can be transformed into nine distinct pyrimidodiazepine- or pyrimidine-containing pyrimidine derivatives via pairing with different functional groups at each reactive site (FIG. 1*c*).

The pyrimidine derivative compounds of the present invention represented by formulas I to IX exhibit much higher structural complexity and skeletal diversity than existing pyrimidine-based drugs, as demonstrated by PMI analysis of the working examples and experiments of the present invention. Using the pyrimidine structures as chemical navigators to efficiently access unexploited regions of bioactive chemical space, the pDOS synthetic pathway provides unique library of polyheterocyclic compounds with superior biological relevancy.

In the present invention, we performed ELISA-based HTS with the pDOS library and identified 21f, a small-molecule PPI inhibitor of the LRS-RagD interaction, which mediates Leu signal sensing in the mTORC1 signalling pathway. Through western blotting and biophysical study using SPR on phosphorylation of S6K1, it was confirmed that 21f could induce cellular autophagy, and reduce cellular proliferation even in the presence of Leu by disrupting the LRS-RagD interaction and subsequently inhibiting Leu-dependent mTORC1 activity. Therefore, this PPI inhibitor could be a powerful tool to specifically delineate unrevealed amino acid-dependent biological processes of mTORC1. Furthermore, the PPI inhibitor could act as a lead structure in the development of novel therapeutic agents to treat diseases linked to the oncogenic activation of mTORC1, thus highlighting the great potential of the pDOS strategy to address unmet therapeutic challenges.

A process for preparing the pyrimidine derivative compound of the present invention may comprise:

Step 1:

for preparing an intermediate substance, tert-(S)-(1-(6-chloro-5-formylpyrimidin-4-yl)amino)-3-((triisopropylsilyl)oxy)propan-2-yl)carbamate;

Step 1a:

for preparing a starting material represented by formula 1 by reacting the intermediate substance prepared in step 1 with cyclic amine or tetrakis palladium; and

[Formula 1]

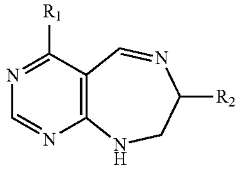

wherein $R_1$ is

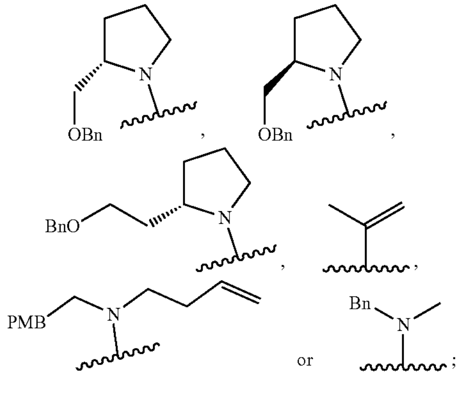

, , , , or ;

and $R_2$ is —$CH_2$—O-TIPS;

Step 2:

for preparing a desired compound from the starting material prepared in step 1a, which, more specifically, further comprises at least one of the following reactions on a compound having formula 1 as a starting material prepared in step 1a: N-alkylation, debenzylation, intramolecular substitution reaction, ring-closing metathesis, nucleophilic addition reaction, allylation reaction of amine, Grubbs' catalyst condensation reaction, alcohol deprotection reaction, intramolecular nucleophilic addition reaction, aziridinium intermediate formation reaction, nucleophilic ring expansion reaction, and bridge head ring formation reaction.

The derived compound in the present invention means a compound represented by formulas I to IX, more specifically, compounds 2a, 3b, 4c, 5d to 6d, 7e to 8e, and 9f to 23f.

According to one example of the present invention, step 2 in the preparation process of the present invention may comprise the steps of Scheme 1 depicted in FIG. 70 or Scheme 2 depicted in FIG. 71:

Each step of scheme 1 can be detailed as follows:

Step 2A: Pairing at the A and B Positions of the Starting Materials

Starting materials 1a to 1e to be discussed below can readily be synthesized through a series of transformations (Scheme 2). For the synthesis of compounds 2a, 3b, and 3c, starting materials 1a to 1c are treated with sodium borohydride (NaBH4) to afford secondary amines on R1; the resulting secondary amines are protected with -Boc and aniline is N-alkylated, which allows for the formation of intermediates A. Compound 2a, 3b, and 4c can efficiently be generated via A-B pairing through an intramolecular substitution reaction, when intermediates A are subjected to debenzylation and the resultant alcohols are subsequently activated with methanesulfonyl chloride (MsCl). Consequently, compounds 2a, 3b and 4c having stereochemically tetracycles, containing a pyrimidinium moiety, can be obtained in moderate yields.

Step 2B: Pairing at the B and C Positions of the Starting Materials

We employed ring-closing metathesis (RCM) for the synthesis of compounds 5d, 6d, 7e, and 8e via B-C pairing. For the RCM reaction, a vinyl group is important and is introduced as a substituent at the C position of the starting materials shown in the scheme above. Starting materials 1d and 1e are subjected to N-alkylation with benzyl bromide to afford iminium ions. Diastereoselective nucleophilic addition of allyl or homoallyl Grignard reagents to the iminium ions generates intermediates B and C. RCM with addition of Grubbs' second-generation catalyst provides the synthesis of compounds 5d, 6d and 7e. 6-, 7- and 10-membered rings are formed by condensation where the condensation reaction through RCM exerted good to excellent diastereoselectivity. Notably, this diastereoselectivity without chiral auxiliaries or catalysts could be rationalized by the preferential approach of Grignard reagents towards the less hindered re-face of the imine in 1d and 1e. The stereochemistry of each product was confirmed by nuclear Overhauser effect (NOE) spectroscopy (FIGS. 6A, 6B, 6C, 7A, 7B, 8A, and 8B).

To generate compound 8e, starting material 1e was treated with $NaBH_4$ to start the synthesis. Allylation of the secondary amine resulting from the treatment reaction with $NaBH_4$ and subsequent RCM with Grubbs' second-generation catalyst yielded compound 8e. 10-membered rings are obtained by condensation in 44% overall yield.

Step 2C: Pairing at the C and D Positions of the Starting Materials 2C-1: Deprotection of the silyltri propyl (TIPS) group from starting material 1f provides an alcohol functional group, which generates the desired compounds 14f, 15f and 16f having the structure of bridged oxazolidine in good yields upon treatment with various N-modifying agents such as Boc anhydride (Boc2O), benzyl isocyanate and 3-nitrobenzene sulfonyl chloride (m-NsCl) to form iminium and subsequent intramolecular nucleophilic addition of the hydroxyl moiety. The structure of bridged oxazolidine 16f was confirmed by X-ray crystallographic analysis (FIG. 3).

2C-2: To synthesize compound 17f, starting material 1f was subjected to N-alkylation with the treatment of methyl iodide, followed by nucleophilic addition of benzylmagnesium bromide to form iminium ion and subsequent removal of the TIPS group of starting material 1f. Then, the hydroxyl moiety of intermediate substance SI-8 (Example 15) was activated with trifluoromethanesulfonic anhydride to provide an aziridium intermediate and the subsequent nucleophilic ring expansion reaction with azide anion afforded to 17f containing an eight-membered diazocane ring. In fact, benzodiazocine is known as an important pharmacophore, but the synthesis of diazocane has not been extensively studied due to the unfavourable transannular strain in medium-sized rings. The stereochemistry of 17f was confirmed by NOE spectroscopy (FIGS. 13A, 13B, 13C, 14A, and 14B).

2C-3: For the synthesis of compounds 18f and 19f, starting material 1f was treated with NaBH4 to afford a secondary amine, which underwent sulfonamide or amide formation upon treatment with chloromethane sulfonyl chloride or chloroacetic anhydride. The subsequent removal of -TIPS group and alcohols, which resulted from intramolecular nucleophilic attack with electrophiles afforded to compounds 18f or 19f, was condensed with and introduced into six-membered lactam rings.

2C-4: Compounds 20f and 21f contain an aziridine ring. Starting material 1f was treated with NaBH4 to result in secondary amine, which was protected with Boc. Aniline was N-alkylated to provide intermediates F ($R^5$=Benzyl or 3,5-dimethylbenzyl). The removal of -TIPS and -Boc group of intermediate F, followed by subsequent cyclization, to produce 20f or 21f in 51 and 53% yields, respectively. Finally, oxazolidinone-containing compound 22f was obtained through the TIPS deprotection of intermediate F ($R^5$=allyl) and subsequent cyclization.

Step 2D: Pairing at the D and E Positions of the Starting Materials

The TIPS group of intermediate F was removed, followed by oxidation reaction with Dess-Martin periodinane to provide an aldehyde. The resulting unstable aldehyde from the oxidation reaction was immediately subjected to Wittig olefination, followed by RCM reaction with Grubbs' second-generation catalyst to afford compound 23f containing bridge-head [4,3,1] ring systems.

Further, the compounds of the present invention exert excellent cytotoxicity against cancer cells and thus can be used as an inhibitor against cancer cell growth, whereby being useful as a treating agent for cancer diseases. As such, the present invention provides a composition for treating cancer comprising a pyrimidine derivative compound represented by any one of formulas I to IX as an active ingredient, which is effective for cancer diseases.

The cancer diseases comprise at least one selected from the group consisting of cervical cancer, lung cancer, pancreatic cancer, non-small cell lung cancer, liver cancer, colon cancer, bone cancer, skin cancer, head or neck cancer, melanoma in skin or eye, uterine cancer, ovarian cancer, rectal cancer, gastric cancer, cancer around anal, colon cancer, breast cancer, fallopian tube carcinoma, endometrial carcinoma, vaginal carcinoma, vulva carcinoma, esophageal cancer, small intestine cancer, endocrine gland cancer, thyroid cancer, parathyroid cancer, adrenal cancer, soft tissues sarcoma, urethral cancer, penile cancer, prostate cancer, bladder cancer, cancer of renal or ureter, renal cell carcinoma, and renal pelvis carcinoma; preferably, lung cancer, liver cancer, skin cancer, or skin melanoma.

The treating agent of the present invention may be formulated as a pharmaceutically conventional formulation for an oral or parenteral administration, for example, a tablet, capsule, troche, solution, suspension, etc., by adding appropriate non-toxic carrier, excipients, adjuvants as generally used into a pyrimidine derivative compound of the present invention. Further, dosage to human of a compound according to the present invention depends on ages, weight, and sex of patients, administration route, health condition, and severity of disease. Based on an adult patient, the dosage is generally from 0.0001 to 1000 mg/kg/day, which may be divided and administered into once or several times per day over a certain interval according to the determination of a doctor or pharmacist. As such, the dosage is not construed to limit the claimed scope at any aspect.

The compound of the present invention may be administered to mammals such as rat, mouse, livestock, or human via different routes. All potential administration routes may be expected, for example, oral, rectal, intravenous, muscular, subcutaneous, intrauterine, intracerebroventricular injection.

Hereinafter, the working examples will be provided for the better understanding of the present invention. However, the examples are merely provided only for a better understanding of the present invention, but are not to be construed as the limitation of the claimed scope.

EXAMPLE

Scheme 3

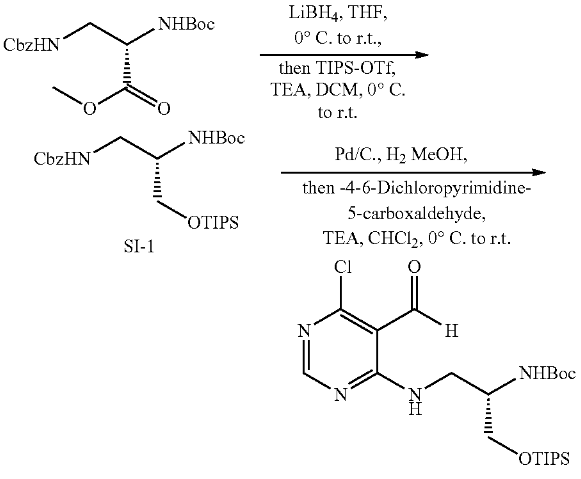

SI-1

SI-2

Scheme 3-1) Preparation of SI-1

(S)-3-(((benzyloxy)carbonyl)amino)-2-((tert-butoxycarbonyl)amino)propanoate (20.00 g, 56.8 mmol) was added to THF (570.0 ml) and stirred. Lithium borohydride (2.0 M solution in THF, 56.8 ml, 113.5 mmol) was slowly added to the solution at 0° C. dropwise. Then, the resulting mixture was left to stir at r.t. After completion of the reaction as indicated by TLC, the mixture was quenched with a saturated ammonium chloride solution. The reaction solution was extracted twice with dichloromethane. The extracted organic solution was dried over anhydrous sodium sulfate and filtered. The filtrate was evaporated under reduced pressure to be condensed and dried. The compound was dissolved in dry dichloromethane (570.0 ml) under argon atmosphere. To this solution were sequentially added triethylamine (15.8 ml, 113.5 mmol) and then TIPS-OTf (22.88 ml, 85.14 mmol) at 0° C. The resulting mixture was left to stir at r.t. After completion of the reaction as indicated by TLC, the mixture was quenched with a saturated ammonium chloride solution. The solution was extracted twice with dichloromethane. The extracted organic solution was dried over anhydrous sodium sulfate and filtered. The filtrate was condensed under reduced pressure, followed by being purified using silica-gel flash column chromatography to afford the desired product SI-1 (22.37 g, 82% yield) as a light colorless oil.

SI-1

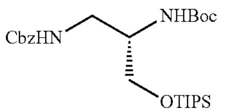

$R_f$=0.4 (hexane/EtOAc 5:1); $^1$H NMR (400 MHz, a $CDCl_3$) δ 7.35-7.29 (m, 5H), 5.32 (br s, 1H), 5.10 (s, 2H), 5.00 (br s, 1H), 3.77-3.73 (m, 3H), 3.47-3.39 (m, 2H), 1.43 (s, 9H), 1.06 (m, 21H); $^{13}$C NMR (100 MHz, a $CDCl_3$) δ 157.0, 156.1, 136.7, 128.6, 128.11, 128.07, 79.6, 66.8, 64.3, 51.8, 43.5, 28.4, 18.0, 11.9; LRMS(ESI+): Calcd for a $C_{25}H_{45}N_2O_5Si^+$ [M+H]$^+$ 481.31, found 481.11. (FIGS. 26A and 26B).

To SI-1 (22.37 g, 46.54 mmol) dissolved in methanol (470.0 ml) was added Pd/C (palladium complex compound: w/w 10%, 11.19 g) and the mixture was stirred with feeding hydrogen atmosphere (1 atm) at r.t. After completion of the reaction as indicated by TLC, the reaction mixture was filtered through Celite® while the filtrate was extracted with ethyl acetate. The filtrate was condensed under reduced pressure and was dissolved in chloroform (470.0 ml). To this solution were added triethylamine (9.74 ml, 69.81 mmol) and 4,6-dichloropyrimidine-5-carboxaldehyde (8.24 g, 46.54 mmol) at 0° C. and left to stir. After stirring over 30 min, the mixture was quenched with a saturated ammonium chloride solution. The mixture was extracted twice with chloroform, and the extracted organic solution was dried over anhydrous sodium sulfate, and filtered. The filtrate was condensed under reduced pressure and the product was purified by silica-gel flash column chromatography to afford the desired product SI-2 (15.19 g, 67% yield) as a light colorless oil.

SI-2

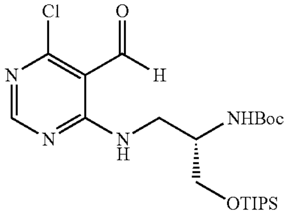

$R_f$=0.5 (hexane/EtOAc 3:1); $^1$H NMR (400 MHz, a $CDCl_3$) δ 10.28 (s, 1H), 9.30 (t, J=5.7 Hz, 1H), 8.34 (s, 1H), 4.99 (d, J=8.6 Hz, 1H), 3.90-3.62 (m, 5H), 1.33 (s, 9H), 1.06 (m, 21H); $^{13}$C NMR (100 MHz, a $CDCl_3$) δ 191.1, 165.3, 161.7, 160.7, 155.6, 108.2, 79.5, 63.7, 51.4, 42.4, 28.3, 17.9, 11.9; LRMS (ESI+): Calcd for a $C_{22}H_{40}ClN_4O_4Si^+$ [M+H]$^+$ 487.25, found 487.03. (FIGS. 27A and 27B).

Scheme 4: Process for preparing derivatives of formla 1 as a starting material, 1a-1c and 1e-1f.

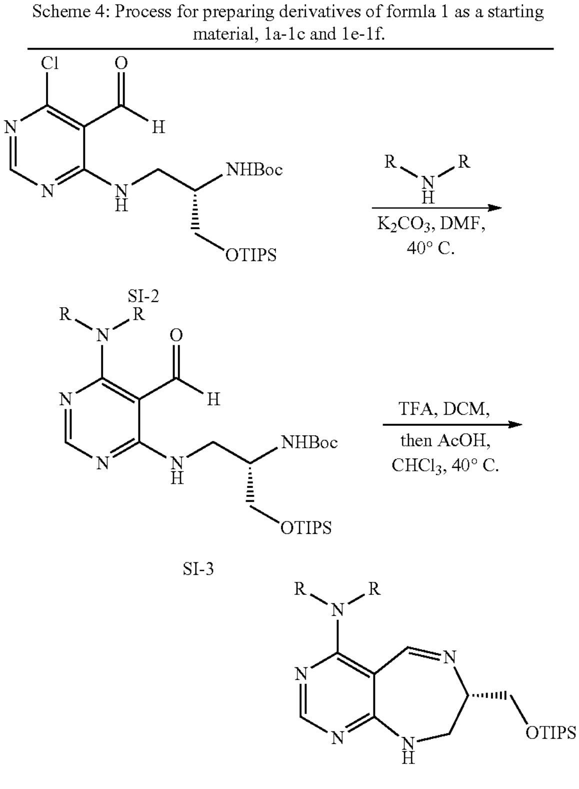

1

Scheme 4-1)

SI-2 (500 mg, 1.026 mmol) and potassium carbonate (283.6 mg, 2.052 mmol) were dissolved to dimethylformamide (10.0 ml) and stirred, followed by adding cyclic amine (1.539 mmol) thereto and stirring at 40° C. After completion of the reaction as indicated by TLC, the mixture was quenched with a saturated ammonium chloride solution. The reaction solution was extracted twice with ethyl acetate. The extracted organic solution was dried over anhydrous sodium sulfate and filtered. The filtrate was condensed under reduced pressure and the product was purified by silica-gel flash column chromatography to afford desired compound SI-3.

Scheme 4-2)

To obtain the cyclic imine product 1, SI-3 was added into 10% trifluoroacetic acid dichloromethane solution (20.0 ml) and stirred at r.t. After completion of the reaction as indicated by TLC, any excess trifluoro acetic acid was removed by azeotropic evaporation with toluene under reduced pressure. The compound was dissolved in 1% acetic acid chloroform (100.0 ml) and stirred at 40° C. After completion of the reaction as indicated by TLC, the reaction was quenched with a saturated sodium bicarbonate solution. The reaction solution was extracted twice with chloroform. The extracted organic solution was dried over anhydrous sodium sulfate and filtered. The filtrate was condensed under reduced pressure and the product was purified by silica-gel flash column chromatography to afford the desired product 1.

1

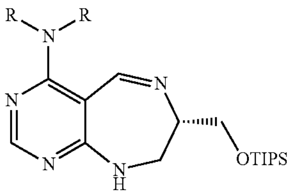

a) Derivative 1a of starting material 1: (S)-4-((S)-2-((benzyloxy)methyl)pyrrolidin-1-yl)-7-(((triisopropylsilyl)oxy)methyl)-8,9-dihydro-7H-pyrimido[4,5-e][1,4]diazepine 1a

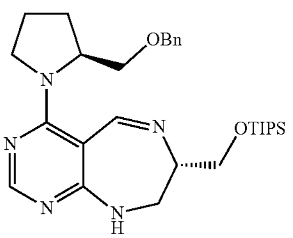

A pale yellow oil; $R_f$=0.2 (DCM/MeOH=20:1); 403.1 mg, 75% overall yield; $^{1}$H NMR (400 MHz, a $CDCl_3$) δ 8.11 (s, 1H), 7.98 (s, 1H), 7.29 (m, 5H), 5.97 (br s, 1H), 4.74 (m, 1H), 4.54, 4.53 (ABq, $J_{AB}$=12.1 Hz, 2H), 4.18 (dd, J=9.8, 4.7 Hz, 1H), 3.90 (m, 1H), 3.80 (dd, J=12.5, 5.5 Hz, 1H), 3.73 (m, 2H), 3.67 (m, 1H), 3.60 (dd, J=9.4, 5.9 Hz, 1H), 3.47 (m, 1H), 3.34 (dd, J=11.3, 7.0 Hz, 1H), 2.15 (m, 1H), 1.96 (m, 2H), 1.71 (m, 1H), 1.08 (m, 21H); $^{13}$C NMR (100 MHz, a $CDCl_3$) δ 164.5, 160.9, 159.1, 157.4, 138.6, 128.4, 127.6, 127.5, 93.1, 73.3, 71.1, 65.1, 64.2, 58.0, 55.2, 47.8, 28.0, 26.1, 18.2, 12.0; HRMS(ESI+): Calcd for a $C_{29}H_{46}N_5O_2Si^+$ $[M+H]^+$ 524.3415, found 524.3414, Δppm −0.19. (FIGS. 28A and 28B).

b) Derivative 1b of starting material 1: (S)-4-((R)-2-((benzyloxy)methyl)pyrrolidin-1-yl)-7-(((triisopropylsilyl)oxy)methyl)-8,9-dihydro-7H-pyrimido[4,5-e][1,4]diazepine 1b

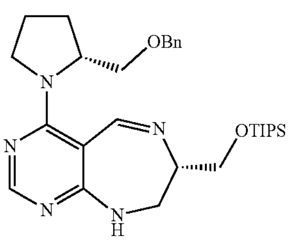

A pale yellow oil; $R_f$=0.2 (DCM/MeOH=20:1); 408.4 mg, 76% overall yield; $^{1}$H NMR (400 MHz, a $CDCl_3$) δ 8.14 (s, 1H), 7.96 (s, 1H), 7.30 (m, 5H), 6.20 (br s, 1H), 4.74 (m, 1H), 4.53 (s, 2H), 4.19 (dd, J=9.7, 3.1 Hz, 1H), 4.02 (m, 1H), 3.84 (m, 1H), 3.74 (m, 2H), 3.63 (m, 2H), 3.46 (t, J=9.7 Hz, 1H), 3.14 (m, 1H), 2.14 (m, 1H), 1.99 (m, 2H), 1.74 (m, 1H), 1.09 (m, 21H); $^{13}$C NMR (100 MHz, a $CDCl_3$) δ 165.0, 164.2, 156.4, 154.0, 138.4, 128.2, 127.4, 127.4, 92.0, 73.1, 70.8, 65.3, 65.0, 57.9, 55.2, 46.6, 27.8, 25.8, 18.0, 11.8; HRMS(ESI+): Calcd for a $C_{29}H_{46}N_5O_2Si^+$ $[M+H]^+$ 524.3415, found 524.3415. (FIGS. 29A and 29B).

c) Derivative 1c of starting material 1: (S)-4-((S)-2-(2-(benzyloxy)ethyl)pyrrolidin-1-yl)-7-(((triisopropylsilyl)oxy)methyl)-8,9-dihydro-7H-pyrimido[4,5-e][1,4]diazepine 1c

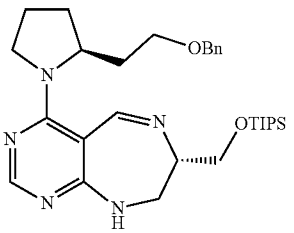

A transparent oil; $R_f$=0.35 (DCM/MeOH=20:1); 419.4 mg, 76% overall yield; 1H NMR (400 MHz, a $CDCl_3$) δ 8.07 (s, 1H), 7.99 (s, 1H), 7.33 (m, 4H), 7.29-7.26 (m, 1H), 6.17 (br s, 1H), 4.61 (m, 1H), 4.53, 4.26 (ABq, $J_{AB}$=11.94 Hz, 2H), 4.18 (dd, J=9.8, 4.3 Hz, 1H), 3.92 (m, 1H), 3.81-3.62 (m, 3H), 3.60-3.56 (m, 2H), 3.45 (m, 1H), 3.33 (m, 1H), 2.33-2.25 (m, 1H), 2.19-2.13 (m, 1H), 1.91-1.87 (m, 1H), 1.80-1.66 (m, 3H), 1.08 (m, 21H); $^{13}$C NMR (100 MHz, a $CDCl_3$) δ 164.8, 161.1, 159.0, 157.4, 138.6, 128.4, 127.8, 127.6, 93.2, 73.0, 67.7, 65.1, 64.3, 56.9, 55.1, 47.6, 34.1, 31.0, 26.2, 18.1, 12.0; HRMS(ESI+): Calcd for a $C_{30}H_{48}N_5O_2Si^+$ $[M+H]^+$ 538.3572, found 538.3571, Δppm −0.19. (FIGS. 30A and 30B).

d) Derivative 1e of starting material 1: (S)—N-(but-3-en-1-yl)-N-(4-methoxyphenethyl)-7-(((triisopropylsilyl)oxy)methyl)-8,9-dihydro-7H-pyrimido[4,5-e][1,4]diazepine-4-amine 1e

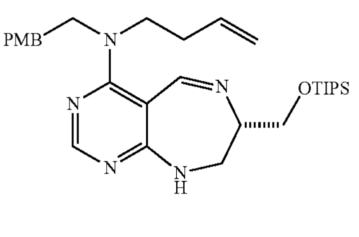

A pale yellow oil; $R_f$=0.4 (DCM/MeOH=20:1); 364.2 mg, 66% overall yield; $^{1}$H NMR (400 MHz, a $CDCl_3$) δ 8.05 (s, 1H), 7.98 (d, J=1.9 Hz, 1H), 7.07 (d, J=8.6 Hz, 2H), 6.80 (d, J=8.6 Hz, 2H), 6.42 (m, 1H), 5.72 (dddd, J=16.8, 10.1, 6.6, 6.6 Hz, 1H), 5.02 (m, 2H), 4.18 (dd, J=9.7, 4.3 Hz, 1H), 3.84 (m, 3H), 3.77 (s, 3H), 3.69 (m, 2H), 3.46 (m, 1H), 3.34 (m, 2H), 2.83 (t, J=7.4 Hz, 2H), 2.33 (q, J=7.0 Hz, 2H), 1.08 (m, 21H); $^{13}C$ NMR (100 MHz, a $CDCl_3$) δ 167.2, 161.9, 158.2, 157.8, 157.1, 135.2, 131.0, 129.7, 117.0, 114.0, 94.3, 65.2, 64.5, 55.3, 53.5, 51.2, 47.6, 33.7, 32.6, 18.1, 12.0; HRMS (ESI+): Calcd for a $C_{30}H_{48}N_5O_2Si^+$ $[M+H]^+$ 538.3572, found 538.3572. (FIGS. 32A and 32B).

e) Derivative 1f of starting material 1: (S)—N-benzyl-N-methyl-7-(((triisopropylsilyl)oxy)methyl)-8,9-dihydro-7H-pyrimido[4,5-e][1,4]diazepine-4-amine 1f

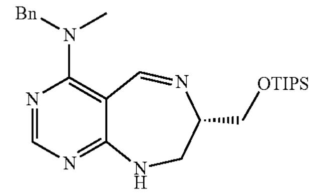

A transparent oil; $R_f$=0.35 (DCM/MeOH=20:1); 349.1 mg, 75% overall yield; $^1H$ NMR (400 MHz, a $CDCl_3$) δ 8.17 (d, J=1.9 Hz, 1H), 8.06 (s, 1H), 7.35-7.25 (m, 5H), 6.99 (br s, 1H), 4.81, 4.71 (ABq, $J_{AB}$=15.2 Hz, 2H), 4.18 (dd, J=9.8, 4.3 Hz, 1H), 3.89 (m, 2H), 3.66 (t, J=10.0 Hz, 1H), 3.32 (ddd, J=13.0, 7.1, 2.5 Hz, 1H), 3.03 (s, 3H), 1.08 (m, 21H); $^{13}C$ NMR (100 MHz, a $CDCl_3$) δ 167.4, 162.4, 157.2, 157.1, 137.3, 128.7, 127.7, 127.4, 92.7, 65.1, 64.5, 56.6, 47.3, 40.1, 18.0, 11.9; HRMS(ESI+): Calcd for a $C_{25}H_{40}N_5OSi^+$ $[M+H]^+$ 454.2997, found 454.2996, Δppm −0.22. (FIGS. 33A and 33B).

Scheme 5: Preparation of compound 1d; (S)-4-(prop-1-en-2-yl)-7-(((triisopropylsilyl)oxy)methyl)-8,9-dihydro-7H-pyrimido[4,5-e][1,4]diazepine

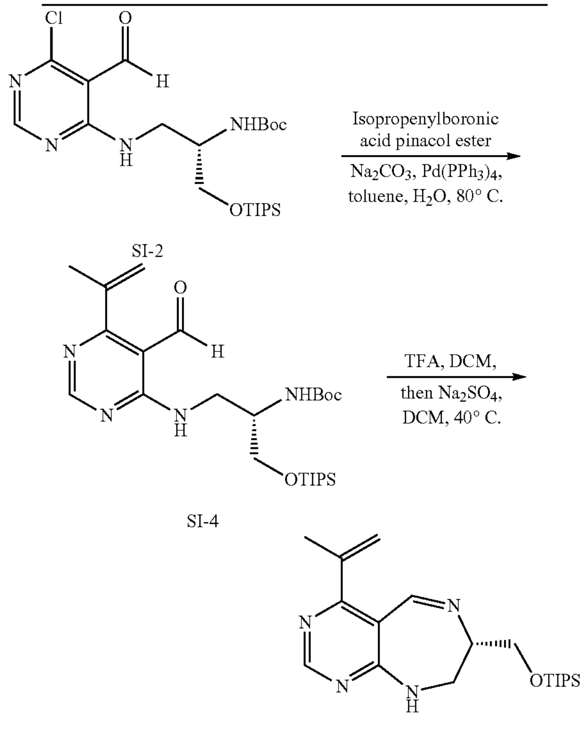

SI-2

SI-4

1d

Scheme 5-1)

SI-2 (500 mg, 1.026 mmol), isopropenyl boronic acid pinacol ester (0.290 ml, 1.539 mmol), and sodium carbonate (380.6 mg, 3.591 mmol) were dissolved in toluene and water (w/w=25.0 ml/25.0 ml). To the stirring solution was added tetrakis palladium (palladium tetrakis; i.e., triphenylphosphine; $Pd((PPh)_3))_4$), 119.0 mg, 0.103 mmol, 10 mol %) at r.t. The compound was heated and stirred at 80° C., followed by the completion of the reaction as indicated by TLC. The reactant was dissolved with ethyl acetate, washed with brine, and then dried over anhydrous magnesium sulfate and filtered. The filtrate was condensed under reduced pressure and the reaction mixture was purified by silica-gel flash column chromatography to obtain SI-4 (379.2 mg, 75% yield).

Scheme 5-2)

SI-4 (379.2 mg, 0.770 mmol) was added to 10% trifluoro acetic acid dichloromethane solution (100.0 ml) and stirred at r.t. After completion of the reaction as indicated by TLC, the reaction was quenched with a saturated sodium bicarbonate solution and extracted twice with dichloromethane. The extracted organic solution was dried with anhydrous sodium sulfate under reduced pressure and filtered. The compound was dissolved in dichloromethane (100.0 ml), adding sodium sulfate (2.915 g, 20.52 mmol), and then stirring at 40° C. The completion of the reaction was indicated by TLC, followed by filtering. The filtrate was condensed under reduced pressure and the product was purified with silica-gel flash column chromatography to obtain cyclic imine compound 1d (234.4 mg, 81% yield) a light colorless oil.

1d

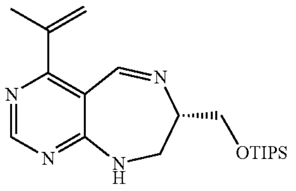

$R_f$=0.2 (DCM/MeOH 20:1); $^1H$ NMR (400 MHz, a $CDCl_3$) δ 8.47 (d, J=2.3 Hz, 1H), 8.43 (s, 1H), 7.37 (br d, J=5.0 Hz, 1H), 5.54 (s, 1H), 5.10 (s, 1H), 4.27 (dd, J=9.7, 4.7 Hz, 1H), 3.95 (dd, J=13.0, 7.0 Hz, 1H), 3.81 (m, 1H), 3.69 (t, J=10.1 Hz, 1H), 3.19 (m, 1H), 2.17 (s, 3H), 1.08 (m, 21H); $^{13}C$ NMR (100 MHz, a $CDCl_3$) δ 172.2, 161.0, 158.0, 157.9, 142.2, 120.9, 107.3, 65.2, 64.8, 47.4, 22.3, 18.1, 11.9; HRMS(ESI+): Calcd for a $C_{20}H_{35}N_4OSi^+$ $[M+H]^+$ 375.2575, found 375.2574, Δppm −0.27. (FIGS. 31A and 31B).

Example 1: Preparation of Compound 2a

To a stirring solution where compound 1a (403.1 mg, 0.770 mmol) was added to methanol (8.0 ml), sodium borohydride (145.6 mg, 3.850 mmol) was added at 0° C. The mixture was stirred at r.t. After completion of the reaction as indicated by TLC, the reaction was quenched with a saturated sodium bicarbonate solution and extracted twice with dichloromethane. The extracted organic solution was dried with anhydrous sodium sulfate under reduced pressure and filtered. The filtrate was condensed under reduced pressure and then dissolved in dichloromethane (8.0 ml). To the solution were added triethylamine (0.215 ml, 1.540 mmol) and di-tert-butyl dicarbonate ($Boc_2O$) (218.5 mg, 1.001 mmol) at 0° C. The compound was stirred at r.t., followed by completion of the reaction as indicated by TLC. The reaction was quenched with a saturated ammonium chloride solution and the reaction solution was extracted twice with dichloromethane. The extracted organic solution was dried over anhydrous magnesium sulfate and filtered. The filtrate was then condensed under reduced pressure and the reaction mixture was purified by silica-gel flash column chromatography to obtain SI-5 (260.3 mg, 54% yield). SI-5 (260.3 mg, 0.416 mmol) was dissolved in DMF (4.0 ml), adding sodium hydride (60% dispersion in mineral oil, 33.28 mg, 0.832 mmol) under argon atmosphere at 0° C. and left to stir. After stirring over 30 min, ethyl iodide (0.067 ml, 0.832 mmol) was added and stirred at r.t. After completion of the reaction as indicated by TLC, the reaction was quenched with a saturated ammonium chloride solution. The reaction solution was extracted twice with ethyl acetate. The extracted organic solution was dried over anhydrous sodium sulfate and filtered. The filtrate was condensed under reduced pressure and the product was purified with silica-gel flash column chromatography to obtain intermediate A (258.5 mg, 95% yield). Intermediate A (258.5 mg, 0.395 mmol) was dissolved in methanol (4.0 ml), adding $Pd(OH)_2/C$ (25.9 mg, 20 wt. %), and then stirring at r.t. while feeding hydrogen atmosphere of 1 atm. The completion of the reaction was as indicated by TLC, followed by filtering through Celite®. The filtrate was extracted with ethyl acetate. The filtrate was condensed under reduced pressure and dissolved in dichloromethane (4.0 ml). To the compound were triethylamine (0.165 ml, 1.185 mmol) and methanesulfonyl chloride (MsCl, 0.061 ml, 0.790 mmol) at 0° C. The compound was stirred at r.t., followed by completion of the reaction as indicated by TLC. The compound after completion of the reaction was diluted with dichloromethane, washing twice with 1N hydrochloric acid. The washed organic solution was dried over anhydrous sodium sulfate and filtered. The filtrate was condensed under reduced pressure and the product was purified with silica-gel flash column chromatography to obtain 2a (280.6 mg, 61% yield) as a white solid.

2a

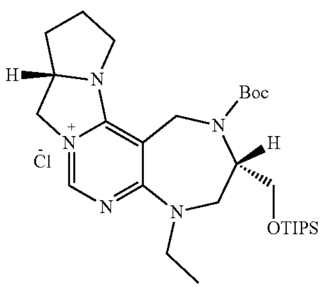

$R_f$=0.1 (DCM/MeOH=10:1); $^1H$ NMR (400 MHz, DMSO-$d_6$, 100° C.) δ 8.50 (s, 1H) 4.64 (m, 2H), 4.48 (m, 2H), 4.33 (m, 2H), 4.13 (m, 1H), 3.82 (m, 2H), 3.76 (m, 1H), 3.69 (m, 1H), 3.62 (dd, J=15.1, 4.6 Hz, 1H), 3.57 (m, 1H), 3.42 (m, 1H), 2.14 (m, 1H), 2.04 (m, 2H), 1.66 (m, 1H), 1.32 (br s, 9H), 1.17 (t, J=7.1 Hz, 3H), 1.08 (m, 21H); $^{13}C$ NMR (100 MHz, DMSO-$d_6$, 100° C.) δ 162.0, 155.8, 154.0, 146.5, 79.3, 62.8, 62.4, 50.8, 50.2, 48.9, 45.1, 29.6, 27.4, 25.7, 17.2, 12.4, 11.0; IR (neat) $v_{max}$: 2940, 2866, 1698, 1638, 1523, 1174 $cm^{-1}$; HRMS(ESI+): Calcd for a $C_{29}H_{52}N_5O_3Si^+$ $[M]^+$ 546.3834, found 546.3831, Δppm −0.55; mp: 136-138° C. (FIGS. 34A and 34B).

Example 2: Preparation of Compound 3b

Compound 3b was prepared based on Example 1, provided that 1b was used in place of 1a.

3b

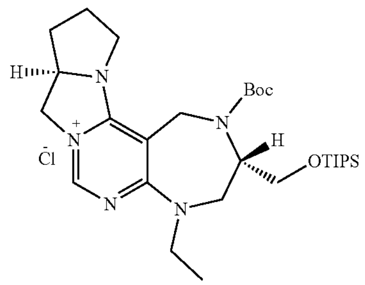

A pale yellow solid; $R_f$=0.1 (DCM/MeOH=10:1); 38% overall yield; $^1H$ NMR (400 MHz, DMSO-$d_6$, 100° C.) δ 8.42 (s, 1H), 4.88 (d, J=16.9 Hz, 1H), 4.58 (d, J=16.9 Hz, 1H), 4.54 (dd, J=10.8, 9.4 Hz, 1H), 4.38 (m, 2H), 4.27 (dd, J=10.9, 8.2 Hz, 1H), 4.16 (dd, J=15.1, 11.9 Hz, 1H), 3.86 (m, 2H), 3.80 (m, 2H), 3.70 (m, 2H), 3.65 (m, 1H), 2.17 (m, 3H), 1.73 (m, 1H), 1.41 (s, 9H), 1.18 (t, J=6.9 Hz, 3H), 1.09 (m, 21H); $^{13}C$ NMR (100 MHz, DMSO-$d_6$, 100° C.) δ 162.3, 153.8, 152.8, 146.5, 93.0, 79.8, 63.2, 62.5, 56.9, 50.6, 49.0, 48.0, 46.1, 36.7, 29.2, 27.5, 26.6, 17.2, 12.3, 10.9; IR (neat) $v_{max}$: 2944, 2863, 1698, 1636, 1517, 1166 $cm^{-1}$; HRMS (ESI+): Calcd for a $C_{29}H_{52}N_5O_3Si^+$ $[M]^+$ 546.3834, found 546.3833, Δppm −0.18; mp: 77-79° C. (FIGS. 35A and 35B).

Example 3: Preparation of Compound 4c

Compound 4c was prepared based on Example 1, provided that 1c was used in place of 1a.

4c

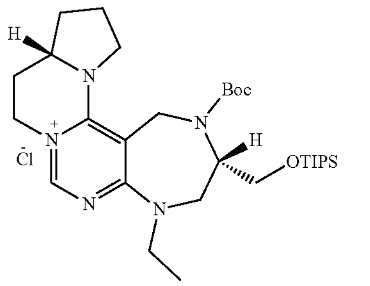

A pale yellow solid; $R_f$=0.2 (DCM/MeOH=10:1); 40% overall yield; $^1H$ NMR (400 MHz, DMSO-$d_6$, 100° C.) δ 8.34 (s, 1H), 4.48 (m, 2H), 4.23 (m, 2H), 4.05 (m, 1H), 3.85 (m, 2H), 3.79 (m, 2H), 3.71 (m, 3H), 3.61 (dd, J=15.0, 4.6 Hz, 1H), 3.53 (m, 1H), 3.06 (br s, 1H), 3.00 (m, 1H), 2.18 (m, 1H), 1.91 (m, 3H), 1.29 (br s, 9H), 1.18 (t, J=7.0 Hz, 3H), 1.09 (m, 21H); $^{13}C$ NMR (100 MHz, DMSO-$d_6$, 100° C.) δ 161.5, 153.1, 149.2, 149.2, 71.7, 63.9, 56.3, 55.8, 49.7, 49.0, 46.8, 30.5, 28.4, 25.0, 23.6, 18.2, 13.7, 12.0; IR (neat) $v_{max}$: 2946, 2867, 1694, 1625, 1529, 1457, 1116 $cm^{-1}$;

HRMS(ESI+): Calcd for a $C_{30}H_{54}N_5O_3Si^+$ $[M]^+$ 560.3990, found 560.3993, Δppm −0.54; mp: 71-73° C. (FIGS. 36A and 36B).

Example 4: Preparation of Compound 5d

1) Formation of intermediate B: 1d (100 mg, 0.267 mmol) was dissolved in acetonitrile (13.5 ml) with stirring and to this solution was added benzyl bromide (0.048 ml, 0.401 mmol). The compound was stirred at 80° C., followed by completion of the reaction as indicated by TLC. The compound after completion of the reaction was condensed under reduced pressure, washed with hexane to remove any excess benzyl bromide, and then condensed. The iminium ion was dissolved in cold anhydrous THF (27.0 ml), to which was added allylmagnesium bromide solution (1.0 M diethyl ether, 1.335 ml, 1.335 mmol) dropwise over 30 min at −78° C. The compound was then stirred for 18 hours at r.t. The reaction was quenched with a saturated ammonium chloride solution and the reaction solution was extracted twice with dichloromethane. The extracted organic solution was dried over anhydrous magnesium sulfate and filtered. The filtrate was condensed under reduced pressure and the reaction mixture was purified by silica-gel flash column chromatography to obtain intermediate B (n=1, 115.0 mg, yield 85%, d.r. >99:1) as a pale yellow oil.

Intermediate B

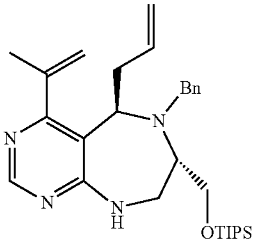

(n = 1)

$R_f$=0.5 (hexane/EtOAc=1:1); $^1H$ NMR (400 MHz, a $CDCl_3$) δ 8.40 (s, 1H), 7.32-7.29 (m, 3H), 7.24-7.20 (m, 2H), 5.88-5.78 (m, 2H), 5.03 (m, 2H), 4.94 (s, 1H), 4.69 (s, 1H), 4.29 (dd, J=9.4, 5.9 Hz, 1H), 3.86 (d, J=15.3 Hz, 1H), 3.78 (dd, J=9.6, 3.7 Hz, 1H), 3.64-3.57 (m, 3H), 3.50-3.40 (m, 2H), 2.84 (m, 1H), 2.22 (m, 1H), 1.81 (s, 3H), 1.01 (s, 21H); $^{13}C$ NMR (100 MHz, a $CDCl_3$) δ 168.4, 164.6, 155.6, 143.0, 140.1, 136.0, 128.4, 127.7, 126.9, 116.7, 116.3, 116.0, 64.4, 59.3, 57.9, 53.0, 43.3, 37.1, 23.0, 18.1, 11.9; HRMS (ESI+): Calcd for a $C_{30}H_{47}N_4OSi^+$ $[M+H]^+$ 507.3514, found 507.3516, Δppm +0.39. (FIGS. 37A and 37B).

The diastereomeric ratio was determined by LC-MS analysis of crude compound, while 1H NMR was analyzed after silica-gel column (FIGS. 22, 37A, and 37B).

2) Preparation of compound 5d: To intermediate B (115.0 mg, 0.227 mmol) dissolved in toluene (11.5 ml) was added $2^{nd}$ generation Grubbs' catalyst (38.20 mg, 0.045 mmol, 20 mol %) and left to stir at reflux. After completion of the reaction as indicated by TLC, the organic solution was condensed under reduced pressure, and the reaction mixture was purified by silica-gel flash column chromatography to obtain desired compound 5d (79.34 mg, yield 73%) as a pale yellow oil.

5d

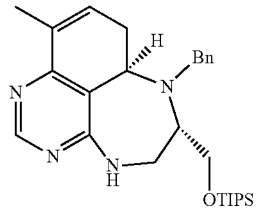

$R_f$=0.4 (hexane/EtOAc=2:1); $^1H$ NMR (400 MHz, a $CDCl_3$) δ 8.43 (s, 1H), 7.34-7.18 (m, 5H), 6.08 (br s, 1H), 5.87 (d, 6.3 Hz, 1H), 5.08 (t, J=11.0 Hz, 1H), 4.16, 3.99 (ABq, $J_{AB}$=14.9 Hz, 2H), 3.87 (t, J=13.3 Hz, 1H), 3.54-3.41 (m, 3H), 3.17 (m, 1H), 2.54 (d, J=10.5 Hz, 2H), 2.03 (s, 3H), 0.97 (m, 21H); $^{13}C$ NMR (100 MHz, a $CDCl_3$) δ 164.2, 160.4, 156.4, 141.1, 132.6, 130.4, 128.3, 128.1, 126.7, 110.9, 66.1, 61.8, 54.6, 50.5, 46.7, 29.5, 18.3, 17.9, 11.8; IR (neat) $v_{max}$: 3241, 3028, 2940, 2865, 1565, 1460, 1116, 1066 $cm^{-1}$; HRMS(ESI+): Calcd for a $C_{28}H_{43}N_4OSi^+$ $[M+H]^+$ 479.3201, found 479.3206, Δppm +1.04. (FIGS. 39A and 39B).

Through Nuclear Overhauser Effect (NOE) spectroscopy, 1D-NOE was analyzed to confirm a chiral center (FIGS. 6A, 6B, and 6C).

Intermediate B

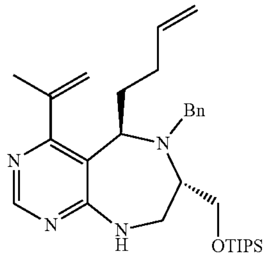

(n = 2)

A yellow oil; $R_f$=0.5 (hexane/EtOAc=1:1); 120.8 mg, 87% yield; d.r. >99:1; $^1H$ NMR (400 MHz, a $CDCl_3$) δ 8.40 (s, 1H), 7.33-7.21 (m, 5H), 5.78 (m, 1H), 5.55 (d, J=5.1 Hz, 1H), 5.01 (dd, J=17.2, 1.2 Hz, 1H), 4.94 (m, 2H), 4.72 (s, 1H), 4.21 (dd, J=10.2, 5.1 Hz, 1H), 3.84 (m, 2H), 3.64-3.54 (m, 3H), 3.48-3.37 (m, 2H), 2.33-2.17 (m, 2H), 2.11-2.04 (m, 1H), 1.83 (s, 3H), 1.45-1.36 (m, 1H), 1.06 (m, 21H); $^{13}C$ NMR (100 MHz, a $CDCl_3$) δ 168.5, 164.7, 155.6, 143.1, 140.2, 138.2, 128.4, 127.8, 127.0, 117.7, 116.0, 114.9, 64.7, 59.2, 57.5, 52.6, 43.4, 31.7, 30.9, 23.1, 18.1, 12.0; HRMS (ESI+): Calcd for a $C_{31}H_{49}N_4OSi^+$ $[M+H]^+$ 521.3670, found 521.3670. (FIGS. 38A and 38B).

Intermediate B (n=2) was synthesized by using 1 d and butyl magnesium bromide solution (0.2 M TFH). The diastereomeric ratio was determined by LC-MS analysis of crude compound, while 1H NMR was analyzed after silica-gel column (FIGS. 23, 38A, and 38B).

6d

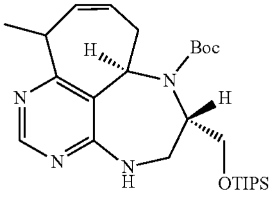

A yellow oil; $R_f$=0.4 (hexane/EtOAc=2:1); 87.95 mg, 72% yield, 63% overall yield; $^1$H NMR (400 MHz, a $CDCl_3$) δ 8.42 (s, 1H), 7.22-7.12 (m, 5H), 6.10 (t, J=6.7 Hz, 1H), 5.82 (d, J=5.5 Hz, 1H), 3.84-3.76 (m, 5H), 3.65 (dd, J=11.7, 7.0 Hz, 1H), 3.49 (m, 1H), 2.89 (m, 1H), 2.48 (m, 1H), 2.10 (m, 2H), 1.91 (s, 3H), 1.84 (m, 1H), 1.26 (m, 21H); $^{13}$C NMR (100 MHz, a $CDCl_3$) δ 164.5, 164.1, 154.9, 140.0, 137.4, 131.8, 128.1, 127.4, 126.7, 117.1, 62.3, 61.2, 57.6, 56.3, 43.0, 35.4, 23.6, 20.1, 17.9, 11.8; IR (neat) $v_{max}$: 3241, 2944, 2865, 1570, 1462, 1102, 883 $cm^{-1}$; HRMS(ESI+): Calcd for a $C_{29}H_{45}N_4OSi^+$ $[M+H]^+$ 493.3357, found 493.3349, Δppm +0.41. (FIGS. 40A and 40B).

Through Nuclear Overhauser Effect (NOE) spectroscopy, 1D-NOE was analyzed to confirm a chiral center of 6d (FIGS. 7A and 7B).

Example 6: Preparation of Compound 7e 1e (10 mg, 0.223 mmol) was dissolved in acetonitrile (11.0 ml) with stirring and to this solution was added benzyl bromide (0.040 ml, 0.335 mmol). The compound was stirred at 80° C., followed by completion of the reaction as indicated by TLC. The compound after completion of the reaction was condensed under reduced pressure, washed with hexane to remove any excess benzyl bromide, and then condensed. The iminium ion was dissolved in cold anhydrous THF (22.0 ml), to which was added 3-butyl magnesium bromide solution (0.2 M THF, 5.575 ml, 1.115 mmol) dropwise over 30 min at −78° C. The compound was then stirred for 18 hours at r.t. The reaction was quenched with a saturated ammonium chloride solution and the reaction solution was extracted twice with dichloromethane. The extracted organic solution was dried over anhydrous magnesium sulfate and filtered. The filtrate was condensed under reduced pressure and the reaction mixture was purified by silica-gel flash column chromatography to obtain intermediate C (122.0 mg, yield 80%, d.r. 95:5). The diastereomeric ratio was determined by LC-MS analysis of crude compound (FIGS. 25A, 25B, and 25C). To intermediate C (122.0 mg, 0.178 mmol) dissolved in toluene (11.5 ml) was added $2^{nd}$ generation Grubbs' catalyst (30.22 mg, 0.036 mmol, 20 mol %) and left to stir at reflux. After completion of the reaction as indicated by TLC, the organic solution was condensed under reduced pressure and the reaction mixture was purified by silica-gel flash column chromatography to obtain desired compound 7e (85.24 mg, yield 73%) as a pale yellow oil.

7e

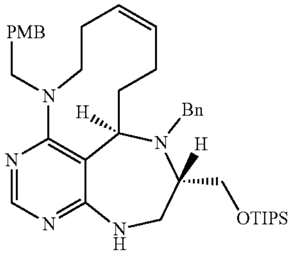

$R_f$=0.2 (hexane/EtOAc=3:1); $^1$H NMR (400 MHz, a $CDCl_3$) δ 8.15 (s, 1H), 7.15-7.05 (m, 5H), 6.99 (d, J=8.6 Hz, 2H), 6.80 (d, J=8.2 Hz, 2H), 5.47 (m, 1H), 5.37 (m, 2H), 4.30 (dd, J=11.9, 2.2 Hz, 1H), 4.13 (m, 1H), 3.80 (s, 3H), 3.75 (m, 2H), 3.72 (m, 1H), 3.39 (m, 4H), 3.11 (m, 1H), 2.80 (m, 1H), 2.59 (m, 3H), 2.33 (m, 1H), 2.01 (m, 1H), 1.88 (m, 1H), 1.77 (m, 2H), 1.50 (m, 1H), 0.92 (m, 21H); $^{13}$C NMR (100 MHz, a $CDCl_3$) δ 167.4, 165.0, 158.0, 155.4, 140.2, 132.1, 131.6, 129.8, 128.8, 128.3, 128.2, 126.8, 113.9, 106.1, 64.5, 60.9, 59.2, 59.1, 57.6, 55.3, 46.9, 43.8, 29.2, 26.3, 23.8, 18.0, 11.9; IR (neat) $v_{max}$: 3245, 3000, 2942, 2865, 1572, 1512, 1247, 1113 $cm^{-1}$; HRMS(ESI+): Calcd for a $C_{39}H_{58}N_5O_2Si^+$ $[M+H]^+$ 656.4354, found 656.4345, Δppm −1.37. (FIGS. 41A and 41B).

Through Nuclear Overhauser Effect (NOE) spectroscopy, 1D-NOE was analyzed to confirm a chiral center of 7e (FIGS. 8A and 8B).

Example 7: Preparation of Compound 8e

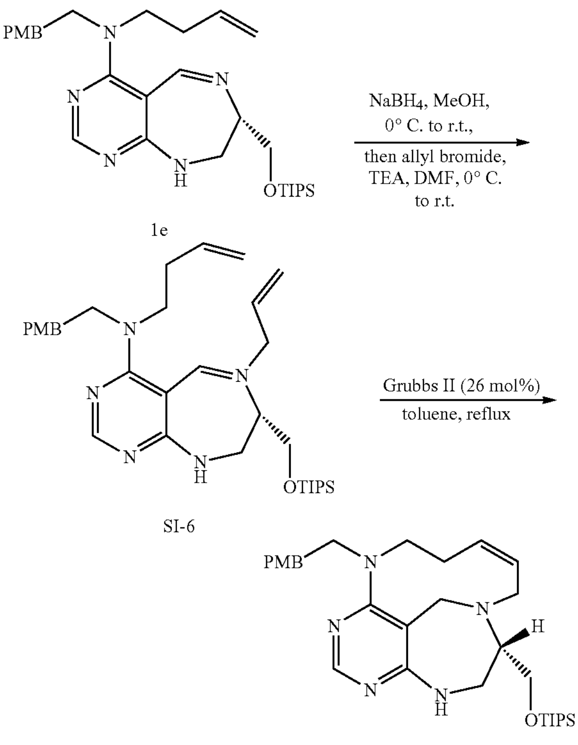

1e

SI-6

8e

A solution of 1e (120 mg, 0.223 mmol) in methanol (MeOH, 2.2 ml) was treated with sodium borohydride ($NaBH_4$, 42.18 mg, 1.115 mmol) at 0° C. and stirred between 0° C. and 25° C. After completion of the reaction as indicated by TLC, the mixture was quenched with addition of sodium bicarbonate ($NaHCO_3$) solution. The reaction solution was extracted twice with dichloromethane (DCM) and the extracted organic solution was dried over anhydrous sodium sulfate ($Na_2SO_4$) and filtered. The filtrate was then evaporated under reduced pressure, condensed, and dried. The compound was dissolved in DMF (2.2 ml), followed sequentially adding triethylamine (TEA, 0.055 ml, 0.396 mmol) and allyl bromide (0.025 ml, 0.290 mmol) at 0° C. and stirring between 0° C. and 25° C. After completion of the reaction as indicated by TLC, the mixture was quenched with addition of ammonium chloride ($NH_4Cl$) solution. The reaction solution was extracted twice with ethyl acetate (EA) and the extracted organic solution was dried over anhydrous sodium sulfate ($Na_2SO_4$) and filtered. The filtrate was then condensed under reduced pressure and the product was purified with silica-gel flash column chromatography to obtain compound SI-6 (81.47 mg, 63% yield).

A solution of SI-6 (81.47 mg, 0.140 mmol) in toluene (28.0 ml) was treated with second generation Grubbs' catalyst (23.77 mg, 0.028 mmol, 20 mol %) and left at reflux. After completion of the reaction as indicated by TLC, the residual solvent was removed under reduced pressure and the product was purified with silica-gel flash column chromatography to obtain compound 8e (54.08 mg, 70% yield, 44% overall yield) as a yellow oil.

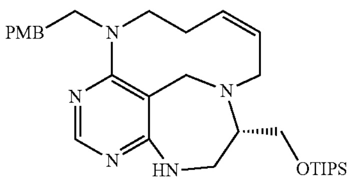

8e $R_f$=0.3 (DCM/MeOH=20:1); $^1$H NMR (400 MHz, a $CDCl_3$) δ 8.35 (s, 1H), 7.02 (d, J=8.6 Hz, 2H), 6.79 (d, J=8.2 Hz, 2H), 5.74 (br d, J=5.1 Hz, 1H), 5.67 (td, J=11.2, 4.5 Hz, 1H), 5.51 (td, J=10.9, 4.5 Hz, 1H), 4.58 (d, J=16.0 Hz, 1H), 4.06 (ddd, J=14.6, 10.9, 3.1 Hz, 1H), 3.97 (d, J=16.0 Hz, 1H), 3.76 (s, 3H), 3.59 (dd, J=10.0, 4.1 Hz, 1H), 3.46 (m, 2H), 3.37 (m, 2H), 3.08 (m, 2H), 2.92 (m, 2H), 2.73 (m, 1H), 2.54 (m, 1H), 2.39 (ddd, J=13.4, 10.7, 5.7, 1H), 2.18 (m, 1H), 1.76 (br d, J=12.1 Hz, 1H), 1.07 (m, 21H); $^{13}$C NMR (100 MHz, a $CDCl_3$) δ 168.2, 165.8, 157.9, 157.7, 134.3, 132.0, 129.5, 127.4, 113.7, 113.3, 69.4, 64.7, 58.1, 55.3, 52.0, 50.5, 43.9, 40.5, 33.8, 25.9, 18.0, 11.9; IR (neat) $v_{max}$: 3239, 3006, 2945, 2866, 1574, 1512, 1265 $cm^{-1}$; HRMS (ESI+): Calcd fora $C_{31}H_{50}N_5O_2Si^+$ [M+H]$^+$ 552.3728, found 552.3722, Δppm −1.09. (FIGS. 42A and 42B).

Example 8: Preparation of Compounds 9f and 10f

In microwave reaction vessel, 1f (90 mg, 0.198 mmol), alkyne (0.5 mmol), 4-picoline N-oxide (54.57 mg, 0.5 mmol), and $Rh(PPh_3)_3Cl$ (18.50 mg, 0.020 mmol, 10 mol %) were dissolved in ACN (3.0 ml) and subjected to the reaction for 35 minutes at 100 watt and 90° C. DCM was added to the mixture and washed with brine. The extracted organic solution was dried over anhydrous sodium sulfate ($Na_2SO_4$) and filtered. The filtrate was then evaporated under reduced pressure, condensed, and dried. The product was purified with silica-gel flash column chromatography to obtain compound 9f or 10f.

9f

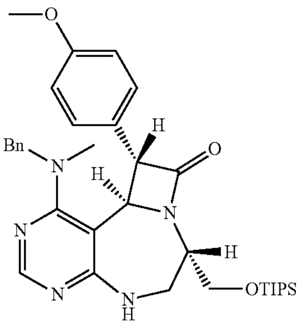

A light yellow oil; $R_f$=0.3 (DCM/MeOH=20:1); 72.69 mg, 61% yield; d.r. >99:1; NMR (400 MHz, a $CDCl_3$) δ 8.10 (s, 1H), 7.25 (m, 3H), 7.11 (d, J=8.2 Hz, 4H), 6.83 (d, J=8.2 Hz, 2H), 6.30 (dd, J=6.5, 4.5 Hz, 1H), 5.06 (s, 1H), 4.43, 4.31 (ABq, $J_{AB}$=14.9 Hz, 2H), 4.21 (dd, J=10.2, 3.5 Hz, 1H), 4.12 (m, 1H), 3.87 (m, 2H). 3.81 (s, 3H), 3.56 (s, 1H), 3.43 (ddd, J=14.2, 7.3, 4.3 Hz, 1H), 2.44 (s, 3H), 1.09 (m, 21H); $^{13}$C NMR (100 MHz, a $CDCl_3$) δ 168.0, 165.3, 163.0, 159.2, 155.0, 137.5, 129.0, 128.5, 128.4, 127.3, 127.1, 114.1, 96.9, 65.2, 63.5, 59.5, 55.3, 55.2, 54.2, 42.9, 38.1, 18.0, 11.8; IR (neat) $v_{max}$: 3250, 3056, 2942, 2865, 1751, 1567, 1119 $cm^{-1}$; HRMS(ESI+): Calcd for a $C_{34}H_{48}N_5O_3Si^+$ [M+H]$^+$ 602.3521, found 602.3528, Δppm +1.16. (FIGS. 43A and 43B).

The diastereomeric ratio was determined by LC-MS analysis of crude compound (FIGS. 20A and 20B).

Through Nuclear Overhauser Effect (NOE) spectroscopy, 1D-NOE was analyzed to confirm a chiral center of 9f (FIGS. 9A, 9B, and 9C).

10f

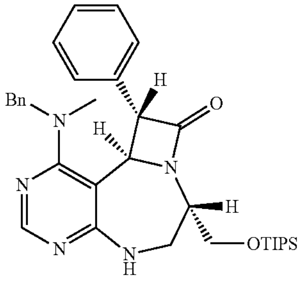

A light yellow oil; $R_f$=0.3 (DCM/MeOH=20:1); 54.35 mg, 48% yield; d.r. 90:10; $^1$H NMR (400 MHz, a $CDCl_3$) δ 8.12 (s, 1H), 7.70-7.65 (m, 1H), 7.53 (m, 1H), 7.46 (m, 1H), 7.30 (m, 2H), 7.23 (m, 3H), 7.09 (m, 2H), 6.35 (dd, J=6.7, 4.7 Hz, 1H), 5.11 (d, J=1.2 Hz, 1H), 4.39 (m, 1H), 4.23 (m, 2H), 4.13 (m, 1H), 3.87 (m, 2H), 3.60 (d, J=1.5 Hz, 1H), 3.43 (ddd, J=14.4, 7.3, 4.5 Hz, 1H), 2.42 (s, 3H), 1.10 (m, 21H); $^{13}$C NMR (100 MHz, a $CDCl_3$) δ 167.6, 165.4, 163.0, 155.0, 137.4, 135.0, 132.1, 132.0, 128.7, 128.4, 127.8, 127.2, 96.9, 65.9, 63.5, 59.4, 55.2, 54.3, 42.8, 37.9, 18.0, 11.8; IR (neat) $v_{max}$: 3239, 3059, 3030, 2942, 2866, 1755, 1567, 1108 $cm^{-1}$; HRMS(ESI+): Calcd for a $C_{33}H_{46}N_5O_2Si^+$ [M+H]$^+$ 572.3415, found 572.3413, Δppm −0.35; mp: 86-88° C. (FIGS. 44A and 44B).

The diastereomeric ratio was determined by LC-MS analysis of crude compound (FIGS. 21A, 21B, and 21C).

Through Nuclear Overhauser Effect (NOE) spectroscopy, 1D-NOE was analyzed to confirm a chiral center of 10f (FIGS. 10A, 10B, and 10C).

Example 9: Preparation of Compound 11f

In microwave reaction vessel, 1f (90 mg, 0.198 mmol), N-benzyl-2-chloroacetamide (54.54 mg, 0.297 mmol), and NaBr (30.56 mg, 0.297 mmol) were dissolved in DMF (3.0 ml) and subjected to the reaction over 30 minutes at 150 watt and 110° C. The mixture was cooled down to r.t., followed by adding 1,8-Diazabicyclo[5.4.0]undec-7-ene (DBU, 0.059 ml, 0.396 mmol) and stirring at r.t. After completion of the reaction as indicated by TLC, the mixture was quenched with addition of sodium bicarbonate (NaHCO3) solution. The reaction solution was extracted twice with ethyl acetate (EA) and the extracted organic solution was dried over anhydrous sodium sulfate (Na2SO4) and filtered. The filtrate was then evaporated under reduced pressure, condensed, and dried. The product was purified by HPLC to obtain 11f (72.57 mg, 61%, d.r. 6:1 (diastereomeric ratio)) as a pale yellow oil.

11f

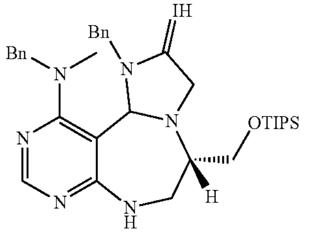

$R_f$=0.3 (hexane/EtOAc=1:1); $^1$H NMR (400 MHz, a $CDCl_3$) δ 8.17 (s, 0.83H, major diastereomer), 8.12 (s, 0.13H, minor diastereomer), 7.28 (br s, 3H), 7.19 (br s, 3H), 6.89 (br s, 2H), 6.73 (br s, 2H), 6.11 (br s, 0.12H, minor diastereomer), 5.90 (s, 0.78H, major diastereomer), 5.28 (s, 0.84H, major diastereomer), 5.08 (s, 0.13H, minor diastereomer), 4.98 (m, 1H), 4.44, 4.34 (ABq, $J_{AB}$=16.2 Hz, 2H), 3.78 (m, 2H), 3.66-3.37 (m, 4H), 3.24 (m, 2H), 2.73 (m, 3H), 1.05-0.95 (m, 21H); $^{13}$C NMR (100 MHz, a $CDCl_3$) δ 173.3, 167.1, 162.9, 157.3, 137.4, 136.0, 128.6, 128.5, 127.8, 127.1, 126.9, 126.7, 88.1, 77.3, 65.0, 59.6, 57.8, 52.0, 44.1, 42.9, 37.9, 18.03, 18.02, 11.9; IR (neat) $v_{max}$: 3290, 3030, 2943, 2865, 1694, 1629, 1571, 1118 $cm^{-1}$; HRMS(ESI+): Calcd fora $C_{34}H_{49}N_6O_2Si^+$ $[M+H]^+$ 601.3681, found 601.3693, Δppm +2.00. (FIGS. 45A and 45B).

The diastereomeric ratio was determined by 1H HMR analysis after silica-gel column (FIGS. 45A and 45B).

Example 10: Preparation of Compounds 12f and 12f'

1f (180.0 mg, 0.397 mmol) was dissolved in acetonitrile solution (ACN, 20.0 ml), followed by treating with benzyl bromide (0.071 ml, 0.596 mmol) and stirring at 80° C. After completion of the reaction as indicated by TLC, the residual solution was removed under reduced pressure, and, sequentially, washed with hexane to remove any excess benzyl bromide. The compound was dissolved in anhydrous THF (40.0 ml) under argon atmosphere, followed by adding ethynylmagnesium bromide solution (0.5 M solution in THF, 3.970 ml, 1.985 mmol) dropwise with a syringe over 30 minutes at −78° C. and stirring over 18 hours between −78° C. and 25° C. After 18 hours, the mixture was quenched with addition of ammonium chloride ($NH_4Cl$) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain compounds 12f (major product) and 12f' (minor product).

12f

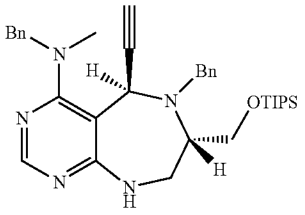

Major product (12f) as a light yellow oil; $R_f$=0.4 (hexane/EtOAc=3:1); 158.4 mg, 70% yield; $^1$H NMR (400 MHz, a $CDCl_3$) δ 8.16 (s, 1H), 7.33-7.24 (m, 5H), 7.17-7.14 (m, 3H), 6.79-6.78 (m, 2H), 6.27 (m, 1H), 4.74 (d, J=2.3 Hz, 1H), 4.64 (d, J=14.9 Hz, 1H), 4.31, 4.26 (ABq, $J_{AB}$=15.1 Hz, 2H), 3.92-3.85 (m, 2H), 3.78 (d, J=14.5 Hz, 1H), 3.73 (dd, J=10.0, 3.3 Hz, 1H), 3.54 (ddd, J=14.4, 7.6, 1.4 Hz 1H), 2.93 (m, 1H), 2.60 (s, 3H), 2.53 (d, J=2.3 Hz, 1H), 1.10-1.00 (m, 21H); $^{13}$C NMR (100 MHz, a $CDCl_3$) δ 167.4, 164.2, 155.8, 138.9, 138.3, 128.5, 128.4, 128.3, 127.6, 127.4, 126.7, 102.0, 83.9, 74.9, 65.3, 62.0, 58.5, 58.2, 48.5, 40.2, 39.6, 18.1, 12.0; IR (neat) $v_{max}$: 3241, 2943, 2865, 1573, 1404, 1101, 669 $cm^{-1}$; HRMS(ESI+) Calcd for a $C_{34}H_{48}N_5OSi^+$ $[M+H]^+$ 570.3623, found 570.3614, Δppm −1.58. (FIGS. 46A and 46B).

Through Nuclear Overhauser Effect (NOE) spectroscopy, 1D-NOE was analyzed to confirm a chiral center of 12f (FIGS. 11A and 11B).

12f'

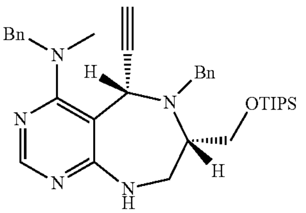

Minor product (12f') as a light yellow oil; $R_f$=0.25 (hexane/EtOAc=3:1); 18.78 mg, 8.3% yield; $^1$H NMR (400 MHz, a $CDCl_3$) δ 8.21 (s, 1H), 7.33-7.31 (m, 3H), 7.21-7.17 (m, 5H), 6.84 (m, 2H), 6.34 (m, 1H), 4.79 (m, 1H), 4.71 (d, J=2.3 Hz, 1H), 4.54, 4.20 (ABq, $J_{AB}$=15.5 Hz, 2H), 4.07 (t, J=10.2 Hz, 1H), 3.84, 3.71 (ABq, $J_{AB}$=13.7 Hz, 2H), 3.64 (dd, J=9.8, 5.1 Hz, 1H), 3.57 (ddd, J=15.0, 7.7, 4.7 Hz 1H), 3.37 (m, 1H), 2.68 (s, 3H), 2.50 (d, J=2.7 Hz, 1H), 1.04 (br s, 21H); $^{13}$C NMR (100 MHz, a $CDCl_3$) δ 168.7, 164.4, 156.1, 139.0, 138.2, 129.0, 128.5, 128.4, 127.6, 127.3, 126.8, 99.9, 87.5, 74.8, 68.3, 64.7, 60.7, 58.5, 46.7, 44.0, 38.9, 18.1, 12.0; IR (neat) $v_{max}$: 3239, 2940, 2865, 1571, 1404, 1102, 698 $cm^{-1}$; HRMS(ESI+): Calcd for a $C_{34}H_{48}N_5OSi^+$ $[M+H]^+$ 570.3623, found 570.3625, Δppm +0.35. (FIGS. 47A and 47B).

Through Nuclear Overhauser Effect (NOE) spectroscopy, 1D-NOE was analyzed to confirm a chiral center of 12f' (FIGS. 12A and 12B).

Example 11: Preparation of Compounds 13f and 13f'

-continued

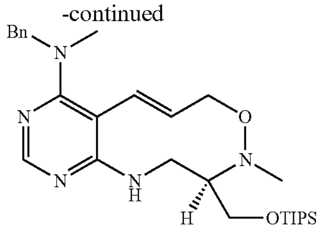

13f

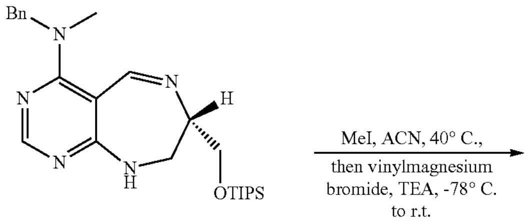

1f

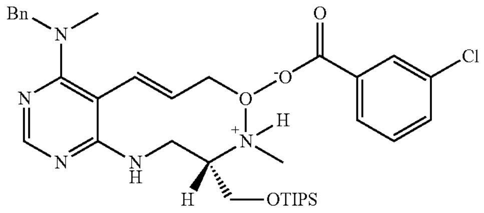

13f

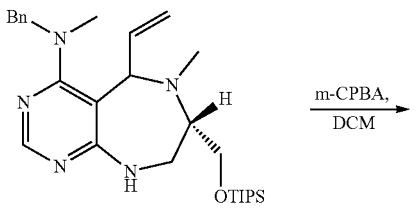

SI-7

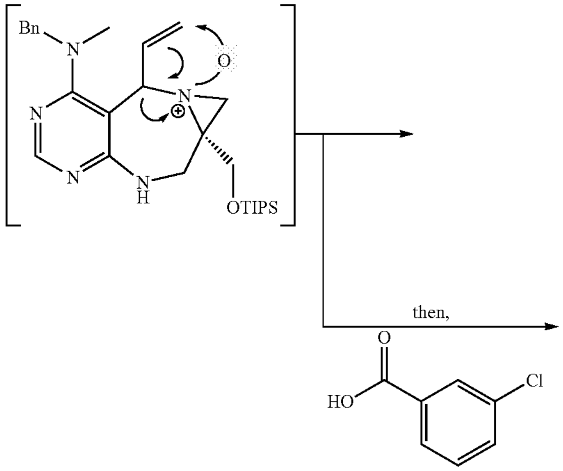

1) Preparation of SI-7: 1f (90 mg, 0.198 mmol) was dissolved in acetonitrile (ACN, 10.0 ml) solution, followed by treating with iodomethane (0.018 ml, 0.297 mmol) and stirring at 40° C. After completion of the reaction as indicated by TLC, any excess iodomethane was removed under reduced pressure. The compound was dissolved in anhydrous THF (20.0 ml) under argon atmosphere, followed by adding benzylmagnesium bromide solution (2.0 m solution in THF, 0.99 ml, 1.98 mmol) dropwise with a syringe over 30 minutes at −78° C. and stirring over 18 hours between −78° C. and 25° C. After 18 hours, the mixture was quenched with addition of ammonium chloride (NH4Cl) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain compound SI-7 (70.68 mg, 72% yield, d.r. 9:1 (diastereomeric ratio)) as a pale yellow oil.

2) Preparation of 13f: SI-7 (70.68 mg, 0.143 mmol) was dissolved in DCM (14.3 ml), treated with 3-chloroperbenzoic acid (m-CPBA, 32.08 mg, 0.186 mmol) and left at reflux. After 1 hour, the residual solution was removed under reduced pressure and the product was then purified with silica-gel flash column chromatography to obtain compound 13f (42.45 mg, 58% yield, 42% overall yield) as a pale transparent oil.

3) Preparation of 13f': SI-7 (70.68 mg, 0.143 mmol) was dissolved in DCM (14.3 ml), treated with 3-chloroperbenzoic acid (m-CPBA, 32.08 mg, 0.186 mmol) and left at reflux. After 1 hour, the above was treated with 3-chlorobenzoic acid (22.39 mg, 0.143 mmol) and left to stir at r.t. After completion of the reaction as indicated by TLC, the residual solution was removed under reduced pressure and the product was purified with silica-gel flash column chromatography to obtain compound 13f (70.72 mg, 74% yield, 53% overall yield) as a pale yellow oil. Eiastereomeric ratio (E:Z=99:1) was confirmed by LS-MS analysis of crude mixture (FIG. 24)

SI-7

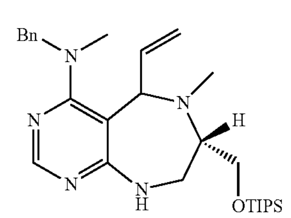

$R_f$=0.27 (DCM/MeOH=20:1); $^1$H NMR (400 MHz, a $CDCl_3$) δ 8.22 (s, 0.08H, minor diastereomer), 8.17 (s, 0.71H, major diastereomer), 7.36-7.24 (m, 6H, major diastereomer+minor diastereomer), 6.25 (m, 1H), 5.64 (br s, 0.12H, minor diastereomer), 5.29 (br s, 0.97H, major diastereomer), 5.20 (d, J=10.2 Hz, 1H), 4.88 (d, J=17.2 Hz, 1H), 4.56-4.45 (m, 3H), 5.20 (d, J=10.2 Hz, 1H), 3.84-3.77 (m, 2H), 3.55 (t, J=9.4 Hz, 1.11H, major diastereomer), 3.43 (t, J=9.8 Hz, 0.15H, minor diastereomer), 3.19 (m, 1H), 2.86-2.81 (m, 4H), 2.74 (s, 0.38H, minor diastereomer), 2.42 (s, 0.38H, minor diastereomer), 2.27 (s, 3H, major diastereomer), 1.10-1.02 (m, 25H, major diastereomer+minor diastereomer); $^{13}$C NMR (100 MHz, a $CDCl_3$) δ 167.6, 165.5, 155.4, 138.7, 136.5, 128.6, 127.3, 127.1, 118.2, 102.9, 64.9, 63.6, 62.8, 58.3, 44.2, 41.4, 39.4, 18.1, 12.0; HRMS(ESI+): Calcd for a $C_{28}H_{46}N_5OSi^+$ $[M+H]^+$ 496.3466, found 496.3465, Δppm −0.20. (FIGS. 48A and 48B).

13f

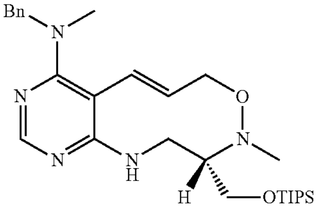

$R_f$=0.3 (hexane/EtOAc=3:1); $^1$H NMR (500 MHz, a $CDCl_3$) δ 8.11 (s, 1H), 7.32 (m, 2H), 7.24 (m, 1H), 7.20 (m, 2H), 6.63 (d, J=16.1 Hz, 1H), 6.09 (m, 1H), 4.82 (br s, 3H), 4.09 (m, 3H), 3.71 (m, 2H), 3.45-3.27 (m, 1H), 3.04 (s, 3H), 2.77 (m, 1H), 2.63-2.55 (m, 3H), 1.08 (m, 21H);); IR (neat) $v_{max}$: 3395, 3254, 3060, 3028, 2926, 1946, 1713, 1567, 1493, 1452, 1266, 1105 $cm^{-1}$; HRMS(ESI+): Calcd for a $C_{28}H_{46}N_5O_2Si^+$ $[M+H]^+$ 512.3415, found 512.3417, Δppm +0.39. (FIG. 49).

The $^1$H NMR spectrum of compound 13f was too broad to analyze. As shown below, the structure of 13f was fully confirmed only when it is in a salt form after treatment of 3-chlorobenzoic acid. The NMR peak of 13f was converted to be sharp to readily analyze.

13f'

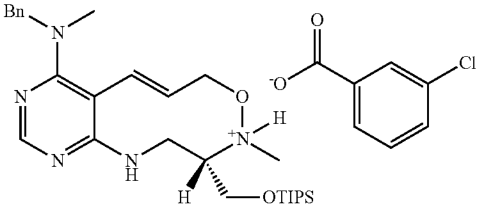

$R_f$=0.3 (hexane/EtOAc 1:1); $^1$H NMR (500 MHz, a $CDCl_3$) δ 8.19 (s, 1H), 7.95 (s, 1H, 3-chlorobenzoic acid-H), 7.85 (d, J=7.8 Hz, 1H, 3-chlorobenzoic acid-H), 7.54 (d, J=8.3 Hz, 1H, 3-chlorobenzoic acid-H), 7.37 (t, J=7.8 Hz, 1H, 3-chlorobenzoic acid-H), 7.29-7.26 (m, 2H), 7.22-7.19 (m, 3H), 6.49 (d, J=16.6 Hz, 1H), 5.96 (dt, J=16.6, 5.9 Hz, 1H), 5.51 (t, J=6.4 Hz, 1H), 4.74 (m, 2H), 4.66, 4.62 (ABq, $J_{AB}$=15.0 Hz, 2H), 3.96 (m, 2H), 3.70 (dd, J=9.8, 8.3 Hz, 1H), 3.55 (dt, J=14.3, 5.6 Hz, 1H), 2.90 (s, 3H), 2.76 (m, 1H), 2.67 (s, 3H), 1.06 (m, 21H), $^{13}$C NMR (100 MHz, a $CDCl_3$) δ 165.1, 162.8, 161.2, 155.4, 138.4, 134.7, 133.3, 131.7, 129.84, 129.75, 128.9, 128.6, 127.8, 127.79, 127.2, 127.1, 96.3, 70.2, 65.6, 61.0, 56.0, 45.2, 40.5, 39.1, 18.1, 11.9; IR (neat) $v_{max}$: 3396, 3062, 3026, 2945, 2863, 1724, 1572, 1253, 1117 $cm^{-1}$; HRMS(ESI+): Calcd for a $C_{35}H_{51}ClN_5O_4Si^+$ $[M+H]^+$ 668.3393, found 668.3387, Δppm −0.90. (FIGS. 50A and 50B).

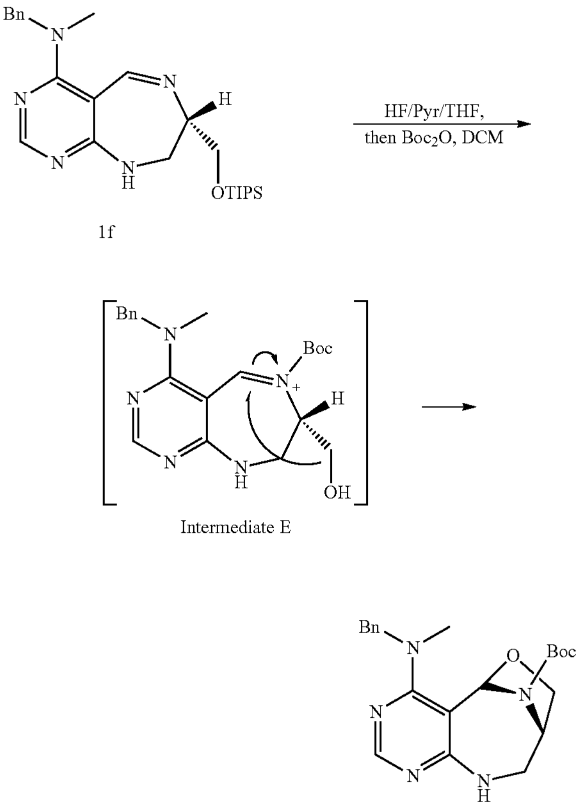

1f

Intermediate E

14f 1f (90.00 mg, 0.198 mmol) was dissolved in HF/pyridine/THF (5/5/90) solution (2 ml) and stirred at r.t. The reaction was completed as indicated by TLC, treated with ethoxytrimethylsilane (2 ml) and stirred over 1 hour to remove any residual excess HF. After 1 hour, the residual solution was removed under reduced pressure. The compound was dissolved in DCM (4 ml), treating with $Boc_2O$ (di-tert-butyl dicarbonate, 56.09 mg, 0.257 mmol), and the mixture was stirred at r.t. After completion of the reaction as indicated by TLC, the residual solution was removed under reduced pressure and the obtained solid was recrystallized with hexane to obtain compound 14f (68.47 mg, 87% overall yield) as a white solid.

14f

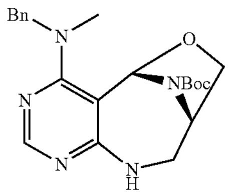

$R_f$=0.3 (EA); $^1$H NMR (400 MHz, a $CDCl_3$) δ 8.13 (s, 1H), 7.35-7.24 (m, 5H), 6.62 (s, 1H), 5.63 (br s, 1H), 4.76 (m, 2H), 4.55 (d, J=15.3 Hz, 1H), 4.01 (d, J=7.0 Hz, 1H), 3.87 (t, J=6.7 Hz, 1H), 3.55 (br d, J=13.6 Hz, 1H), 3.48-3.43 (m, 1H), 2.98 (s, 3H), 1.43 (s, 9H); $^{13}$C NMR (100 MHz, a $CDCl_3$) δ 166.7, 164.0, 155.8, 153.0, 138.3, 128.6, 127.9, 127.2, 103.0, 85.2, 81.6, 68.5, 57.5, 53.7, 48.0, 40.7, 28.5, 28.4, 28.3; IR (neat) $v_{max}$: 3248, 2975, 2931, 1700, 1571, 1403, 1162, 1048, 699 $cm^{-1}$; HRMS(ESI+): Calcd for a $C_{21}H_{28}N_5O_3^+$ [M+H]$^+$ 398.2187, found 398.2174, Δppm −3.26; mp: 50-52° C. (FIGS. 51A and 51B).

Example 13: Preparation of Compound 15f

The compound was prepared based on Example 12, provided that benzyl isocyanate was used in place of $Boc_2O$.

15f

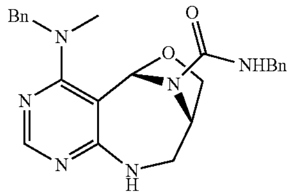

A white solid; $R_f$=0.4 (EA); 77.57 mg, 91% yield; $^1$H NMR (500 MHz, a $CDCl_3$) δ 8.18 (s, 1H), 7.29-7.28 (m, 2H), 7.25-7.24 (m, 4H), 7.19-7.18 (m, 2H), 7.14 (d, J=6.4 Hz, 2H), 6.57 (s, 1H), 5.55 (br s, 1H), 4.86 (t, J=5.4 Hz, 1H), 4.74 (m, 1H), 4.46 (br d, J=1.5 Hz, 2H), 4.32 (d, J=5.4 Hz, 2H), 4.02 (dd, J=7.3, 1.0 Hz, 1H), 3.91 (m, 1H), 3.55 (m, 1H), 3.38 (dt, J=13.2, 4.2 Hz, 1H), 2.83 (s, 3H); $^{13}$C NMR (100 MHz, a $CDCl_3$) δ 166.8, 164.1, 156.0, 154.9, 138.8, 137.8, 128.7, 128.6, 127.7, 127.5, 127.4, 127.3, 104.3, 84.0, 68.7, 58.2, 53.7, 48.0, 44.7, 40.3; IR (neat) $v_{max}$: 3258, 2971, 1633, 1542, 1405, 1049, 698 $cm^{-1}$; HRMS(ESI+): Calcd for a $C_{24}H_{27}N_6O_2^+$ [M+H]$^+$ 431.2190, found 431.2184, Δppm −1.39; mp: 67-69° C. (FIGS. 52A and 52B).

Example 14: Preparation of Compound 16f

The compound was prepared based on Example 12, provided that 3-nitrobenzene sulfonyl chloride (m-NsCl) was used in place of $Boc_2O$. The product was purified with silica-gel flash column chromatography to obtain compound 16f.

The structure 16f was confirmed by X-ray crystallographic analysis (FIGS. 3 and 64, a CCDC number 1500586).

16f

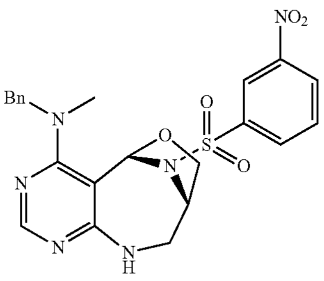

A white solid; $R_f$=0.3 (EA); 59.2 mg, 62% yield; $^1$H NMR (400 MHz, DMSO-$d_6$) δ 8.54-8.53 (m, 2H), 8.02 (s, 1H), 7.98 (d, J=7.8 Hz, 1H), 7.83 (t, J=8.2 Hz, 1H), 7.39 (m, 2H), 7.26 (m, 4H), 6.63 (s, 1H), 4.84 (br s, 1H), 4.65, 4.54 (ABq, $J_{AB}$=15.6 Hz, 2H), 3.61 (d, J=7.4 Hz, 1H), 3.51-3.45 (m, 1H), 3.28 (d, J=14.1 Hz, 1H), 2.88 (m, 4H); $^{13}$C NMR (400 MHz, DMSO-$d_6$) δ 165.6, 163.2, 155.8, 148.0, 138.9, 138.1, 133.3, 131.7, 128.5, 127.4, 127.1, 122.4, 122.3, 101.4, 87.3, 66.7, 57.4, 55.8, 54.9, 47.8, 40.0; IR (neat) $v_{max}$: 2920, 1573, 1535, 1354, 1176, 734 $cm^{-1}$; HRMS(ESI+): Calcd for a $C_{22}H_{23}N_6O_5S^+$ [M+H]$^+$ 483.1445, found 483.1450, Δppm +1.03; mp: 101-103° C. (FIGS. 53A and 53B).

Example 15: Preparation of Compounds 17f and 17f'

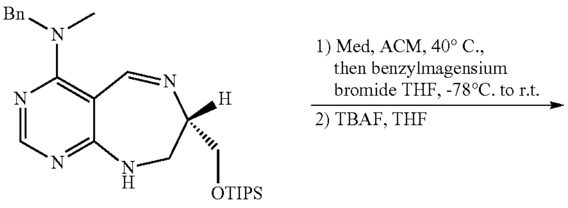

1f

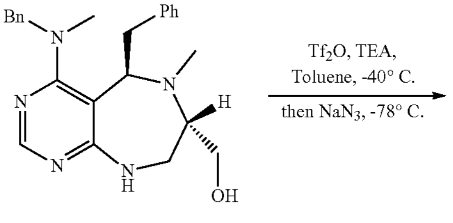

SI-8

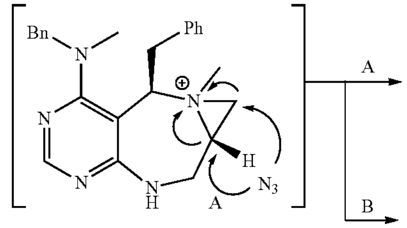

-continued

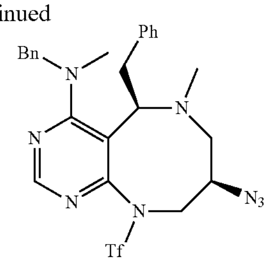

17f

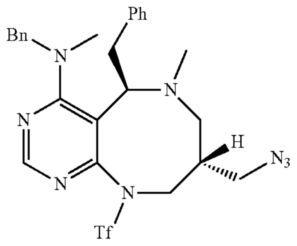

17f

1) Preparation of Compound SI-8

1f (180 mg, 0.397 mmol) was dissolved in acetonitrile solution (ACN, 20.0 ml), treating with iodomethane (0.036 ml, 0.594 mmol) and stirring at 40° C. After completion of the reaction as indicated by TLC, any excess iodomethane was removed under reduced pressure. The compound was dissolved in anhydrous THF (40.0 ml) under argon atmosphere, followed by adding benzylmagnesium bromide solution (2.0 m solution in THF, 0.99 ml, 1.98 mmol) dropwise with a syringe over 30 minutes at −78° C. and stirring over 18 hours between −78° C. and 25° C. After 18 hours, the mixture was quenched with addition of ammonium chloride ($NH_4Cl$) solution. The reaction solution was extracted twice with dichloromethane (DCM) and the extracted organic solution was dried over anhydrous sodium sulfate ($Na_2SO_4$) and filtered. The filtrate was then condensed under reduced pressure and the product was first purified by a short silica gel flash column chromatography. The compound was dissolved in THF solution (4 ml), treating with TBAF solution (Tetrabutylammonium fluoride, 1.0 M solution in THF, 0.516 ml, 0.516 mmol) and stirring at r.t. After completion of the reaction as indicated by TLC, the residual solution was removed under reduced pressure and the product was purified with silica-gel flash column chromatography to obtain compound SI-8 (121.8 mg, 76% yield) as white powder.

2) Preparation of 17f' from SI-8

SI-8 (121.8 mg, 0.302 mmol) was dissolved, under argon atmosphere, in anhydrous toluene (3.0 ml), sequentially adding triethylamine (Et3N, 0.126 ml, 0.906 mmol) and trifluoromethanesulfonic anhydride ($Tf_2O$) (0.112 ml, 0.664 mmol) at −40° C. and stirring at −40° C. over 1 hour. After 1 hour, $NaN_3$ (58.9 mg, 0.906 mmol) was added at −78° C. and stirred between −78° C. and 25° C. over 18 hours. After 18 hours, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain, respectively, 17f (path A, 8-membered ring)) and 17f' (path B, 7-membered ring)).

SI-8

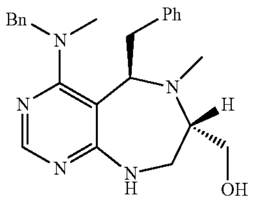

$R_f$=0.4 (DCM/MeOH=10:1); $^1$H NMR (400 MHz, a $CDCl_3$) δ 8.13 (s, 1H), 7.32-7.25 (m, 3H), 7.20-7.13 (m, 3H), 6.99 (d, J=7.2 Hz, 2H), 6.73 (d, J=6.7 Hz, 2H), 5.40 (d, J=5.9 Hz, 1H), 4.35, 4.28 (ABq, $J_{AB}$=16.0, 15.6 Hz, 2H), 4.19 (dd, J=9.6, 4.5 Hz, 1H), 3.60 (dd, J=10.6, 5.1 Hz, 1H), 3.46 (dd, J=10.8, 5.7 Hz, 1H), 3.31-3.04 (m, 4H), 2.88 (dd, J=12.9, 4.3 Hz, 1H), 2.62 (s, 3H), 2.51 (br s, 1H), 2.32 (s, 3H); $^{13}$C NMR (100 MHz, a $CDCl_3$) δ 168.4, 166.1, 154.9, 139.3, 138.1, 129.0, 128.6, 128.1, 127.4, 127.1, 126.2, 103.3, 65.0, 61.7, 58.5, 58.0, 46.2, 38.7, 38.6, 34.5; HRMS (ESI+): Calcd for a $C_{24}H_{30}H_5O^+$ $[M+H]^+$ 404.2445, found 404.2446, Δppm +0.25; mp: 70-72° C. (FIGS. 54A and 54B).

17f

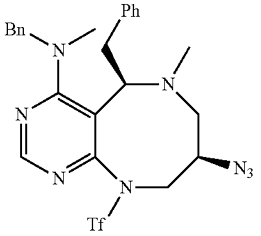

(Path A, 8-membered ring). A white solid; $R_f$=0.6 (hexane/EtOAc=3:1); 37.2 mg, 22% yield, 17% overall yield; $^1$H NMR (800 MHz, a $CDCl_3$) δ 8.29 (s, 1H), 7.32 (m, 2H), 7.28 (m, 1H), 7.17 (m, 2H), 7.13 (m, 1H), 7.00 (d, J=7.3 Hz, 2H), 6.74 (d, J=7.3 Hz, 2H), 4.33, 4.27 (ABq, $J_{AB}$=15.7 Hz, 2H), 4.23 (dd, J=14.9, 6.6 Hz, 1H), 3.99 (dd, J=10.3, 3.9 Hz, 1H), 3.96 (dd, J=15.7, 1.5 Hz, 1H), 3.89 (m, 1H), 3.38 (dd, J=14.9, 10.5 Hz, 1H), 3.07 (m, 1H), 2.98 (dd, J=12.5, 3.7 Hz, 1H), 2.84 (br dd, J=16.0, 1.6 Hz, 1H), 2.66 (s, 3H), 2.59 (s, 3H); $^{13}$C NMR (100 MHz, a $CDCl_3$) δ 169.2, 160.3, 154.0, 138.1, 136.7, 129.1, 128.8, 128.3, 127.64, 127.57, 126.5, 120.7 (q, $^1J_{C,F}$=324.4 Hz), 115.0, 66.0, 59.9, 57.4, 56.0, 52.1, 49.1, 38.8, 37.5; IR (neat) $v_{max}$: 3028, 2929, 2868, 2108, 1566, 1393 $cm^{-1}$; HRMS(ESI+) Calcd for $C_{25}H_{28}F_3N_8O_2S^+$ $[M+H]^+$ 561.2003, found 561.2009, Δppm +1.07; mp: 103-105° C. (FIGS. 56A and 56B).

Through Nuclear Overhauser Effect (NOE) spectroscopy, 1D-NOE was analyzed to confirm a chiral center of 17f (FIGS. 13A, 13B, and 13C).

17f'

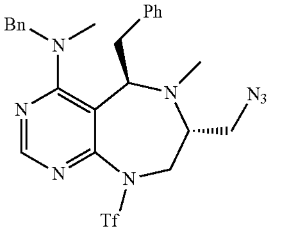

(Path B, 7-membered ring). A white solid; $R_f$=0.5 (hexane/EtOAc=3:1); 55.9 mg, 33% yield, 25% overall yield; $^1$H NMR (500 MHz, a $CDCl_3$) δ 8.32 (s, 1H), 7.34 (m, 2H), 7.29 (m, 1H), 7.14 (m, 3H), 6.96 (d, J=7.3 Hz, 2H), 6.73 (br d, J=7.3 Hz, 2H), 4.56, 4.49 (ABq, $J_{AB}$=16.5 Hz, 2H), 4.23 (d, J=15.2 Hz, 1H), 3.91 (dd, J=11.2, 2.9 Hz, 1H), 3.67 (dd, J=13.7, 4.4 Hz, 1H), 3.50 (dd, J=14.9, 10.5 Hz, 1H), 3.32 (m, 1H), 3.19 (dd, J=13.7, 2.4 Hz, 1H), 3.10 (t, J=11.8 Hz, 1H), 2.96 (dd, J=13.0, 3.2 Hz, 1H), 2.78 (s, 3H), 2.31 (s, 3H); $^{13}$C NMR (100 MHz, a $CDCl_3$) δ 168.1, 159.7, 154.7, 138.3, 137.2, 129.1, 128.8, 128.3, 127.5, 127.0, 126.5, 120.1 (q, $^1J_{C,F}$=322.6 Hz), 110.1, 66.6, 59.6, 57.4, 56.3, 51.5, 42.1, 38.0, 31.5; IR (neat) $v_{max}$: 3030, 2930, 2869, 2105, 1578, 1529, 1391, 1212, 1043 $cm^{-1}$; HRMS (ESI+) Calcd for a $C_{25}H_{28}F_3N_8O_2S^+$ $[M+H]^+$ 561.2003, found 561.2011, Δppm +1.43; mp: 140-142° C. (FIGS. 55A and 55B).

Through Nuclear Overhauser Effect (NOE) spectroscopy, 1D-NOE was analyzed to confirm a chiral center of 17f (FIGS. 14A and 14B).

Example 16: Preparation of Compound 18f

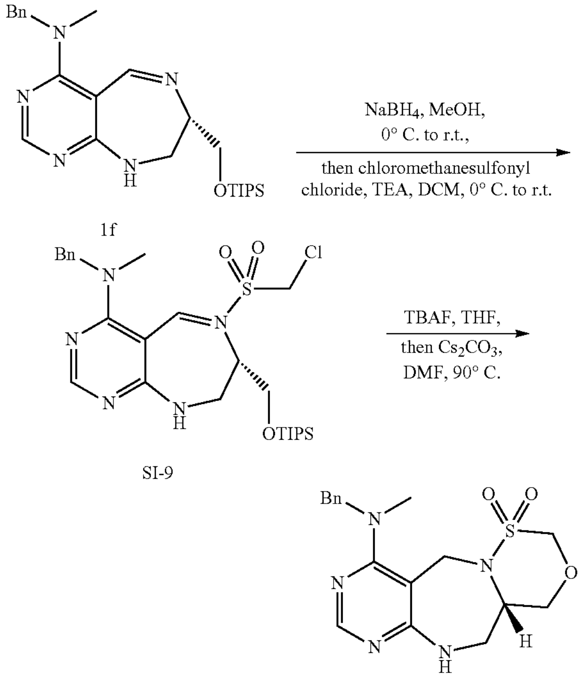

1f

SI-9

18f

1) Preparation of Compound SI-9

A solution of 1f (90 mg, 0.198 mmol) in methanol (MeOH, 2 ml) was treated with sodium borohydride (NaBH4, 36.88 mg, 0.975 mmol) at 0° C. and stirred between 0° C. and 25° C. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then evaporated under reduced pressure, condensed, and dried. The compound was dissolved in dichloromethane (DCM, 2 ml), followed by adding, at 0° C., triethylamine (TEA, 0.055 ml, 0.396 mmol) and then chloromethane sulfonyl chloride (0.023 ml, 0.257 mmol), and stirring between 0° C. and 25° C. After completion of the reaction as indicated by TLC, the mixture was quenched with addition of ammonium chloride ($NH_4Cl$) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain compound SI-9 (97.89 mg, 87% yield).

SI-9

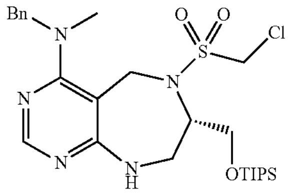

2) Preparation of Compound 18f

A solution of SI-9 (97.89 mg, 0.172 mmol) in THF was treated with TBAF solution (Tetrabutylammonium fluoride, 1.0 M solution in THF, 0.224 ml, 0.224 mmol) and stirred at r.t. After completion of the reaction as indicated by TLC, the residual solution was removed under reduced pressure. The compound was dissolved in DMF (2 ml), treating with $Cs_2CO_3$ (168.1 mg, 0.516 mmol) and stirring at 90° C. After completion of the reaction as indicated by TLC, the reaction solution was extracted twice with ethyl acetate (EA) and the extracted organic solution was dried over anhydrous sodium sulfate (Na2SO4) and filtered. The filtrate was then condensed under reduced pressure and the product was purified with silica-gel flash column chromatography to compound 18f (51.02 mg, 79% yield, 69% overall yield) as white powder.

18f

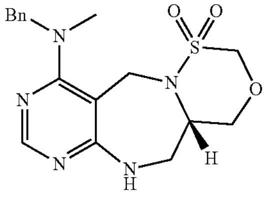

$R_f$=0.4 (DCM/MeOH=20:1); $^1$H NMR (400 MHz, DMSO-$d_6$) δ 7.98 (s, 1H), 7.34-7.23 (m, 6H), 4.84 (d, J=11.7 Hz, 1H), 4.71-4.59 (m, 3H), 4.47 (d, J=15.3 Hz, 1H), 4.33 (d, J=15.7 Hz, 1H), 4.19 (br s, 1H), 3.89 (d, J=10.4 Hz, 1H), 3.80 (t, J=11.2 Hz, 1H), 3.54 (br s, 1H), 3.38 (br s, 1H), 2.81 (s, 3H); $^{13}$C NMR (100 MHz, DMSO-$d_6$) δ 165.0, 163.2, 153.5, 138.1, 128.4, 127.5, 127.0, 95.6, 62.0, 55.4, 40.2, 39.4; IR (neat) $v_{max}$: 3230, 2926, 1574, 1409, 1155, 736 $cm^{-1}$; HRMS(ESI+): Calcd for a $C_{17}H_{22}N_5O_3S^+$ [M+H]$^+$ 376.1438, found 376.1437, Δppm −0.27; mp: 196-198° C. (FIGS. 57A and 57B).

Example 17: Preparation of Compound 19f

Compound 19f was prepared based on Example 18, provided that chloroacetic anhydride was used in place of chloromethane sulfonyl chloride.

19f

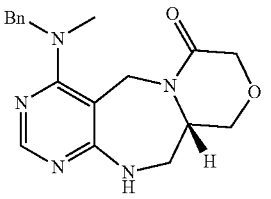

A transparent oil; $R_f$=0.5 (DCM/MeOH=20:1); 50.40 mg, 75% overall yield; $^1$H NMR (400 MHz, a $CDCl_3$) δ 8.02 (s, 1H), 7.39-7.33 (m, 4H), 7.27-7.23 (m, 1H), 6.97 (m, 1H), 5.23 (d, J=15.7 Hz, 1H), 4.78, 4.41 (ABq, $J_{AB}$=15.7 Hz, 2H), 4.21, 4.12 (ABq, $J_{AB}$=16.4 Hz, 2H), 4.09-4.01 (m, 2H), 3.97-3.87 (m, 2H), 3.78 (t, J=11.0 Hz, 1H), 3.00 (dd, J=15.3, 7.4 Hz, 1H), 2.89 (s, 3H); $^{13}$C NMR (100 MHz, a $CDCl_3$) δ 166.7, 166.5, 164.3, 154.7, 137.8, 128.5, 127.5, 127.1, 95.4, 67.7, 66.5, 57.5, 56.2, 42.2, 40.7, 39.1; IR (neat) $v_{max}$: 3237, 2908, 1653, 1573, 1408, 1119, 737 $cm^{-1}$; HRMS (ESI+): Calcd for a $C_{18}H_{22}N_5O_2^+$ [M+H]$^+$ 340.1768, found 340.1765, Δppm −0.88. (FIGS. 58A and 58B).

Example 18: Preparation of Compound 20f

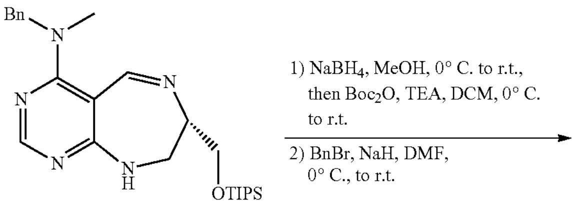

1f

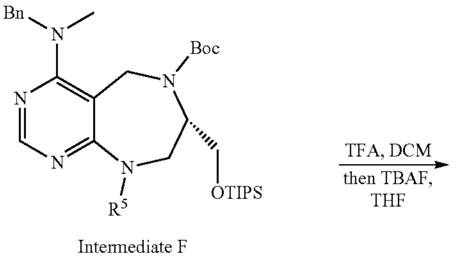

Intermediate F ($R^5$ = Benzyl)

-continued

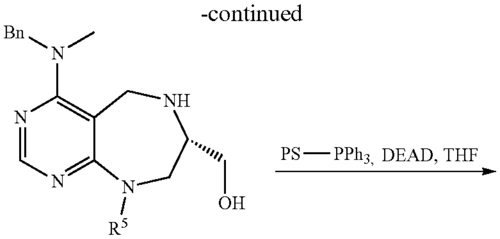

SI-10

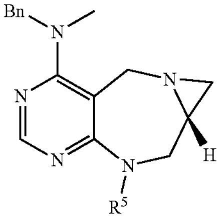

20f ($R^5$ = Benzyl)

1) Preparation of Intermediate F

A solution of 1f (135.0 mg, 0.298 mmol) in methanol (MeOH) was treated with sodium borohydride ($NaBH_4$, 56.37 mg, 1.490 mmol) at 0° C. and stirred between 0° C. and 25° C. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then evaporated under reduced pressure, condensed, and dried. The compound was dissolved in dichloromethane (DCM, 3 ml), followed by sequentially adding, at 0° C., triethylamine (TEA, 0.083 ml, 0.596 mmol) and $Boc_2O$ (Di-tert-butyl dicarbonate, 84.55 mg, 0.387 mmol), and stirring between 0° C. and 25° C. After completion of the reaction as indicated by TLC, the mixture was quenched with addition of ammonium chloride ($NH_4Cl$) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain Boc-protected compound (162.3 mg, 98% yield). Boc-protected compound (162.3 mg, 0.292 mmol) was dissolved, under argon atmosphere, in anhydrous DMF solution (3.0 ml), treated with sodium hydride (NaH, 60% dispersion in mineral oil, 23.36 mg, 0.584 mmol) at 0° C., and stirred at 0° C. over 30 minutes. After 30 minutes, the mixture was slowly treated with benzyl bromide (0.052 ml, 0.438 mmol) at 0° C. and stirred between 0° C. and 25° C. After completion of the reaction as indicated by TLC, the mixture was quenched with addition of ammonium chloride (NH4Cl) solution. The reaction solution was extracted twice with ethyl acetate (EA) and the extracted organic solution was dried over anhydrous sodium sulfate (Na2SO4) and filtered. The filtrate was then condensed under reduced pressure and the product was purified with silica-gel flash column chromatography to obtain intermediate F ($R^5$=benzyl, 164.1 mg, 87% yield).

2) Preparation of Compound SI-10

Intermediate F ($R^5$=benzyl, 164.1 mg, 0.254 mmol) was dissolved in 10% trifluoroacetic acid (TFA) DCM (12.5 ml)

solution and then stirred at r.t. After completion of the reaction as indicated by TLC, any excess TFA was removed by azeotropic evaporation with toluene under reduced pressure. The compound was dissolved in THF (2.5 ml), treating with Tetra-n-butylammonium fluoride solution (TBAF, 1.0 m solution in THF, 0.330 ml, 0.330 mmol) and stirred at r.t. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain compound SI-10 (73.21 mg, 74% yield).

3) Preparation of Compound 20f

Compound SI-10 (73.21 mg, 0.188 mmol) was dissolved, under argon atmosphere, in anhydrous DMF solution (20.0 ml), treated with solid triphenylphosphine ($PPh_3$) (polymer-bound triphenylphosphine (587.5 mg, 0.94 mmol)) and stirred over 30 minutes. After 30 minutes, the above was slowly treated with diethyl azodicarboxylate (DEAD, 0.058 ml, 0.376 mmol) and stirred over 18 hours. The resultant solid after the reaction was removed by using Celite® and the filtrate was condensed under reduced pressure. The product was purified with silica-gel flash column chromatography to obtain compound 20f ($R^5$=benzyl) (56.57 mg, 81% yield, 52% overall yield) compound as a pale yellow oil.

20f

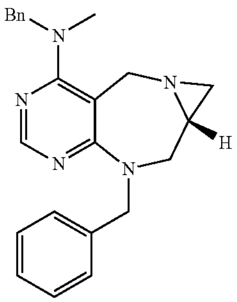

$R_f$=0.4 (DCM/MeOH 20:1); $^1H$ NMR (400 MHz, a $CDCl_3$) δ 8.24 (s, 1H), 7.35-7.27 (m, 10H), 5.10, 4.88 (ABq, $J_{AB}$=15.3 Hz, 2H), 4.61, 4.39 (ABq, $J_{AB}$=15.3 Hz, 2H), 4.26 (d, J=13.7, 1H), 4.09 (dd, J=15.3, 11.3 Hz, 1H), 3.58 (d, J=13.7, 1H), 3.42 (dd, J=15.5, 4.1 Hz, 1H), 2.82 (s, 3H), 2.43 (m, 1H), 1.78 (d, J=5.1, 1H), 1.30 (d, J=3.1, 1H); $^{13}C$ NMR (100 MHz, a $CDCl_3$) δ 167.4, 163.8, 155.4, 138.8, 138.7, 128.7, 128.6, 127.8, 127.6, 127.3, 127.1, 100.3, 57.8, 53.9, 51.5, 48.7, 39.7, 34.4, 32.8; IR (neat) $v_{max}$:3027, 2920, 2853, 1559, 1356, 735, 700 $cm^{-1}$; HRMS(ESI+): Calcd fora $C_{23}H_{26}N_5^+$ $[M+H]^+$ 372.2183, found 372.2189, Δppm +1.61. (FIGS. 59A and 59B).

Example 19: Preparation of Compound 21f

Compound 21f was prepared based on Example 18, provided that 3,5-dimethylbenzyl bromide was used in place of benzyl bromide.

21f

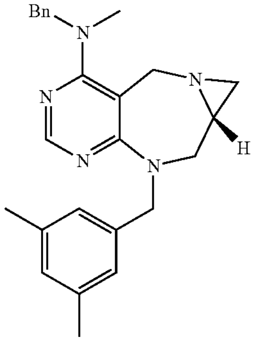

Intermediate F ($R^5$=3,5-dimethylbenzyl). A light yellow oil; $R_f$=0.5 (DCM/MeOH=20:1); 49.82 mg, 81% yield, 53% overall yield; $^1H$ NMR (500 MHz, a $CDCl_3$) δ 8.25 (s, 1H), 7.34-7.25 (m, 5H), 6.91 (m, 3H), 5.04, 4.78 (ABq, $J_{AB}$=15.2 Hz, 2H), 4.61, 4.38 (ABq, $J_{AB}$=15.2 Hz, 2H), 4.26 (d, J=13.7, 1H), 4.04 (dd, J=14.2, 11.7 Hz, 1H), 3.57 (d, J=13.7, 1H), 3.41 (dd, J=15.4, 2.2 Hz, 1H), 2.81 (s, 3H), 2.43 (m, 1H), 2.29 (s, 6H), 1.77 (d, J=2.9, 1H), 1.28 (s, 1H); $^{13}C$ NMR (100 MHz, a $CDCl_3$) δ 167.4, 163.8, 155.4, 138.8, 138.6, 138.3, 129.0, 128.6, 127.8, 127.1, 125.4, 100.3, 57.9, 53.7, 51.5, 48.4, 39.7, 34.5, 32.7, 21.5; IR (neat) $v_{max}$: 3026, 2922, 2863, 1564, 1355, 735, 700 $cm^{-1}$; HRMS(ESI+): Calcd for a $C_{25}H_{30}N_5^+$ $[M+H]^+$ 400.2496, found 400.2495, Δppm −0.25. (FIGS. 60A and 60B).

Example 20: Preparation of Compound 22f

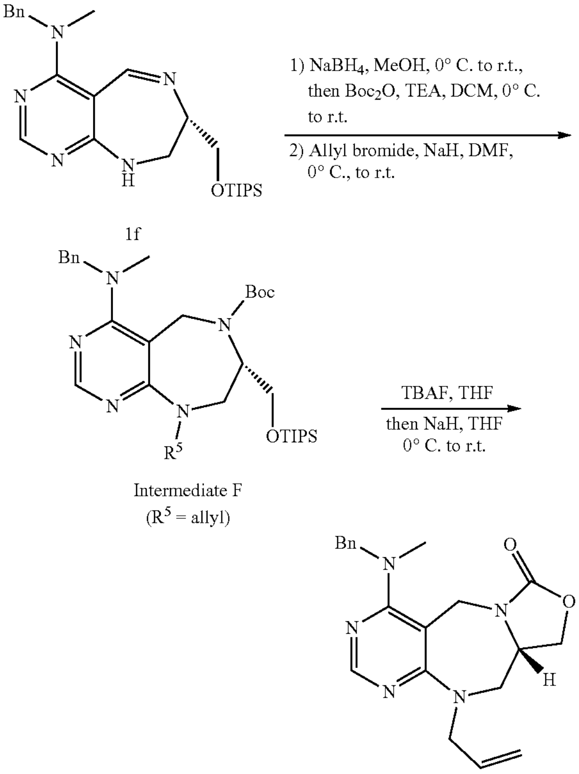

1f

Intermediate F ($R^5$ = allyl)

22f

1) Preparation of Intermediate F ($R^5$=Allyl)

A solution of 1f (135.0 mg, 0.298 mmol) in methanol (MeOH) was treated with sodium borohydride ($NaBH_4$ (56.37 mg, 1.490 mmol)) at 0° C. and stirred between 0° C. and 25° C. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then evaporated under reduced pressure, condensed, and dried. The compound was dissolved in dichloromethane (DCM 3 ml), followed by sequentially adding, at 0° C., triethylamine (TEA, 0.083 ml, 0.596 mmol) and $Boc_2O$ (Di-tert-butyl dicarbonate, 84.55 mg, 0.387 mmol), and stirring between 0° C. and 25° C. After completion of the reaction as indicated by TLC, the mixture was quenched with addition of ammonium chloride (NH4Cl) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain Boc-protected compound (162.3 mg, 98% yield).

The Boc-protected compound (162.3 mg, 0.292 mmol) was dissolved, under argon atmosphere, in anhydrous DMF solution (3.0 ml), treating with sodium hydride (NaH (60% dispersion in mineral oil, 23.36 mg, 0.584 mmol)) at 0° C., and stirring at 0° C. over 30 minutes. After 30 minutes, the mixture was slowly treated with allyl bromide (0.038 ml, 0.438 mmol) at 0° C. and stirred between 0° C. and 25° C. After completion of the reaction as indicated by TLC, the mixture was quenched with addition of ammonium chloride (NH4Cl) solution. The reaction solution was extracted twice with ethyl acetate (EA) and the extracted organic solution was dried over anhydrous sodium sulfate (Na2SO4) and filtered. The filtrate was then condensed under reduced pressure and the product was purified with silica-gel flash column chromatography to obtain intermediate F ($R^5$=allyl, 141.2 mg, 81% yield).

2) Preparation of Compound 22f

A solution of intermediate F (R5=allyl, 243.1 mg, 0.408 mmol) was treated with TBAF solution (Tetrabutylammonium fluoride, 1.0 M solution in THF, 0.530 ml, 0.530 mmol) and stirred at r.t. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then evaporated under reduced pressure, condensed, and dried. The compound was dissolved, under argon atmosphere, in anhydrous THF (2.5 ml), treating with sodium hydride (NaH (60% dispersion in mineral oil, 14.22 mg, 0.356 mmol)) at 0° C., and stirring between 0° C. and 25° C. After completion of the reaction as indicated by TLC, the mixture was quenched with addition of ammonium chloride (NH4Cl) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain 22f (56.30 mg, 65% yield, 53% overall yield) as white powder.

22f

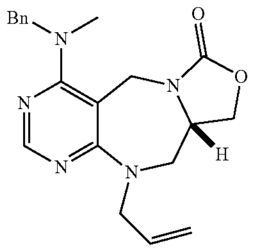

$R_f$— 0.2 (EA); $^1$H NMR (400 MHz, a $CDCl_3$) δ 8.23 (s, 1H), 7.36-7.31 (m, 4H), 7.28 (m, 1H), 5.92 (m, 1H), 5.21 (d, J=10.2 Hz, 1H), 5.15 (dd, J=17.2, 1.2 Hz, 1H), 4.72-4.65 (m, 2H), 4.61 (dd, J=15.5, 4.9 Hz, 1H), 4.55-4.44 (m, 2H), 4.11-4.07 (m, 2H), 4.02 (d, J=16.0 Hz, 1H), 3.91 (dd, J=15.5, 6.5 Hz, 1H), 3.76 (dd, J=14.9, 2.0 Hz, 1H), 3.25 (dd, J=15.1, 3.3 Hz, 1H), 2.91 (s, 3H); $^{13}$C NMR (100 MHz, a $CDCl_3$) δ 166.9, 164.9, 157.3, 155.0, 138.1, 134.2, 128.7, 127.9, 127.3, 117.8, 97.0, 65.1, 56.9, 56.7, 54.5, 52.4, 42.1, 39.7; IR (neat) $v_{max}$: 3049, 2976, 2917, 1758, 1561, 1410, 1266, 746 $cm^{-1}$; HRMS(ESI+): Calcd for a $C_{20}H_{24}N_5O_2^+$ $[M+H]^+$ 366.1925, found 366.1924, Δppm −0.27; mp: 89-91° C. (FIGS. 61A and 61B).

Example 21: Preparation of Compound 23f

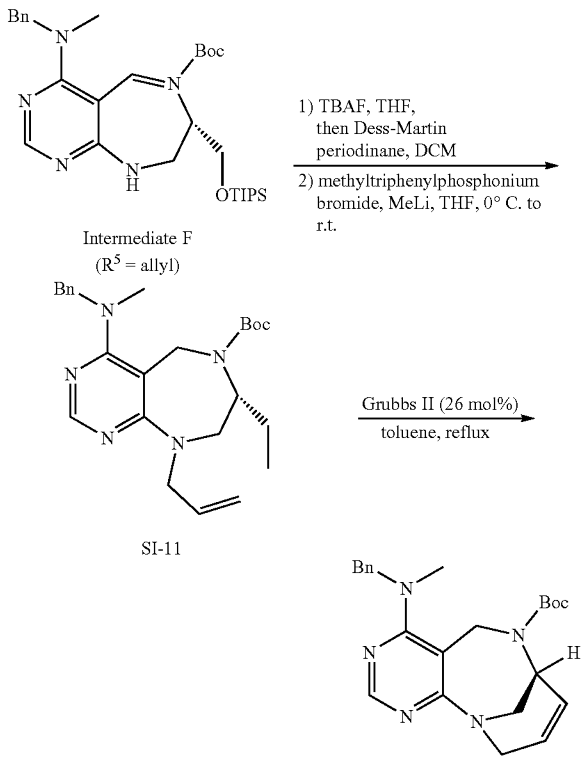

Intermediate F ($R^5$ = allyl)

SI-11

23f

1) Preparation of SI-11

A solution of intermediate F (R5=allyl, 243.1 mg, 0.408 mmol) in THF was treated with TBAF solution (Tetrabutylammonium fluoride, 1.0 M solution in THF, 0.530 ml, 0.530 mmol) and stirred at r.t. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then evaporated under reduced pressure, condensed, and dried. The compound was dissolved in dichloromethane (8.2 ml), treating with Dess-Martin periodinane (259.6 mg, 0.612 mmol) and stirred at r.t. After completion of the reaction as indicated by TLC, the mixture was quenched with addition of sodium bicarbonate (NaHCO3) solution. The reaction solution was extracted twice with dichloromethane (DCM) and the extracted organic solution was dried over anhydrous sodium sulfate (Na2SO4) and filtered. The filtrate was then condensed under reduced pressure and the product was purified with silica-gel flash column chromatography to obtain aldehyde compound (148.3 mg, 83% yield).

Next, methyltriphenylphosphonium bromide (363.3 mg, 1.017 mmol) was dissolved, under argon atmosphere, in anhydrous THF, followed by adding, at 0° C., MeLi (1.6 M in diethyl ether, 0.530 ml, 0.848 mmol) solution, and the mixture was stirred over 30 minutes at 0° C. After 30 minutes, the above was treated with the resultant aldehyde compound and stirred over 12 hours between 0° C. and 25° C. After 12 hours, to the mixture was added ammonium chloride solution to quench the reaction. The reaction solution was extracted twice with ethyl acetate (EA) and the extracted organic solution was dried over anhydrous sodium sulfate (Na2SO4) and filtered. The filtrate was then condensed under reduced pressure and the product was purified with silica-gel flash column chromatography to obtain compound SI-11 (130.0 mg, 88% yield).

2) Preparation of Compound 23f

A solution of SI-11 (130.0 mg, 0.298 mmol) in toluene was treated with second generation Grubbs' catalyst (50.94 mg, 0.060 mmol, 20 mol %) and left at reflux. After 4 hours, the resultant was condensed under reduced pressure and the product was purified with silica-gel flash column chromatography to obtain compound 23f (44.83 mg, 52% recovery yield, 31% overall yield) as a yellow oil.

23f

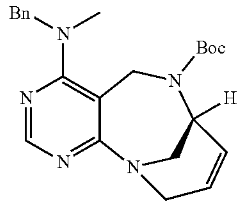

$R_f$=0.2 (hexane/EA=1:1); $^1$H NMR (400 MHz, DMSO-$d_6$, 100° C.) δ 8.06 (s, 1H), 7.35-7.29 (m, 4H), 7.27-7.23 (m, 1H), 6.35 (ddd, J=9.9, 5.3, 1.8 Hz, 1H), 5.78 (ddd, J=10.1, 3.9, 1.8 Hz, 1H), 4.92 (d, J=16.5 Hz, 1H), 4.86-4.81 (m, 1H), 4.76 (d, J=15.3 Hz, 1H), 4.56 (d, J=15.9 Hz, 1H), 4.42 (dd, J=15.3, 1.2 Hz, 1H), 4.34 (d, J=15.3 Hz, 1H), 4.00 (dd, J=4.9, 1.8 Hz, 1H), 3.77 (dq, J=18.3, 2.2 Hz, 1H), 3.30 (dd, J=15.3, 2.4 Hz, 1H), 2.84 (s, 3H), 1.42 (s, 9H); $^{13}$C NMR (100 MHz, DMSO-$d_6$, 100° C.) δ 166.0, 163.6, 154.6, 153.5, 137.9, 128.0, 127.7, 127.3, 127.1, 126.3, 99.7, 79.0, 55.4, 49.9, 49.4, 45.7, 41.9, 38.7, 27.7; IR (neat) $v_{max}$: 3031, 2978, 2928, 1690, 1588, 1408, 1164 $cm^{-1}$; HRMS(ESI+): Calcd for a $C_{23}H_{30}N_5O_2^+$ $[M+H]^+$ 408.2394, found 408.2382, Δppm −2.94. (FIGS. 62A and 62B).

Experiment 1: Cell Culture

HEK293T cell was cultured in Dulbecco modified eagle medium (DMEM) with 10% (v/v) fetal bovine serum (FBS) and 1% (v/v) antibiotic-antimycotic solution. HeLa, DU145, and Ca Ski cells were cultured in RPMI 1640 medium with 10% (v/v) FBS and 1% (v/v) antibiotic-antimycotic solution. The cells were cultured in 100-mm culture dish in an incubator at 37° C., in 5% $CO_2$.

Experiment 2: ELISA

His-tagged human LRS proteins were diluted in carbonate buffer (100 mM, pH 9.6) to the concentration of 0.5 ng $\mu l^{-1}$. The proteins were distributed to the plate (half-bottom 96 well clear plate) from CORNING 3690 and subjected to incubation overnight at 4° C. refrigerator under sealed. Protein from each well was removed and washed three times with PBS mixed with 0.05% Tweed® 20 (PBST), subjected to blocking with PBS containing 5% bovine serum albumin (BSA) for 2 hours. Each well was washed with PBST, followed by the treatment of a compound and GST-tagged human RagD protein simultaneously for 3 hours. GST protein itself was used as a negative control. Each well was treated with GST antibody diluted in PBST and incubated at room temperature for 1 h. After washing with PBST, the HRP-conjugated anti-horse IgG secondary antibody was incubated at room temperature for 1 h. TMB was added to each well for colorimetric development. Blue color was found in positive wells. To stop the chemical reaction, the treatment with 1 m $H_3PO_4$ was done. Finally, absorbance at 450 nm were measured.

The experiment result shows that compound 21f inhibits the LRS-RagD interaction in a dose-dependent manner (FIG. 15).

Experiment 3: Western Blotting

Cells were lysed with Radio-ImmunoPrecipitation Assay (RIPA) buffer (50 mM Tris, pH 7.8, 150 mM NaCl, 0.5% deoxycholate, 1% IGEPAL CA-630, protease inhibitor cocktail, and phosphatase inhibitors). Protein was obtained by transferring supernatant after centrifugation at 15000 rpm for 20 min. Protein concentration was measured with Micro BCA™ protein assay kit. Overall protein sampling procedure was done at 4° C. Prepared protein samples were analyzed with SDS-PAGE. Protein after electrophoresis was transferred into nitrocellulose membrane. Membrane was blocked with TBST mixed with 2% BSA over at least 1 h at r.t. Primary antibodies were incubated overnight at 4° C. The treatment concentration was as follows: Anti-LC3B (ab51520); 1:1000, anti-S6K1 (ab32359); 1:1000, anti-phospho-T389 S6K1 (ab2571); 1:800, anti-p62 (CST 5114); 1:1000, anti-glyceraldehyde-3-phosphate dehydrogenase (GAPDH) (CST 2118); 1:1000, anti-phospho-S65 4E-BP1 (CST 9451); 1:1000, anti-phospho-S757 ULK1 (CST 6888); 1:800, anti-phospho-S473 Akt (CST 4058); 1:1000, anti-phospho-T172 AMPKα (CST 2531). After washing with TBST, HRP-labeled anti-rabbit IgG secondary antibody was treated at room temperature for 1 h. After washing with TBST, developing by Amersham ECL prime solution was done. Chemiluminescent signal was imaged by ChemiDoc™ MP imaging system.

It was confirmed from the experiment that 21f inhibits an activation of mTORC1 in a dose-dependent manner as discussed below.

The effect of rapamycin on mTORC1 within cells was reviewed over 0 to 24 hours. HEK293T cells were treated with 500 nM of rapamycin. Phospho-T389 S6K1 and phospho-S65 4E-BP1 were reduced as the time passed wherein the effect lasted for at least about 12 hours. This is similar to the result with 21f. However, against phospho-S757 ULK1, it was confirmed that 21f exerted high inhibition degree, while rapamycin not so high. This shows that 21f functions in a different mechanism from rapamycin (FIG. 18).

Experiment 4: Surface Plasmon Resonance (SPR) Assay

The dissociation rate constant ($K_D$) toward His-LRS proteins was determined by using SPR instrument (Biacore T100) at the national center for inter-university research facilities (NCIRF) in Seoul National University. The carboxyl group on the surface of CMS chip was able to be replaced with protein by forming reactive succinimide ester with 1-ethyl-3-(3-dimethylaminopropyl)-carbodiimide (EDC) and N-hydroxysuccinimide (NHS). Human LRS proteins (1.5×PBS, pH 7.3) were immobilized on flow cell 2 (imed RU; 12000) by leading to amide bond formation with NHS ester. The residual NHS ester was quenched with 1 M ethanolamine-HCl (pH 8.0). Amide bond formation alone, without any protein t, was performed on flow cell 1 as a control. The immobilization process was proceeded on PBS buffer. After the immobilization of hLRS, compounds were flowed for 60 s at a flow rate of 20 μl $min^{-1}$ in various concentrations from 1 μM to 15 Buffer was then flowed at the same flow rate for 200 s for dissociation of compounds. As a running buffer, 1×PBS (pH 7.3) containing 3% DMSO and 0.005% $P_2O$ was used. The experiment was performed at 25° C. Data analysis was done by using Biacore T100 Evaluation software. Final sensorgrams were obtained after the elimination of results from flow cell control and buffer-only control. The dissociation constant ($K_D$) was calculated by fitting to the 1:1 binding model.

It was confirmed from the experiment that 21f binds LRS in a dose-dependent manner (FIG. 15).

Experiment 5: Transfection

HeLa cells were seeded in chambered coverglass from Nunc and incubated for 24 h. mCherry-GFP-LC3 plasmid was transfected to the cells using Lipofectamine™ 2000 solution. Transfection was proceeded according to manufacturer's protocol.

Experiment 6: mCherry-GFP-LC3 Puncta Imaging

DeltaVision Elite imaging system was used for the imaging of mCherry-GFP-LC3 transfected HeLa cell. For live-cell imaging, chamber was maintained at 37° C. and in 5% $CO_2$. Cells were observed with 60× scale, using mCherry/mCherry, GFP/GFP (Excitation/Emission) filter sets. The wavelength range of the used filters is as follows: mCherry (Excitation: 575/25 nm, Emission: 625/45 nm); GFP (Excitation: 475/28 nm, Emission: 525/48 nm). Images were processed and analyzed with SoftWorks deconvolution software.

Experiment 7: Cell Proliferation Assay

HEK293T cells were seeded in 96-well plate from CORNING. 24 h after seeding, the compound diluted with DMEM at 5 μM of final concentration was treated in cells while leucine-free DMEM was treated in cells as a control. Cell division assay was done with WSTs assay and BrdU colorimetric kit, following the manufacturer's protocol.

Hereinafter, the detailed results and analysis of the experiments are discussed.

Results of Experiments

The present inventors found from the experiments that LRS can play a noncanonical role of in amino acid-dependent mTORC1 activation by sensing intracellular Leu concentration. According to this study, LRS can mediate Leu signalling to mTORC1 via direct binding to RagD-GTP protein and form an LRS-RagD protein complex in a Leu-dependent manner, which leads to the translocation of mTORC1 to the lysosome cellular membrane and subsequent activation of mTORC1 (FIG. 15*a*). Thus, LRS-RagD interactions could serve as a Leu-sensing mechanism in the nutrition-dependent activation of mTORC1. Further, novel small-molecule PPI inhibitors could serve as lead compounds for the development of potential therapeutic agents with new modes of action to treat human diseases linked to the oncogenic activation of mTORC1.

To identify novel small-molecule PPI modulators towards the LRS-RagD interaction, the pDOS library was subjected to ELISA-based HTS using purified LRS and GST (glutathione-S-transferase) where aziridine-containing 20f and 21f were identified as dose-dependent inhibitors of the LRS-RagD interaction (FIG. 15*b*). On the basis of this data, we hypothesized that 20f and 21f inhibit the LRS-mediated Leu signalling to mTORC1 via direct disruption of the LRS-RagD interaction, which resulted in decreasing phosphorylated S6K1, a dominant substrate of mTORC1 kinase. As shown in FIG. 15*c*, the level of phosphorylated S6K1 was decreased in the absence of Leu. Similarly, 20f and 21f suppressed the phosphorylation of S6K1 even in the presence of Leu. On the basis of the reduction of LRS-RagD interaction by ELISA (20f 15.5%; 21f 30.2%) and the phosphorylation suppression of S6K1 by western blotting (20f 16.4%; 21f 48.9%; FIG. 15*d*), we selected 21f as the candidate compound and subjected it to further western blot analysis and biophysical study using surface plasmon resonance (SPR; FIG. 15*e*) spectroscopy. As shown in FIG. 15*d*, compound 21f downregulated the phosphorylation of S6K1 in a dose-dependent manner. Further, compound 21f directly bound to LRS with 4.5(±0.78) of $K_D$ when measured by SPR. This clearly supported that 21f directly binds to LRS and disrupts the interaction between LRS and RagD (FIG. 15).

It was examined whether compound 21f stimulates cellular autophagy through the inhibition of LRS-mediated activation of mTORC1. HeLa human cervical cancer cells were treated with rapamycin (Rap), bafilomycin (Baf), or 21f in the presence of Leu. Autophagic activity was evaluated using western blot analysis with autophagosome biomarker wherein microtubule-associated proteins 1 light chain 3 (LC3) and ubiquitin-binding protein p62 are used as the autophagosome biomarker. This is because conversion of LC3 I to LC3 II is associated with the formation of autophagosome and the degradation of p62 reflects autolysosome formation indicating the final progression of the autophagic processes. Baf is a known inhibitor of vacuolar-type H+-ATPase, which inhibits the autolysosomal degradation of cellular contents as well as autophagosomal-lysosomal fusion through the inhibition of acidification, thereby blocking the final-stage flux of autophagy. As shown in FIG. 16*a*, the treatment with Baf resulted in an increased ratio of LC3 I/LC3 II, and accumulation of p62 compared with the DMSO control. In contrast, the treatment with Rap or 21f as an inhibitor of mTORC1 increased the cellular level of LC3 II and stimulated the degradation of p62, which was consistent with their suppressive effects on mTORC1 activity. To monitor autophagy in living cells, we performed the mCherry-green fluorescent protein (GFP)-LC3 assay. Because of the difference in acid sensitivity of mCherry (acid-stable) and GFP (acid-sensitive), the entire autophagy process from autophagosome to autolysosome formation could be differentiated by the fluorescence emission pattern (FIG. 16*b*). For instance, cells expression of mCherry-GFP-LC3 show yellow puncta when autophagosomes are formed.

In contrast, the formation of autolysosome via autophagosomal-autolysosomal fusion results in red puncta because the acidic environment of autolysosomes quenches GFP fluorescence. As shown in FIG. 16*c*, yellow puncta were clearly observed upon treatment with Baf, which is consistent with the inhibitory effect of Baf on autophagosomal-autolysosomal fusion. When cells were treated with Rap or 21f, red puncta were clearly observed, which indicates that compound 21f could activate autophagy via the suppression of LRS-mediated activation of mTORC1. Finally, we evaluated whether compound 21f could inhibit Leu-mediated cell proliferation by using BrdU and WST assay, because Leu plays a critical role in promoting cellular proliferation through the activation of mTORC1. As shown in FIG. 16*d* (BrdU assay), compound 21f suppressed cell proliferation even in the presence of Leu, similar to in the Leu-deprived medium, which indicated that compound 21f could inhibit Leu-mediated signalling to mTORC1 by disrupting the LRS-RagD interaction (FIG. 16).

The invention claimed is:

1. A pyrimidine derivative compound represented by Formula VIII:

[Formula VIII]

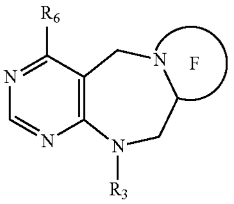

wherein

F is —X—$(CH_2)$n-(O—$CH_2$)m- and forms a 3- to 6-membered heterocyclic ring together with adjacent N and C atoms wherein X is

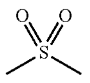,
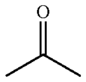

or —$CH_2$—, and wherein (i) when n is 0, m is 0 or 1, (ii) when n is 1, m is 0 or 1, and (iii) when n is 2, m is 0;

$R_3$ is hydrogen, a —$C_1$ to $C_3$ alkyl group, an allyl group, -Tf, a $C_1$ to $C_3$ alkyl benzyl group, or

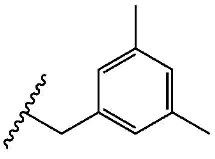;

and $R_6$ is

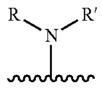

wherein R and R' are each independently a benzyl group or a $C_1$ to $C_3$ alkyl group.

2. The compound according to claim 1, wherein the compound is represented by Formula VIII-1:

[Formula VIII-1]

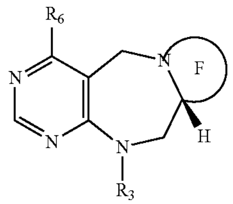

wherein

F is —X—$(CH_2)$n-(O—$CH_2$)m- and forms a 3- to 6-membered heterocyclic ring together with adjacent N and C atoms wherein X is

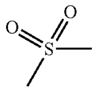,
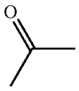

or —$CH_2$—, and wherein (i) when n is 0, m is 0 or 1, (ii) when n is 1, m is 0 or 1, and (iii) when n is 2, m is 0;

$R_3$ is hydrogen, a —$C_1$ to $C_3$ alkyl group, an allyl group, -Tf, a $C_1$ to $C_3$ alkyl benzyl group, or

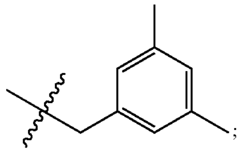 [SMILES: *Cc1cc(C)cc(C)c1];

and $R_6$ is

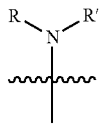

wherein R and R' are each independently a benzyl group or a $C_1$ to $C_3$ alkyl group.

3. A compound represented by any one of the following formulas:

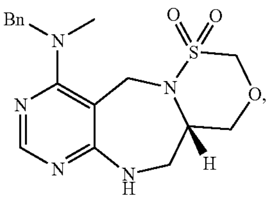
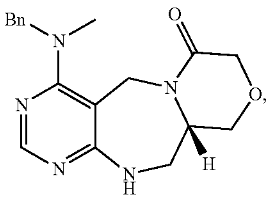

-continued

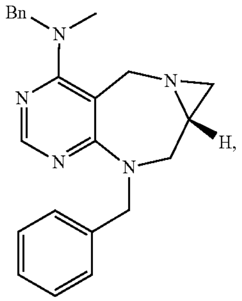
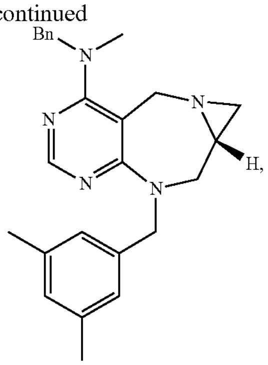
and
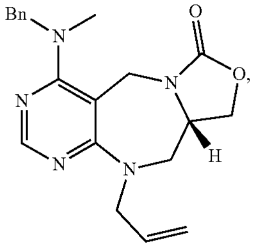

or a pharmaceutically acceptable salt thereof.

4. A process for preparing the pyrimidine derivative compound according to claim 1 or a pharmaceutically acceptable salt thereof, comprising:

step 1 for preparing an intermediate substance, tert-(S)-(1-(6-chloro-5-formylpyrimidin-4-yl)amino)-3-((tri-isopropylsilyl)oxy)propan-2-yl)carbamate;

step 1a for preparing a starting material represented by Formula 1 by reacting the intermediate substance prepared in step 1 with cyclic amine or tetrakis palladium:

[Formula 1]

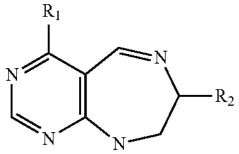

wherein $R_1$ is

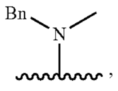

and $R_2$ is —$CH_2$—O-TIPS; and step 2 for preparing a desired compound from the starting material prepared in step 1a.

5. The process for preparing according to claim 4, wherein step 2 comprises at least one of the following reactions on the starting material of step 1a: N-alkylation, debenzylation, intramolecular substitution reaction, ring-closing metathesis, nucleophilic addition reaction, allylation reaction of amine, Grubbs' catalyst condensation reaction, alcohol deprotection reaction, intramolecular nucleophilic addition reaction, aziridinium intermediate formation reaction, nucleophilic ring expansion reaction, and bridge head ring formation reaction.

6. A composition for treating cervical cancer comprising as an active ingredient the pyrimidine derivative compound according to claim 1 or a pharmaceutically acceptable salt thereof.

* * * * *